United States Patent
Smith et al.

(10) Patent No.: US 10,626,081 B2
(45) Date of Patent: Apr. 21, 2020

(54) FARNESOID X RECEPTOR AGONISTS AND USES THEREOF

(71) Applicant: Metacrine, Inc., San Diego, CA (US)

(72) Inventors: Nicholas D. Smith, San Diego, CA (US); Steven P. Govek, San Diego, CA (US); Johnny Y. Nagasawa, San Diego, CA (US)

(73) Assignee: METACRINE, INC., San Diego, CA (US)

( * ) Notice: Subject to any disclaimer, the term of this patent is extended or adjusted under 35 U.S.C. 154(b) by 0 days.

(21) Appl. No.: 15/758,709

(22) PCT Filed: Sep. 16, 2016

(86) PCT No.: PCT/US2016/052268
§ 371 (c)(1),
(2) Date: Mar. 8, 2018

(87) PCT Pub. No.: WO2017/049172
PCT Pub. Date: Mar. 23, 2017

(65) Prior Publication Data
US 2018/0244606 A1    Aug. 30, 2018

Related U.S. Application Data

(60) Provisional application No. 62/219,422, filed on Sep. 16, 2015.

(51) Int. Cl.
*C07C 233/54*    (2006.01)
*C07C 255/57*    (2006.01)
(Continued)

(52) U.S. Cl.
CPC ............ *C07C 233/54* (2013.01); *A61K 31/16* (2013.01); *A61K 31/216* (2013.01); *A61K 31/27* (2013.01); *A61K 31/277* (2013.01); *A61K 31/337* (2013.01); *A61K 31/351* (2013.01); *A61K 31/36* (2013.01); *A61K 31/382* (2013.01); *A61K 31/397* (2013.01); *A61K 31/402* (2013.01); *A61K 31/404* (2013.01); *A61K 31/415* (2013.01); *A61K 31/416* (2013.01); *A61K 31/4184* (2013.01); *A61K 31/4192* (2013.01); *A61K 31/42* (2013.01); *A61K 31/426* (2013.01); *A61K 31/4406* (2013.01); *A61K 31/4453* (2013.01); *A61K 31/45* (2013.01); *A61K 31/4965* (2013.01); *A61K 31/50* (2013.01); *A61K 31/505* (2013.01); *A61K 31/5375* (2013.01); *A61K 45/06* (2013.01); *A61P 1/16* (2018.01); *C07C 233/63* (2013.01); *C07C 233/65* (2013.01); *C07C 233/81* (2013.01); *C07C 233/87* (2013.01); *C07C 235/04* (2013.01); *C07C 235/16* (2013.01); *C07C 235/40* (2013.01); *C07C 235/56* (2013.01); *C07C 235/64* (2013.01); *C07C 235/82* (2013.01); *C07C 237/24* (2013.01); *C07C 255/57* (2013.01); *C07C 255/60* (2013.01); *C07C 271/24* (2013.01); *C07C 271/28* (2013.01); *C07C 311/07* (2013.01); *C07C 311/08* (2013.01); *C07C 317/32* (2013.01); *C07C 317/44* (2013.01); *C07C 323/50* (2013.01); *C07C 323/61* (2013.01); *C07C 335/02* (2013.01); *C07D 205/04* (2013.01); *C07D 209/04* (2013.01); *C07D 211/06* (2013.01); *C07D 211/62* (2013.01); *C07D 211/76* (2013.01); *C07D 211/94* (2013.01); *C07D 211/96* (2013.01); *C07D 213/40* (2013.01); *C07D 231/12* (2013.01); *C07D 231/56* (2013.01); *C07D 235/04* (2013.01); *C07D 235/08* (2013.01); *C07D 237/20* (2013.01); *C07D 239/42* (2013.01); *C07D 241/20* (2013.01); *C07D 249/18* (2013.01); *C07D 261/08* (2013.01); *C07D 265/30* (2013.01); *C07D 277/28* (2013.01); *C07D 295/088* (2013.01); *C07D 295/135* (2013.01);
(Continued)

(58) Field of Classification Search
None
See application file for complete search history.

(56) References Cited

U.S. PATENT DOCUMENTS

| 7,671,085 B2 | 3/2010 | Downes et al. | |
|---|---|---|---|
| 2015/0258052 A1* | 9/2015 | Evans | A61K 31/216 514/155 |

(Continued)

FOREIGN PATENT DOCUMENTS

| EP | 0656355 A1 | 6/1995 |
|---|---|---|
| WO | WO-03037865 A1 | 5/2003 |

(Continued)

OTHER PUBLICATIONS

Ali et al. Recent advances in the development of farnesoid X receptor agonists. Ann Tranl Med 3(1):5 (2015).

(Continued)

*Primary Examiner* — Heidi Reese
(74) *Attorney, Agent, or Firm* — Wilson Sonsini Goodrich & Rosati

(57) ABSTRACT

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

18 Claims, No Drawings

(51) Int. Cl.

| | | |
|---|---|---|
| C07C 271/28 | (2006.01) | |
| C07C 317/44 | (2006.01) | |
| C07C 235/40 | (2006.01) | |
| C07D 309/08 | (2006.01) | |
| C07C 335/02 | (2006.01) | |
| C07D 205/04 | (2006.01) | |
| C07D 277/28 | (2006.01) | |
| C07D 213/40 | (2006.01) | |
| C07D 305/08 | (2006.01) | |
| C07C 233/63 | (2006.01) | |
| C07C 323/61 | (2006.01) | |
| C07C 233/87 | (2006.01) | |
| A61K 31/16 | (2006.01) | |
| C07D 295/088 | (2006.01) | |
| C07D 211/62 | (2006.01) | |
| C07C 235/56 | (2006.01) | |
| C07D 235/04 | (2006.01) | |
| C07D 319/12 | (2006.01) | |
| C07D 211/76 | (2006.01) | |
| C07C 235/64 | (2006.01) | |
| C07D 211/96 | (2006.01) | |
| C07C 311/07 | (2006.01) | |
| C07C 235/16 | (2006.01) | |
| C07C 317/32 | (2006.01) | |
| C07C 271/24 | (2006.01) | |
| C07C 233/65 | (2006.01) | |
| C07C 237/24 | (2006.01) | |
| C07C 233/81 | (2006.01) | |
| C07C 255/60 | (2006.01) | |
| C07C 311/08 | (2006.01) | |
| A61P 1/16 | (2006.01) | |
| A61K 31/216 | (2006.01) | |
| A61K 31/27 | (2006.01) | |
| A61K 31/277 | (2006.01) | |
| A61K 31/337 | (2006.01) | |
| A61K 31/351 | (2006.01) | |
| A61K 31/36 | (2006.01) | |
| A61K 31/382 | (2006.01) | |
| A61K 31/397 | (2006.01) | |
| A61K 31/402 | (2006.01) | |
| A61K 31/404 | (2006.01) | |
| A61K 31/415 | (2006.01) | |
| A61K 31/416 | (2006.01) | |
| A61K 31/4184 | (2006.01) | |
| A61K 31/4192 | (2006.01) | |
| A61K 31/42 | (2006.01) | |
| A61K 31/426 | (2006.01) | |
| A61K 31/4406 | (2006.01) | |
| A61K 31/4453 | (2006.01) | |
| A61K 31/45 | (2006.01) | |
| A61K 31/4965 | (2006.01) | |
| A61K 31/50 | (2006.01) | |
| A61K 31/505 | (2006.01) | |
| A61K 31/5375 | (2006.01) | |
| A61K 45/06 | (2006.01) | |
| C07C 235/04 | (2006.01) | |
| C07C 235/82 | (2006.01) | |
| C07C 323/50 | (2006.01) | |
| C07D 209/04 | (2006.01) | |
| C07D 211/06 | (2006.01) | |
| C07D 211/94 | (2006.01) | |
| C07D 231/12 | (2006.01) | |
| C07D 231/56 | (2006.01) | |
| C07D 235/08 | (2006.01) | |
| C07D 237/20 | (2006.01) | |
| C07D 239/42 | (2006.01) | |
| C07D 241/20 | (2006.01) | |
| C07D 249/18 | (2006.01) | |
| C07D 261/08 | (2006.01) | |
| C07D 265/30 | (2006.01) | |
| C07D 295/135 | (2006.01) | |
| C07D 295/195 | (2006.01) | |
| C07D 295/26 | (2006.01) | |
| C07D 317/58 | (2006.01) | |

(52) U.S. Cl.
CPC ....... *C07D 295/195* (2013.01); *C07D 295/26* (2013.01); *C07D 305/08* (2013.01); *C07D 309/08* (2013.01); *C07D 317/58* (2013.01); *C07D 319/12* (2013.01); *C07C 2601/04* (2017.05); *C07C 2601/08* (2017.05); *C07C 2601/14* (2017.05); *C07C 2601/18* (2017.05); *C07C 2602/16* (2017.05); *C07C 2602/42* (2017.05); *C07C 2603/74* (2017.05)

(56) References Cited

U.S. PATENT DOCUMENTS

| | | | |
|---|---|---|---|
| 2018/0251429 | A1 | 9/2018 | Smith et al. |
| 2018/0282263 | A1 | 10/2018 | Smith et al. |
| 2019/0062277 | A1 | 2/2019 | Smith et al. |

FOREIGN PATENT DOCUMENTS

| | | | |
|---|---|---|---|
| WO | WO-2004045511 | A2 | 6/2004 |
| WO | WO-2004046162 | A2 | 6/2004 |
| WO | WO-2005037216 | A2 | 4/2005 |
| WO | WO-2007093603 | A1 | 8/2007 |
| WO | WO-2007110237 | A2 | 10/2007 |
| WO | WO-2008066097 | A1 | 6/2008 |
| WO | WO-2008073936 | A1 | 6/2008 |
| WO | WO-2008156715 | A1 | 12/2008 |
| WO | WO-2011006935 | A2 | 1/2011 |
| WO | WO-2012129495 | A1 | 9/2012 |
| WO | WO-2014133414 | A2 | 9/2014 |
| WO | WO-2015138969 | A1 | 9/2015 |
| WO | WO-2016149111 | A1 | 9/2016 |
| WO | WO-2017049172 | A1 | 3/2017 |
| WO | WO-2017049173 | A1 | 3/2017 |
| WO | WO-2017049176 | A1 | 3/2017 |
| WO | WO-2017049177 | A1 | 3/2017 |
| WO | WO-2018170165 | A1 | 9/2018 |
| WO | WO-2018170166 | A1 | 9/2018 |
| WO | WO-2018170167 | A1 | 9/2018 |
| WO | WO-2018170173 | A1 | 9/2018 |
| WO | WO-2018170182 | A1 | 9/2018 |

OTHER PUBLICATIONS

Berge et al. Pharmaceutical Salts. Journal of Pharmaceutical Sciences 66(1):1-19 (Jan. 1977).

Bundgaard. Design and Application of Prodrugs. Textbook of Drug Design and Development. Krosgaard-Larsen and Bundgaard. Chapter 5. pp. 113-191 (1991).

Bundgaard. Means to Enhance Penetration: Prodrugs as a Means to Improve the Delivery of Peptide Drugs. Advanced Drug Delivery Review 8:1-38 (1992).

Chemical Abstract compound, STN express RN 1026708-50-8 (Entered STN: Jun. 9, 2008).

Chemical Abstract compound, STN express. RN 1347920-07-3 (Entered STN: Dec. 4, 2011).

Costantino et al. Molecular Dynamics Simulation of the Ligand Binding Domain of Farnesoid X Receptor. Insights into Helix-12 Stability and Coactivator Peptide Stabilization in Response to Agonist Binding. J Med Chem 48:3251-3259 (2005).

(56) References Cited

OTHER PUBLICATIONS

Downes et al. A Chemical, Genetic, and Structural Analysis of the Nuclear Bile Acid Receptor FXR. Molecular Cell 11:1079-1092 (2003).
Erb et al. Sequential One-Pot Access to Molecular Diversity through Aniline Aqueous Borylation. J Organ Chem 79:10568-10580 (2014).
Fang et al. Intestinal FXR agonism promotes adipose tissue browning and reduces obesity and insulin resistance. Nat Med 21(2):159-165 (2015).
Fu et al. Discovery of new non-steroidal FXR ligands via a virtual screening workflow based on Phase shape and induced fit docking. Bioorg Med Chem Lett 22(22):6848-6853 (2012).
Fu et al. Fibroblast growth factor 19 increases metabolic rate and reverses dietary and leptin-deficient diabetes. Endocrinology 145:2594-2603 (2004).
Gege et al. Knocking on FXR's Door: The "Hammerhead"-Structure Series of FXR Agonists—Amphiphilic Isoxazoles with Potent In Vitro and In Vivo Activi-ties. Current Topics in Medicinal Chemistry 14:2143-2158 (2014).
Hambruch et al. On the Pharmacology of Farnesoid X Receptor Agonists: Give me an "A", Like an "Acid". Nuclear Receptor Research 3:Article ID 101207 (2016).
Honorio et al. 3D QSAR Comparative molecular field analysis on nonsteroidal farnesoid X receptor activators. J Mol Graph Model 25:921-927 (2007).
Honorio et al. Hologram quantitative structure-activity relationships for a series of farnesoid X receptor activators. Bioorg Med Chem Letts 15:3119-3125 (2005).
Hu et al. Predicting biological Functions of Compounds based on Chemical-Chemical Interactions. PLoS One 6(12):e29491 (2011).
Inagaki et al. Regulation of antibacterial defense in the small intestine by the nuclear bile acid receptor. PNA USA 103:3920-3925 (2006).
Kim et al. Inhibitory Effects of Bile Acides and Synthetic Farnesoid X Receptor Agonists on Rotavirus Replication. J Virol 85(23):12570-12577 (2011).
Lam et al. Bile acids inhibit duodenal secretin expression via orphan nuclear receptor small heterodimer partner (SHP). Am J Physol Gastrointest Liver Physiol 287:G90-G97 (2009).
Li et al. Microbiome remodelling leads to inhibition of intestinal farnesoid X receptor signalling and decreased obesity. Nat Commun 4:2384 (2013).
Li et al. Progress in the ligands and their complex structures of farnesoid X receptor. ACTA Pharmaceutica Sinica 47(6):704-715 (2012) (English Abstract).
Misawa et al. Discovery and structural development of small molecules that enhance transport activity of bile salt export pump mutant associated with progressive familial intrahepatic cholestasis type 2. Bioorg Med Chem 20:2940-2949 (2012).
Morkved. Intramolecular O→N acyl migration. Preparation of unsymmetrical imides derived from isoquinoline-1-carboxylic acid and substituted picolinic acids. Acta Chemica Scandinavica B 33(7):544-546 (1979).
Nicolaou et al. Discovery and optimization of non-steroidal FXR agonists from natural product-like libraries. Org Biomol Chem 1:908-920 (2003).
PCT/US2016/052268 International Preliminary Report on Patentability dated Mar. 29, 2018.
PCT/US2016/052268 International Search Report and Written Opinion dated Dec. 28, 2016.
Reschly et al. Ligand specificity and evolution of liver X receptors. J Steroid Biochem Mol Biol 110(1-2):83-94 (2008).
Schuster et al. Pharmacophore-based discovery of FXR agonists. Part I: Model development and experimental validation. Bioorg Med Chem 19:7168-7180 (2011).
Science IP—The CAS Search Service. Jul. 17, 2015 (316 pgs).
Steri et al. Antidiabetic sulfonylureas modulate farnesoid X receptor activation and target gene transcription. Future Med Chem 2(4):575-589 (2010).
Widder et al. Section III: Prodrugs Kinetics. Method in Enzymology. 112:309-396 (1985).
Yang et al. Syntheses of nicotinamide riboside and derivatives: effective agents for increasing nicotinamide adenine dinucleotide concentrations in mammalian cells. J. Med. Chem. 50:6458-61 (2007).
Zhang et al. 3D-QSAR studies with the aid of molecular docking for a series of non-steroidal FXR agonists. 17(8):2156-2160 (2007).
Merk et al. Medicinal chemistry of farnesoid X receptor ligands: from agonists and antagonists to modulators. Future Med Chem 4(8):1015-1036 (2012).

* cited by examiner

FARNESOID X RECEPTOR AGONISTS AND USES THEREOF

RELATED APPLICATIONS

This application is the U.S. National Stage entry of International Application No. PCT/US2016/052268, filed on Sep. 16, 2016, which claims the benefit of U.S. Provisional Patent Application No. 62/219,422 filed on Sep. 16, 2015, both of which are incorporated herein by reference in their entireties.

FIELD OF THE INVENTION

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

BACKGROUND OF THE INVENTION

Farnesoid X receptor (FXR) is a nuclear receptor highly expressed in the liver, intestine, kidney, adrenal glands, and adipose tissue. FXR regulates a wide variety of target genes involved in the control of bile acid synthesis and transport, lipid metabolism, and glucose homeostasis. FXR agonism is a treatment modality for many metabolic and liver conditions.

SUMMARY OF THE INVENTION

In one aspect, described herein are farnesoid X receptor agonists and uses thereof.

In some embodiments, the farnesoid X receptor agonists described herein have the structure of Formula (I), or a pharmaceutically acceptable salt thereof, or solvate thereof:

Formula (I)

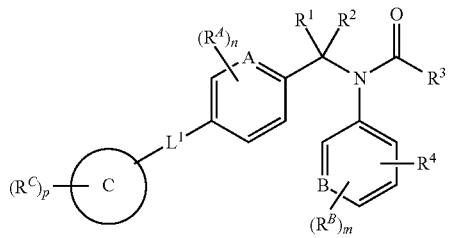

wherein
- $R^1$ and $R^2$ are each independently selected from H, D, F, $C_1$-$C_4$alkyl, or $C_1$-$C_4$fluoroalkyl;
- or $R^1$ and $R^2$ are taken together with the carbon atom to which they are attached to form a substituted or unsubstituted $C_3$-$C_{10}$cycloalkyl, or substituted or unsubstituted $C_2$-$C_{10}$heterocycloalkyl;
- or $R^1$ and $R^2$ are taken together with the carbon atom to which they are attached to form a carbonyl (C=O);
- $R^3$ is selected from substituted or unsubstituted $C_1$-$C_{10}$alkyl, substituted or unsubstituted $C_2$-$C_{10}$alkenyl, substituted or unsubstituted $C_2$-$C_{10}$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl, wherein if $R^3$ is substituted then $R^3$ is substituted with one or more $R^{12}$ groups;
- each $R^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -L$^4$-L$^5$-R$^{13}$;
- $L^4$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;
- $L^5$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;
- $R^{13}$ is H, halogen, —N(R$^{10}$)$_2$, unsubstituted or substituted $C_1$-$C_{10}$alkyl, unsubstituted or substituted $C_1$-$C_{10}$alkenyl, unsubstituted or substituted $C_1$-$C_{10}$alkynyl, unsubstituted or substituted $C_1$-$C_{10}$cycloalkyl, unsubstituted or substituted $C_1$-$C_{10}$heterocycloalkyl, unsubstituted or substituted aryl, or unsubstituted or substituted heteroaryl;
- $R^4$ is -L$^3$-Y;
- $L^3$ is —C(R$^5$)(R$^6$)—, —C(R$^5$)(R$^6$)—C(R$^7$)(R$^8$)—, —C≡C—, —O—C(R$^7$)(R$^8$)—, or —C(R$^5$)(R$^6$)—O—;
- $R^5$ and $R^7$ are each independently selected from H, D, $C_1$-$C_4$alkyl and $C_3$-$C_6$cycloalkyl;
- or $R^5$ and $R^7$ are taken together with the intervening atoms to form a double bond;
- or $R^5$ and $R^7$ are taken together with the intervening atoms to form an epoxide or a substituted or unsubstituted $C_3$-$C_6$cycloalkyl;
- $R^6$ and $R^8$ are each independently selected from H, D, $C_1$-$C_4$alkyl or $C_3$-$C_6$cycloalkyl;
- Y is —CH$_2$OR$^9$, —C(=O)OR$^9$,

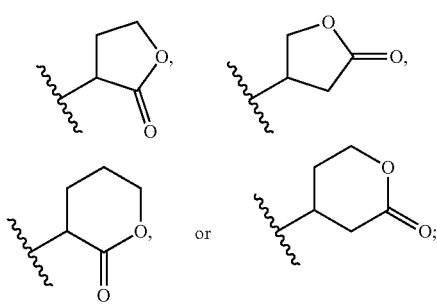

R⁹ is selected from H, substituted or unsubstituted C₁-C₆alkyl, substituted or unsubstituted C₁-C₆heteroalkyl, substituted or unsubstituted C₂-C₆alkenyl, substituted or unsubstituted C₃-C₆cycloalkyl, substituted or unsubstituted phenyl, or substituted or substituted or unsubstituted heterocycle;

L¹ is —X¹-L²-, -L²-X¹—;

X¹ is —O—, —S—, —S(=O)—, —S(=O)₂—, —S(=O)₂NR¹⁰—, —CH₂—, —C≡C—, —C(=O)—, —C(=O)O—, —OC(=O)—, —OC(=O)O—, —C(=O)NR¹⁰—, —NR¹⁰C(=O)—, —OC(=O)NR¹⁰—, —NR¹⁰C(=O)O—, —NR¹⁰C(=O)NR¹⁰—, —NR¹⁰S(=O)₂—, or —NR¹⁰—;

L² is absent or substituted or unsubstituted C₁-C₄alkylene;

A is CR$^A$, or N;

each R$^A$ is independently selected from H, D, halogen, —CN, —OH, —OR¹⁰, —SR¹⁰, —S(=O)R¹¹, —S(=O)₂R¹¹, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl;

B is CR$^B$, or N;

each R$^B$ is independently selected from H, D, halogen, —CN, —OH, —OR¹⁰, —SR¹⁰, —S(=O)R¹¹, —S(=O)₂R¹¹, —N(R¹⁰)₂, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl;

ring C is monocyclic carbocycle, bicyclic carbocycle, monocyclic N-containing heterocycle, or bicyclic heterocycle;

each R$^C$ is independently selected from H, D, halogen, —CN, —OH, —OR¹⁰, —SR¹⁰, —S(=O)R¹¹, —NO₂, —N(R¹⁰)₂, —S(=O)₂R¹¹, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl, substituted or unsubstituted phenyl and substituted or unsubstituted monocyclic heteroaryl;

each R¹⁰ is independently selected from H, substituted or unsubstituted C₁-C₆alkyl, substituted or unsubstituted C₁-C₆fluoroalkyl, substituted or unsubstituted C₃-C₆cycloalkyl, substituted or unsubstituted phenyl, substituted or unsubstituted monocyclic heteroaryl, and substituted or unsubstituted benzyl;

or two R¹⁰ on the same N atom are taken together with the N atom to which they are attached to form a N-containing heterocycle;

each R¹¹ is independently selected from substituted or unsubstituted C₁-C₆alkyl, substituted or unsubstituted C₁-C₆heteroalkyl, substituted or unsubstituted C₁-C₆fluoroalkyl, substituted or unsubstituted C₃-C₆cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

In some embodiments, the farnesoid X receptor agonists described herein have the structure of Formula (II), or a pharmaceutically acceptable salt thereof, or solvate thereof:

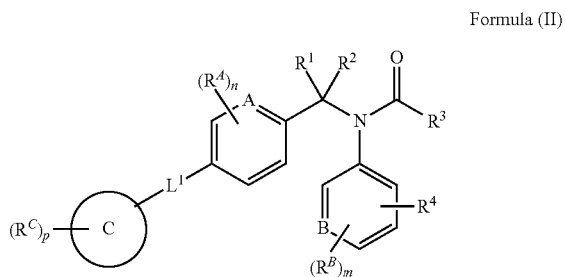

Formula (II)

wherein
R¹ and R² are each independently selected from H, D, F, C₁-C₄alkyl, or C₁-C₄fluoroalkyl;
or R¹ and R² are taken together with the carbon atom to which they are attached to form a substituted or unsubstituted C₃-C₁₀cycloalkyl, or substituted or unsubstituted C₂-C₁₀heterocycloalkyl;
or R¹ and R² are taken together with the carbon atom to which they are attached to form a carbonyl (C=O);

R³ is selected from substituted or unsubstituted C₄-C₁₀alkyl, substituted or unsubstituted C₁-C₁₀alkoxy, substituted or unsubstituted C₂-C₁₀alkenyl, or unsubstituted substituted C₂-C₁₀alkynyl, substituted or unsubstituted cyclopropyl, substituted or unsubstituted cyclobutyl, substituted or unsubstituted cyclopentyl, substituted cyclohexyl, substituted or unsubstituted cycloheptyl, substituted or unsubstituted cyclooctyl, substituted or unsubstituted C₂-C₁₀heterocycloalkyl containing 1 O or S atom, substituted aryl, or substituted or unsubstituted heteroaryl, wherein if R³ is substituted then R³ is substituted with one or more R¹² groups;

each R¹² is independently selected from D, halogen, —CN, —NO₂, —OR¹⁰, —SR¹⁰, —S(=O)R¹¹, —S(=O)₂R¹¹, —S(=O)₂N(R¹⁰)₂, —NR¹⁰S(=O)₂R¹¹, —C(=O)R¹¹, —OC(=O)R¹¹, —CO₂R¹⁰, —OCO₂R¹¹, —N(R¹⁰)₂, —C(=O)N(R¹⁰)₂, —OC(=O)N(R¹⁰)₂, —NR¹⁰C(=O)R¹¹, —NR¹⁰C(=O)OR¹¹, unsubstituted or substituted C₁-C₁₀alkyl, unsubstituted or substituted C₁-C₁₀fluoroalkyl, unsubstituted or substituted C₂-C₁₀alkenyl, unsubstituted or substituted C₂-C₁₀alkynyl, unsubstituted or substituted C₁-C₁₀heteroalkyl, unsubstituted or substituted C₃-C₁₀cycloalkyl, unsubstituted or substituted aryl, unsubstituted or substituted heteroaryl, and -L⁴-L⁵-R¹³;

L⁴ is absent, —O—, —S—, —S(=O)—, —S(=O)₂—, —NR¹⁰—, —C(=O)—, —C(=O)NH—, —NHC(=O)—, —C(=O)O—, —OC (=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;

$L^5$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;

$R^{13}$ is H, halogen, —N(R$^{10}$)$_2$, unsubstituted or substituted C$_1$-C$_{10}$alkyl, unsubstituted or substituted C$_1$-C$_{10}$alkenyl, unsubstituted or substituted C$_1$-C$_{10}$alkynyl, unsubstituted or substituted C$_1$-C$_{10}$cycloalkyl, unsubstituted or substituted C$_1$-C$_{10}$heterocycloalkyl, unsubstituted or substituted aryl, or unsubstituted or substituted heteroaryl;

or $R^3$ is —N(R$^{14}$)$_2$, wherein each $R^{14}$ is independently selected from H, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_6$cycloalkyl, and substituted or unsubstituted benzyl, or two $R^{13}$ on the same N atom are taken together with the N atom to which they are attached to form a N-containing heterocycle, provided that $R^3$ is not —NHCH(CH$_3$)$_2$;

$R^4$ is -L$^3$-Y;

$L^3$ is —C(R$^5$)(R$^6$)—, —C(R$^5$)(R$^6$)—C(R$^7$)(R$^8$)—, —C≡C—, —O—C(R$^7$)(R$^8$)—, or —C(R$^5$)(R$^6$)—O—;

$R^5$ and $R^7$ are each independently selected from H, D, C$_1$-C$_4$alkyl and C$_3$-C$_6$cycloalkyl;

or $R^5$ and $R^7$ are taken together with the intervening atoms to form a double bond;

or $R^5$ and $R^7$ are taken together with the intervening atoms to form an epoxide or a substituted or unsubstituted C$_3$-C$_6$cycloalkyl;

$R^6$ and $R^8$ are each independently selected from H, D, C$_1$-C$_4$alkyl or C$_3$-C$_6$cycloalkyl;

Y is —CH$_2$OR$^9$, —C(=O)OR$^9$,

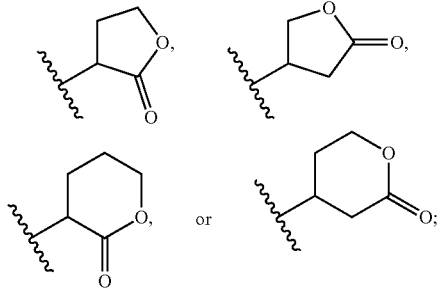

$R^9$ is selected from H, substituted or unsubstituted C$_1$-C$_6$alkyl, substituted or unsubstituted C$_1$-C$_6$heteroalkyl, substituted or unsubstituted C$_2$-C$_6$alkenyl, substituted or unsubstituted C$_3$-C$_6$cycloalkyl, substituted or unsubstituted phenyl, or substituted or unsubstituted heterocycle;

$L^1$ is —X$^1$-L$^2$-, -L$^2$-X$^1$—;

$X^1$ is absent, —O—, —S—, —S(=O)—, —S(=O)$_2$—, —S(=O)$_2$NR$^{10}$—, —CH$_2$—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

$L^2$ is absent or substituted or unsubstituted C$_1$-C$_4$alkylene;

A is CR$^A$, or N;

each $R^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

B is CR$^B$, or N;

each $R^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

ring C is monocyclic carbocycle, bicyclic carbocycle, monocyclic N-containing heterocycle, or bicyclic heterocycle;

each $R^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;

each $R^{10}$ is independently selected from H, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

In some embodiments, the farnesoid X receptor agonists described herein have the structure of Formula (III), or a pharmaceutically acceptable salt thereof, or solvate thereof:

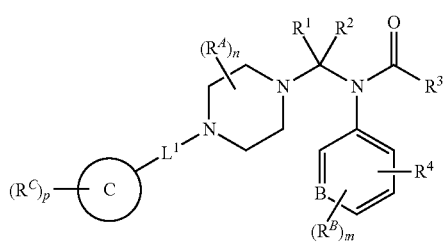

Formula (III)

wherein
- $R^1$ and $R^2$ are each independently selected from H, D, F, $C_1$-$C_4$alkyl, or $C_1$-$C_4$fluoroalkyl;
- or $R^1$ and $R^2$ are taken together with the carbon atom to which they are attached to form a substituted or unsubstituted $C_3$-$C_{10}$cycloalkyl, or substituted or unsubstituted $C_2$-$C_{10}$heterocycloalkyl;
- or $R^1$ and $R^2$ are taken together with the carbon atom to which they are attached to form a carbonyl (C=O);
- $R^3$ is selected from substituted or unsubstituted $C_1$-$C_{10}$alkyl, substituted or unsubstituted $C_2$-$C_{10}$alkenyl, substituted or unsubstituted $C_2$-$C_{10}$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl, wherein if $R^3$ is substituted then $R^3$ is substituted with one or more $R^{12}$ groups;
- each $R^{12}$ is independently selected from D, halogen, —CN, —$NO_2$, —$OR^{10}$, —$SR^{10}$, —S(=O)$R^{11}$, —S(=O)$_2R^{11}$, —S(=O)$_2N(R^{10})_2$, —$NR^{10}$S(=O)$_2R^{11}$, —C(=O)$R^{11}$, —OC(=O)$R^{11}$, —$CO_2R^{10}$, —$OCO_2R^{11}$, —N($R^{10})_2$, —C(=O)N($R^{10})_2$, —OC(=O)N($R^{10})_2$, —$NR^{10}$C(=O)$R^{11}$, —$NR^{10}$C(=O)$OR^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -$L^4$-$L^5$-$R^{13}$;
- $L^4$ is absent, —O—, —S—, —S(=O)—, —S(=O)$_2$—, —$NR^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;
- $L^5$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;
- $R^{13}$ is H, halogen, —N($R^{10})_2$, unsubstituted or substituted $C_1$-$C_{10}$alkyl, unsubstituted or substituted $C_1$-$C_{10}$alkenyl, unsubstituted or substituted $C_1$-$C_{10}$alkynyl, unsubstituted or substituted $C_1$-$C_{10}$cycloalkyl, unsubstituted or substituted $C_1$-$C_{10}$heterocycloalkyl, unsubstituted or substituted aryl, or unsubstituted or substituted heteroaryl;
- $R^4$ is -$L^3$-Y;
- $L^3$ is —C($R^5$)($R^6$)—, —C($R^5$)($R^6$)—C($R^7$)($R^8$)—, —C≡C—, —O—C($R^7$)($R^8$)—, or —C($R^5$)($R^6$)—O—;
- $R^5$ and $R^7$ are each independently selected from H, D, $C_1$-$C_4$alkyl and $C_3$-$C_6$cycloalkyl;
- or $R^5$ and $R^7$ are taken together with the intervening atoms to form a double bond;
- or $R^5$ and $R^7$ are taken together with the intervening atoms to form an epoxide or a substituted or unsubstituted $C_3$-$C_6$cycloalkyl;
- $R^6$ and $R^8$ are each independently selected from H, D, $C_1$-$C_4$alkyl or $C_3$-$C_6$cycloalkyl;
- Y is —$CH_2OR^9$, —C(=O)$OR^9$,

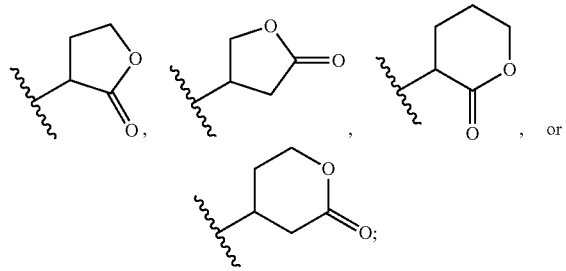

- $R^9$ is selected from H, substituted or unsubstituted $C_1$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted phenyl, or substituted or substituted or unsubstituted heterocycle;
- $L^1$ is —$X^1$-$L^2$-, -$L^2$-$X^1$—;
- $X^1$ is —S(=O)—, —S(=O)$_2$—, —$CH_2$—, —C(=O)—, —OC(=O)—, —$NR^{10}$C(=O)—, or —$NR^{10}$S(=O)$_2$—;
- $L^2$ is absent or substituted or unsubstituted $C_1$-$C_4$alkylene;
- each $R^A$ is independently selected from H, D, halogen, —CN, —OH, —$OR^{10}$, —$SR^{10}$, —S(=O)$R^{11}$, —S(=O)$_2R^{11}$, —NHS(=O)$_2R^{11}$, —S(=O)$_2N(R^{10})_2$, —C(=O)$R^{11}$, —OC(=O)$R^{11}$, —$CO_2R^{10}$, —$OCO_2R^{11}$, —C(=O)N($R^{10})_2$, —OC(=O)N($R^{10})_2$, —$NR^{10}$C(=O)N($R^{10})_2$, —$NR^{10}$C(=O)$R^{11}$, —$NR^{10}$C(=O)$OR^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;
- B is $CR^B$, or N;
- each $R^B$ is independently selected from H, D, halogen, —CN, —OH, —$OR^{10}$, —$SR^{10}$, —S(=O)$R^{11}$, —S(=O)$_2R^{11}$, —N($R^{10})_2$, —NHS(=O)$_2R^{11}$, —S(=O)$_2N(R^{10})_2$, —C(=O)$R^{11}$, —OC(=O)$R^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

ring C is monocyclic carbocycle, bicyclic carbocycle, or bicyclic heterocycle;

each R$^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;

each R$^{10}$ is independently selected from H, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

or two R$^{10}$ on the same N atom are taken together with the N atom to which they are attached to form a N-containing heterocycle;

each R$^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

In some embodiments, the farnesoid X receptor agonists described herein have the structure of Formula (IV), or a pharmaceutically acceptable salt thereof, or solvate thereof:

Formula (IV)

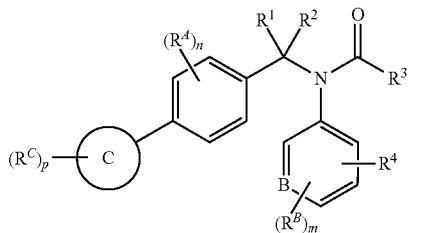

wherein
R$^1$ and R$^2$ are each independently selected from H, D, F, C$_1$-C$_4$alkyl, or C$_1$-C$_4$fluoroalkyl;
or R$^1$ and R$^2$ are taken together with the carbon atom to which they are attached to form a substituted or unsubstituted C$_3$-C$_{10}$cycloalkyl, or substituted or unsubstituted C$_2$-C$_{10}$heterocycloalkyl;

or R$^1$ and R$^2$ are taken together with the carbon atom to which they are attached to form a carbonyl (C=O);

R$^3$ is selected from substituted or unsubstituted C$_1$-C$_{10}$alkyl, substituted or unsubstituted C$_2$-C$_{10}$alkenyl, substituted or unsubstituted C$_2$-C$_{10}$alkynyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, wherein if R$^3$ is substituted then R$^3$ is substituted with one or more R$^{12}$ groups;

each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^4$-L$^5$-R$^{13}$;

L$^4$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;

L$^5$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;

R$^{13}$ is H, halogen, —N(R$^{10}$)$_2$, unsubstituted or substituted C$_1$-C$_{10}$alkyl, unsubstituted or substituted C$_1$-C$_{10}$alkenyl, unsubstituted or substituted C$_1$-C$_{10}$alkynyl, unsubstituted or substituted C$_1$-C$_{10}$cycloalkyl, unsubstituted or substituted C$_1$-C$_{10}$heterocycloalkyl, unsubstituted or substituted aryl, or unsubstituted or substituted heteroaryl;

R$^4$ is -L$^3$-Y;
L$^3$ is —C(R$^5$)(R$^6$)—, —C(R$^5$)(R$^6$)—C(R$^7$)(R$^8$)—, —C≡C—, —O—C(R$^7$)(R$^8$)—, or —C(R$^5$)(R$^6$)—O—;

R$^5$ and R$^7$ are each independently selected from H, D, C$_1$-C$_4$alkyl and C$_3$-C$_6$cycloalkyl;
or R$^5$ and R$^7$ are taken together with the intervening atoms to form a double bond;
or R$^5$ and R$^7$ are taken together with the intervening atoms to form an epoxide or a substituted or unsubstituted C$_3$-C$_6$cycloalkyl;
R$^6$ and R$^8$ are each independently selected from H, D, C$_1$-C$_4$alkyl or C$_3$-C$_6$cycloalkyl;
Y is —CH$_2$OR$^9$, —C(=O)OR$^9$,

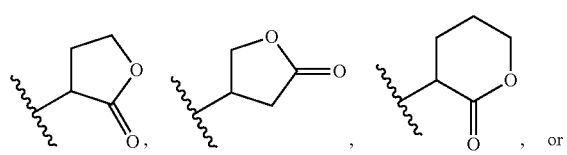

, or

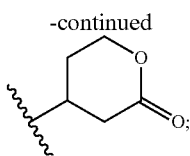

R$^9$ is selected from H, substituted or unsubstituted C$_1$-C$_6$alkyl, substituted or unsubstituted C$_1$-C$_6$heteroalkyl, substituted or unsubstituted C$_2$-C$_6$alkenyl, substituted or unsubstituted C$_3$-C$_6$cycloalkyl, substituted or unsubstituted phenyl, or substituted or substituted or unsubstituted heterocycle;

L$^1$ is —X$^1$-L$^2$-, or -L$^2$-X$^1$—;

X$^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

L$^2$ is absent or substituted or unsubstituted C$_1$-C$_4$alkylene;

each R$^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

B is CR$^B$, or N;

each R$^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

ring C is a 5-membered N-containing heteroaryl, or a N-containing C$_2$-C$_8$heterocycloalkyl;

each R$^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;

each R$^{10}$ is independently selected from H, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_6$cycloalkyl, substituted or unsubstituted phenyl, substituted or unsubstituted monocyclic heteroaryl, and substituted or unsubstituted benzyl;

or two R$^{10}$ on the same N atom are taken together with the N atom to which they are attached to form a N-containing heterocycle;

each R$^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

In some embodiments, the farnesoid X receptor agonists described herein have the structure of Formula (VI), or a pharmaceutically acceptable salt thereof, or solvate thereof:

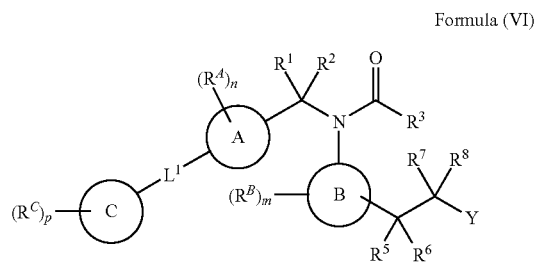

Formula (VI)

wherein

R$^1$ and R$^2$ are each independently selected from H, D, F, C$_1$-C$_4$alkyl, or C$_1$-C$_4$fluoroalkyl;

or R$^1$ and R$^2$ are taken together with the carbon atom to which they are attached to form a substituted or unsubstituted C$_3$-C$_{10}$cycloalkyl, or substituted or unsubstituted C$_2$-C$_{10}$heterocycloalkyl;

or R$^1$ and R$^2$ are taken together with the carbon atom to which they are attached to form a carbonyl (C=O);

R$^3$ is selected from substituted or unsubstituted C$_1$-C$_{10}$alkyl, substituted or unsubstituted C$_2$-C$_{10}$alkenyl, substituted or unsubstituted C$_2$-C$_{10}$alkynyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, wherein if R$^3$ is substituted then R$^3$ is substituted with one or more R$^{12}$ groups;

each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$^2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^5$-L$^6$-R$^{13}$;

L⁵ is absent, —O—, —S—, —S(=O)—, —S(=O)₂—, —NR¹⁰—, —C(=O)—, —C(=O)NH—, —NHC(=O)—, —C(=O)O—, —OC(=O)—, —OC(=O)NH—, —NHC(=O)NH—, —NHC(=O)O—, —(CH₂)ᵣ—, or —(OCH₂CH₂)ᵣ—, r is 1, 2, 3, or 4;

L⁶ is absent, unsubstituted or substituted C₁-C₁₀alkylene, unsubstituted or substituted C₁-C₁₀heteroalkylene, unsubstituted or substituted C₂-C₁₀alkenylene, unsubstituted or substituted C₂-C₁₀alkynylene, unsubstituted or substituted C₃-C₁₀cycloalkylene, unsubstituted or substituted C₂-C₁₀heterocycloalkylene, unsubstituted or substituted arylene, or unsubstituted or substituted heteroarylene;

R¹³ is H, halogen, —N(R¹⁰)₂, unsubstituted or substituted C₁-C₁₀alkyl, unsubstituted or substituted C₁-C₁₀alkenyl, unsubstituted or substituted C₁-C₁₀alkynyl, unsubstituted or substituted C₁-C₁₀cycloalkyl, unsubstituted or substituted C₁-C₁₀heterocycloalkyl, unsubstituted or substituted aryl, or unsubstituted or substituted heteroaryl;

ring A is a monocyclic carbocycle, monocyclic heterocycle, or bicyclic heterocycle;

each R^A is independently selected from H, D, halogen, —CN, —OH, —OR¹⁰, —SR¹⁰, —S(=O)R¹¹, —S(=O)₂R¹¹, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl;

L¹ is —X¹-L²-, or -L²-X¹—;

X¹ is absent, —O—, —S—, —S(=O)—, —S(=O)₂—, —S(=O)₂NR¹⁰—, —CH₂—, —CH=CH—, —C≡C—, —C(=O)—, —C(=O)O—, —OC(=O)—, —OC(=O)O—, —C(=O)NR¹⁰—, —NR¹⁰C(=O)—, —OC(=O)NR¹⁰—, —NR¹⁰C(=O)O—, —NR¹⁰C(=O)NR¹⁰—, —NR¹⁰S(=O)₂—, or —NR¹⁰—;

L² is absent or substituted or unsubstituted C₁-C₄alkylene;

ring C is monocyclic carbocycle, bicyclic carbocycle, monocyclic heterocycle, or bicyclic heterocycle;

each R^C is independently selected from H, D, halogen, —CN, —OH, —OR¹⁰, —SR¹⁰, —S(=O)R¹¹, —NO₂, —N(R¹⁰)₂, —S(=O)₂R¹¹, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl, substituted or unsubstituted phenyl and substituted or unsubstituted monocyclic heteroaryl;

ring B is a monocyclic carbocycle, bicyclic carbocycle, monocyclic heterocycle or bicyclic heterocycle;

each R^B is independently selected from H, D, halogen, —CN, —OH, —OR¹⁰, —SR¹⁰, —S(=O)R¹¹, —S(=O)₂R¹¹, —N(R¹⁰)₂, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl;

R⁵ and R⁷ are each independently selected from H, D, C₁-C₄alkyl and C₃-C₆cycloalkyl;

or R⁵ and R⁷ are taken together with the intervening atoms to form a double bond;

or R⁵ and R⁷ are taken together with the intervening atoms to form an epoxide or a substituted or unsubstituted C₃-C₆cycloalkyl;

R⁶ and R⁸ are each independently selected from H, D, C₁-C₄alkyl or C₃-C₆cycloalkyl;

Y is —CH₂OR⁹, —C(=O)OR⁹, —CH₂C(=O)OR⁹,

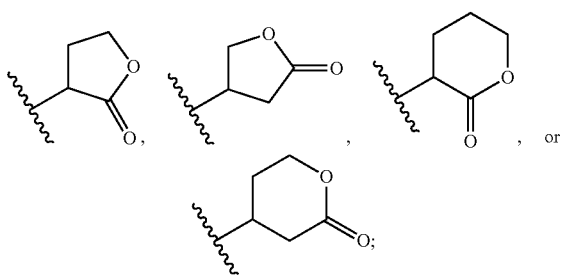

, or each R⁹ is independently selected from H, substituted or unsubstituted C₂-C₆alkyl, substituted or unsubstituted C₁-C₆heteroalkyl, substituted or unsubstituted C₂-C₆alkenyl, substituted or unsubstituted C₃-C₆cycloalkyl, substituted or unsubstituted phenyl, or substituted or substituted or unsubstituted heterocycle;

each R¹⁰ is independently selected from H, substituted or unsubstituted C₁-C₆alkyl, substituted or unsubstituted C₁-C₆fluoroalkyl, substituted or unsubstituted C₃-C₆cycloalkyl, substituted or unsubstituted phenyl, substituted or unsubstituted monocyclic heteroaryl, and substituted or unsubstituted benzyl;

or two R¹⁰ on the same N atom are taken together with the N atom to which they are attached to form a N-containing heterocycle;

each R¹¹ is independently selected from substituted or unsubstituted C₁-C₆alkyl, substituted or unsubstituted C₁-C₆heteroalkyl, substituted or unsubstituted C₁-C₆fluoroalkyl, substituted or unsubstituted C₃-C₆cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In another aspect, described herein is a method of treating a disease or condition in a mammal that would benefit from FXR agonism comprising administering a compound as described herein, or pharmaceutically acceptable salt, or solvate thereof, to the mammal in need thereof. In some embodiments, the disease or condition is a metabolic condition. In some embodiments, the disease or condition is a liver condition.

In some embodiments, the compound is administered to the mammal by intravenous administration, subcutaneous administration, oral administration, inhalation, nasal administration, dermal administration, or ophthalmic administration.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In one aspect, described herein is a method for the treatment or prevention of a metabolic or liver condition in a mammal comprising administering a therapeutically effective amount of a compound described herein, or a pharmaceutically acceptable salt, or solvate thereof, to the mammal in need thereof. In other embodiments, the metabolic or liver condition is amenable to treatment with a FXR agonist. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

In some embodiments, described herein is method of treating or preventing a metabolic disorder in a subject, comprising: administering to a gastrointestinal tract of the subject a therapeutically effective amount of one or more of the compounds described herein, or a pharmaceutically acceptable salt or solvate thereof, thereby activating farnesoid X receptors (FXR) in the intestines, and treating or preventing a metabolic disorder in the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound. In some embodiments, the method reduces or prevents diet-induced weight gain. In some embodiments, the method increases a metabolic rate in the subject. In some embodiments, the increasing the metabolic rate comprises enhancing oxidative phosphorylation in the subject. In some embodiments, the method further comprises improving glucose and/or lipid homeostasis in the subject. In some embodiments, the method results in no substantial change in food intake and/or fat consumption in the subject. In some embodiments, the method results in no substantial change in appetite in the subject. In some embodiments, the metabolic disorder is selected from obesity, diabetes, insulin resistance, dyslipidemia, or any combination thereof. In some embodiments, the metabolic disorder is non-insulin dependent diabetes mellitus. In some embodiments, the method protects against diet-induced weight gain, reduces inflammation, enhances thermogenesis, enhances insulin sensitivity in the liver, reduces hepatic steatosis, promotes activation of BAT, decreases blood glucose, increases weight loss, or any combination thereof. In some embodiments, the method enhances insulin sensitivity in the liver and promotes brown adipose tissue (BAT) activation. In some embodiments, the method further comprises administering to the subject an insulin sensitizing drug, an insulin secretagogue, an alpha-glucosidase inhibitor, a glucagon-like peptide (GLP) agonist, a dipeptidyl peptidase-4 (DPP-4) inhibitor, nicotinamide ribonucleoside, an analog of nicotinamide ribonucleoside, or combinations thereof.

In some embodiments, described herein is a method of treating or preventing inflammation in an intestinal region of a subject, comprising: administering to a gastrointestinal tract of the subject a therapeutically effective amount of one or more of the compounds described herein, or a pharmaceutically acceptable salt or solvate thereof, thereby activating FXR receptors in the intestines, and thereby treating or preventing inflammation in the intestinal region of the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the inflammation is associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, or any combination thereof. In some embodiments, the method further comprises administering a therapeutically effective amount of an antibiotic therapy to the subject, wherein the method treats or prevents inflammation associated with pseudomembranous colitis in the subject. In some embodiments, the method further comprises administering to the subject a therapeutically effective amount of an oral corticosteroid, other anti-inflammatory or immunomodulatory therapy, nicotinamide ribonucleoside, an analog of nicotinamide ribonucleoside, or combinations thereof. In some embodiments, the method increases HSL phosphorylation and β3-adrenergic receptor expression. In some embodiments, a serum concentration of the compound in the subject remains below its $EC_{50}$ following administration of the compound.

In some embodiments, described herein is a method of treating or preventing a cell proliferation disease in a subject, comprising administering to a gastrointestinal tract of the subject a therapeutically effective amount of one or more of the compounds described herein or a pharmaceutically acceptable salt or solvate thereof. In some embodiments, the cell proliferation disease is an adenocarcinoma. In some embodiments, the adenocarcinoma is a colon cancer. In some embodiments, the treating the adenocarcinoma reduces the size of the adenocarcinoma, the volume of the adenocarcinoma, the number of adenocarcinomas, cachexia due to the adenocarcinoma, delays progression of the adenocarcinoma, increases survival of the subject, or combinations thereof. In some embodiments, the method further comprises administering to the subject an additional therapeutic compound selected from the group consisting of a chemotherapeutic, a biologic, a radiotherapeutic, or combinations thereof.

In some embodiments, described herein is a method of treating or preventing a liver disease or condition in a subject, comprising administering to the subject a therapeutically effective amount of one or more of the compounds described herein, or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is intrahepatic cholestasis or extrahepatic cholestasis.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for the treatment, prevention or amelioration of one or more symptoms of a disease or condition that would benefit from FXR agonism, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

The nuclear hormone receptor farnesoid X receptor (also known as FXR or nuclear receptor subfamily 1, group H, member 4 (NR1H4)) (OMIM: 603826) functions as a regulator for bile acid metabolism. FXR is a ligand-activated transcriptional receptor expressed in diverse tissues including the adrenal gland, kidney, stomach, duodenum, jejunum, ileum, colon, gall bladder, liver, macrophages, and white and brown adipose tissue. Bile acids function as endogenous ligands for FXR such that enteric and systemic release of bile acids induces FXR-directed changes in gene expression networks. Bile acids are the primary oxidation product of cholesterol, and in some cases, upon secretion into the intestines, are regulators of cholesterol absorption. The rate-limiting step for conversion of cholesterol into bile acids is catalyzed by cytochrome p450 enzyme cholesterol 7-α-hydroxylase (CYP7A1) and occurs in the liver. Activation of FXR represses the transcription of CYP7A1 by increasing the expression level of the hepatic small heterodimer partner (SHP) (also known as nuclear receptor subfamily 0, group B, member 2; or NR0B2) and intestinal expression of fibroblast growth factor 15 (FGF15) in mice and fibroblast growth factor 19 (FGF19) in human. SHP represses the liver receptor homolog (LRH-1), a nuclear receptor necessary for CYP7A1 gene expression, through its interaction with LRH-1 to form a non-functional heterodimer. In some cases, FGF15/19 released from the intestine then activates the fibroblast growth factor receptor 4 in the liver, leading to activation of the mitogen-activated protein kinase (MAPK) signaling pathway which suppress Cyp7A1.

In some embodiments, elevated levels of bile acids have been associated with insulin resistance. For example, insulin resistance sometimes leads to a decreased uptake of glucose from the blood, and increased de novo glucose production in the liver. In some instances, intestinal sequestration of bile acids has been shown to improve insulin resistance by promoting the secretion of glucagon-like peptide-1 (GLP1) from intestinal L-cells. GLP-1 is an incretin derived from the transcription product of the proglucagon gene. It is released in response to the intake of food and exerts control in appetite and gastrointestinal function, and promotes insulin secretion from the pancreas. The biologically active forms of GLP-1 include GLP-1-(7-37) and GLP-1-(7-36)NH$_2$, which result from selective cleavage of the proglucagon molecule. In such cases, activation of FXR leading to decreased production of bile acids correlates to a decrease in insulin resistance.

In some embodiments, the activation of FXR also correlates to the secretion of pancreatic polypeptide-fold such as peptide YY (PYY or PYY3-36). In some instances, peptide YY is a gut hormone peptide that modulates neuronal activity within the hypothalamic and brainstem, regions of the brain involved in reward processing. In some instances, reduced level of PYY correlates to increased appetite and weight gain.

In some instances, the activation of FXR indirectly leads to a reduction of plasma triglycerides. The clearance of triglycerides from the bloodstream is due to lipoprotein lipase (LPL). LPL activity is enhanced by the induction of its activator apolipoprotein CII, and the repression of its inhibitor apolipoprotein CIII in the liver occurs upon FXR activation.

In some cases, the activation of FXR further modulates energy expenditure such as adipocyte differentiation and function. Adipose tissue comprises adipocytes or fat cells. In some instances, adipocytes are further differentiated into brown adipose tissue (BAT) or white adipose tissue (WAT). The function of BAT is to generate body heat, while WAT functions as fat storing tissues.

In some instances, FXR is widely expressed in the intestine. In some cases, the activation of FXR has been shown to induce the expression and secretion of FGF19 (or FGF15 in mouse) in the intestine. FGF19 is a hormone that regulates bile acid synthesis as well as exerts an effect on glucose metabolism, lipid metabolism, and on energy expenditure. In some instances, FGF19 has also been observed to modulate adipocyte function and differentiation. Indeed, a study has shown that the administration of FGF19 to high-fat diet-fed mice increased energy expenditure, modulated adipocytes differentiation and function, reversed weight gain, and improved insulin resistance (see, Fu et al., "Fibroblast growth factor 19 increases metabolic rate and reverses dietary and leptin-deficient diabetes." *Endocrinology* 145: 2594-2603 (2004)).

In some cases, intestinal FXR activity has also been shown to be involved in reducing overgrowth of the microbiome, such as during feeding (Li et al., *Nat Commun* 4:2384, 2013). For example, a study had shown that activation of FXR correlated with increased expression of several genes in the ileum such as Ang2, iNos, and Il18, which have established antimicrobial actions (Inagaki et al., *Proc Natl Acad Sci USA* 103:3920-3925, 2006).

G protein-coupled bile acid receptor 1 (also known as GPBAR2, GPCR19, membrane-type receptor for bile acids or M-BAR, or TGR5) is a cell surface receptor for bile acids. Upon activation with bile acid, TGR5 induces the production of intracellular cAMP, which then triggers an increase in triiodothyronine due to the activation of deiodinase (DIO2) in BAT, resulting in increased energy expenditure.

Hence in some embodiments, regulation of metabolic processes such as bile acid synthesis, bile-acid circulation, glucose metabolism, lipid metabolism, or insulin sensitivity is modulated by the activation of FXR. Furthermore, in some embodiments, dis-regulation of metabolic processes such as bile acid synthesis, bile-acid circulation, glucose metabolism, lipid metabolism, or insulin sensitivity results in metabolic diseases such as diabetes or diabetes-related conditions or disorders, alcoholic or non-alcoholic liver disease or condition, intestinal inflammation, or cell proliferative disorders.

Disclosed herein, in certain embodiments, are compounds that have activity as FXR agonists. In some embodiments, the FXR agonists described herein are structurally distinct from bile acids, other synthetic FXR ligands, and other natural FXR ligands.

In some embodiments, also disclosed herein are methods of treating or preventing a metabolic disorder, such as diabetes, obesity, impaired glucose tolerance, dyslipidemia, or insulin resistance by administering a therapeutically effective amount of an FXR agonist. In some instances, the compounds are administered to the GI tract of a subject.

In additional embodiments, disclosed herein are methods for treating or preventing alcoholic or non-alcoholic liver disease or conditions (e.g., cholestasis, primary biliary cirrhosis, steatosis, cirrhosis, alcoholic hepatitis, non-alcoholic steatohepatitis (NASH), non-alcoholic fatty liver disease (NAFLD), primary sclerosing cholangitis (PSC) or elevated liver enzymes) by administering a therapeutically effective amount of an FXR agonist to a subject in need thereof (e.g., via the GI tract). In additional embodiments, disclosed herein include methods for treating or preventing cholestasis, cirrhosis, primary biliary cirrhosis, non-alcoholic steatohepatitis (NASH), non-alcoholic fatty liver disease (NAFLD), or primary sclerosing cholangitis (PSC) by administering a therapeutically effective amount of an FXR agonist to a subject in need thereof. In some embodiments, disclosed herein include methods for treating or preventing cholestasis by administering a therapeutically effective amount of an FXR agonist to a subject in need thereof. In some embodiments, disclosed herein include methods for treating or preventing primary biliary cirrhosis by administering a therapeutically effective amount of an FXR agonist to a subject in need thereof. In some embodiments, disclosed herein include methods for treating or preventing NASH by administering a therapeutically effective amount of an FXR agonist to a subject in need thereof. In some embodiments, disclosed herein include methods for treating or preventing NAFLD by administering a therapeutically effective amount of an FXR agonist to a subject in need thereof.

In further embodiments, disclosed herein include methods for treating or preventing inflammation in the intestines and/or a cell proliferative disorder, such as cancer, by administering a therapeutically effective amount of an FXR agonist to a subject in need thereof (e.g., via the GI tract).

In still further embodiments, disclosed herein include FXR agonists that modulate one or more of the proteins or genes associated with a metabolic process such as bile acid synthesis, glucose metabolism, lipid metabolism, or insulin sensitivity, such as for example, increase in the activity of FGF19 (FGF15 in mouse), increase in the secretion of GLP-1, or increase in the secretion of PYY.

Metabolic Disorders

Disclosed herein, in certain embodiments, are methods of treating a metabolic disorder in a subject in need thereof. Also described herein include methods of preventing a metabolic disorder in a subject in need thereof. In some instances, these methods include administering to the subject in need thereof a therapeutically effective amount of one or more of the compounds disclosed herein. In some instances, the one or more compounds disclosed herein are absorbed in the gastrointestinal (GI) tract. In additional instances, the one or more disclosed compounds absorbed in the GI tract activates FXR receptors thereby treating or preventing a metabolic disorder in the subject.

In some embodiments, the disclosed compounds demonstrate systemic exposure. In some instances, the disclosed compounds have local exposure in the intestines, but limited exposure in the liver or systemically. In some embodiments, local exposure of the disclosed compounds in the intestines may be demonstrated by regulation of FXR target genes in the intestines. In some embodiments, the target genes may include: SHP, FGF19 (FGF15), IBABP, C3, OST α/β. In some embodiments, exposure of the disclosed compounds is about 40%, 50%, 55%, 60%, 65%, 70%, 75%, 80%, 85%, 90%, 95%, 99%, 99.5%, or more in the intestines. In some instances, exposure of the disclosed compounds is about 0.5%, 1%, 5%, 10%, 15%, 20%, 25%, 30%, 40%, 50%, or less in the systemic circulation. In some embodiments, the exposure of the FXR agonists to the intestinal lumen reduces the chance of side effects which results from systemic action, thereby improving the safety profile of the therapy. In additional embodiments, the disclosed compounds enhance FXR target gene expression in the intestines. In additional embodiments, the disclosed compounds further modulate gene expressions in the FXR-mediated pathway, such as for example, FGF19 (FGF15) which inhibits CYP7A1 and CYP8B1 gene expression in the liver. In some instances, the disclosed compounds enhance gene expression in the FXR-mediated pathway. In other instances, the disclosed compounds reduce or inhibit gene expression in the FXR-mediated pathway. In some instances, enhancing is about 1%, 5%, 10%, 15%, 20%, 25%, 30%, 40%, 50%, 60%, 70%, 80%, 90%, 100%, 200%, 300%, 500%, 1,000%, 5,000%, 10,000%, 50,000%, 100,000%, 500,000% or higher in gene expression in the intestines, liver, kidney, or other tissues relative to the gene expression in the absence of the disclosed compound. In some cases, reducing is about 100%, 90%, 80%, 70%, 60%, 50%, 40%, 30%, 25%, 20%, 15%, 10%, 5%, 1%, or less in gene expression in the intestines, liver, kidney, or other tissues relative to the gene expression in the absence of the disclosed compound.

In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound.

In some embodiments, metabolic disorder refers to any disorder that involves an alteration in the normal metabolism of carbohydrates, lipids, proteins, nucleic acids or a combination thereof. In some instances, a metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, oxyntomodulin, PYY or the like), or the neural control system (e.g., GLP-1 in the brain). Exemplary metabolic disorders include, but are not limited to, diabetes, insulin resistance, dyslipidemia, liver disease, inflammation related intestinal conditions, cell proliferative disorders, or the like.

Diabetes Mellitus and Diabetes-Related Conditions or Disorders

In some embodiments, disclosed herein are methods of treating a subject having diabetes mellitus or diabetes-related condition or disorder with administration of a FXR agonist described herein. In some instances, diabetes is type II diabetes or non-insulin-dependent diabetes mellitus (NIDDM). In some instances, diabetes-related conditions or disorders include obesity, impaired glucose tolerance, dyslipidemia, and insulin resistance. In some instances, diabetes-related conditions or disorders further include secondary complications such as atherosclerosis, stroke, fatty liver disease, blindness, gallbladder disease, or polycystic ovary disease. In some cases, a FXR agonist is administered for the treatment of type II diabetes, obesity, impaired glucose tolerance, dyslipidemia, insulin resistance, or secondary complications such as atherosclerosis, stroke, fatty liver disease, blindness, gallbladder disease, or polycystic ovary disease.

In some embodiments, a diabetic subject (e.g., a type II diabetic subject) is further characterized with a body mass index (BMI) of 25 or greater, 30 or greater, 35 or greater, 40 or greater, such as a BMI of 25 to 29, 30 to 34, or 35 to 40.

In some examples, a FXR agonist described herein reduces or prevents weight gain in a subject. In some instances, the weight gain is diet-induced weight gain. In other instances, the weight gain is non diet-related, such as familial/genetic obesity or obesity resulting from medication. In some examples, such methods reduce or prevent weight gain in the subject by at least 5%, at least 10%, at least 15%, at least 20%, at least 30%, at least 40%, at least 50%, or more. In some instances, weight gain is reduced or prevented by about 5% to about 50%, by about 5% to about 25%, by about 10% to about 20%, or by about 10% to about 30%. In some cases, the reduction or prevention of weight gain is relative to the reduction or prevention of weight gain observed in a subject not treated with the FXR agonist.

Similarly, in some cases, the FXR agonist reduces the BMI of a subject. In some examples, such methods reduce the BMI of a subject by at least 5%, at least 10%, at least 15%, at least 20%, at least 25%, at least 30%, or more, relative to a subject not treated with the FXR agonist. In some instances, the subject is overweight but not obese. In other instances, the subject is neither overweight nor obese.

In some instances, administration of a FXR agonist results in a decrease in the amount of serum lipids. In some examples, the decrease in the amount of serum lipids is by at least 5%, at least 10%, at least 15%, at least 20%, at least 30%, at least 50%, at least 60%, at least 70%, at least 75%, or more. In some cases, the decrease in the amount of serum lipids is by about 5% to about 50%, by about 5% to about 25%, by about 10% to about 20%, by about 10% to about 70%, or by about 10% to about 30%. In some cases, the decrease in the amount of serum lipids is relative to the amount of serum lipids observed in a subject not treated with the FXR agonist.

In some examples, administration of a FXR agonist results in a decrease in triglyceride (e.g., hepatic triglyceride) level. In some instances, the decrease in triglyceride (e.g., hepatic triglyceride) level is by at least 5%, at least 10%, at least 15%, at least 20%, at least 30%, at least 50%, at least 60%, at least 70%, at least 75%, or more. In some instances, the decrease in triglyceride (e.g., hepatic triglyceride) level is by about 5% to about 50%, by about 5% to about 25%, by about 10% to about 20%, by about 10% to about 70%, or by about 10% to about 30%. In some cases, the decrease in triglyceride (e.g., hepatic triglyceride) level is relative to the triglyceride (e.g., hepatic triglyceride) level observed in a subject not treated with the FXR agonist.

In some examples, administration of a FXR agonist results in an increased insulin sensitivity to insulin in the liver. In some instances, the increase in insulin sensitivity is by at least 5%, at least 10%, at least 15%, at least 20%, at least 30%, at least 40%, at least 50%, or more. In some cases, the increase in insulin sensitivity is by about 5% to about 50%, by about 5% to about 25%, by about 10% to about 20%, or by about 10% to about 30%. In some cases, the increase in insulin sensitivity is relative to sensitivity observed in a subject not treated with the FXR agonist.

In some embodiments, administration of a FXR agonist results in a decrease in the amount of serum insulin in the subject. In some examples, the decrease in serum insulin is by at least 5%, at least 10%, at least 15%, at least 20%, at least 30%, at least 50%, at least 60%, at least 70%, at least 75%, or more. In some instances, serum insulin is decreased by about 5% to about 50%, by about 5% to about 25%, by about 10% to about 20%, by about 10% to about 70%, or by about 10% to about 30%. In some cases, the decrease in serum insulin level is relative to levels observed in a subject not treated with the FXR agonist.

In some embodiments, administration of a FXR agonist results in a decrease in the amount of serum glucose in the subject. In some examples, the decrease in serum glucose is by at least 5%, at least 10%, at least 15%, at least 20%, at least 30%, at least 50%, at least 60%, at least 70%, at least 75%, or more. In some instances, serum glucose is decreased by about 5% to about 50%, by about 5% to about 25%, by about 10% to about 20%, by about 10% to about 70%, or by about 10% to about 30%. In some cases, the decrease in serum glucose level is relative to levels observed in a subject not treated with the FXR agonist.

In some examples, a FXR agonist described herein increases browning of white adipose tissue in a subject. In some examples, the rate of increase of browning of white adipose tissue in the subject is by at least 5%, at least 10%, at least 15%, at least 20%, at least 30%, at least 40%, at least 50%, or more, relative to a subject not treated with the FXR agonist.

In some embodiments, administration of a FXR agonist does not result in substantial change in food intake and/or fat consumption in the subject. In some instances, food intake and/or fat consumption is reduced, such as by less than 15%, less than 10%, or less than 5%. In some embodiments, no substantial change in appetite in the subject results. In other embodiments, reduction in appetite is minimal as reported by the subject.

In some embodiments, administration of a FXR agonist results in an increase in the metabolic rate in the subject. In some instances, the FXR agonist increases the metabolic rate in a subject. In some cases, the metabolic rate in the subject is increased by at least 5%, at least 10%, at least 15%, at least 20%, at least 30%, at least 40%, at least 50%, at least 60%, at least 70%, at least 75%, or more. In some instances, the metabolic rate is increased by about 5% to about 50%, by about 5% to about 25%, by about 10% to about 20%, by about 10% to about 70%, or by about 10% to about 30%). In some cases, the increase in metabolic rate is relative to the rate observed in a subject not treated with the FXR agonist.

In some embodiments, the increase in metabolism results from enhanced oxidative phosphorylation in the subject, which in turn leads to increased energy expenditure in tissues (such as BAT). In such instances, the FXR agonist helps to increase the activity of BAT. In some examples, the activity of BAT is increased by at least 5%, at least 10%, at least 15%, at least 20%, at least 30%, at least 50%, at least 60%, at least 70%, at least 75%, or more. In some instances, the activity of BAT is increased by about 5% to about 50%, by about 5% to about 25%, by about 10% to about 20%, by about 10% to about 70%, or by about 10% to about 30%. In some cases, the increase in BAT activity is relative to the activity of BAT observed in a subject not treated with the FXR agonist.

Alcoholic and Non-Alcoholic Liver Disease or Condition

Disclosed herein include methods of preventing and/or treating alcoholic or non-alcoholic liver diseases or conditions. Exemplary alcoholic or non-alcoholic liver diseases or conditions include, but are not limited to cholestasis, cirrhosis, steatosis, alcoholic hepatitis, non-alcoholic steatohepatitis (NASH), non-alcoholic fatty liver disease (NAFLD), primary sclerosing cholangitis (PSC), elevated liver enzymes, and elevated triglyceride levels. In some embodiments, a FXR agonist is used in the prevention or treatment of alcoholic or non-alcoholic liver diseases. In some embodiments, a FXR agonist is used in the prevention or treatment of cholestasis, cirrhosis, steatosis, alcoholic hepatitis, non-alcoholic steatohepatitis (NASH), non-alcoholic fatty liver disease (NAFLD), or primary sclerosing cholangitis (PSC).

Cholestasis

In some embodiments, a FXR agonist disclosed herein is used in the treatment of cholestasis in a subject. Cholestasis, an impairment or cessation in the flow of bile, which in some cases, causes hepatotoxicity due to the buildup of bile acids and other toxins in the liver. In some instances, cholestasis is a component of many liver diseases, including cholelithiasis, cholestasis of pregnancy, primary biliary cirrhosis (PBC), and primary sclerosing cholangitis (PSC). In some instances, the obstruction is due to gallstone, biliary trauma, drugs, one or more additional liver diseases, or to cancer. In some cases, the enterohepatic circulation of bile acids enables the absorption of fats and fat-soluble vitamins from the intestine and allows the elimination of cholesterol, toxins, and metabolic by-products such as bilirubin from the liver. In some cases, activation of FXR induces expression of the canalicular bile transporters BSEP (ABCB11) and multidrug resistancerelated protein 2 (MRP2; ABCC2, cMOAT), and represses genes involved in bile acid biosynthesis, such as for example sterol 12α-hydroxylase (CYP8B1) and CYP7A1.

In some examples, the FXR agonist reduces cholestasis in the subject by at least 5%, at least 10%, at least 15%, at least 20%, at least 30%, at least 40%, at least 50%, or more. In some cases, cholestasis is reduced by about 5% to about 50%, by about 5% to about 25%, by about 10% to about 20%, or by about 10% to about 30%. In some instances, the level of cholestasis is relative to the level of cholestasis in a subject not treated with the FXR agonist.

Primary Biliary Cirrhosis and Cirrhosis

In some embodiments, a FXR agonist disclosed herein is used in the treatment of primary biliary cirrhosis (PBC) in a subject. PBC is a liver disease that primarily results from autoimmune destruction of the bile ducts that transport bile acids (BAs) out of the liver, resulting in cholestasis. As PBC progresses, persistent toxic buildup of BAs causes progressive liver damage. Chronic inflammation and fibrosis can advance to cirrhosis. In some examples, the FXR agonist reduces PBC in the subject by at least 5%, at least 10%, at least 15%, at least 20%, at least 30%, at least 40%, at least 50%, or more. In some cases, PBC is reduced by about 5% to about 50%, by about 5% to about 25%, by about 10% to about 20%, or by about 10% to about 30%. In some instances, the level of PBC is relative to the level of PBC in a subject not treated with the FXR agonist.

In some embodiments, a FXR agonist disclosed herein reduces cirrhosis in a subject. In some examples, the FXR agonist reduces cirrhosis in the subject by at least 5%, at least 10%, at least 15%, at least 20%, at least 30%, at least 40%, at least 50%, or more. In some cases, cirrhosis is reduced by about 5% to about 50%, by about 5% to about 25%, by about 10% to about 20%, or by about 10% to about 30%. In some instances, the level of cirrhosis is relative to the level of cirrhosis in a subject not treated with the FXR agonist.

Non-Alcoholic Fatty Liver Disease and Non-Alcoholic Steatohepatitis

Non-alcoholic fatty liver disease (NAFLD) is associated with excessive fat in the liver (steatosis) and in some cases progresses to NASH, which is defined by the histologic hallmarks of inflammation, cell death, and fibrosis. In some instances, primary NASH is associated with insulin resistance, while secondary NASH is caused by medical or surgical conditions, or drugs such as, but not limited to, tamoxifen. In some cases, NASH progresses to advanced fibrosis, hepatocellular carcinoma, or end-stage liver disease requiring liver transplantation.

In some instances, NASH develops as a result of triglyceride (TGs) imbalance. For example, dysfunctional adipocytes secrete pro-inflammatory molecules such as cytokines and chemokines leading to insulin resistance and a failure of lipolysis suppression in the adipocytes. In some instances, this failure of lipolysis suppression leads to a release of free fatty acids (FFAs) into the circulation and uptake within the liver. In some cases, overaccumulation of FFAs in the form of triglycerides (TGs) in lipid droplets leads to oxidative stress, mitochondrial dysfunction, and upregulation of pro-inflammatory molecules.

In some instances, activation of FXR inhibits triglyceride (TG)/fatty acid (FA) synthesis facilitated by suppressing sterol regulatory element-binding protein 1c (SREBP1c) via activation of SHP. In some cases, FXR additionally increases the clearance of TG by stimulating lipoprotein lipase (LPL) activity as well as the hepatic uptake of remnants and low-density lipoprotein by inducing syndecan 1 (SDC1) and the VLDL receptor (VLDLR).

In some embodiments, a FXR agonist disclosed herein is used in the treatment of non-alcoholic steatohepatitis (NASH). In some examples, the FXR agonist reduces NASH the subject by at least 5%, at least 10%, at least 15%, at least 20%, at least 30%, at least 40%, at least 50%, or more. In some cases, NASH is reduced by about 5% to about 50%, by about 5% to about 25%, by about 10% to about 20%, or by about 10% to about 30%. In some instances, the level of NASH is relative to the level of NASH in a subject not treated with the FXR agonist.

In some embodiments, a FXR agonist disclosed herein is used in the treatment of NAFLD. In some examples, the FXR agonist reduces NAFLD in the subject by at least 5%, at least 10%, at least 15%, at least 20%, at least 30%, at least 40%, at least 50%, or more. In some cases, NAFLD is reduced by about 5% to about 50%, by about 5% to about 25%, by about 10% to about 20%, or by about 10% to about 30%. In some instances, the level of NAFLD is relative to the level of NAFLD in a subject not treated with the FXR agonist.

Steatosis

In some embodiments, a FXR agonist disclosed herein reduces fatty liver (steatosis) in a subject. In some examples, the FXR agonist reduces steatosis in the subject by at least 5%, at least 10%, at least 15%, at least 20%, at least 30%, at least 40%, at least 50%, or more. In some instances, steatosis is reduced by about 5% to about 50%, by about 5% to about 25%, by about 10% to about 20%, or by about 10% to about 30%. In some instances, the level of steatosis is relative to the level of steatosis in a subject not treated with the FXR agonist.

Alcoholic Hepatitis

In some embodiments, a FXR agonist disclosed herein reduces alcoholic hepatitis in a subject. In some examples, the FXR agonist reduces alcoholic hepatitis in the subject by at least 5%, at least 10%, at least 15%, at least 20%, at least 30%, at least 40%, at least 50%, or more. In some instances, the level of alcoholic hepatitis is reduced by about 5% to about 50%, by about 5% to about 25%, by about 10% to about 20%, or by about 10% to about 30%. In some instances, the level of alcoholic hepatitis is relative to the level of alcoholic hepatitis in a subject not treated with the FXR agonist.

Primary Sclerosing Cholangitis

In some embodiments, a FXR agonist disclosed herein is used in the treatment of primary sclerosing cholangitis (PSC). PSC is a chronic and progressive cholestatic liver disease. PSC is characterized by progressive inflammation, fibrosis, and stricture formation in liver ducts. Common symptoms include pruritus and jaundice. The disease is strongly associated with inflammatory bowel disease (IBD)—about 5% of patients with ulcerative colitis will have PSC. Up to 70% of patients with PSC also have IBD, most commonly ulcerative colitis.

Additional Alcoholic and Non Alcoholic Liver Diseases or Conditions

In some embodiments, a FXR agonist disclosed herein reduces liver enzymes in a subject. In some examples, the FXR agonist reduce liver enzymes (e.g., serum ALT and/or AST levels) in the subject by at least 5%, at least 10%, at least 15%, at least 20%, at least 30%, at least 40%, at least 50%, or more. In some instances, the level of liver enzymes is reduced by about 5% to about 50%, by about 5% to about 25%, by about 10% to about 20%, or by about 10% to about 30%. In some instances, the level of liver enzymes is relative to the level of liver enzymes in a subject not treated with the FXR agonist.

In some embodiments, a FXR agonist disclosed herein reduces liver triglycerides in a subject. In some examples, the FXR agonist reduces liver triglycerides in the subject by at least 5%, at least 10%, at least 15%, at least 20%, at least 30%, at least 40%, at least 50%, or more. In some instances, the level of liver triglycerides is reduced by about 5% to about 50%, by about 5% to about 25%, by about 10% to about 20%, or by about 10% to about 30%. In some instances, the level of liver triglycerides is relative to the level of liver triglycerides in a subject not treated with the FXR agonist.

Inflammatory Intestinal Condition

Disclosed herein are methods of treating or preventing an inflammatory intestinal condition. Exemplary inflammatory conditions include necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, a FXR agonist disclosed herein is administered to a subject having an inflammatory intestinal condition. In some embodiments, a FXR agonist disclosed herein is administered to a subject having necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection.

In some embodiments, a FXR agonist disclosed herein reduces inflammation of the intestines in a subject (such as a human). In some examples, the FXR agonist reduces intestinal inflammation in the subject by at least 5%, at least 10%, at least 15%, at least 20%, at least 30%, at least 40%, at least 50%, or more. In some instances, intestinal inflammation is reduced by about 5% to about 50%, by about 5% to about 25%, by about 10% to about 20%, or by about 10% to about 30%. In some instances, the level of intestinal inflammation is relative to the level of intestinal inflammation in a subject not treated with the FXR agonist.

Cell Proliferation Disease

Further disclosed herein are methods of preventing or treating cell proliferation diseases, for example, in certain types of cancer. In some embodiments, the FXR agonists disclosed herein are used in the prevention or treatment of adenocarcinomas, or a carcinoma derived from glandular tissue or in which the tumor cells form recognizable glandular structures. In some embodiments, adenocarcinomas are classified according to the predominant pattern of cell arrangement, as papillary, alveolar, or according to a particular product of the cells, as mucinous adenocarcinoma. In some instances, adenocarcinomas are observed for example, in colon, kidney, breast, cervix, esophagus, gastric, pancreas, prostate, or lung.

In some embodiments, the compounds disclosed herein are used in the prevention or treatment of a cancer of the intestine, such as colon cancer, e.g. cancer that forms in the tissues of the colon (the longest part of the large intestine), or a cancer of another part of the intestine, such as the jejunum, and/or ileum. In some instances, colon cancer is also referred to as "colorectal cancer." In some instances, the most common type of colon cancer is colon adenocarcinoma.

In some cases, cancer progression is characterized by stages, or the extent of cancer in the body. Staging is usually based on the size of the tumor, the presence of cancer in the lymph nodes, and the presence of the cancer in a site other than the primary cancer site. Stages of colon cancer include stage I, stage II, stage III and stage IV. In some embodiments, colon adenocarcinoma is from any stage. In other embodiments, colon adenocarcinoma is a stage I cancer, a stage II cancer or a stage III cancer.

In some embodiments, a FXR agonist described herein is administered to a subject having a stage I, stage II, stage III, or stage IV cancer. In some instances, a FXR agonist described herein is administered to a subject having a stage I, stage II, or stage III colon adenocarcinoma.

In some embodiments, a FXR agonist disclosed herein further reduces the tumor burden in a subject. In some examples, the FXR agonist reduces tumor burden (such as colon tumor burden) in the subject by at least 5%, at least 10%, at least 15%, at least 20%, at least 30%, at least 40%, at least 50%, or more. In some instances, tumor burden is reduced by about 5% to about 50%, by about 5% to about 25%, by about 10% to about 20%, or by about 10% to about 30%. In some instances, the level of tumor burden is relative to the level of tumor burden in a subject not treated with the FXR agonist.

In some instances, a FXR agonist disclosed herein further reduces tumor size and/or volume in a subject. In some cases, the FXR agonist reduces tumor size and/or volume (such as a colon tumor) in the subject by at least 5%, at least 10%, at least 15%, at least 20%, at least 30%, at least 40%, at least 50%, or more. In some instances, tumor size is reduced by about 5% to about 50%, by about 5% to about 25%, by about 10% to about 20%, or by about 10% to about 30%. In some instances, the tumor size is relative to the tumor size in a subject not treated with the FXR agonist.

In additional embodiments, a FXR agonist disclosed herein reduces effects of cachexia due to a tumor in a subject. In some examples, the FXR agonist reduce the effect of cachexia (such as due to a colon tumor) in the subject by at least 5%, at least 10%, at least 15%, at least 20%, at least 30%, at least 40%, at least 50%, or more. In some instances, the effect of cachexia is reduced by about 5% to about 50%, by about 5% to about 25%, by about 10% to about 20%, or by about 10% to about 30%. In some instances, the effect of cachexia is relative to the effect of cachexia in a subject not treated with the FXR agonist.

In other embodiments, a FXR agonist disclosed herein increases survival rates of a subject with a tumor. In some cases, the FXR agonist increases the survival rate of a subject with a tumor (such as a colon cancer) in the subject by at least 5%, at least 10%, at least 15%, at least 20%, at least 30%, at least 40%, at least 50%, or more. In some instances, survival rate is increased by about 5% to about 50%, by about 5% to about 25%, by about 10% to about 20%, or by about 10% to about 30%. In some instances, the survival rate is relative to the survival rate in a subject not treated with the FXR agonist.

Compounds

Compounds described herein, including pharmaceutically acceptable salts, prodrugs, active metabolites and pharmaceutically acceptable solvates thereof, are farnesoid X receptor agonists.

In one aspect, described herein is a compound of Formula (I), or a pharmaceutically acceptable salt, or solvate thereof:

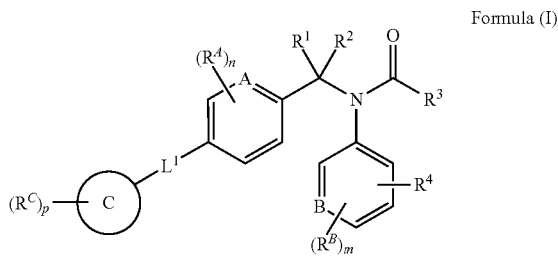

Formula (I)

wherein
$R^1$ and $R^2$ are each independently selected from H, D, F, $C_1$-$C_4$alkyl, or $C_1$-$C_4$fluoroalkyl;
or $R^1$ and $R^2$ are taken together with the carbon atom to which they are attached to form a substituted or unsubstituted C$_3$-C$_{10}$cycloalkyl, or substituted or unsubstituted C$_2$-C$_{10}$heterocycloalkyl;

or R$^1$ and R$^2$ are taken together with the carbon atom to which they are attached to form a carbonyl (C=O);

R$^3$ is selected from substituted or unsubstituted C$_1$-C$_{10}$alkyl, substituted or unsubstituted C$_2$-C$_{10}$alkenyl, substituted or unsubstituted C$_2$-C$_{10}$alkynyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, wherein if R$^3$ is substituted then R$^3$ is substituted with one or more R$^{12}$ groups;

each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NHC(=O)R$^{11}$, —NHC(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^4$-L$^5$-R$^{13}$;

L$^4$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;

L$^5$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;

R$^{13}$ is H, halogen, unsubstituted or substituted C$_1$-C$_{10}$alkyl, unsubstituted or substituted C$_1$-C$_{10}$alkenyl, unsubstituted or substituted C$_1$-C$_{10}$alkynyl, unsubstituted or substituted C$_1$-C$_{10}$cycloalkyl, unsubstituted or substituted C$_1$-C$_{10}$heterocycloalkyl, unsubstituted or substituted aryl, or unsubstituted or substituted heteroaryl;

R$^4$ is -L$^3$-Y;

L$^3$ is —C(R$^5$)(R$^6$)—, —C(R$^5$)(R$^6$)—C(R$^7$)(R$^8$)—, —O—C(R$^7$)(R$^8$)—, or —C(R$^5$)(R$^6$)—O—;

R$^5$ and R$^7$ are each independently selected from H, D, C$_1$-C$_4$alkyl and C$_3$-C$_6$cycloalkyl;

or R$^5$ and R$^7$ are taken together with the intervening atoms to form a double bond;

or R$^5$ and R$^7$ are taken together with the intervening atoms to form an epoxide or a substituted or unsubstituted C$_3$-C$_6$cycloalkyl;

R$^6$ and R$^8$ are each independently selected from H, D, C$_1$-C$_4$alkyl or C$_3$-C$_6$cycloalkyl;

Y is —CH$_2$OR$^9$, —C(=O)OR$^9$,

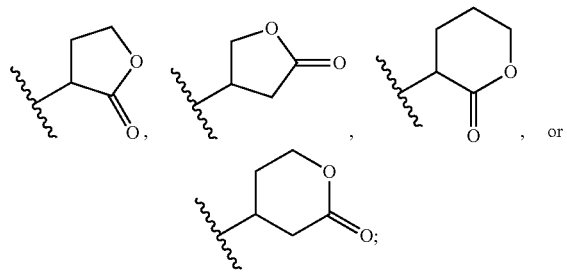

R$^9$ is selected from H, substituted or unsubstituted C$_1$-C$_6$alkyl, substituted or unsubstituted C$_1$-C$_6$heteroalkyl, substituted or unsubstituted C$_2$-C$_6$alkenyl, substituted or unsubstituted C$_3$-C$_6$cycloalkyl, substituted or unsubstituted phenyl, or substituted or substituted or unsubstituted heterocycle;

L$^1$ is —X$^1$-L$^2$-, -L$^2$-X$^1$—;

X$^1$ is —O—, —S—, —S(=O)—, —S(=O)$_2$—, —S(=O)$_2$NR$^{10}$—, —CH$_2$—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

L$^2$ is absent or substituted or unsubstituted C$_1$-C$_4$alkylene;

A is CR$^A$, or N;

each R$^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

B is CR$^B$, or N;

each R$^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

ring C is monocyclic carbocycle, bicyclic carbocycle, monocyclic N-containing heterocycle, or bicyclic heterocycle;

each R$^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

For any and all of the embodiments, substituents are selected from among a subset of the listed alternatives. For example, in some embodiments, $R^1$ and $R^2$ are each independently selected from H, D, F, $C_1$-$C_4$alkyl, or $C_1$-$C_4$fluoroalkyl. In other embodiments, $R^1$ and $R^2$ are each independently selected from H, D, F, $CH_3$, or $CF_3$. In some other embodiments, $R^1$ and $R^2$ are each independently selected from H, or D. In some other embodiments, $R^1$ and $R^2$ are each H.

In some embodiments, A is $CR^A$. In some embodiments, A is N.

In some embodiments, $L^1$ is —$X^1$-$L^2$-, -$L^2$-$X^1$—; $X^1$ is —O—, —S—, —S(=O)—, —S(=O)$_2$—, —S(=O)$_2$NR$^{10}$—, —CH$_2$—, —C≡C—, —C(=O)—, —C(=O)O—, —OC(=O)—, —C(=O)NR$^{10}$—, —NR$^{10}$C(=O)—, —NR$^{10}$S(=O)$_2$—, or —NR$^{10}$—; $L^2$ is absent or —CH$_2$—.

In some embodiments, $L^1$ is absent, —O—, —S—, —S—CH$_2$—, —CH$_2$—S—, —CH$_2$—, —CH=CH—, —C≡C—, —C(=O)—, —C(=O)O—, —OC(=O)—, —C(=O)NR$^{10}$—, —NR$^{10}$C(=O)—, —NR$^{10}$S(=O)$_2$—, —NR$^{10}$—, —NR$^{10}$—CH$_2$—, or —CH$_2$—NR$^{10}$—.

In some embodiments, $L^1$ is absent, —O—, —S—, —S—CH$_2$—, —CH$_2$—S—, —CH$_2$—, —CH=CH—, —C≡C—, —NR$^{10}$—, —NR$^{10}$—CH$_2$—, or —CH$_2$—NR$^{10}$—.

In some embodiments, $L^1$ is absent, —O—, —S—, —CH=CH—, —C≡C—, or —NR$^{10}$—.

In some embodiments, $L^1$ is absent, —O—, —S—, or —NR$^{10}$—.

In some embodiments, $R^3$ is selected from substituted or unsubstituted $C_1$-$C_{10}$alkyl, substituted or unsubstituted $C_3$-$C_{10}$cycloalkyl, or substituted or unsubstituted aryl, wherein if $R^3$ is substituted then $R^3$ is substituted with one or more $R^{12}$ groups.

In some embodiments, $R^3$ is selected from methyl, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

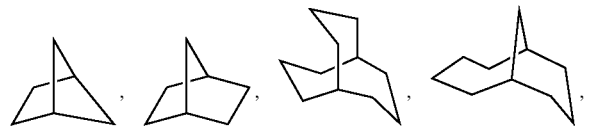

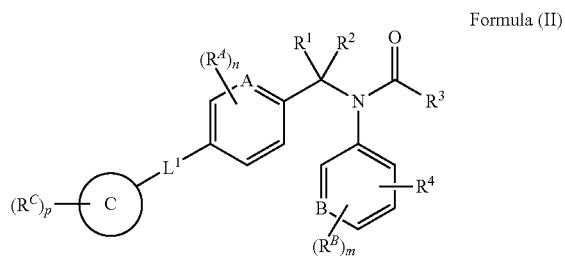

and adamantyl.

In some embodiments, $R^3$ is selected from substituted or unsubstituted cyclohexyl, substituted or unsubstituted phenyl, and

In some embodiments, $R^3$ is selected from substituted or unsubstituted cyclohexyl, or substituted or unsubstituted phenyl. In some embodiments, $R^3$ is substituted or unsubstituted cyclohexyl. In some embodiments, $R^3$ is substituted or unsubstituted phenyl.

In another aspect, described herein is a compound that has the structure of Formula (I), or a pharmaceutically acceptable salt or solvate thereof:

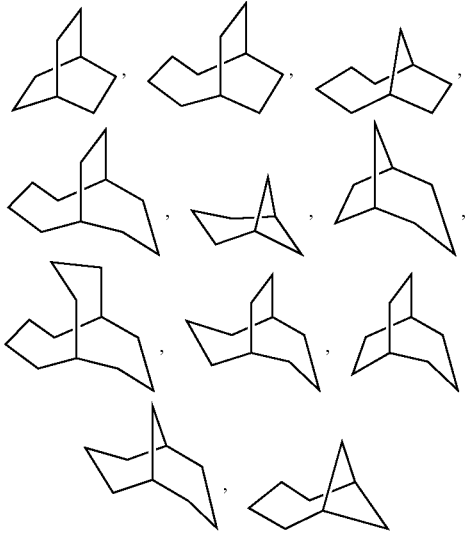

Formula (II)

wherein
$R^1$ and $R^2$ are each independently selected from H, D, F, $C_1$-$C_4$alkyl, or $C_1$-$C_4$fluoroalkyl;
or $R^1$ and $R^2$ are taken together with the carbon atom to which they are attached to form a substituted or unsubstituted $C_3$-$C_{10}$cycloalkyl, or substituted or unsubstituted $C_2$-$C_{10}$heterocycloalkyl;
or $R^1$ and $R^2$ are taken together with the carbon atom to which they are attached to form a carbonyl (C=O);
$R^3$ is selected from substituted or unsubstituted $C_4$-$C_{10}$alkyl, substituted or unsubstituted $C_1$-$C_{10}$alkoxy, substituted or unsubstituted $C_2$-$C_{10}$alkenyl, or unsubstituted substituted $C_2$-$C_{10}$alkynyl, substituted or unsubstituted cyclopropyl, substituted or unsubstituted cyclobutyl, substituted or unsubstituted cyclopentyl, substituted or unsubstituted cyclohexyl, substituted or unsubstituted cycloheptyl, substituted or unsubstituted cyclooctyl, substituted or unsubstituted $C_2$-$C_{10}$heterocycloalkyl containing 1 O or S atom, substituted aryl, or substituted or unsubstituted heteroaryl, wherein if $R^3$ is substituted then $R^3$ is substituted with one or more $R^{12}$ groups;

each $R^{12}$ is independently selected from D, halogen, —CN, —$NO_2$, —$OR^{10}$, —$SR^{10}$, —S(═O)$R^{11}$, —S(═O)$_2R^{11}$, —S(═O)$_2N(R^{10})_2$, —$NR^{10}$S(═O)$_2R^{11}$, —C(═O)$R^{11}$, —OC(═O)$R^{11}$, —$CO_2R^{10}$, —$OCO_2R^{11}$, —N($R^{10})_2$, —C(═O)N($R^{10})_2$, —OC(═O)N($R^{10})_2$, —NHC(═O)$R^{11}$, —NHC(═O)$OR^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -$L^4$-$L^5$-$R^{13}$;

$L^4$ is absent, —O—, —S—, —S(═O)—, —S(═O)$_2$—, —$NR^{10}$—, —C(═O)—, —C(═O)NH—, —NHC(═O)—, —C(═O)O—, —OC(═O)—, —OC(═O)NH—, —NHC(═O)NH—, —NHC(═O)O—, —(CH$_2$)$_r$—, or —(OCH$_2$CH$_2$)$_r$—, r is 1, 2, 3, or 4;

$L^5$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;

$R^{13}$ is H, halogen, unsubstituted or substituted $C_1$-$C_{10}$alkyl, unsubstituted or substituted $C_1$-$C_{10}$alkenyl, unsubstituted or substituted $C_1$-$C_{10}$alkynyl, unsubstituted or substituted $C_1$-$C_{10}$cycloalkyl, unsubstituted or substituted $C_1$-$C_{10}$heterocycloalkyl, unsubstituted or substituted aryl, or unsubstituted or substituted heteroaryl;

or $R^3$ is —N($R^{14})_2$, wherein each $R^{14}$ is independently selected from H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, and substituted or unsubstituted benzyl, or two $R^{13}$ on the same N atom are taken together with the N atom to which they are attached to form a N-containing heterocycle, provided that $R^3$ is not —NHCH($CH_3)_2$;

$R^4$ is -$L^3$-Y;

$L^3$ is —C($R^5$)($R^6$)—, —C($R^5$)($R^6$)—C($R^7$)($R^8$)—, —O—C($R^7$)($R^8$)—, or —C($R^5$)($R^6$)—O—;

$R^5$ and $R^7$ are each independently selected from H, D, $C_1$-$C_4$alkyl and $C_3$-$C_6$cycloalkyl;

or $R^5$ and $R^7$ are taken together with the intervening atoms to form a double bond;

or $R^5$ and $R^7$ are taken together with the intervening atoms to form an epoxide or a substituted or unsubstituted $C_3$-$C_6$cycloalkyl;

$R^6$ and $R^8$ are each independently selected from H, D, $C_1$-$C_4$alkyl or $C_3$-$C_6$cycloalkyl;

Y is —$CH_2OR^9$, —C(═O)$OR^9$,

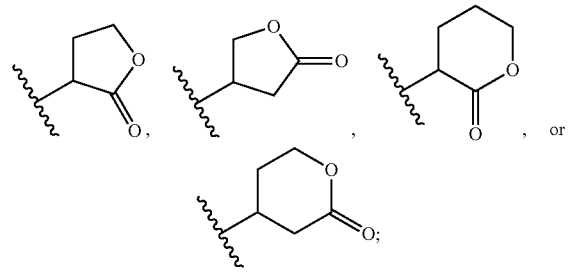

$R^9$ is selected from H, substituted or unsubstituted $C_1$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted phenyl, or substituted or substituted or unsubstituted heterocycle;

$L^1$ is —$X^1$-$L^2$-, -$L^2$-$X^1$—;

$X^1$ is absent, —O—, —S—, —S(═O)—, —S(═O)$_2$—, —S(═O)$_2NR^{10}$—, —$CH_2$—, —C≡C—, —C(═O)—, —C(═O)O—, —OC(═O)—, —OC(═O)O—, —C(═O)$NR^{10}$—, —$NR^{10}$C(═O)—, —OC(═O)$NR^{10}$—, —$NR^{10}$C(═O)O—, —$NR^{10}$C(═O)$NR^{10}$—, —$NR^{10}$S(═O)$_2$—, or —$NR^{10}$—;

$L^2$ is absent or substituted or unsubstituted $C_1$-$C_4$alkylene;

A is $CR^A$, or N;

each $R^A$ is independently selected from H, D, halogen, —CN, —OH, —$OR^{10}$, —$SR^{10}$, —S(═O)$R^{11}$, —S(═O)$_2R^{11}$, —NHS(═O)$_2R^{11}$, —S(═O)$_2N(R^{10})_2$, —C(═O)$R^{11}$, —OC(═O)$R^{11}$, —$CO_2R^{10}$, —$OCO_2R^{11}$, —C(═O)N($R^{10})_2$, —OC(═O)N($R^{10})_2$, —$NR^{10}$C(═O)N($R^{10})_2$, —$NR^{10}$C(═O)$R^{11}$, —$NR^{10}$C(═O)$OR^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

B is $CR^B$, or N;

each $R^B$ is independently selected from H, D, halogen, —CN, —OH, —$OR^{10}$, —$SR^{10}$, —S(═O)$R^{11}$, —S(═O)$_2R^{11}$, —N($R^{10})_2$, —NHS(═O)$_2R^{11}$, —S(═O)$_2N(R^{10})_2$, —C(═O)$R^{11}$, —OC(═O)$R^{11}$, —$CO_2R^{10}$, —$OCO_2R^{11}$, —C(═O)N($R^{10})_2$, —OC(═O)N($R^{10})_2$, —$NR^{10}$C(═O)N($R^{10})_2$, —$NR^{10}$C(═O)$R^{11}$, —$NR^{10}$C(═O)$OR^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

ring C is monocyclic carbocycle, bicyclic carbocycle, monocyclic N-containing heterocycle, or bicyclic heterocycle;

each $R^C$ is independently selected from H, D, halogen, —CN, —OH, —$OR^{10}$, —$SR^{10}$, —S(═O)$R^{11}$, —$NO_2$, —N($R^{10})_2$, —S(═O)$_2R^{11}$, —NHS(═O)$_2R^{11}$, —S(═O)$_2N(R^{10})_2$, —C(═O)$R^{11}$, —OC(═O)$R^{11}$, —$CO_2R^{10}$, —$OCO_2R^{11}$, —C(═O)N($R^{10})_2$, —OC(═O)N($R^{10})_2$, —$NR^{10}$C(═O)N($R^{10})_2$, —$NR^{10}$C (=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;

each R$^{10}$ is independently selected from H, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

or two R$^{10}$ on the same N atom are taken together with the N atom to which they are attached to form a N-containing heterocycle;

each R$^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4.

In some embodiments, R$^3$ is selected from substituted or unsubstituted C$_1$-C$_{10}$alkyl, substituted or unsubstituted C$_3$-C$_{10}$cycloalkyl, or substituted or unsubstituted aryl, wherein if R$^3$ is substituted then R$^3$ is substituted with one or more R$^{12}$ groups. In some embodiments, R$^3$ is selected from substituted or unsubstituted C$_4$-C$_{10}$alkyl, substituted or unsubstituted C$_3$-C$_{10}$cycloalkyl, or substituted or unsubstituted aryl, wherein if R$^3$ is substituted then R$^3$ is substituted with one or more R$^{12}$ groups.

In some embodiments, R$^3$ is selected from n-butyl, isobutyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted cyclohexyl, and substituted phenyl.

In some embodiments, R$^3$ is selected from substituted cyclohexyl and substituted phenyl.

In some embodiments, R$^4$ is

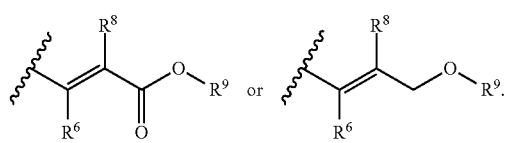

In some embodiments, R$^4$ is

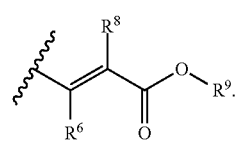

In some embodiments, R$^4$ is

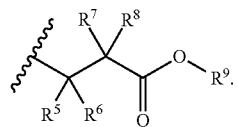

In some embodiments, R$^4$ is

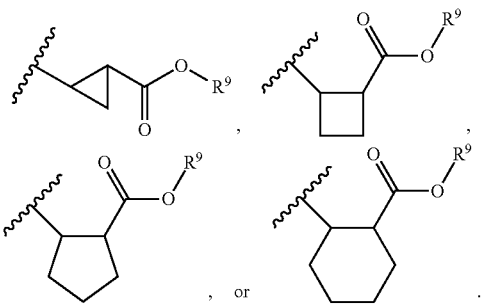

In some embodiments, R$^4$ is -L$^3$-Y; L$^3$ is —CH$_2$—; Y is

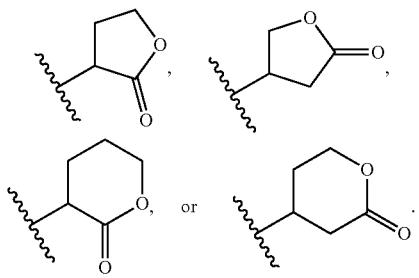

In some embodiments, ring C is monocyclic carbocycle, or bicyclic carbocycle.

In some embodiments, ring C is monocyclic carbocycle selected from cyclopropyl, cyclobutyl, cyclopentyl, cyclohexyl, and phenyl.

In some embodiments, ring C is phenyl.

In some embodiments, ring C is bicyclic carbocycle selected from indanyl, indenyl, and naphthyl.

In some embodiments, ring C is monocyclic heterocycle, or bicyclic heterocycle.

In some embodiments, ring C is monocyclic heterocycle, or bicyclic heterocycle selected from pyridinyl, pyrazolyl, pyrrolyl, imidazolyl, oxazolyl, isoxazolyl, thiazolyl, isothiazolyl, triazolyl, pyrimidinyl, pyrazinyl, triazinyl, benzotriazolyl, benzimidazolyl, indolyl, quinolinyl, indazolyl, purinyl, quinoxalinyl, and acridinyl.

In some embodiments, ring C is monocyclic heterocycle, or bicyclic heterocycle selected from pyridinyl, pyrazolyl, pyrrolyl, imidazolyl, oxazolyl, isoxazolyl, thiazolyl, isothiazolyl, triazolyl, pyrimidinyl, pyrazinyl, and triazinyl.

In some embodiments,

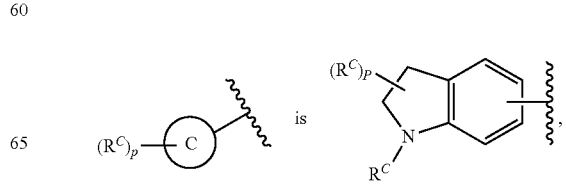

-continued

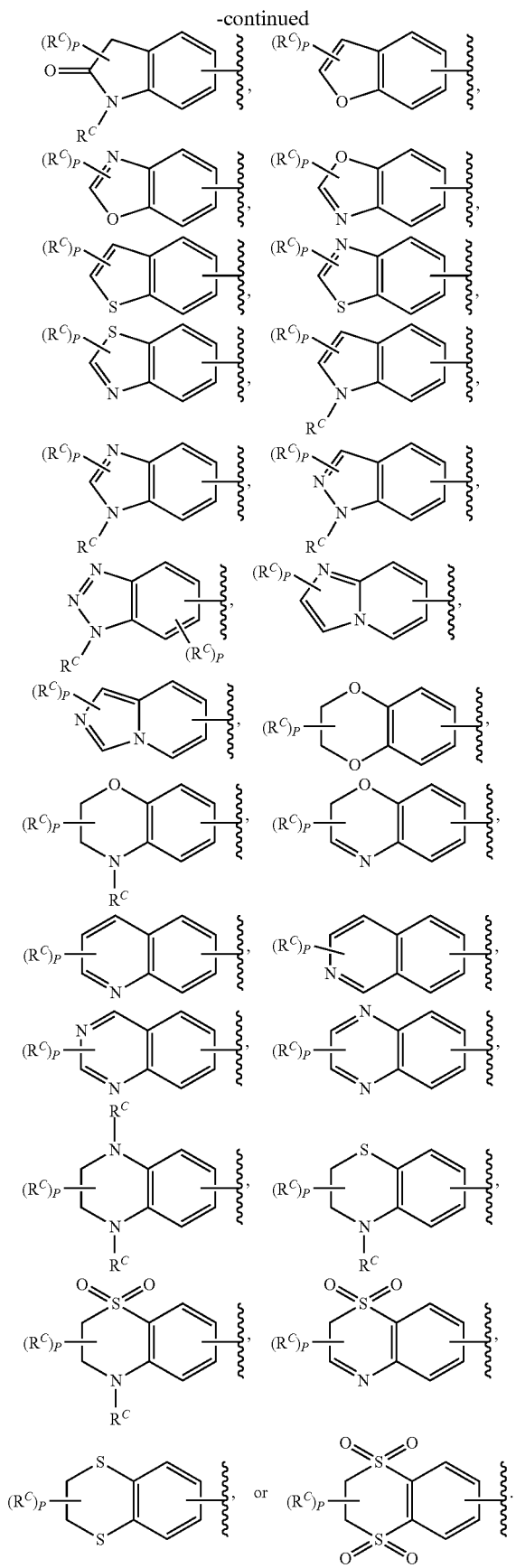

In some embodiments,

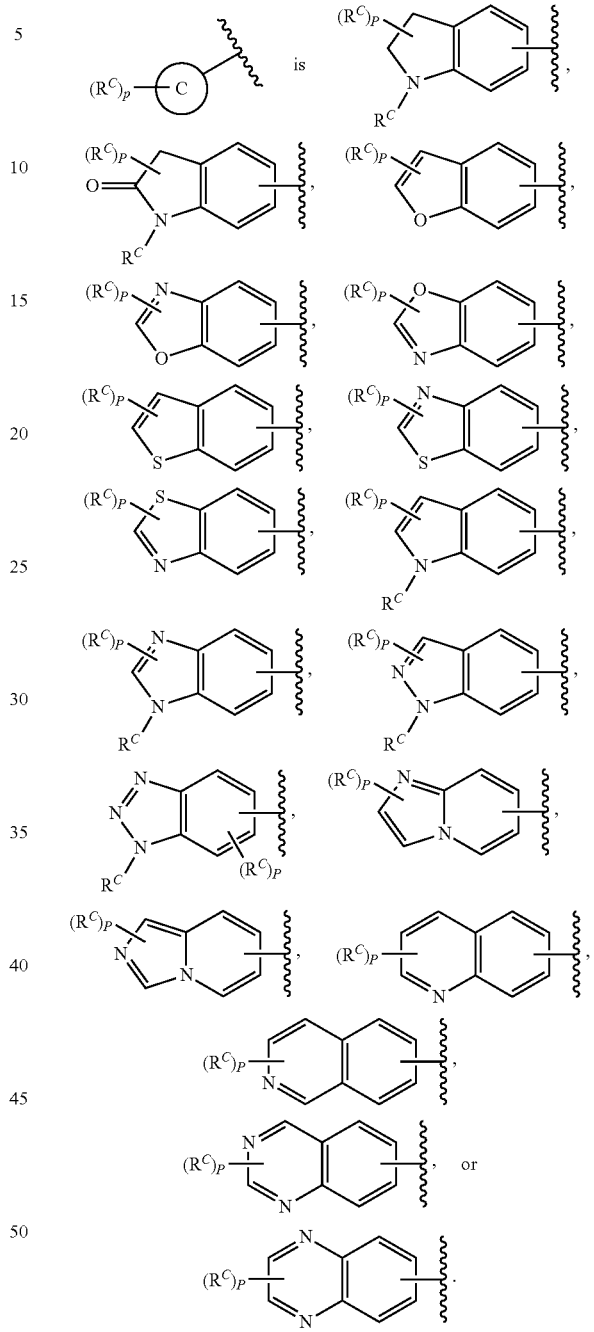

In some embodiments, ring C is monocyclic heterocycle selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, and 1,2,3,6-tetrahydropyridinyl.

In another aspect, described herein is a compound that has the structure of Formula (II), or a pharmaceutically acceptable salt or solvate thereof:

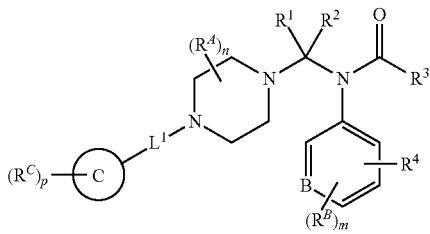

Formula (III)

wherein
R$^1$ and R$^2$ are each independently selected from H, D, F, C$_1$-C$_4$alkyl, or C$_1$-C$_4$fluoroalkyl;
or R$^1$ and R$^2$ are taken together with the carbon atom to which they are attached to form a substituted or unsubstituted C$_3$-C$_{10}$cycloalkyl, or substituted or unsubstituted C$_2$-C$_{10}$heterocycloalkyl;
or R$^1$ and R$^2$ are taken together with the carbon atom to which they are attached to form a carbonyl (C=O);
R$^3$ is selected from substituted or unsubstituted C$_1$-C$_{10}$alkyl, substituted or unsubstituted C$_2$-C$_{10}$alkenyl, substituted or unsubstituted C$_2$-C$_{10}$alkynyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, wherein if R$^3$ is substituted then R$^3$ is substituted with one or more R$^{12}$ groups;
each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NHC(=O)R$^{11}$, —NHC(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^4$-L$^5$-R$^{13}$;
L$^4$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;
L$^5$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;
R$^{13}$ is H, halogen, unsubstituted or substituted C$_1$-C$_{10}$alkyl, unsubstituted or substituted C$_1$-C$_{10}$alkenyl, unsubstituted or substituted C$_1$-C$_{10}$alkynyl, unsubstituted or substituted C$_1$-C$_{10}$cycloalkyl, unsubstituted or substituted C$_1$-C$_{10}$heterocycloalkyl, unsubstituted or substituted aryl, or unsubstituted or substituted heteroaryl;

R$^4$ is -L$^3$-Y;
L$^3$ is —C(R$^5$)(R$^6$)—, —C(R$^5$)(R$^6$)—C(R$^7$)(R$^8$)—, —O—C(R$^7$)(R$^8$)—, or —C(R$^5$)(R$^6$)—O—;
R$^5$ and R$^7$ are each independently selected from H, D, C$_1$-C$_4$alkyl and C$_3$-C$_6$cycloalkyl;
or R$^5$ and R$^7$ are taken together with the intervening atoms to form a double bond;
or R$^5$ and R$^7$ are taken together with the intervening atoms to form an epoxide or a substituted or unsubstituted C$_3$-C$_6$cycloalkyl;
R$^6$ and R$^8$ are each independently selected from H, D, C$_1$-C$_4$alkyl or C$_3$-C$_6$cycloalkyl;
Y is —CH$_2$OR$^9$, —C(=O)OR$^9$,

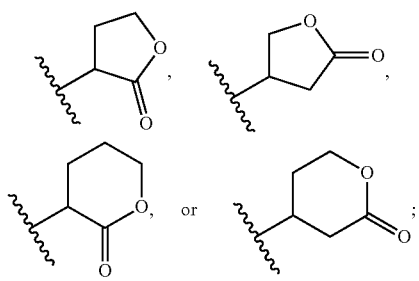

R$^9$ is selected from H, substituted or unsubstituted C$_1$-C$_6$alkyl, substituted or unsubstituted C$_1$-C$_6$heteroalkyl, substituted or unsubstituted C$_2$-C$_6$alkenyl, substituted or unsubstituted C$_3$-C$_6$cycloalkyl, substituted or unsubstituted phenyl, or substituted or substituted or unsubstituted heterocycle;
L$^1$ is —X$^1$-L$^2$-, -L$^2$-X$^1$—;
X$^1$ is —S(=O)—, —S(=O)$_2$—, —CH$_2$—, —C(=O)—, —OC(=O)—, —NR$^{10}$C(=O)—, or —NR$^{10}$S(=O)$_2$—;
L$^2$ is absent or substituted or unsubstituted C$_1$-C$_4$alkylene;
each R$^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;
B is CR$^B$, or N;
each R$^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;
ring C is monocyclic carbocycle, bicyclic carbocycle, or bicyclic heterocycle;
each R$^C$ is independently selected from H, D, halogen, —CN, —OH, —OR$^{10}$, —SR$^{10}$, —S(=O)R$^{11}$, —NO$_2$, —N($R^{10}$)$_2$, —S(=O)$_2$$R^{11}$, —NHS(=O)$_2$$R^{11}$, —S(=O)$_2$N($R^{10}$)$_2$, —C(=O)$R^{11}$, —OC(=O)$R^{11}$, —CO$_2$$R^{10}$, —OCO$_2$$R^{11}$, —C(=O)N($R^{10}$)$_2$, —OC(=O)N($R^{10}$)$_2$, —N$R^{10}$C(=O)N($R^{10}$)$_2$, —N$R^{10}$C(=O)$R^{11}$, —N$R^{10}$C(=O)O$R^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4.

In some embodiments, $L^1$ is —$X^1$-$L^2$-, -$L^2$-$X^1$—; $X^1$ is —S(=O)$_2$—, —CH$_2$—, or —C(=O)—; $L^2$ is absent or —CH$_2$—.

In some embodiments, $R^4$ is

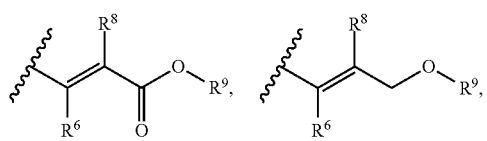

or —C≡C—C(=O)O$R^9$.

In some embodiments, $R^4$ is

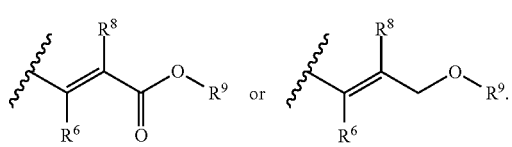

In some embodiments, $R^4$ is

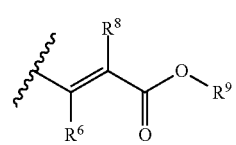

or —C≡C—C(=O)O$R^9$. In some embodiments, $R^4$ is

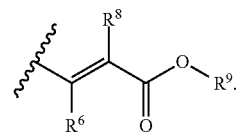

In some embodiments, $R^4$ is

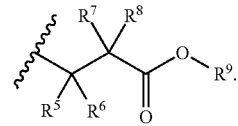

In some embodiments, $R^4$ is

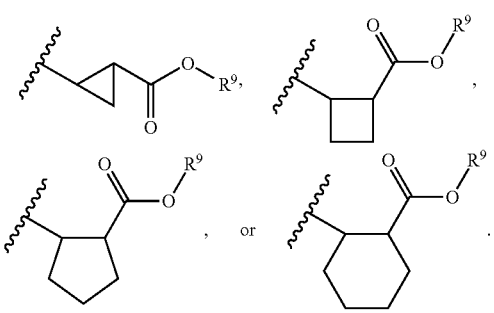

In some embodiments, $R^4$ is -$L^3$-Y; $L^3$ is —CH$_2$—; Y is

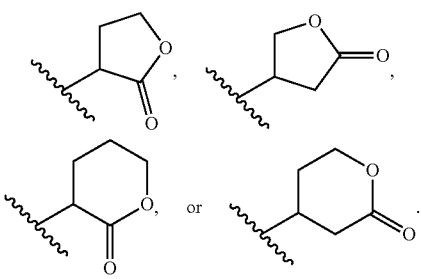

In some embodiments, ring C is monocyclic carbocycle, or bicyclic carbocycle.

In some embodiments, ring C is monocyclic carbocycle selected from cyclopropyl, cyclobutyl, cyclopentyl, cyclohexyl, and phenyl.

In some embodiments, ring C is phenyl.

In some embodiments, ring C is bicyclic carbocycle selected from indanyl, indenyl, and naphthyl.

In some embodiments, ring C is monocyclic heterocycle, or bicyclic heterocycle.

In some embodiments, ring C is monocyclic heterocycle, or bicyclic heterocycle selected from pyridine, pyrazole, pyrrole, imidazole, oxazole, isoxazole, thiazole, isothiazole, triazole, pyrimidine, pyrazine, triazine, benzotriazole, benzimidazole, indole, quinoline, indazole, purine, quinoxaline, and acridine.

In some embodiments, ring C is monocyclic heterocycle, or bicyclic heterocycle selected from pyridine, pyrazole, pyrrole, imidazole, oxazole, isoxazole, thiazole, isothiazole, triazole, pyrimidine, pyrazine, and triazine.

In some embodiments,

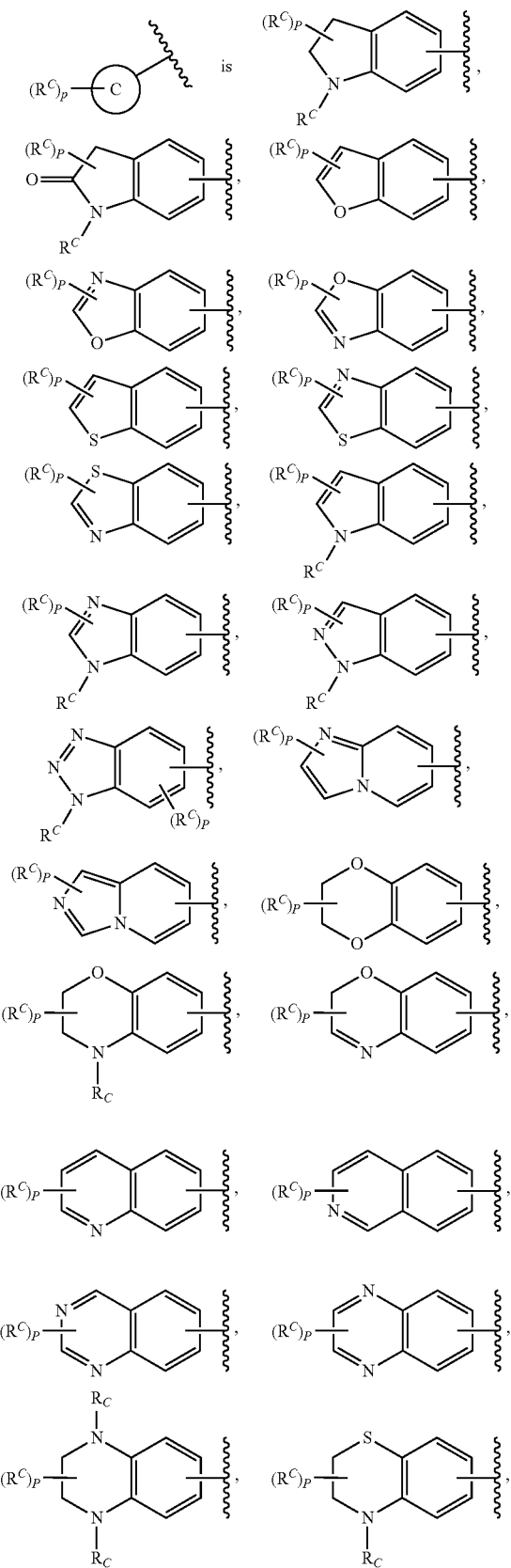

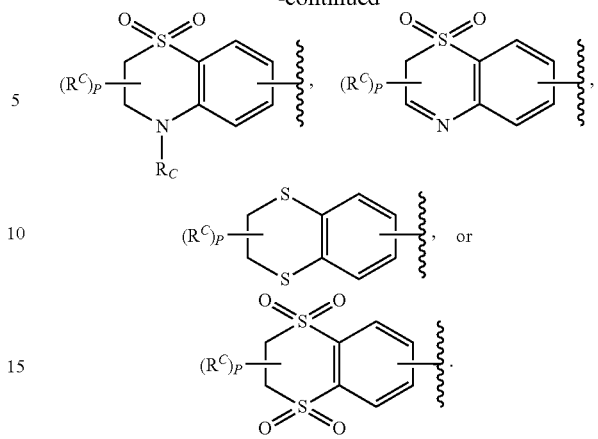

In some embodiments, ring C is monocyclic heterocycle selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, and 1,2,3,6-tetrahydropyridinyl.

In some embodiments, $R^3$ is selected from substituted or unsubstituted $C_1$-$C_{10}$alkyl, substituted or unsubstituted $C_3$-$C_{10}$cycloalkyl, or substituted or unsubstituted aryl, wherein if $R^3$ is substituted then $R^3$ is substituted with one or more $R^{12}$ groups.

In some embodiments, $R^3$ is selected from methyl, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

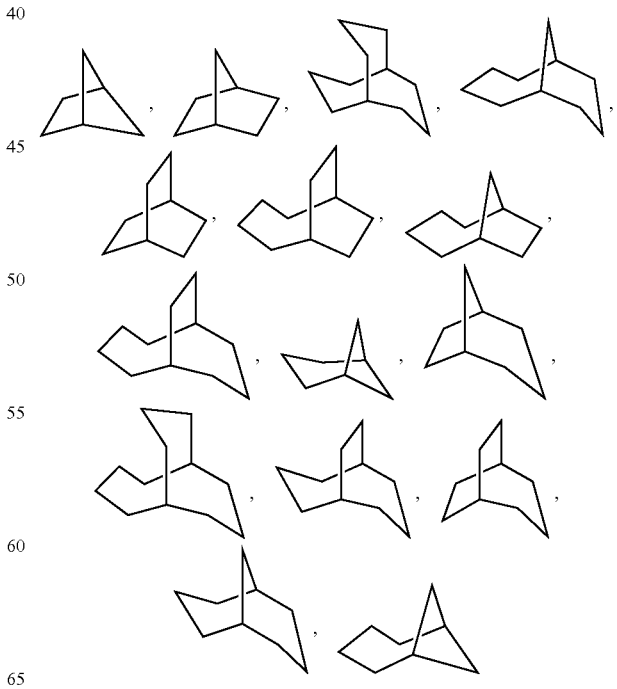

and adamantyl.

In some embodiments, R³ is selected from substituted or unsubstituted cyclohexyl, substituted or unsubstituted phenyl, and

In yet another aspect, described herein is a compound that has the structure of Formula (IV), or a pharmaceutically acceptable salt or solvate thereof:

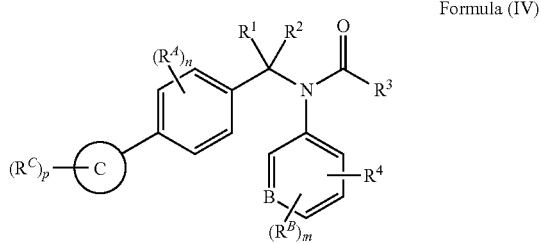

Formula (IV)

wherein
R¹ and R² are each independently selected from H, D, F, $C_1$-$C_4$alkyl, or $C_1$-$C_4$fluoroalkyl;
or R¹ and R² are taken together with the carbon atom to which they are attached to form a substituted or unsubstituted $C_3$-$C_{10}$cycloalkyl, or substituted or unsubstituted $C_2$-$C_{10}$heterocycloalkyl;
or R¹ and R² are taken together with the carbon atom to which they are attached to form a carbonyl (C=O);
R³ is selected from substituted or unsubstituted $C_1$-$C_{10}$alkyl, substituted or unsubstituted $C_2$-$C_{10}$alkenyl, substituted or unsubstituted $C_2$-$C_{10}$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl, wherein if R³ is substituted then R³ is substituted with one or more R¹² groups;
each R¹² is independently selected from D, halogen, —CN, —NO₂, —OR¹⁰, —SR¹⁰, —S(=O)R¹¹, —S(=O)₂R¹¹, —S(=O)₂N(R¹⁰)₂, —NR¹⁰S(=O)₂R¹¹, —C(=O)R¹¹, —OC(=O)R¹¹, —CO₂R¹⁰, —OCO₂R¹¹, —N(R¹⁰)₂, —C(=O)N(R¹⁰)₂, —OC(=O)N(R¹⁰)₂, —NHC(=O)R¹¹, —NHC(=O)OR¹¹, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -L⁴-L⁵-R¹³;
L⁴ is absent, —O—, —S—, —S(=O)—, —S(=O)₂—, —NR¹⁰—, —C(=O)—, —C(=O)NH—, —NHC(=O)—, —C(=O)O—, —OC(=O)—, —OC(=O)NH—, —NHC(=O)NH—, —NHC(=O)O—, —(CH₂)ᵣ—, or —(OCH₂CH₂)ᵣ—, r is 1, 2, 3, or 4;
L⁵ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;
R¹³ is H, halogen, unsubstituted or substituted $C_1$-$C_{10}$alkyl, unsubstituted or substituted $C_1$-$C_{10}$alkenyl, unsubstituted or substituted $C_1$-$C_{10}$alkynyl, unsubstituted or substituted $C_1$-$C_{10}$cycloalkyl, unsubstituted or substituted $C_1$-$C_{10}$heterocycloalkyl, unsubstituted or substituted aryl, or unsubstituted or substituted heteroaryl;
R⁴ is -L³-Y;
L³ is —C(R⁵)(R⁶)—, —C(R⁵)(R⁶)—C(R⁷)(R⁸)—, —O—C(R⁷)(R⁸)—, or —C(R⁵)(R⁶)—O—;
R⁵ and R⁷ are each independently selected from H, D, $C_1$-$C_4$alkyl and $C_3$-$C_6$cycloalkyl;
or R⁵ and R⁷ are taken together with the intervening atoms to form a double bond;
or R⁵ and R⁷ are taken together with the intervening atoms to form an epoxide or a substituted or unsubstituted $C_3$-$C_6$cycloalkyl;
R⁶ and R⁸ are each independently selected from H, D, $C_1$-$C_4$alkyl or $C_3$-$C_6$cycloalkyl;
Y is —CH₂OR⁹, —C(=O)OR⁹,

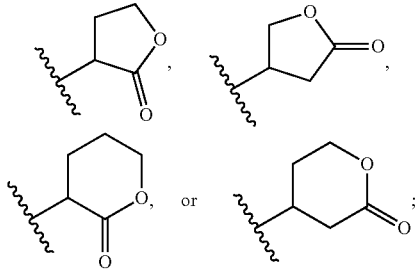

R⁹ is selected from H, substituted or unsubstituted $C_1$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted phenyl, or substituted or unsubstituted heterocycle;
L¹ is —X¹-L²-, or -L²-X¹—;
X¹ is absent, —O—, —S—, —S(=O)—, —S(=O)₂—, —S(=O)₂NR¹⁰, —CH₂—, —CH=CH—, —C≡C—, —C(=O)—, —C(=O)O—, —OC(=O)—, —OC(=O)O—, —C(=O)NR¹⁰—, —NR¹⁰C(=O)—, —OC(=O)NR¹⁰—, —NR¹⁰C(=O)O—, —NR¹⁰C(=O)NR¹⁰—, —NR¹⁰S(=O)₂—, or —NR¹⁰—;
L² is absent or substituted or unsubstituted $C_1$-$C_4$alkylene;
each Rᴬ is independently selected from H, D, halogen, —CN, —OH, —OR¹⁰, —SR¹⁰, —S(=O)R¹¹, —S(=O)₂R¹¹, —NHS(=O)₂R¹¹, —S(=O)₂N(R¹⁰)₂, —C(=O)R¹¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

B is $CR^B$, or N;

each $R^B$ is independently selected from H, D, halogen, —CN, —OH, —$OR^{10}$, —$SR^{10}$, —$S(=O)R^{11}$, —$S(=O)_2R^{11}$, —$N(R^{10})_2$, —$NHS(=O)_2R^{11}$, —$S(=O)_2N(R^{10})_2$, —$C(=O)R^{11}$, —$OC(=O)R^{11}$, —$CO_2R^{10}$, —$OCO_2R^{11}$, —$C(=O)N(R^{10})_2$, —$OC(=O)N(R^{10})_2$, —$NR^{10}C(=O)N(R^{10})_2$, —$NR^{10}C(=O)R^{11}$, —$NR^{10}C(=O)OR^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

ring C is a 5-membered N-containing heteroaryl, or a N-containing $C_2$-$C_8$heterocycloalkyl;

each $R^C$ is independently selected from H, D, halogen, —CN, —OH, —$OR^{10}$, —$SR^{10}$, —$S(=O)R^{11}$, —$NO_2$, —$N(R^{10})_2$, —$S(=O)_2R^{11}$, —$NHS(=O)_2R^{11}$, —$S(=O)_2N(R^{10})_2$, —$C(=O)R^{11}$, —$OC(=O)R^{11}$, —$CO_2R^{10}$, —$OCO_2R^{11}$, —$C(=O)N(R^{10})_2$, —$OC(=O)N(R^{10})_2$, —$NR^{10}C(=O)N(R^{10})_2$, —$NR^{10}C(=O)R^{11}$, —$NR^{10}C(=O)OR^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

In some embodiments, ring C is a monocyclic 5-membered $C_1$-$C_4$heteroarylene containing 1-4 N atoms, 0 or 1 O or S atom.

In some embodiments, ring C is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

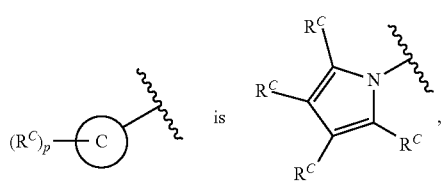

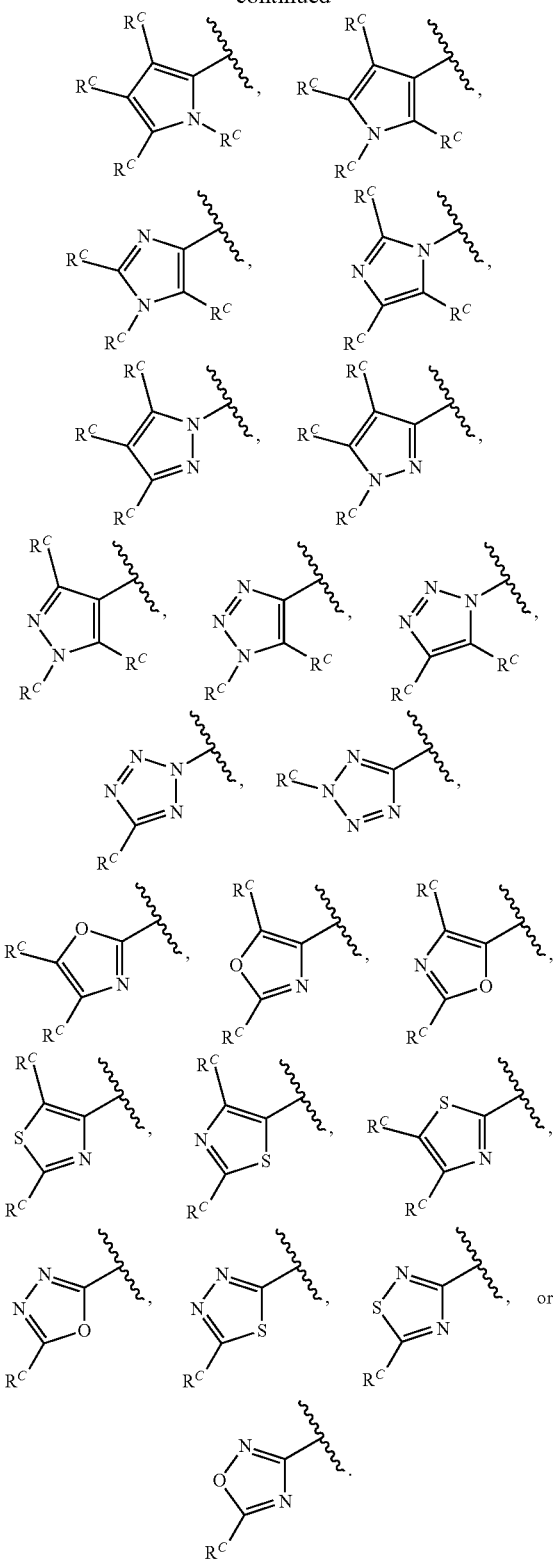

In some embodiments, ring C is a monocyclic $C_2$-$C_8$heterocycloalkyl containing at least 1 N atom in the ring.

In some embodiments, ring C is a monocyclic $C_2$-$C_8$heterocycloalkyl containing at least 1 N atom in the ring that is selected from aziridinyl, azetidinyl, pyrrolidinyl, morpholinyl, thiomorpholinyl, piperidinyl, piperazinyl, or azepanyl.

In some embodiments.

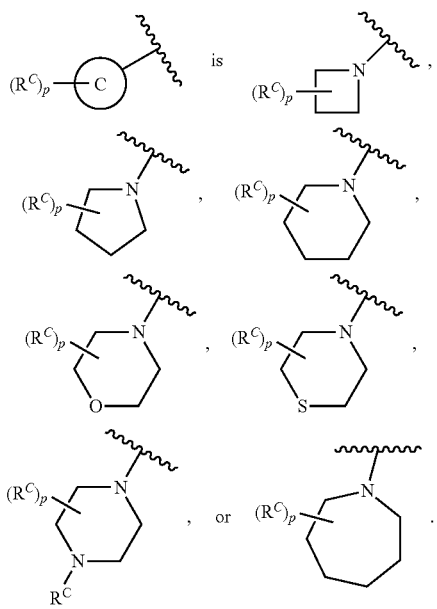

In some embodiments, the compound of Formula (IV) has the structure of Formula (V), or a pharmaceutically acceptable salt or solvate thereof:

Formula (V)

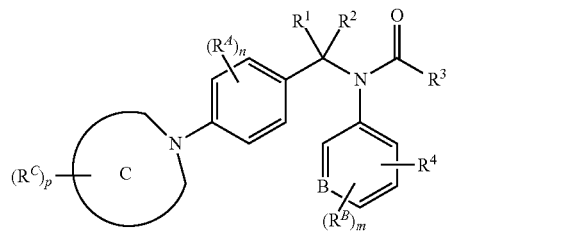

wherein, ring C is a 5-membered N-containing heteroaryl, or a N-containing $C_2$-$C_8$heterocycloalkyl.

In some embodiments, ring C is a 5-membered N-containing heteroaryl containing 1-4 N atoms.

In some embodiments,

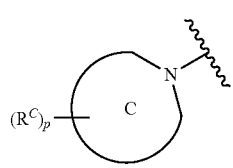

is a monocyclic 5-membered $C_1$-$C_4$heteroarylene containing 1-4 N atoms that has the structure

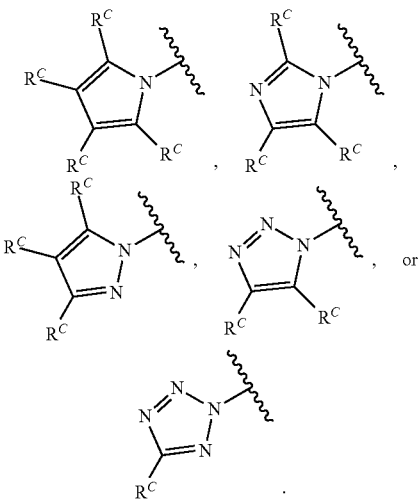

In some embodiments, ring C is a monocyclic $C_2$-$C_8$heterocycloalkyl containing at least 1 N atom in the ring that is selected from aziridinyl, azetidinyl, pyrrolidinyl, morpholinyl, thiomorpholinyl, piperidinyl, piperazinyl, or azepanyl.

In some embodiments,

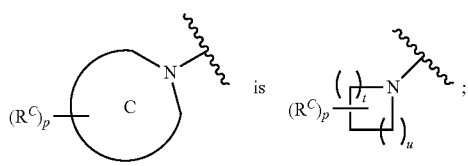

wherein, t is 1, 2, or 3; u is 1, 2, or 3.

In some embodiments,

In some embodiments, ring C is a monocyclic $C_2$-$C_8$heterocycloalkyl containing 1 N atom in the ring that is selected from a β-lactam, γ-lactam, δ-lactam or ε-lactam.

In some embodiments, ring C is a bicyclic $C_5$-$C_8$heterocycloalkyl that is a fused bicyclic $C_5$-$C_8$heterocycloalkyl, bridged bicyclic $C_5$-$C_8$heterocycloalkyl, or spiro bicyclic $C_5$-$C_8$heterocycloalkyl.

In some embodiments,

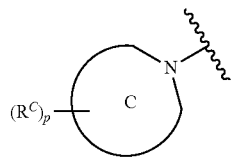

is a bridged bicyclic $C_5$-$C_8$heterocycloalkyl that is

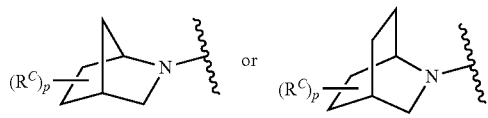

In some embodiments,

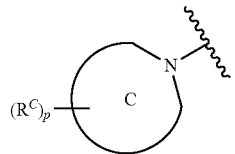

is spiro bicyclic $C_5$-$C_8$heterocycloalkyl that is

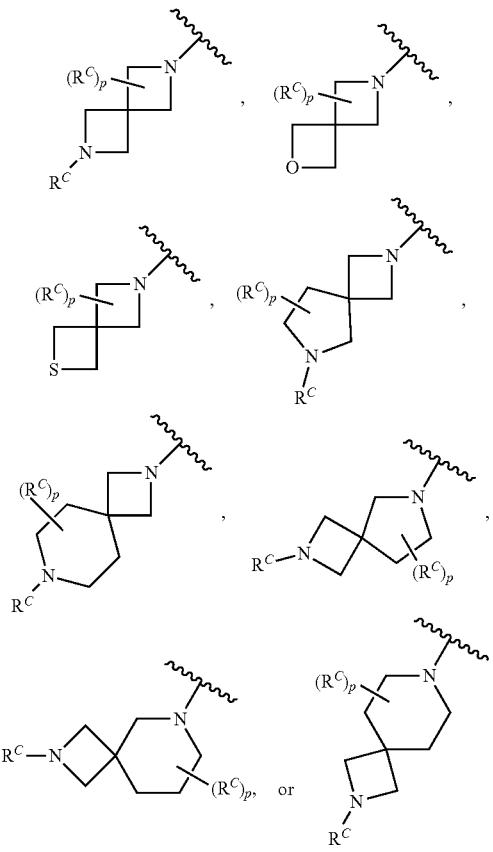

In some embodiments, $R^4$ is

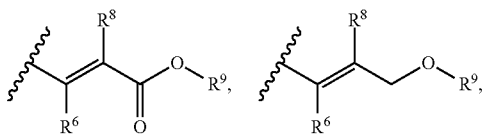

or —C≡C—C(=O)OR$^9$.

In some embodiments, $R^4$ is

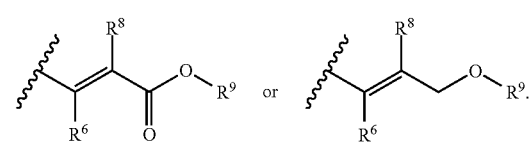

In some embodiments, $R^4$ is

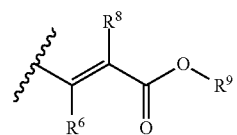

or —C≡C—C(=O)OR$^9$. In some embodiments, $R^4$ is

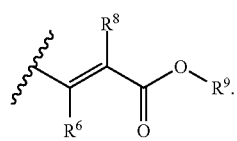

In some embodiments, $R^4$ is —C≡C—C(=O)OR$^9$.

In some embodiments, $R^4$ is

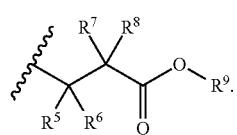

In some embodiments, $R^4$ is

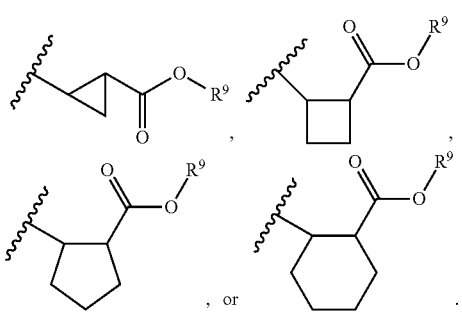

53

In some embodiments, R⁴ is -L³-Y; L³ is —CH₂—; Y is

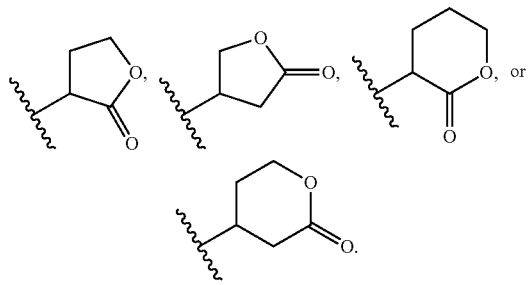

In some embodiments, R³ is selected from substituted or unsubstituted $C_1$-$C_{10}$alkyl, substituted or unsubstituted $C_3$-$C_{10}$cycloalkyl, or substituted or unsubstituted aryl, wherein if R³ is substituted then R³ is substituted with one or more $R^{12}$ groups.

In some embodiments, R³ is selected from methyl, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

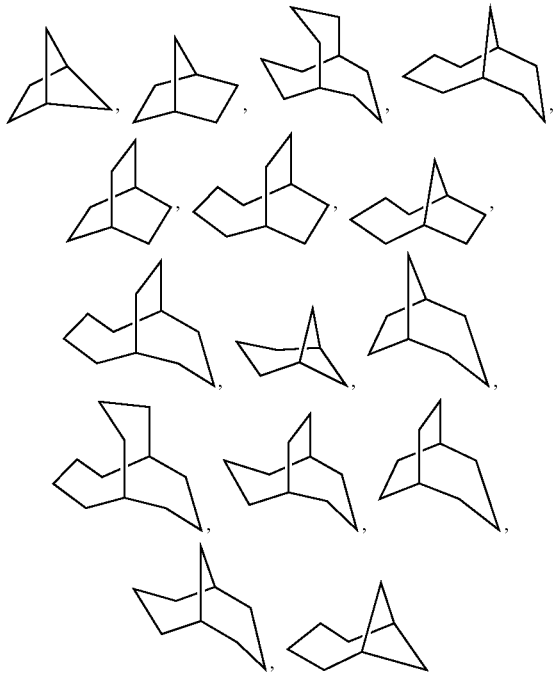

and adamantyl.

In some embodiments, R³ is selected from substituted or unsubstituted cyclohexyl, substituted or unsubstituted phenyl, and

54

In yet another aspect, described herein is a compound that has the structure of Formula (VI), or a pharmaceutically acceptable salt or solvate thereof:

Formula (VI)

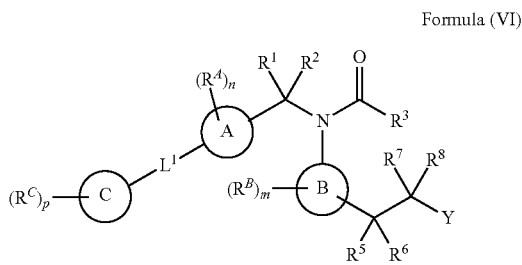

wherein
R¹ and R² are each independently selected from H, D, F, $C_1$-$C_4$alkyl, or $C_1$-$C_4$fluoroalkyl;
or R¹ and R² are taken together with the carbon atom to which they are attached to form a substituted or unsubstituted $C_3$-$C_{10}$cycloalkyl, or substituted or unsubstituted $C_2$-$C_{10}$heterocycloalkyl;
or R¹ and R² are taken together with the carbon atom to which they are attached to form a carbonyl (C=O);
R³ is selected from substituted or unsubstituted $C_1$-$C_{10}$alkyl, substituted or unsubstituted $C_2$-$C_{10}$alkenyl, substituted or unsubstituted $C_2$-$C_{10}$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl, wherein if R³ is substituted then R³ is substituted with one or more $R^{12}$ groups;
each $R^{12}$ is independently selected from D, halogen, —CN, —NO₂, —OR¹⁰, —SR¹⁰, —S(=O)R¹¹, —S(=O)₂R¹¹, —S(=O)₂N(R¹⁰)₂, —NR¹⁰S(=O)₂R¹¹, —C(=O)R¹¹, —OC(=O)R¹¹, —CO₂R¹⁰, —OCO₂R¹¹, —N(R¹⁰)₂, —C(=O)N(R¹⁰)₂, —OC(=O)N(R¹⁰)₂, —NHC(=O)R¹¹, —NHC(=O)OR¹¹, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -L⁵-L⁶-R¹³;
L⁵ is absent, —O—, —S—, —S(=O)—, —S(=O)₂—, —NR¹⁰—, —C(=O)—, —C(=O)NH—, —NHC(=O)—, —C(=O)O—, —OC(=O)—, —OC(=O)NH—, —NHC(=O)NH—, —NHC(=O)O—, —(CH₂)ᵣ—, or —(OCH₂CH₂)ᵣ—, r is 1, 2, 3, or 4;
L⁶ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;
R¹³ is H, halogen, unsubstituted or substituted $C_1$-$C_{10}$alkyl, unsubstituted or substituted $C_1$-$C_{10}$alkenyl, unsubstituted or substituted $C_1$-$C_{10}$alkynyl, unsubstituted or substituted $C_1$-$C_{10}$cycloalkyl, unsubstituted or substituted $C_1$-$C_{10}$heterocycloalkyl, unsubstituted or substituted aryl, or unsubstituted or substituted heteroaryl;

ring A is a monocyclic carbocycle, monocyclic heterocycle, or bicyclic heterocycle;

each $R^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

$L^1$ is —$X^1$-$L^2$-, or -$L^2$-$X^1$—;

$X^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

$L^2$ is absent or substituted or unsubstituted $C_1$-$C_4$alkylene;

ring C is monocyclic carbocycle, bicyclic carbocycle, monocyclic heterocycle, or bicyclic heterocycle;

each $R^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;

ring B is a monocyclic carbocycle, bicyclic carbocycle, monocyclic heterocycle or bicyclic heterocycle;

each $R^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

$R^5$ and $R^7$ are each independently selected from H, D, $C_1$-$C_4$alkyl and $C_3$-$C_6$cycloalkyl;

or $R^5$ and $R^7$ are taken together with the intervening atoms to form a double bond;

or $R^5$ and $R^7$ are taken together with the intervening atoms to form an epoxide or a substituted or unsubstituted $C_3$-$C_6$cycloalkyl;

$R^6$ and $R^8$ are each independently selected from H, D, $C_1$-$C_4$alkyl or $C_3$-$C_6$cycloalkyl;

Y is —CH$_2$OR$^9$, —C(=O)OR$^9$, —CH$_2$C(=O)OR$^9$,

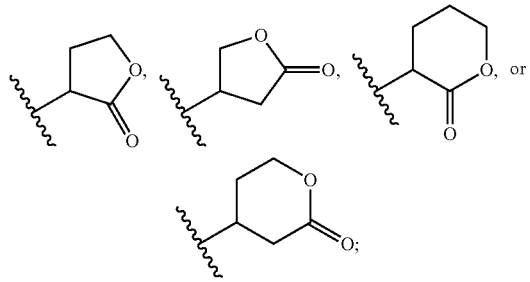

each $R^9$ is independently selected from H, substituted or unsubstituted $C_2$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted phenyl, and substituted or substituted or unsubstituted heterocycle;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4.

In some embodiments, ring B is a monocyclic carbocycle or monocyclic heterocycle wherein the groups

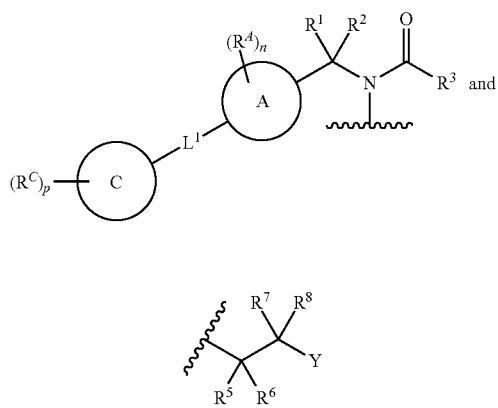

are in a 1,3-relationship on ring B.

In some embodiments, ring B is a monocyclic carbocycle or monocyclic heterocycle wherein the groups

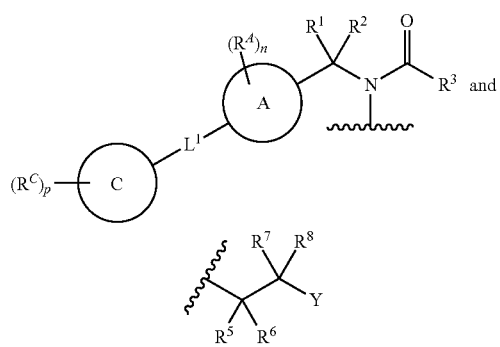

are in a 1,4-relationship on ring B.

In some embodiments, ring B is phenyl.

In some embodiments, ring B is monocyclic heteroaryl.

In some embodiments, ring B is monocyclic 6-membered heteroaryl selected from pyridinyl, pyrimidinyl, pyrazinyl, and pyridazinyl.

In some embodiments,

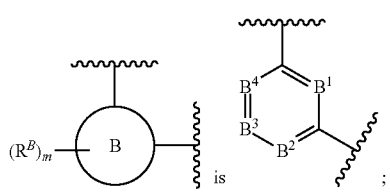

$B^1$ is $CR^B$ or N; $B^2$ is $CR^B$ or N; $B^3$ is $CR^B$ or N; $B^4$ is $CR^B$ or N.

In some embodiments, $B^1$ is $CR^B$; $B^2$ is $CR^B$; $B^3$ is $CR^B$; $B^4$ is $CR^B$.

In some embodiments, $B^1$ is N; $B^2$ is $CR^B$ or N; $B^3$ is $CR^B$; $B^4$ is $CR^B$.

In some embodiments, $B^1$ is $CR^B$ or N; $B^2$ is $CR^B$; $B^3$ is $CR^B$ or N; $B^4$ is $CR^B$.

In some embodiments, $B^1$ is $CR^B$ or N; $B^2$ is $CR^B$; $B^3$ is $CR^B$; $B^4$ is $CR^B$ or N.

In some embodiments, $B^1$ is $CR^B$ or N; $B^2$ is N; $B^3$ is $CR^B$; $B^4$ is $CR^B$ or N.

In some embodiments,

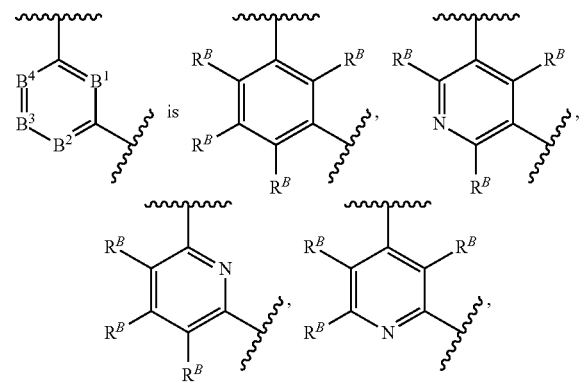

In some embodiments, ring A is a monocyclic carbocycle.

In some embodiments, ring A is monocyclic carbocycle that is phenyl or a $C_3$-$C_8$cycloalkyl.

In some embodiments, ring A is phenyl.

In some embodiments,

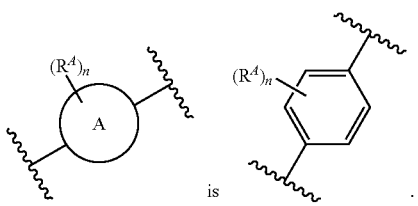

In some embodiments, the compound has the following structure:

Formula (VII)

In some embodiments, ring A is $C_3$-$C_8$cycloalkyl that is selected from cyclopropyl, cyclobutyl, cyclopentyl, cyclohexyl, cycloheptyl, and cyclooctyl.

In some embodiments, ring A is

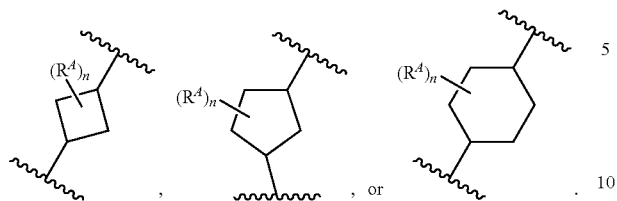

In some embodiments, ring A is a monocyclic heterocycle.

In some embodiments, ring A is a monocyclic heterocycle that is a monocyclic $C_1$-$C_5$heteroarylene containing 1-4 N atoms, and 0 or 1 O or S atom.

In some embodiments, ring A is a monocyclic heterocycle that is a monocyclic $C_1$-$C_5$heteroarylene containing 0-4 N atoms, and 1 O or S atom.

In some embodiments, ring A is a monocyclic heterocycle that is a monocyclic 6-membered heteroarylene selected from pyridinylene, pyrimidinylene, pyrazinylene, or pyridazinylene.

In some embodiments,

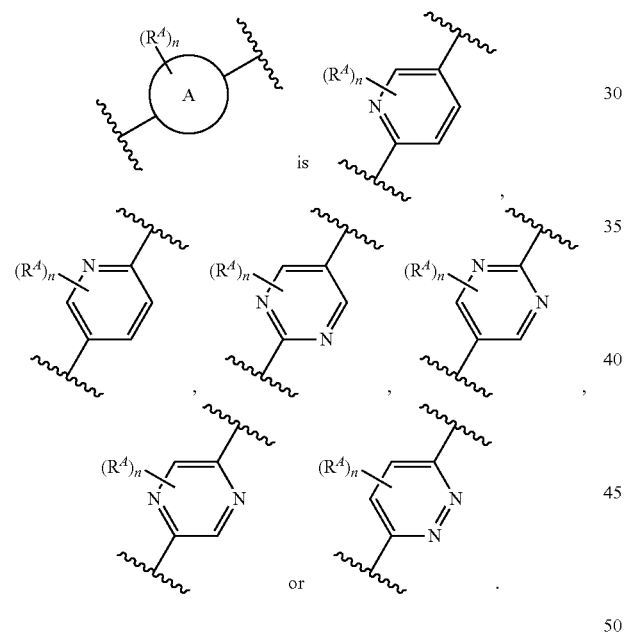

In some embodiments, ring A is a monocyclic heterocycle that is a monocyclic 5-membered heteroarylene selected from furanylene, thienylene, pyrrolylene, oxazolylene, thiazolylene, imidazolylene, pyrazolylene, triazolylene, tetrazolylene, isoxazolylene, isothiazolylene, oxadiazolylene, and thiadiazolylene.

In some embodiments,

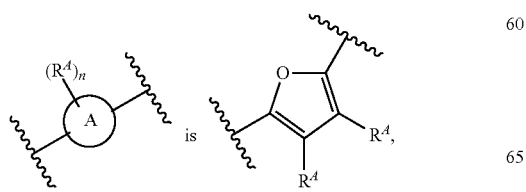

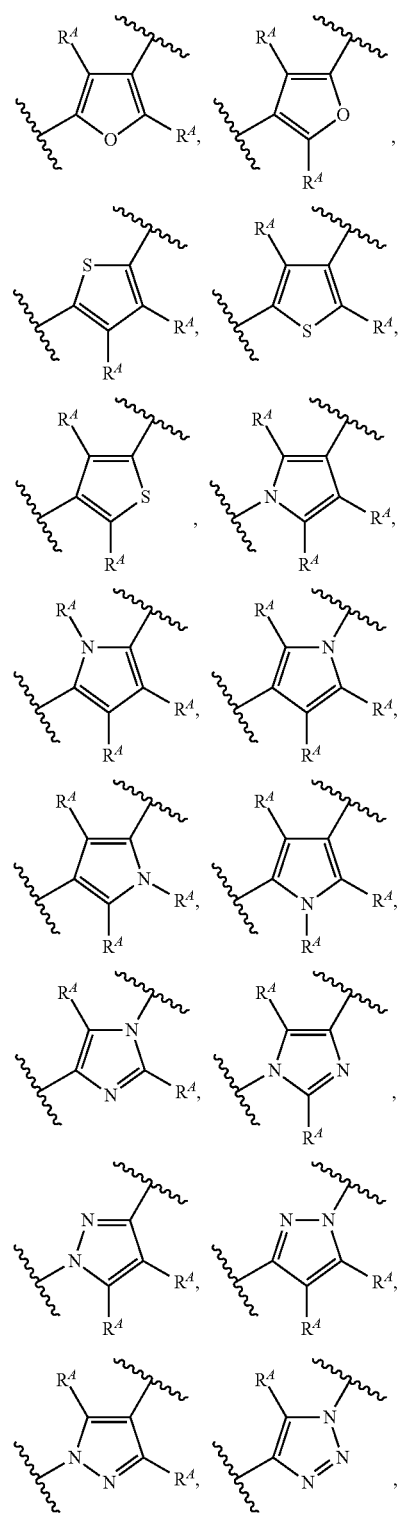

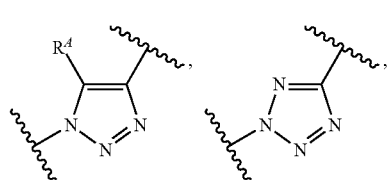

-continued

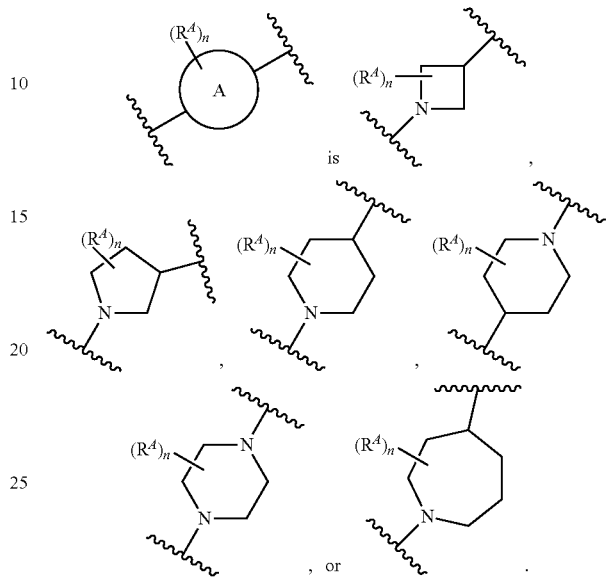

In some embodiments, L¹ is —X¹-L²-, -L²-X¹—; X¹ is absent, —O—, —S—, —S(=O)—, —S(=O)₂—, —S(=O)₂NR¹⁰—, —CH₂—, —CH=CH—, —C≡C—, —C(=O)—, —C(=O)O—, —OC(=O)—, —C(=O)NR¹⁰—, —NR¹⁰C(=O)—, —NR¹⁰S(=O)₂—, or —NR¹⁰—; L² is absent or —CH₂—.

In some embodiments, L¹ is absent, —O—, —S—, —S—CH₂—, —CH₂—S—, —CH₂—, —CH=CH—, —C≡C—, —NR¹⁰—, —NR¹⁰—CH₂—, or —CH₂—NR¹⁰—.

In some embodiments, L¹ is absent, —O—, —S—, —CH=CH—, —C≡C—, or —NR¹⁰—.

In some embodiments, L¹ is absent, —O—, —S—, or —NR¹⁰—.

In some embodiments, L¹ is absent.

In some embodiments, ring A is a monocyclic heterocycle that is a monocyclic C₂-C₈heterocycloalkyl containing at least 1 N atom in the ring.

In some embodiments, ring A is a monocyclic heterocycle that is a monocyclic C₂-C₈heterocycloalkyl containing at least 1 N atom in the ring that is selected from aziridinyl, azetidinyl, pyrrolidinyl, piperidinyl, piperazinyl, or azepanyl.

In some embodiments,

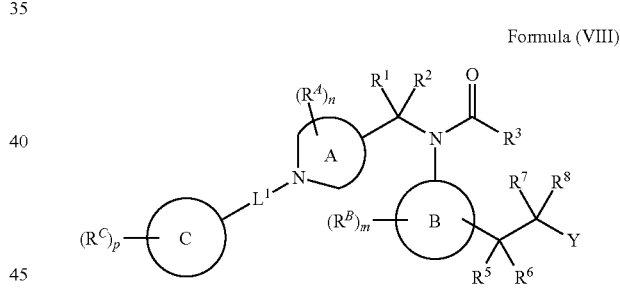

is

In some embodiments, the compound of Formula (VI) has the structure of Formula (VIII), or a pharmaceutically acceptable salt or solvate thereof:

Formula (VIII)

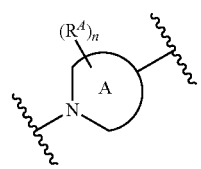

wherein, ring A is a monocyclic heterocycle containing 1-4 N atoms or a bicyclic heterocycle containing 1-4 N atoms.

In some embodiments, ring A is a monocyclic heterocycle that is a monocyclic 5-membered C₁-C₄heteroarylene containing 1-4 N atoms.

In some embodiments, is a monocyclic 5-membered C₁-C₄heteroarylene containing 1-4 N atoms that has the structure

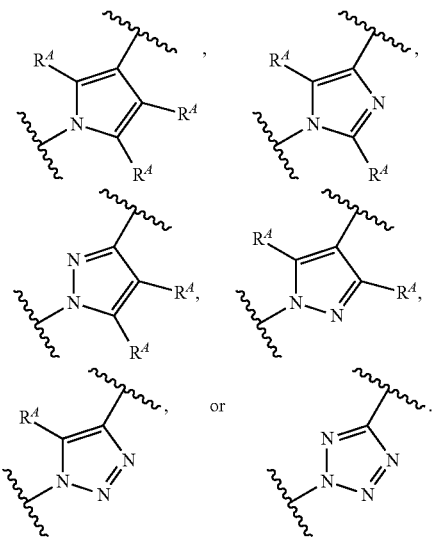

In some embodiments, ring A is a monocyclic heterocycle that is a monocyclic $C_2$-$C_8$heterocycloalkyl containing at least 1 N atom in the ring that is selected from aziridinyl, azetidinyl, pyrrolidinyl, piperidinyl, piperazinyl, or azepanyl.

In some embodiments,

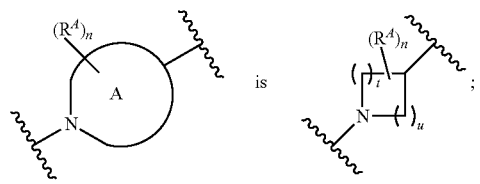

wherein, t is 1, 2, or 3; u is 1, 2, or 3.

In some embodiments,

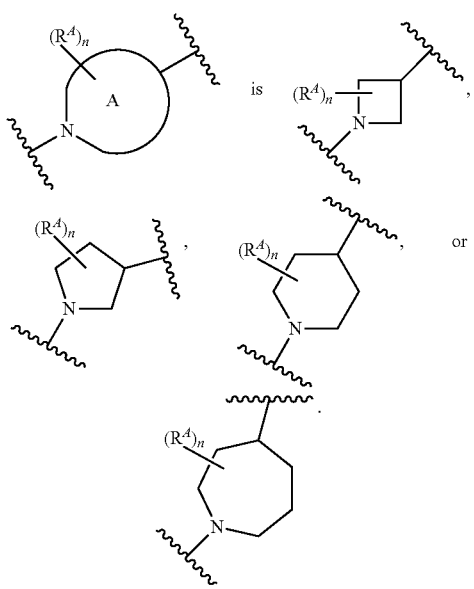

In some embodiments,

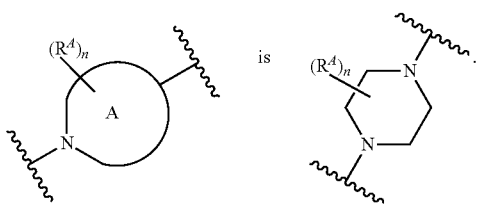

In some embodiments, ring A is a monocyclic heterocycle containing 1-4 N atoms or a bicyclic heterocycle containing 1-4 N atoms that is selected from a β-lactam, γ-lactam, δ-lactam or ε-lactam.

In some embodiments, ring A is a bicyclic $C_5$-$C_8$heterocycloalkyl that is a fused bicyclic $C_5$-$C_8$heterocycloalkyl, bridged bicyclic $C_5$-$C_8$heterocycloalkyl, or spiro bicyclic $C_5$-$C_8$heterocycloalkyl.

In some embodiments,

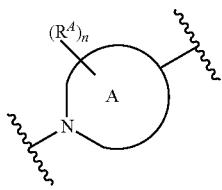

is a bridged bicyclic $C_5$-$C_8$heterocycloalkyl that is

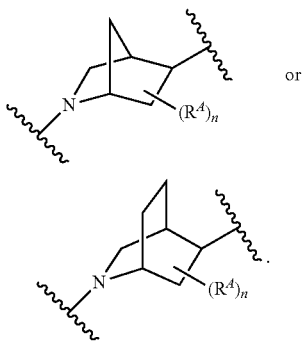

In some embodiments,

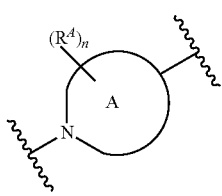

is spiro bicyclic $C_5$-$C_8$heterocycloalkyl that is

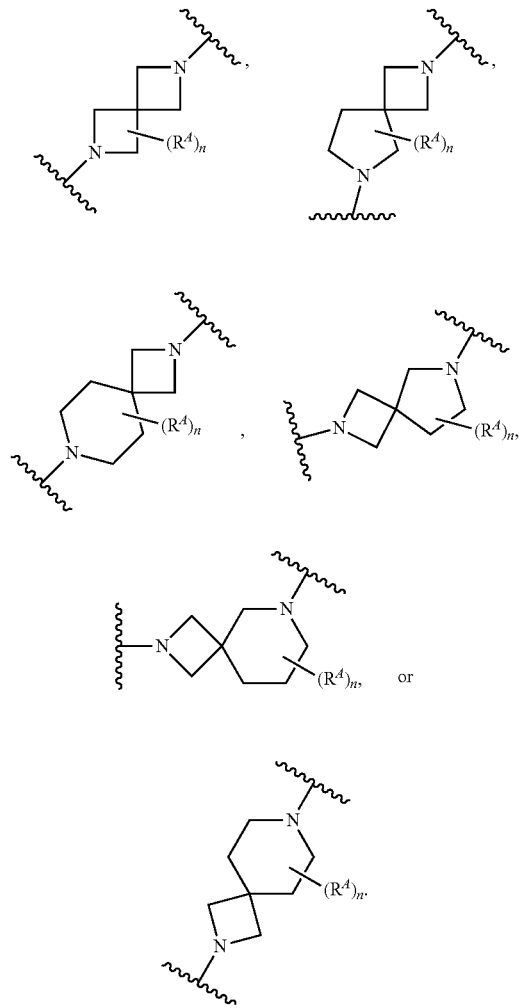

In some embodiments, L$^1$ is —X$^1$-L$^2$-, -L$^2$-X$^1$—; X$^1$ is absent, —S(=O)—, —S(=O)$_2$—, —CH$_2$—, —C(=O)—, —OC(=O)—, —NR$^{10}$C(=O)—, or —NR$^{10}$S(=O)$_2$—; L$^2$ is absent or substituted or unsubstituted C$_1$-C$_4$alkylene.

In some embodiments, L$^1$ is —X$^1$-L$^2$-, -L$^2$-X$^1$—; X$^1$ is absent, —S(=O)$_2$—, —CH$_2$—, or —C(=O)—; L$^2$ is absent or —CH$_2$—.

In some embodiments, ring C is monocyclic carbocycle, or bicyclic carbocycle.

In some embodiments, ring C is monocyclic carbocycle selected from cyclopropyl, cyclobutyl, cyclopentyl, cyclohexyl, and phenyl.

In some embodiments, ring C is phenyl.

In some embodiments, ring C is bicyclic carbocycle selected from indanyl, indenyl, and naphthyl.

In some embodiments, ring C is monocyclic heterocycle, or bicyclic heterocycle.

In some embodiments, ring C is a monocyclic heteroaryl selected from furanyl, thienyl, pyrrolyl, oxazolyl, thiazolyl, imidazolyl, pyrazolyl, triazolylene, tetrazolyl, isoxazolyl, isothiazolyl, oxadiazolyl, thiadiazolyl, pyridinyl, pyrimidinyl, pyrazinyl, pyridazinyl, and triazinyl.

In some embodiments,

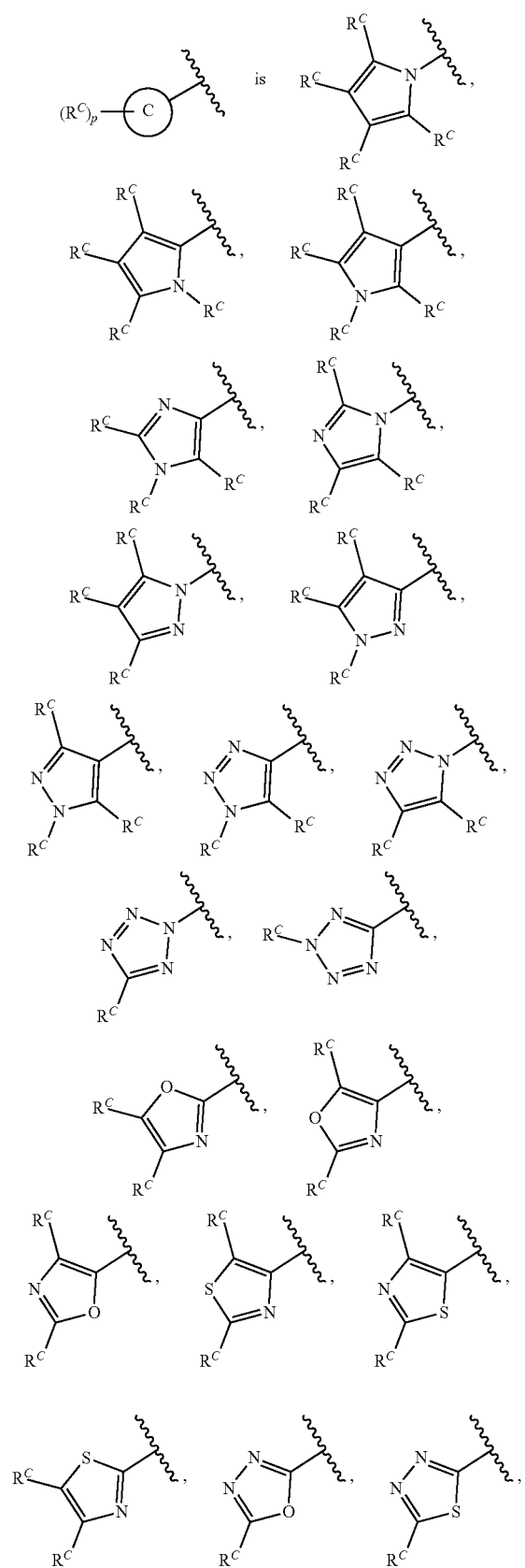

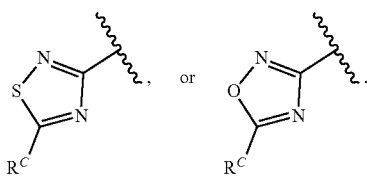

In some embodiments, ring C is a bicyclic heteroaryl selected from quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments,

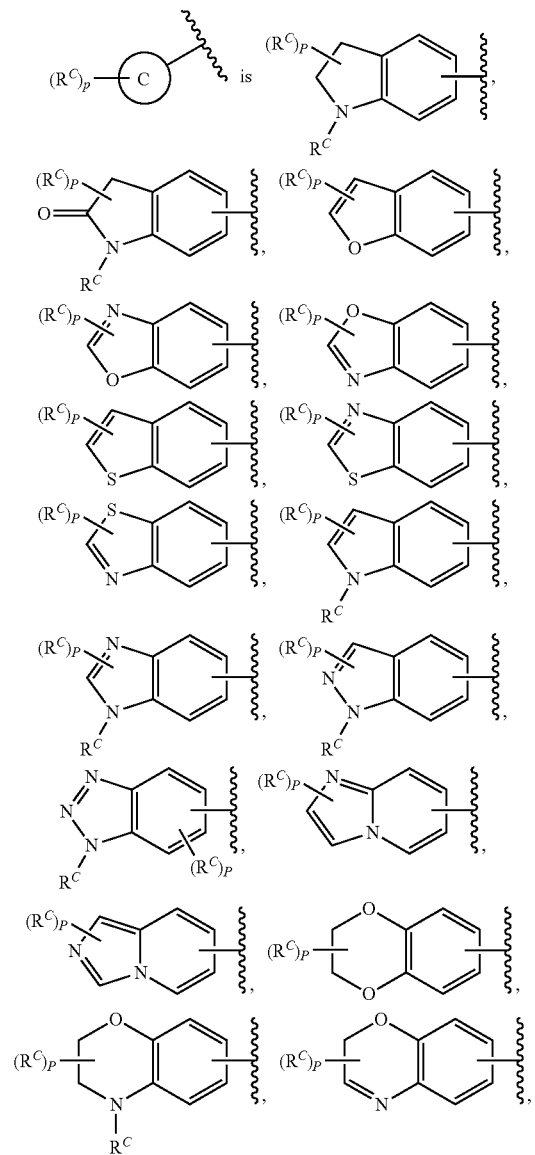

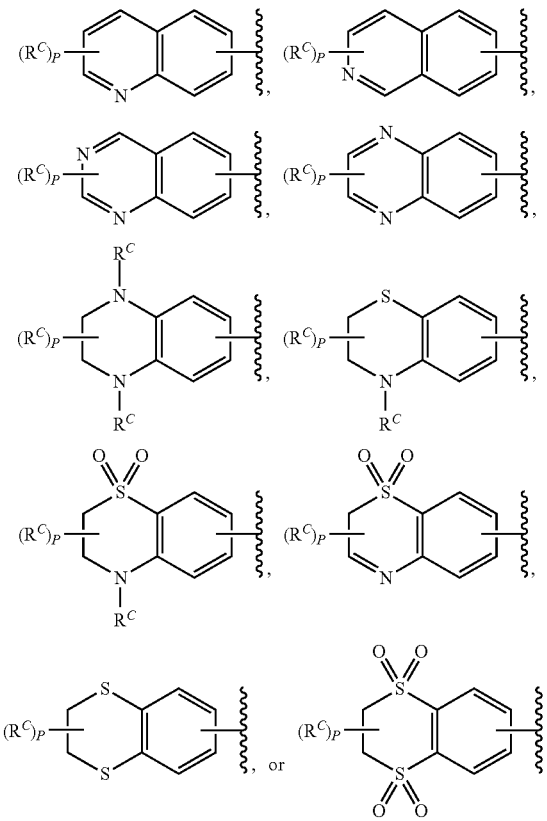

In some embodiments,

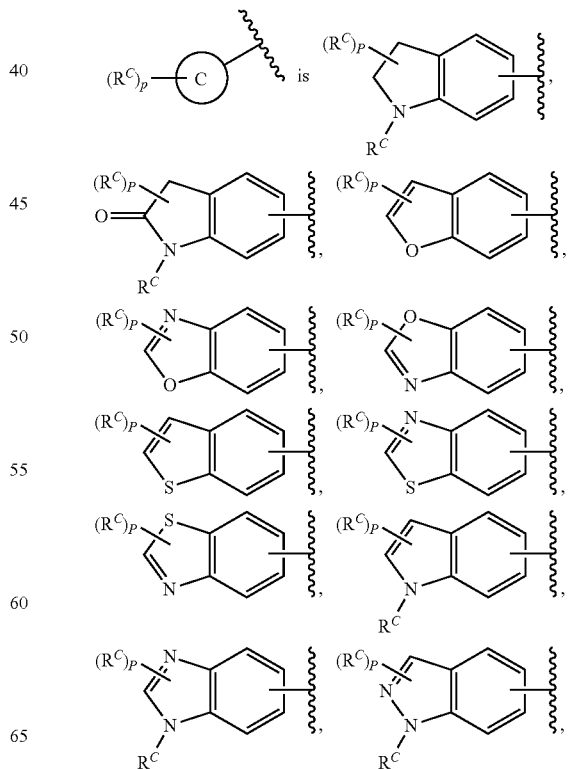

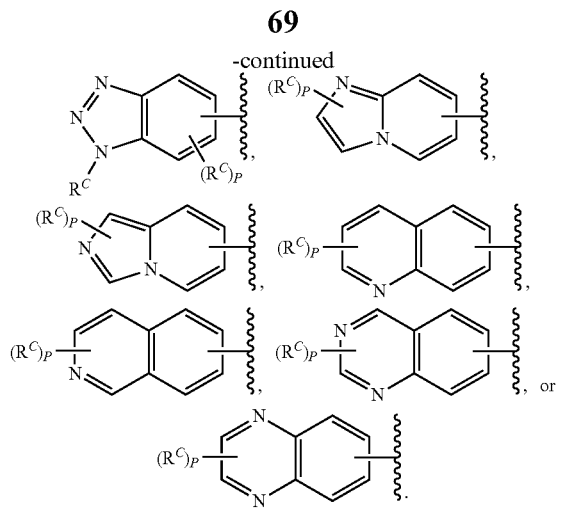

In some embodiments, ring C is monocyclic heteroaryl selected from furanyl, thienyl, pyridinyl, pyrazolyl, pyrrolyl, imidazolyl, oxazolyl, isoxazolyl, thiazolyl, isothiazolyl, triazolyl, pyrimidinyl, pyrazinyl, and triazinyl.

In some embodiments, ring C is a monocyclic 6-membered heteroaryl containing 1-3 N atoms.

In some embodiments,

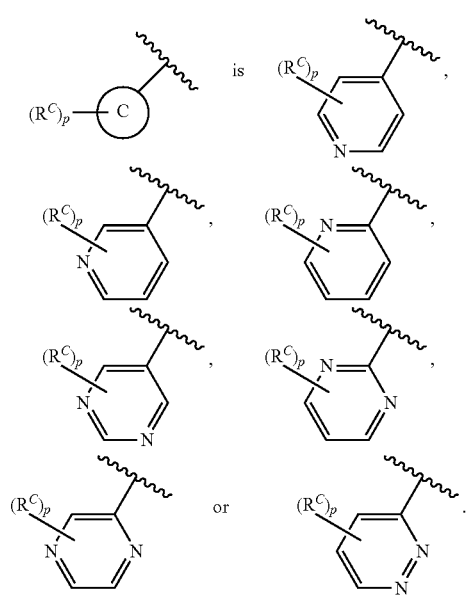

In some embodiments, ring C is a monocyclic 5-membered $C_1$-$C_4$ heteroaryl.

In some embodiments, ring C is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

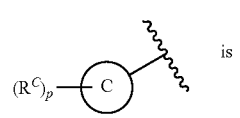

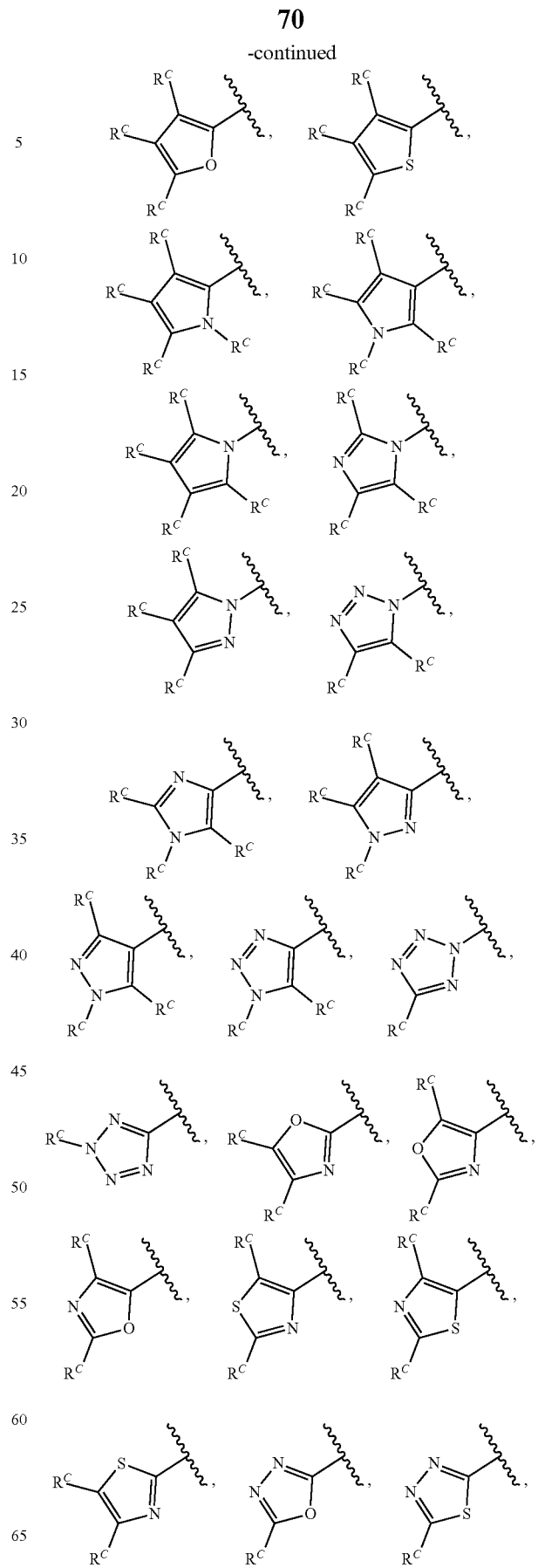

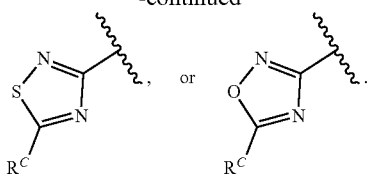

In some embodiments, ring C is monocyclic heterocycle selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, and 1,2,3,6-tetrahydropyridinyl.

In some embodiments, ring C is a monocyclic $C_2$-$C_8$heterocycloalkyl containing at least 1 N atom in the ring.

In some embodiments, ring C is a monocyclic $C_2$-$C_8$heterocycloalkyl containing at least 1 N atom in the ring that is selected from aziridinyl, azetidinyl, pyrrolidinyl, morpholinyl, thiomorpholinyl, piperidinyl, piperazinyl, or azepanyl.

In some embodiments,

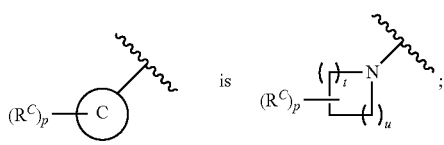

wherein, t is 1, 2, or 3; u is 1, 2, or 3.

In some embodiments,

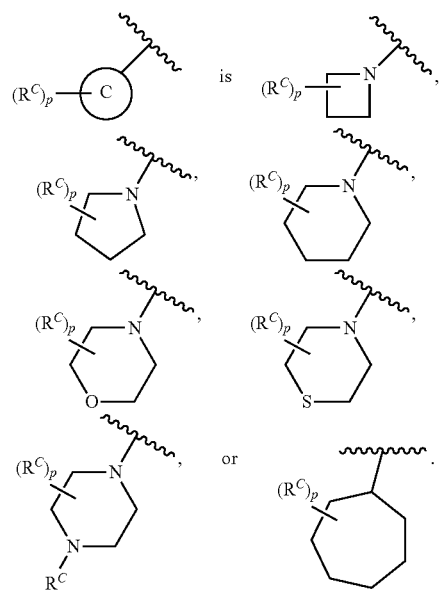

In some embodiments, ring C is a $C_2$-$C_8$heterocycloalkyl containing 1 N atom in the ring that is selected from a β-lactam, γ-lactam, δ-lactam or ε-lactam.

In some embodiments, ring C is a bicyclic $C_5$-$C_8$heterocycloalkyl that is a fused bicyclic $C_5$-$C_8$heterocycloalkyl, bridged bicyclic $C_5$-$C_8$heterocycloalkyl, or spiro bicyclic $C_5$-$C_8$heterocycloalkyl.

In some embodiments,

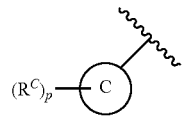

is a bridged bicyclic $C_5$-$C_8$heterocycloalkyl that is

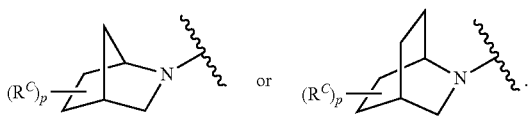

In some embodiments,

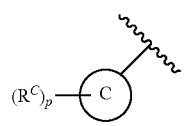

is spiro bicyclic $C_5$-$C_8$heterocycloalkyl that is

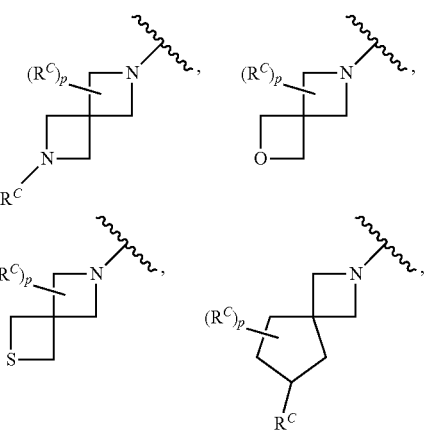

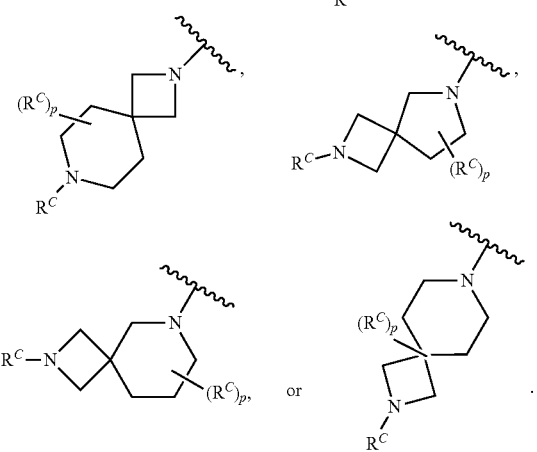

In some embodiments, R³ is selected from substituted or unsubstituted C₁-C₁₀alkyl, substituted or unsubstituted C₃-C₁₀cycloalkyl, or substituted or unsubstituted aryl, wherein if R³ is substituted then R³ is substituted with one or more R¹² groups.

In some embodiments, R³ is selected from substituted or unsubstituted C₃-C₁₀cycloalkyl, or substituted or unsubstituted phenyl, wherein if R³ is substituted then R³ is substituted with one or more R¹² groups.

In some embodiments, R³ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

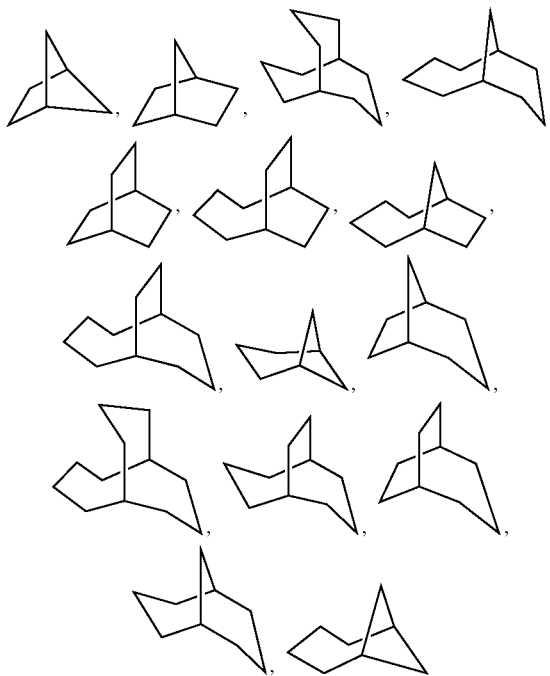

and adamantyl. In some embodiments, R³ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl. In some embodiments, R³ is selected from iso-propyl, iso-butyl, tert-butyl, tert-pentyl, neopentyl, isopentyl, sec-pentyl, 3-pentyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl. In some embodiments, R³ is selected from iso-propyl, iso-butyl, tert-butyl, tert-pentyl, neopentyl, isopentyl, sec-pentyl, 3-pentyl, isohexyl, 3-methylpentyl, 2,3-dimethylbutyl, neohexyl, substituted or unsubstituted cyclohexyl. In some embodiments, R³ is substituted or unsubstituted cyclohexyl.

In some embodiments, R³ is selected from methyl, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

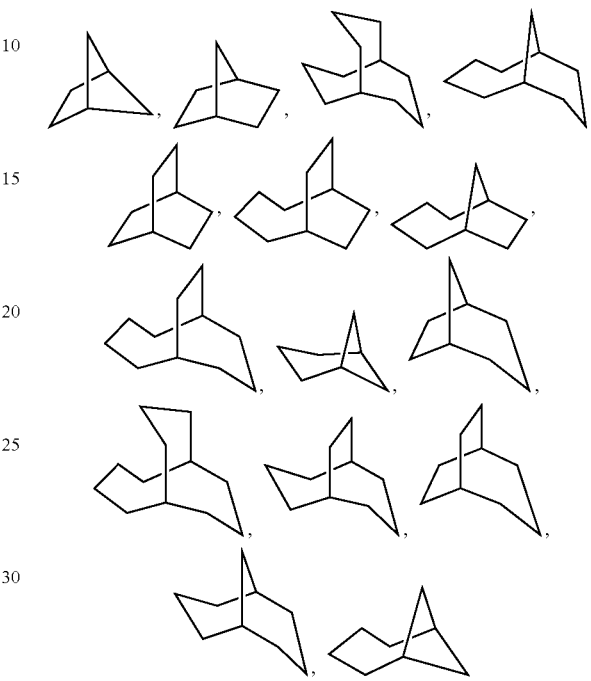

and adamantyl.

In some embodiments, R³ is selected from methyl, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, substituted or unsubstituted cyclohexyl, substituted or unsubstituted phenyl. In some embodiments, R³ is selected iso-propyl, iso-butyl, tert-butyl, substituted or unsubstituted cyclopropyl, substituted or unsubstituted cyclobutyl, substituted or unsubstituted cyclopentyl, substituted or unsubstituted cyclohexyl, substituted or unsubstituted phenyl.

In some embodiments, R⁵ and R⁷ are taken together with the intervening atoms to form a double bond; Y is —CH₂OR⁹, or —C(=O)OR⁹.

In some embodiments, R⁵ and R⁷ are taken together with the intervening atoms to form a double bond; Y is —C(=O)OR⁹.

In some embodiments, R⁹ is selected from H, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, or substituted or unsubstituted cyclohexyl.

In some embodiments, R⁹ is selected from ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, or substituted or unsubstituted cyclohexyl.

In some embodiments, R⁹ is selected from ethyl, propyl, iso-propyl, n-butyl, iso-butyl, or tert-butyl.

In some embodiments, R⁹ is selected from H, substituted or unsubstituted C₁-C₆alkyl, substituted or unsubstituted C₁-C₆heteroalkyl, substituted or unsubstituted $C_3$-$C_6$cycloalkyl, substituted or unsubstituted phenyl, or substituted or substituted or unsubstituted heterocycle. In some embodiments, $R^9$ is selected from substituted or unsubstituted $C_1$-$C_6$alkyl, or substituted or unsubstituted $C_1$-$C_6$heteroalkyl. In some embodiments, $R^9$ is substituted or unsubstituted $C_1$-$C_6$alkyl.

In some embodiments, $R^9$ is substituted or unsubstituted $C_1$-$C_6$heteroalkyl. In some embodiments, $R^9$ is selected from substituted or unsubstituted $C_3$-$C_6$cycloalkyl, substituted or unsubstituted phenyl, or substituted or substituted or unsubstituted heterocycle. In some embodiments, $R^9$ is substituted or substituted or unsubstituted heterocycle. In some embodiments, $R^9$ is selected from H, $C_2$-$C_6$alkenyl, and $C_3$-$C_6$cycloalkyl.

In some embodiments, $R^9$ is methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, or neohexyl. In some embodiments, $R^9$ is ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, or neohexyl.

Any combination of the groups described above for the various variables is contemplated herein. Throughout the specification, groups and substituents thereof are chosen by one skilled in the field to provide stable moieties and compounds.

In some embodiments, compounds described herein include, but are not limited to, those described in Table 1 and Table 2.

TABLE 1

| Cmpd | Structure | Name |
| --- | --- | --- |
| 1 | 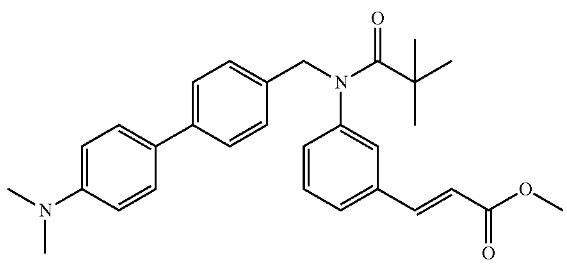 | (E)-Methyl 3-(3-(N-((4'-(dimethylamino)-[1,1'-biphenyl]-4-yl)methyl)pivalamido)phenyl)acrylate |
| 2 | 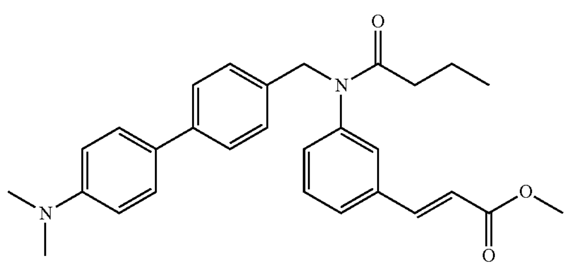 | (E)-Methyl 3-(3-(N-((4'-(dimethylamino)-[1,1'-biphenyl]-4-yl)methyl)butyramido)phenyl)acrylate |
| 3 | 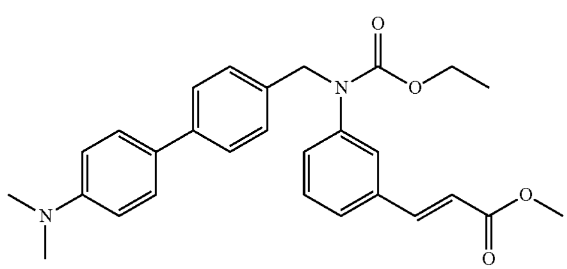 | (E)-Methyl 3-(3-(((4'-(dimethylamino)-[1,1'-biphenyl]-4-yl)methyl)(ethoxycarbonyl)amino)phenyl)acrylate |
| 4 | 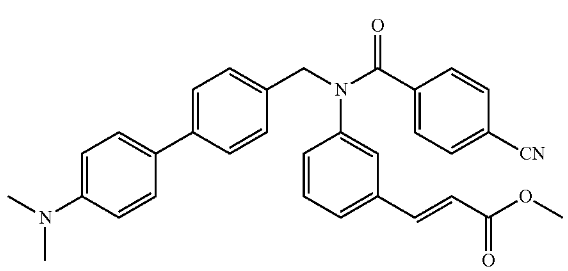 | (E)-Methyl 3-(3-(4-cyano-N-((4'-(dimethylamino)-[1,1'-biphenyl]-4-yl)methyl)benzamido)phenyl)acrylate |

TABLE 1-continued

| Cmpd | Structure | Name |
|---|---|---|
| 5 | 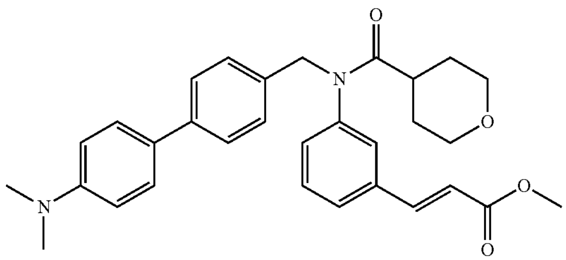 | (E)-Methyl 3-(3-(N-((4'-(dimethylamino)-[1,1'-biphenyl]-4-yl)methyl)tetrahydro-2H-pyran-4-carboxamido)phenyl)acrylate |
| 6 | 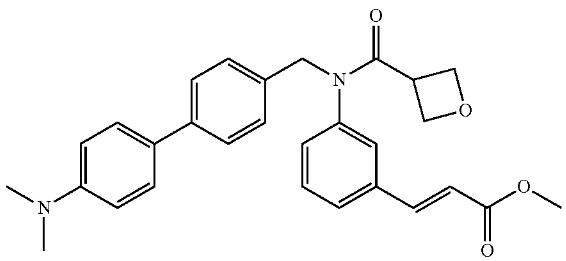 | (E)-Methyl 3-(3-(N-((4'-(dimethylamino)-[1,1'-biphenyl]-4-yl)methyl)oxetane-3-carboxamido)phenyl)acrylate |
| 7 | 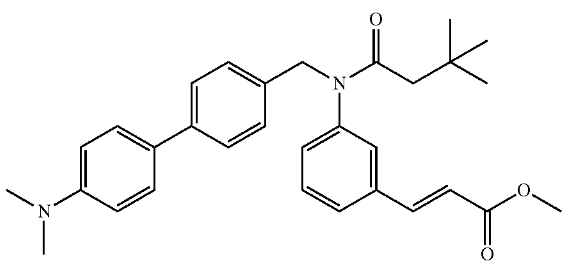 | (E)-Methyl 3-(3-(N-((4'-(dimethylamino)-[1,1'-biphenyl]-4-yl)methyl)-3,3-dimethylbutanamido)phenyl)acrylate |
| 8 | 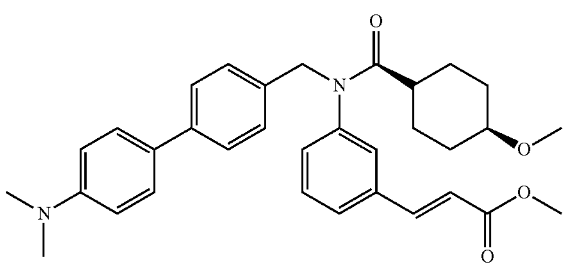 | (E)-Methyl 3-(3-((1r,4r)-N-((4'-(dimethylamino)-[1,1'-biphenyl]-4-yl)methyl)-4-methoxycyclohexanecarboxamido)phenyl)acrylate |
| 9 | 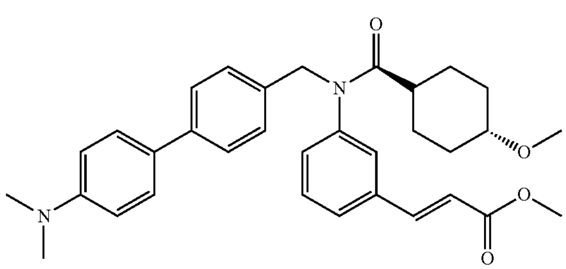 | (E)-Methyl 3-(3-((1s,4s)-N-((4'-(dimethylamino)-[1,1'-biphenyl]-4-yl)methyl)-4-methoxycyclohexanecarboxamido)phenyl)acrylate |
| 10 | 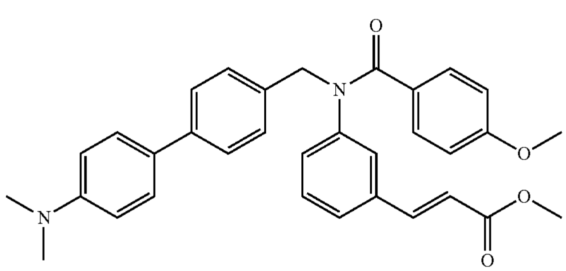 | (E)-Methyl 3-(3-(N-((4'-(dimethylamino)-[1,1'-biphenyl]-4-yl)methyl)-4-methoxybenzamido)phenyl)acrylate |

TABLE 1-continued

| Cmpd | Structure | Name |
| --- | --- | --- |
| 11 | 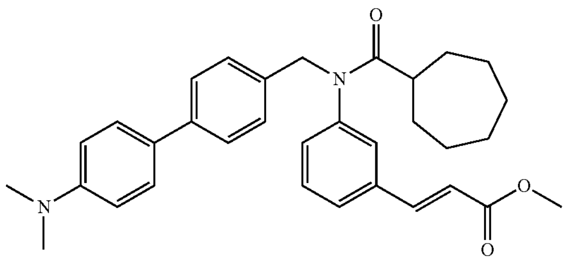 | (E)-Methyl 3-(3-(N-((4'-(dimethylamino)-[1,1'-biphenyl]-4-yl)methyl)cycloheptanecarboxamido)phenyl)acrylate |
| 12 | 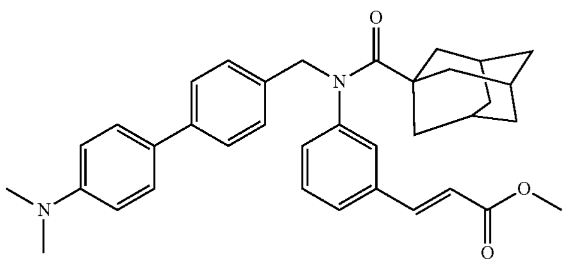 | (E)-Methyl 3-(3-(-N-((4'-(dimethylamino)-[1,1'-biphenyl]-4-yl)methyl)adamantane-1-carboxamido)phenyl)acrylate |
| 13 | 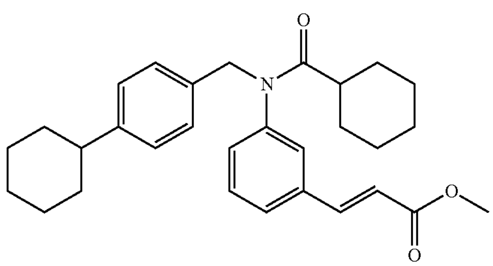 [SMILES: COC(=O)/C=C/c1cccc(N(Cc2ccc(C3CCCCC3)cc2)C(=O)C2CCCCC2)c1] | (E)-methyl 3-(3-(N-(4-cyclohexylbenzyl)cyclohexanecarboxamido)phenyl)acrylate |
| 13.1 | 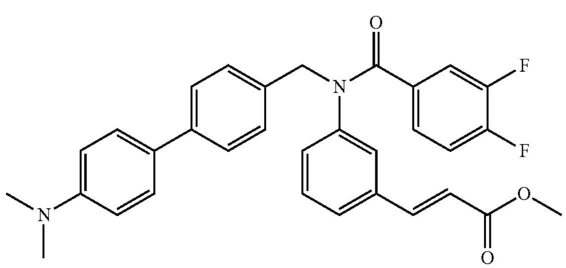 | (E)-Methyl 3-(3-(N-((4'-(dimethylamino)-[1,1'-biphenyl]-4-yl)methyl)-3,4-difluorobenzamido)phenyl)acrylate |
| 13.2 | 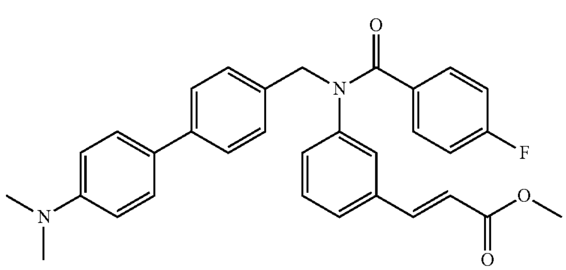 | (E)-Methyl 3-(3-(N-((4'-(dimethylamino)-[1,1'-biphenyl]-4-yl)methyl)-4-fluorobenzamido)phenyl)acrylate |
| 13.3 | 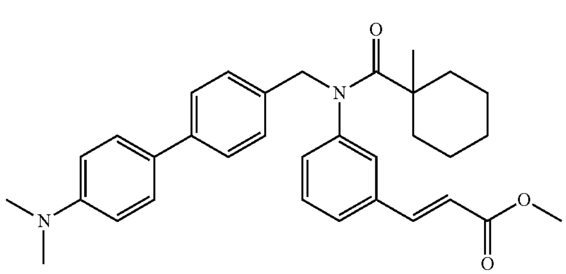 | (E)-Methyl 3-(3-(N-((4'-(dimethylamino)-[1,1'-biphenyl]-4-yl)methyl)-1-methylcyclohexane-carboxamido)phenyl)acrylate |

TABLE 1-continued

| Cmpd | Structure | Name |
| --- | --- | --- |
| 13.4 | 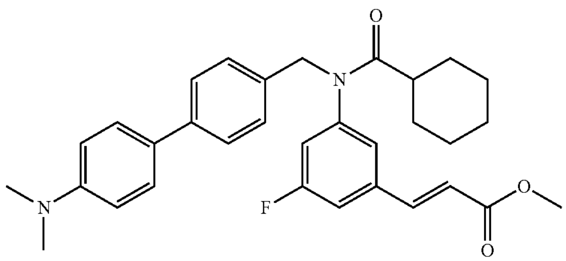 | (E)-Methyl 3-(3-(N-((4'-(dimethylamino)-[1,1'-biphenyl]-4-yl)methyl)cyclohexanecarboxamido)-5-fluorophenyl)acrylate |
| 13.5 | 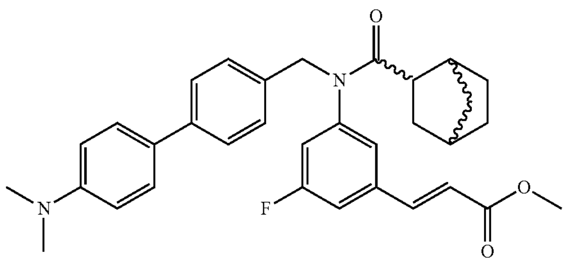 | (E)-Methyl 3-(3-(N-((4'-(dimethylamino)-[1,1'-biphenyl]-4-yl)methyl)bicyclo[2.2.1]heptane-2-carboxamido)-5-fluorophenyl)acrylate |
| 13.6 | 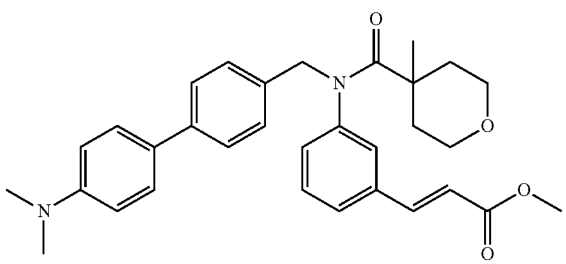 | (E)-Methyl 3-(3-(N-((4'-(dimethylamino)-[1,1'-biphenyl]-4-yl)methyl)-4-methyltetrahydro-2H-pyran-4-carboxamido)phenyl)acrylate |
| 13.7 | 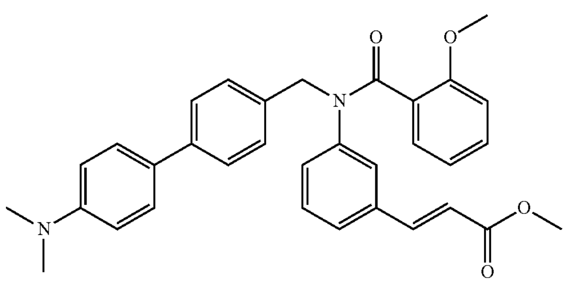 | (E)-Methyl 3-(3-(N-((4'-(dimethylamino)-[1,1'-biphenyl]-4-yl)methyl)-2-methoxybenzamido)phenyl)acrylate |
| 13.8 | 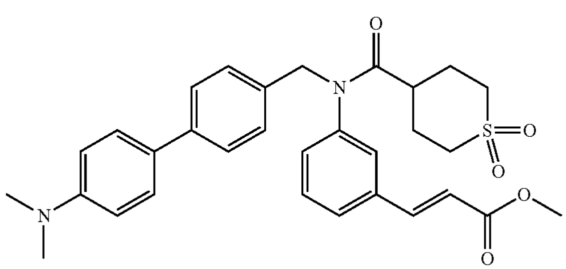 | (E)-Methyl 3-(3-(N-((4'-(dimethylamino)-[1,1'-biphenyl]-4-yl)methyl)-1,1-dioxidotetrahydro-2H-thiopyran-4-carboxamido)phenyl)acrylate |
| 13.9 | 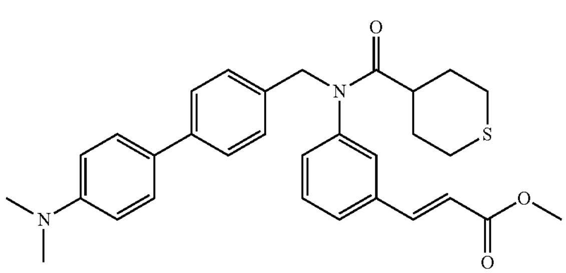 | (E)-Methyl 3-(3-(N-((4'-(dimethylamino)-[1,1'-biphenyl]-4-yl)methyl)tetrahydro-2H-thiopyran-4-carboxamido)phenyl)acrylate |

TABLE 1-continued

| Cmpd | Structure | Name |
| --- | --- | --- |
| 13.10 | 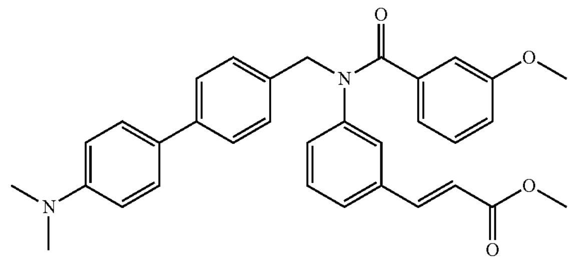 | (E)-Methyl 3-(3-(N-((4'-(dimethylamino)-[1,1'-biphenyl]-4-yl)methyl)-3-methoxybenzamido)phenyl)acrylate |
| 13.11 | 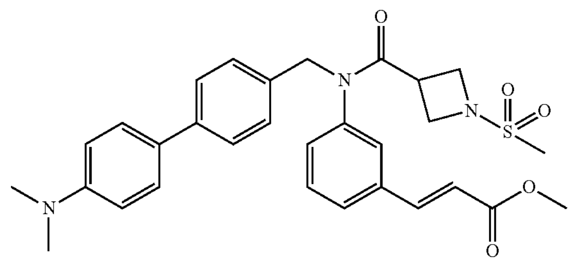 | (E)-Methyl 3-(3-(N-((4'-(dimethylamino)-[1,1'-biphenyl]-4-yl)methyl)-1-(methylsulfonyl)azetidine-3-carboxamido)phenyl)acrylate |
| 13.12 | 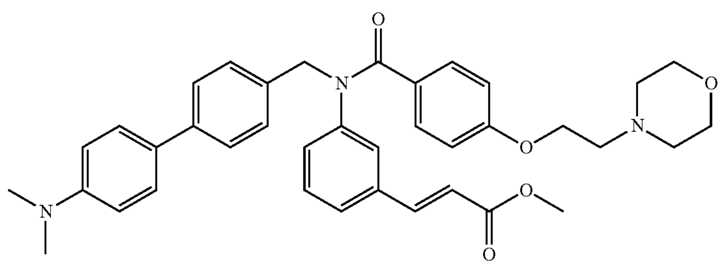 [SMILES: COC(=O)/C=C/c1cccc(N(Cc2ccc(-c3ccc(N(C)C)cc3)cc2)C(=O)c2ccc(OCCN3CCOCC3)cc2)c1] | (E)-Methyl 3-(3-(N-((4'-(dimethylamino)-[1,1'-biphenyl]-4-yl)methyl)-4-(2-morpholinoethoxy)benzamido)phenyl)acrylate |
| 13.13 | 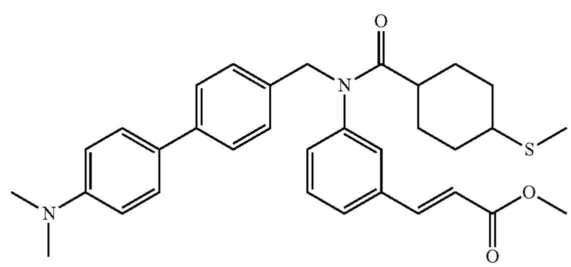 | (E)-Methyl 3-(3-(N-((4'-(dimethylamino)-[1,1'-biphenyl]-4-yl)methyl)-4-(methylthio)cyclohexanecarboxamido)phenyl)acrylate |
| 13.14 | 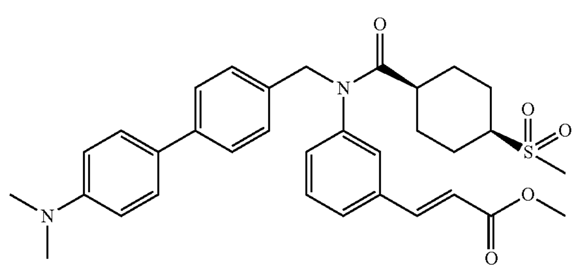 [SMILES: COC(=O)/C=C/c1cccc(N(Cc2ccc(-c3ccc(N(C)C)cc3)cc2)C(=O)[C@H]2CC[C@@H](S(C)(=O)=O)CC2)c1] | cis-(E)-Methyl 3-(3-(N-((4'-(dimethylamino)-[1,1'-biphenyl]-4-yl)methyl)-4-(methylsulfonyl)cyclohexanecarboxamido)phenyl)acrylate |
| 13.15 | 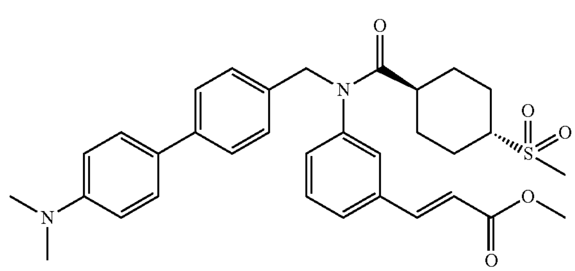 [SMILES: COC(=O)/C=C/c1cccc(N(Cc2ccc(-c3ccc(N(C)C)cc3)cc2)C(=O)[C@H]2CC[C@H](S(C)(=O)=O)CC2)c1] | trans-(E)-methyl 3-(3-(N-((4'-(dimethylamino)-[1,1'-biphenyl]-4-yl)methyl)-4-(methylsulfonyl)cyclohexanecarboxamido)phenyl)acrylate |

TABLE 1-continued

| Cmpd | Structure | Name |
| --- | --- | --- |
| 13.16 | 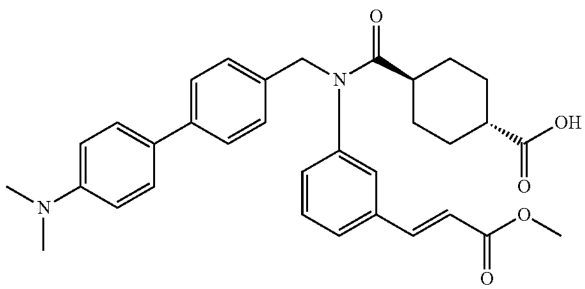 [SMILES: COC(=O)/C=C/c1cccc(N(Cc2ccc(-c3ccc(N(C)C)cc3)cc2)C(=O)[C@H]2CC[C@H](C(=O)O)CC2)c1] | trans-4-(((4'-(Dimethylamino)-[1,1'-biphenyl]-4-yl)methyl)(3-((E)-3-methoxy-3-oxoprop-1-en-1-yl)phenyl)carbamoyl)cyclohexanecarboxylic acid |
| 13.17 | 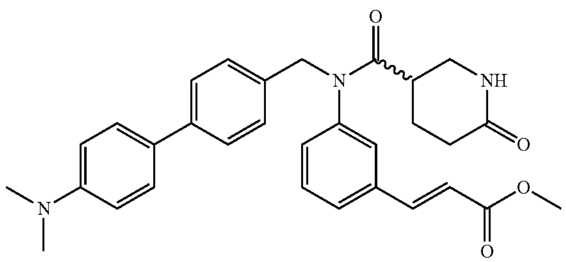 | (E)-Methyl 3-(3-(N-((4'-(dimethylamino)-[1,1'-biphenyl]-4-yl)methyl)-6-oxopiperidine-3-carboxamido)phenyl)acrylate |
| 13.18 | 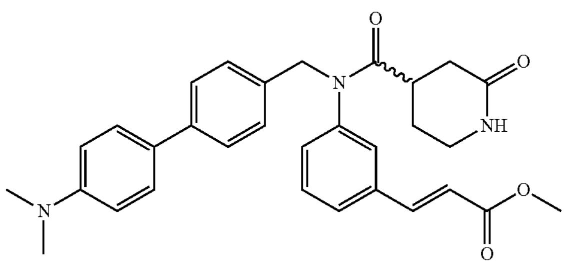 | (E)-Methyl 3-(3-(N-((4'-(dimethylamino)-[1,1'-biphenyl]-4-yl)methyl)-2-oxopiperidine-4-carboxamido)phenyl)acrylate |
| 13.19 | 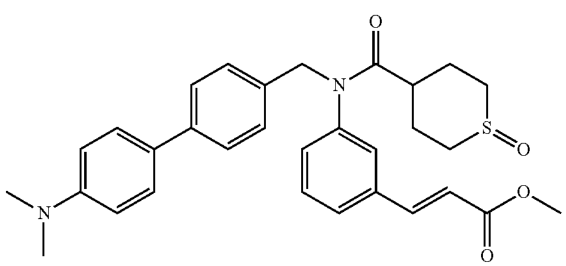 | (E)-Methyl 3-(3-(N-((4'-(dimethylamino)-[1,1'-biphenyl]-4-yl)methyl)-1-oxidotetrahydro-2H-thiopyran-4-carboxamido)phenyl)acrylate |
| 13.20 | 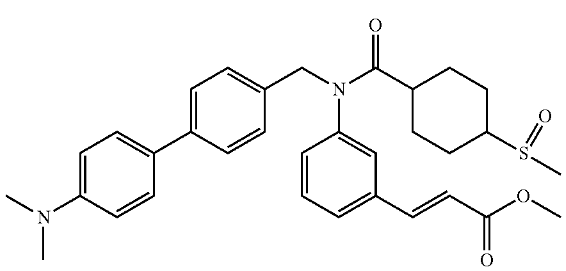 | (E)-Methyl 3-(3-(N-((4'-(dimethylamino)-[1,1'-biphenyl]-4-yl)methyl)-4-(methylsulfinyl)cyclohexanecarboxamido)phenyl)acrylate |
| 13.21 | 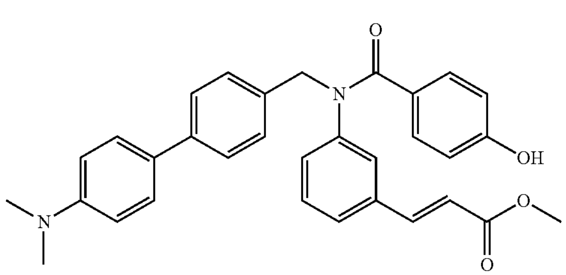 | (E)-Methyl 3-(3-(N-((4'-(dimethylamino)-[1,1'-biphenyl]-4-yl)methyl)-4-hydroxybenzamido)phenyl)acrylate |

TABLE 1-continued

| Cmpd | Structure | Name |
|---|---|---|
| 13.22 | 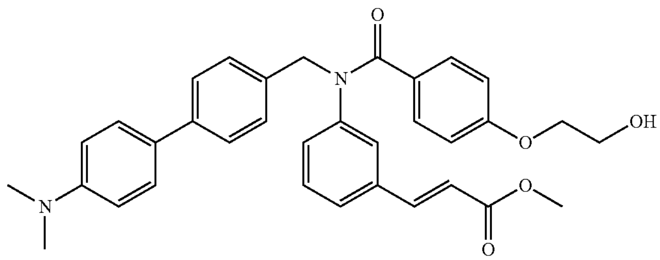 [SMILES: COC(=O)/C=C/c1cccc(N(Cc2ccc(-c3ccc(N(C)C)cc3)cc2)C(=O)c2ccc(OCCO)cc2)c1] | (E)-Methyl 3-(3-(N-((4'-(dimethylamino)-[1,1'-biphenyl]-4-yl)methyl)-4-(2-hydroxyethoxy)benzamido)phenyl)acrylate |
| 13.23 | 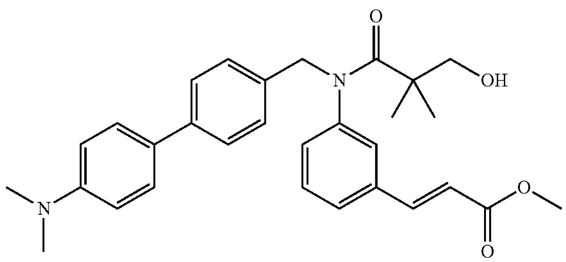 | (E)-Methyl 3-(3-(N-((4'-(dimethylamino)-[1,1'-biphenyl]-4-yl)methyl)-3-hydroxy-2,2-dimethylpropanamido)phenyl)acrylate |
| 13.24 | 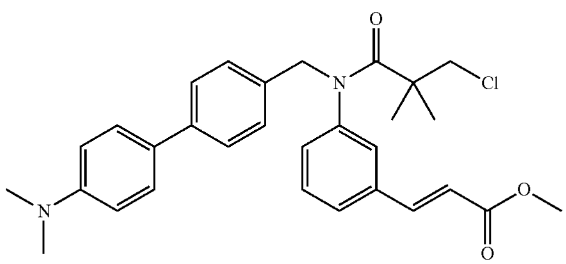 | (E)-Methyl 3-(3-(3-chloro-N-((4'-(dimethylamino)-[1,1'-biphenyl]-4-yl)methyl)-2,2-dimethylpropanamido)phenyl)acrylate |
| 13.25 | 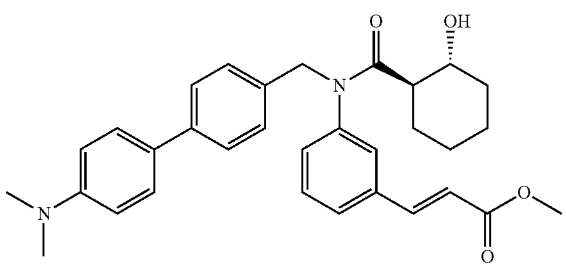 | trans-(E)-Methyl 3-(3-(N-((4'-(dimethylamino)-[1,1'-biphenyl]-4-yl)methyl)-2-hydroxycyclohexanecarboxamido)phenyl)acrylate |
| 13.26 | 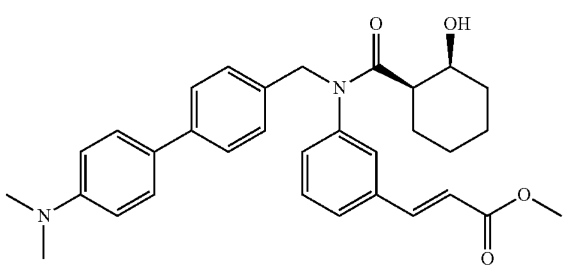 | cis-(E)-Methyl 3-(3-(N-((4'-(dimethylamino)-[1,1'-biphenyl]-4-yl)methyl)-2-hydroxycyclohexanecarboxamido)phenyl)acrylate |
| 13.27 | 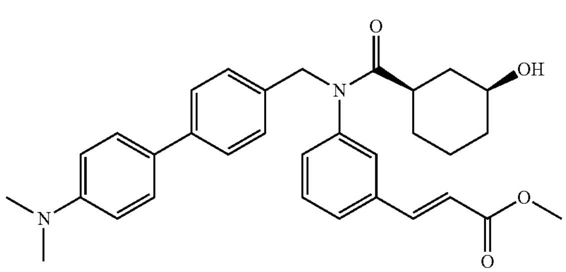 | cis-(E)-Methyl 3-(3-(N-((4'-(dimethylamino)-[1,1'-biphenyl]-4-yl)methyl)-3-hydroxycyclohexanecarboxamido)phenyl)acrylate |

TABLE 1-continued

| Cmpd | Structure | Name |
|---|---|---|
| 13.28 | 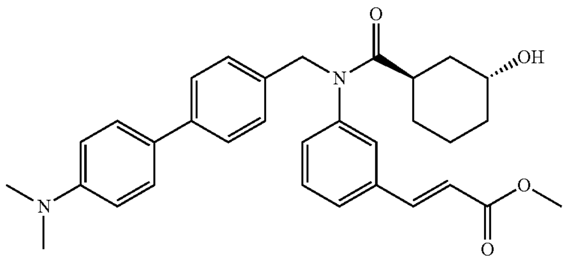 | trans-(E)-Methyl 3-(3-(N-((4'-(dimethylamino)-[1,1'-biphenyl]-4-yl)methyl)-3-hydroxycyclohexanecarboxamido)phenyl)acrylate |
| 14 | 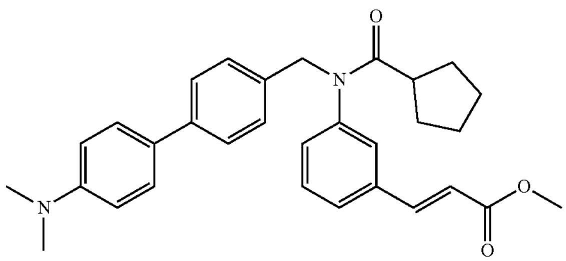 | (E)-Methyl 3-(3-(N-((4'-(dimethylamino)-[1,1'-biphenyl]-4-yl)methyl)cyclopentanecarboxamido)phenyl)acrylate |
| 15 | 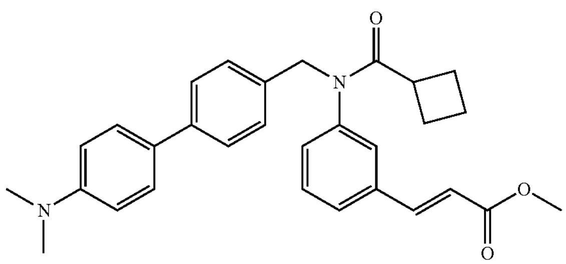 | (E)-Methyl 3-(3-(N-((4'-(dimethylamino)-[1,1'-biphenyl]-4-yl)methyl)cyclobutanecarboxamido)phenyl)acrylate |
| 16 | 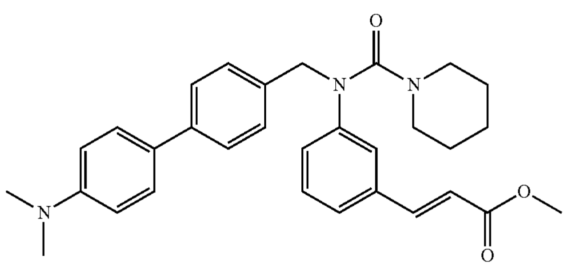 | (E)-Methyl 3-(3-(((4'-(dimethylamino)-[1,1'-biphenyl]-4-yl)methyl)amino)phenyl)acrylate |
| 17 | 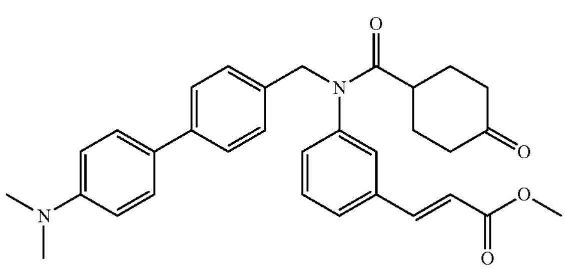 | (E)-Methyl 3-(3-(N-((4'-(dimethylamino)-[1,1'-biphenyl]-4-yl)methyl)-4-oxocyclohexanecarboxamido)phenyl)acrylate |
| 17.1 | 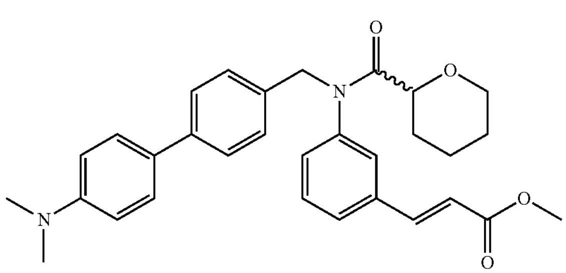 | (E)-Methyl 3-(3-(N-((4'-(dimethylamino)-[1,1'-biphenyl]-4-yl)methyl)tetrahydro-2H-pyran-2-carboxamido)phenyl)acrylate |

TABLE 1-continued

| Cmpd | Structure | Name |
|---|---|---|
| 17.2 | 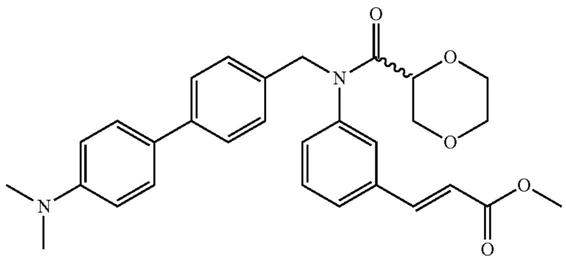 | (E)-Methyl 3-(3-(N-((4'-(dimethylamino)-[1,1'-biphenyl]-4-yl)methyl)-1,4-dioxane-2-carboxamido)phenyl)acrylate |
| 17.3 | 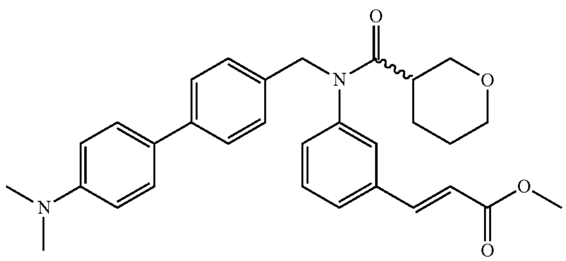 | (E)-Methyl 3-(3-(N-((4'-(dimethylamino)-[1,1'-biphenyl]-4-yl)methyl)tetrahydro-2H-pyran-3-carboxamido)phenyl)acrylate |
| 18 | 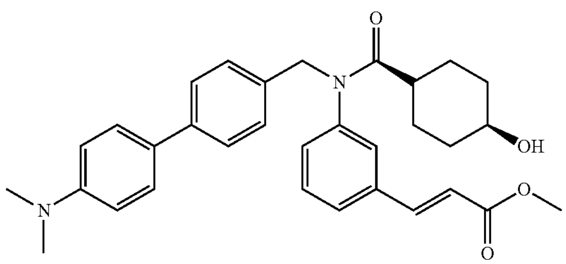 | cis-(E)-Methyl 3-(3-(N-((4'-(dimethylamino)-[1,1'-biphenyl]-4-yl)methyl)-4-hydroxycyclohexanecarboxamido)phenyl)acrylate |
| 19 | 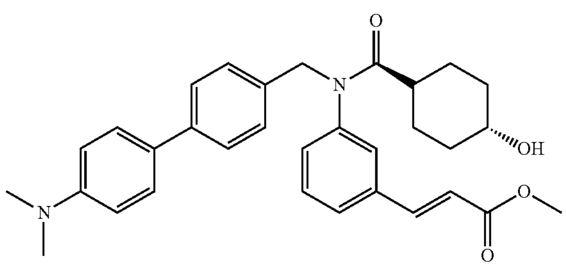 | trans-(E)-Methyl 3-(3-(N-((4'-(dimethylamino)-[1,1'-biphenyl]-4-yl)methyl)-4-hydroxycyclohexanecarboxamido)phenyl)acrylate |
| 20 | 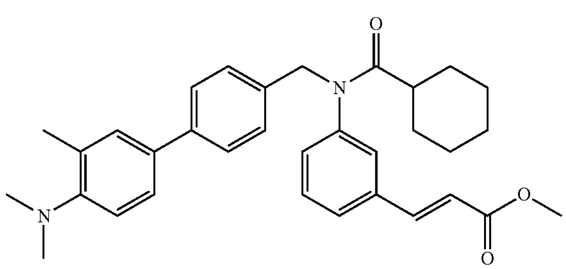 | (E)-Methyl 3-(3-(N-((4'-(dimethylamino)-3'-methyl-[1,1'-biphenyl]-4-yl)methyl)cyclohexanecarboxamido)phenyl)acrylate |
| 21 | 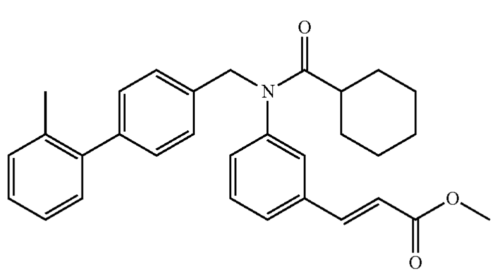 [SMILES: COC(=O)/C=C/c1cccc(N(Cc2ccc(-c3ccccc3C)cc2)C(=O)C2CCCCC2)c1] | (E)-Methyl 3-(3-(N-((2'-methyl-[1,1'-biphenyl]-4-yl)methyl)cyclohexanecarboxamido)phenyl)acrylate |

TABLE 1-continued

| Cmpd | Structure | Name |
|---|---|---|
| 22 | 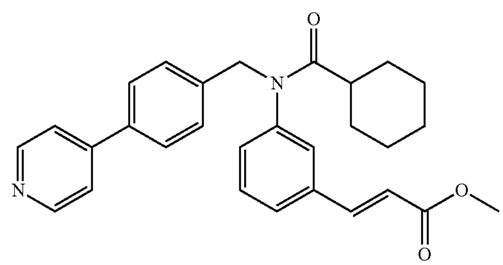 | (E)-Methyl 3-(3-(N-(4-(pyridin-4-yl)benzyl)cyclohexanecarboxamido)phenyl)acrylate |
| 23 | 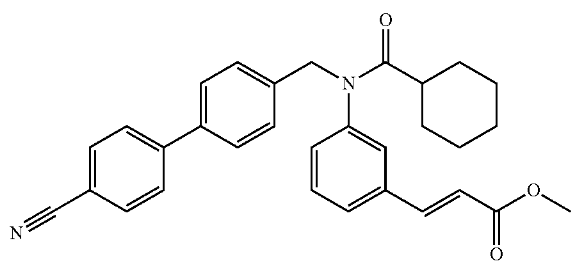 [SMILES: COC(=O)/C=C/c1cccc(N(Cc2ccc(-c3ccc(C#N)cc3)cc2)C(=O)C2CCCCC2)c1] | (E)-Methyl 3-(3-(N-((4'-cyano-[1,1'-biphenyl]-4-yl)methyl)cyclohexanecarboxamido)phenyl)acrylate |
| 24 | 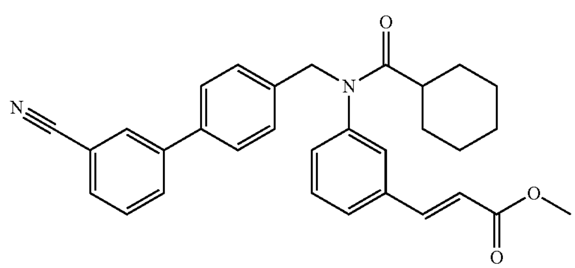 [SMILES: COC(=O)/C=C/c1cccc(N(Cc2ccc(-c3cccc(C#N)c3)cc2)C(=O)C2CCCCC2)c1] | (E)-Methyl 3-(3-(N-((3'-cyano-[1,1'-biphenyl]-4-yl)methyl)cyclohexanecarboxamido)phenyl)acrylate |
| 25 | 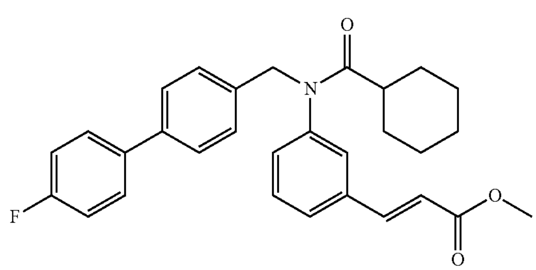 [SMILES: COC(=O)/C=C/c1cccc(N(Cc2ccc(-c3ccc(F)cc3)cc2)C(=O)C2CCCCC2)c1] | (E)-Methyl 3-(3-(N-((4'-fluoro-[1,1'-biphenyl]-4-yl)methyl)cyclohexanecarboxamido)phenyl)acrylate |
| 26 | 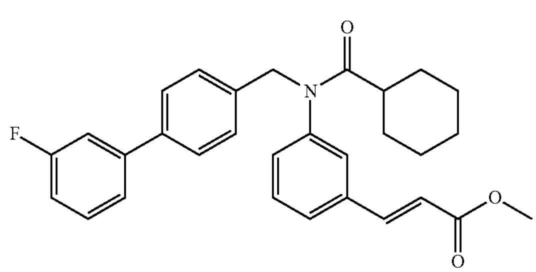 [SMILES: COC(=O)/C=C/c1cccc(N(Cc2ccc(-c3cccc(F)c3)cc2)C(=O)C2CCCCC2)c1] | (E)-Methyl 3-(3-(N-((3'-fluoro-[1,1'-biphenyl]-4-yl)methyl)cyclohexanecarboxamido)phenyl)acrylate |
| 27 | 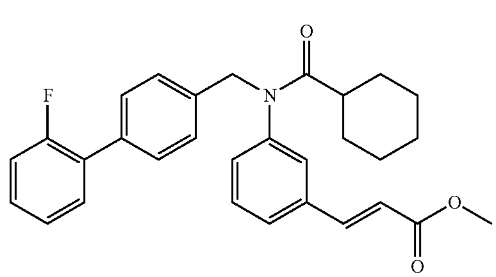 [SMILES: COC(=O)/C=C/c1cccc(N(Cc2ccc(-c3ccccc3F)cc2)C(=O)C2CCCCC2)c1] | (E)-Methyl 3-(3-(N-((2'-fluoro-[1,1'-biphenyl]-4-yl)methyl)cyclohexanecarboxamido)phenyl)acrylate |

TABLE 1-continued

| Cmpd | Structure | Name |
|---|---|---|
| 28 | 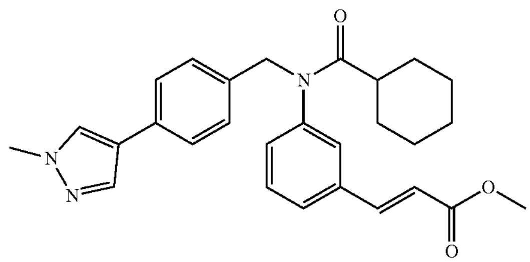 | (E)-Methyl 3-(3-(N-(4-(1-methyl-1H-pyrazol-4-yl)benzyl)cyclohexanecarboxamido)phenyl)acrylate |
| 29 | 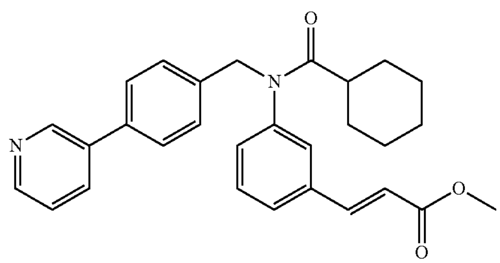 | (E)-Methyl 3-(3-(N-(4-(pyridin-3-yl)benzyl)cyclohexanecarboxamido)phenyl)acrylate |
| 30 | 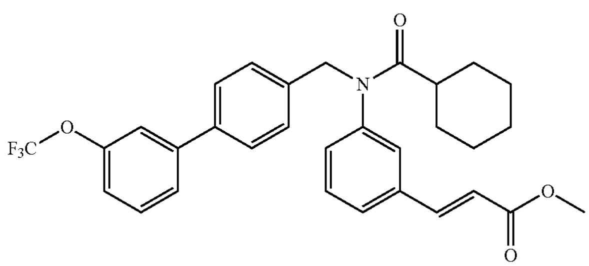 [SMILES: COC(=O)/C=C/c1cccc(N(Cc2ccc(-c3cccc(OC(F)(F)F)c3)cc2)C(=O)C2CCCCC2)c1] | (E)-Methyl 3-(3-(N-((3'-(trifluoromethoxy)-[1,1'-biphenyl]-4-yl)methyl)cyclohexanecarboxamido)phenyl)acrylate |
| 31 | 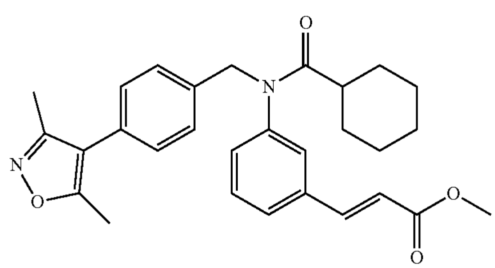 [SMILES: COC(=O)/C=C/c1cccc(N(Cc2ccc(-c3c(C)noc3C)cc2)C(=O)C2CCCCC2)c1] | (E)-Methyl 3-(3-(N-(4-(3,5-dimethylisoxazol-4-yl)benzyl)cyclohexanecarboxamido)phenyl)acrylate |
| 32 | 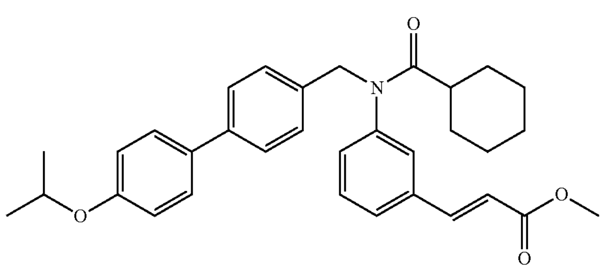 [SMILES: COC(=O)/C=C/c1cccc(N(Cc2ccc(-c3ccc(OC(C)C)cc3)cc2)C(=O)C2CCCCC2)c1] | (E)-Methyl 3-(3-(N-((4'-isopropoxy-[1,1'-biphenyl]-4-yl)methyl)cyclohexanecarboxamido)phenyl)acrylate |
| 33 | 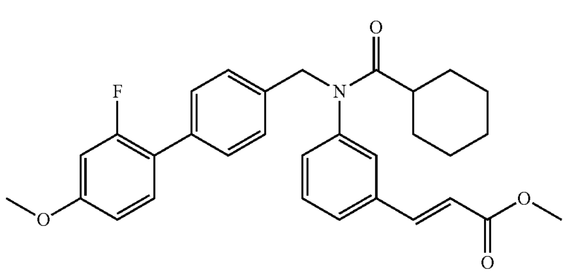 | (E)-Methyl 3-(3-(N-((2'-fluoro-4'-methoxy-[1,1'-biphenyl]-4-yl)methyl)cyclohexanecarboxamido)phenyl)acrylate |

TABLE 1-continued

| Cmpd | Structure | Name |
|---|---|---|
| 34 | 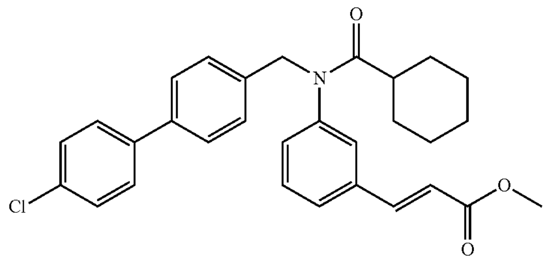 [SMILES: COC(=O)/C=C/c1cccc(N(Cc2ccc(-c3ccc(Cl)cc3)cc2)C(=O)C2CCCCC2)c1] | (E)-Methyl 3-(3-(N-((4'-chloro-[1,1'-biphenyl]-4-yl)methyl)cyclohexanecarboxamido)phenyl)acrylate |
| 35 | 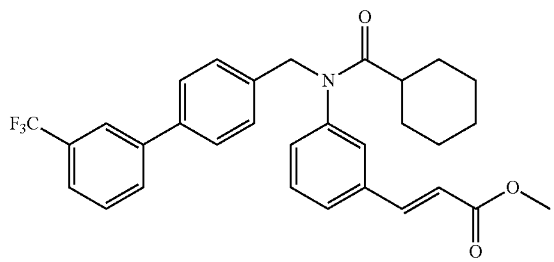 [SMILES: COC(=O)/C=C/c1cccc(N(Cc2ccc(-c3cccc(C(F)(F)F)c3)cc2)C(=O)C2CCCCC2)c1] | (E)-Methyl 3-(3-(N-((3'-(trifluoromethyl)-[1,1'-biphenyl]-4-yl)methyl)cyclohexanecarboxamido)phenyl)acrylate |
| 36 | 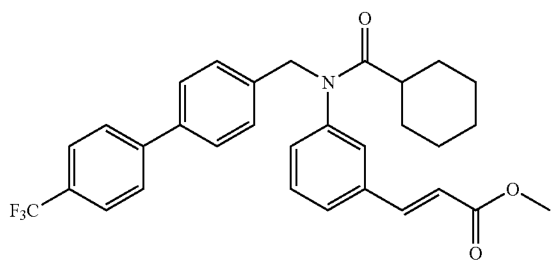 [SMILES: COC(=O)/C=C/c1cccc(N(Cc2ccc(-c3ccc(C(F)(F)F)cc3)cc2)C(=O)C2CCCCC2)c1] | (E)-Methyl 3-(3-(N-((4'-(trifluoromethyl)-[1,1'-biphenyl]-4-yl)methyl)cyclohexanecarboxamido)phenyl)acrylate |
| 37 | 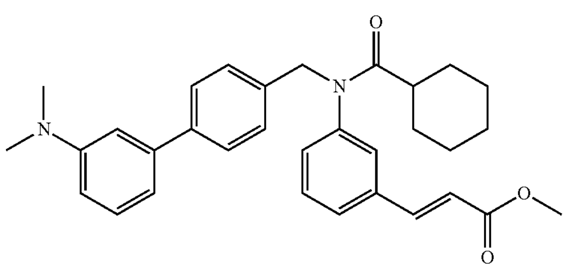 | (E)-Methyl 3-(3-(N-((3'-(dimethylamino)-[1,1'-biphenyl]-4-yl)methyl)cyclohexanecarboxamido)phenyl)acrylate |
| 38 | 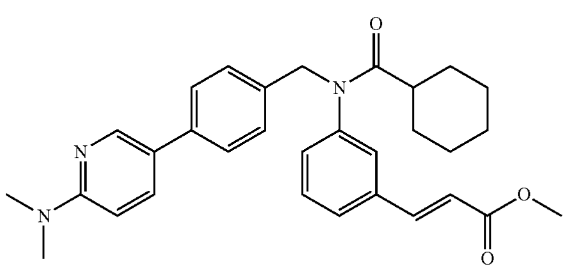 | (E)-Methyl 3-(3-(N-(4-(6-(dimethylamino)pyridin-3-yl)benzyl)cyclohexanecarboxamido)phenyl)acrylate |
| 39 | 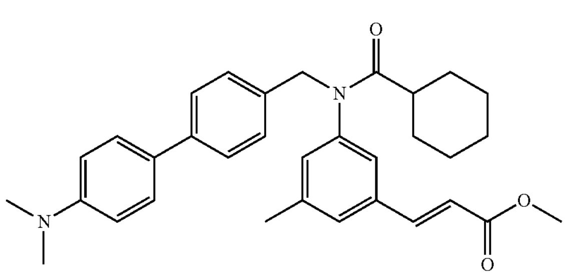 | (E)-Methyl 3-(3-(N-((4'-(dimethylamino)-[1,1'-biphenyl]-4-yl)methyl)cyclohexanecarboxamido)-5-methylphenyl)acrylate |

TABLE 1-continued

| Cmpd | Structure | Name |
|---|---|---|
| 40 | 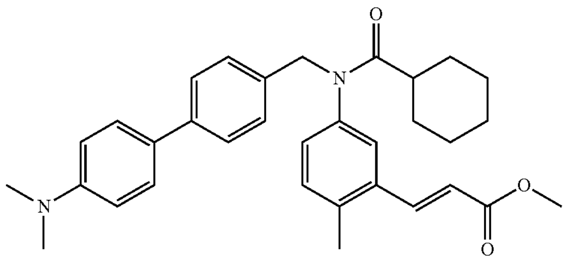 | (E)-Methyl 3-(5-(N-((4'-(dimethylamino)-[1,1'-biphenyl]-4-yl)methyl)cyclohexanecarboxamido)-2-methylphenyl)acrylate |
| 41 | 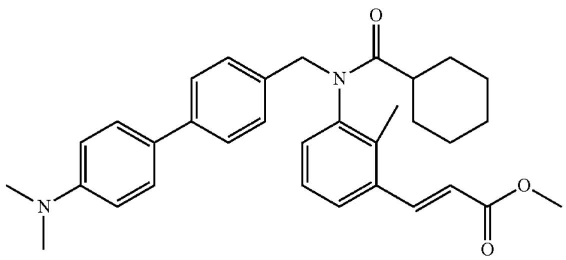 | (E)-Methyl 3-(3-(N-((4'-(dimethylamino)-[1,1'-biphenyl]-4-yl)methyl)cyclohexanecarboxamido)-2-methylphenyl)acrylate |
| 42 | 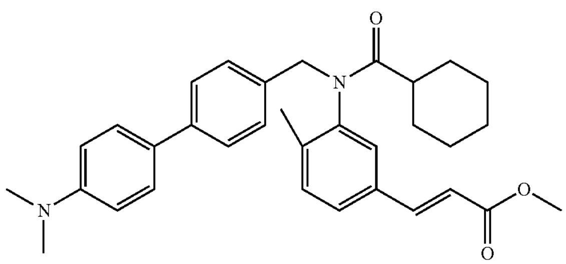 | (E)-Methyl 3-(3-(N-((4'-(dimethylamino)-[1,1'-biphenyl]-4-yl)methyl)cyclohexanecarboxamido)-4-methylphenyl)acrylate |
| 43 | 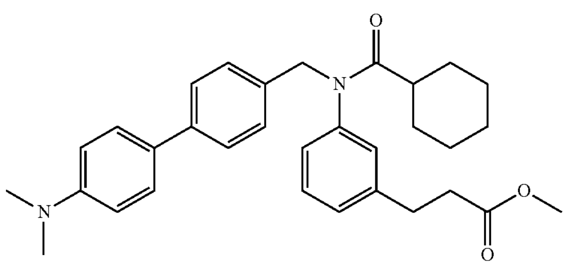 | Methyl 3-(3-(N-((4'-(dimethylamino)-[1,1'-biphenyl]-4-yl)methyl)cyclohexanecarboxamido)phenyl)propanoate |
| 44 | 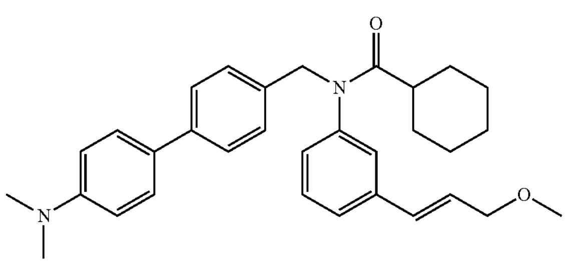 | (E)-N-((4'-(Dimethylamino)-[1,1'-biphenyl]-4-yl)methyl)-N-(3-(3-methoxyprop-1-en-1-yl)phenyl)cyclohexanecarboxamide |
| 45 | 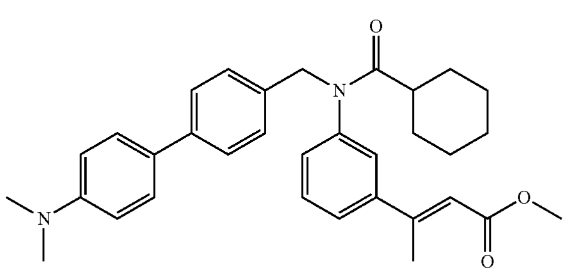 | (E)-Methyl 3-(3-(N-((4'-(dimethylamino)-[1,1'-biphenyl]-4-yl)methyl)cyclohexanecarboxamido)phenyl)but-2-enoate |

TABLE 1-continued

| Cmpd | Structure | Name |
|---|---|---|
| 46 | 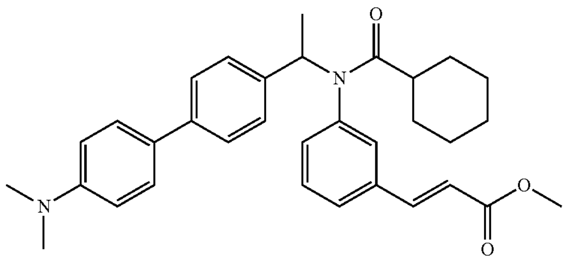 | (E)-Methyl 3-(3-(N-(1-(4'-(dimethylamino)-[1,1'-biphenyl]-4-yl)ethyl)cyclohexanecarboxamido)phenyl)acrylate |
| 47 | 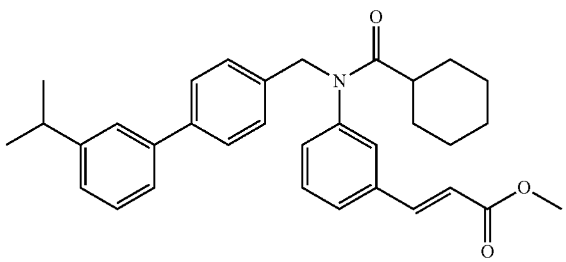 | (E)-Methyl 3-(3-(N-((3'-isopropyl-[1,1'-biphenyl]-4-yl)methyl)cyclohexanecarboxamido)phenyl)acrylate |
| 48 | 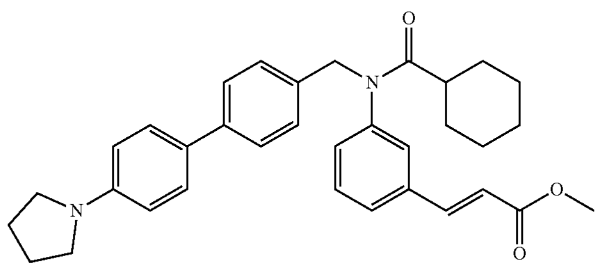 [SMILES: COC(=O)/C=C/c1cccc(N(Cc2ccc(-c3ccc(N4CCCC4)cc3)cc2)C(=O)C2CCCCC2)c1] | (E)-Methyl 3-(3-(N-((4'-(pyrrolidin-1-yl)-[1,1'-biphenyl]-4-yl)methyl)cyclohexanecarboxamido)phenyl)acrylate |
| 49 | 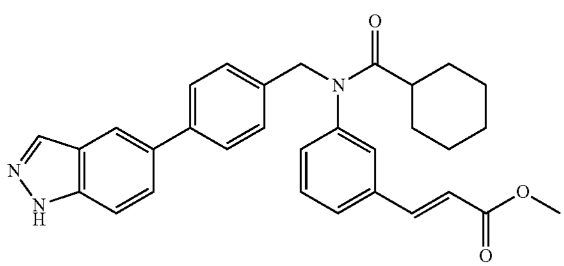 | (E)-Methyl 3-(3-(N-(4-(1H-indazol-5-yl)benzyl)cyclohexanecarboxamido)phenyl)acrylate |
| 50 | 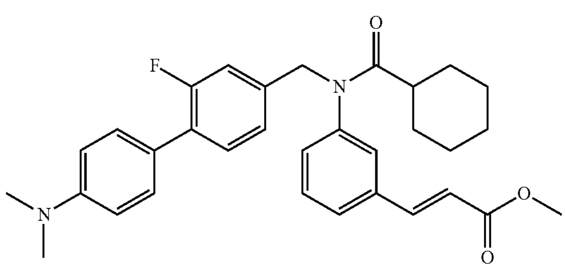 | (E)-methyl 3-(3-(N-((4'-(dimethylamino)-2-fluoro-[1,1'-biphenyl]-4-yl)methyl)cyclohexanecarboxamido)phenyl)acrylate |
| 51 | 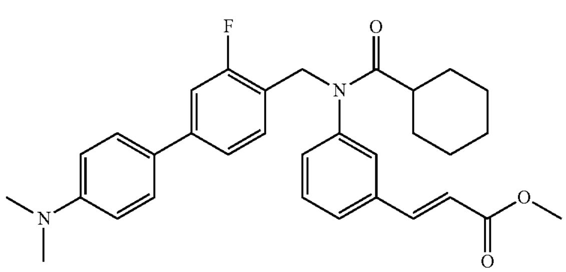 | (E)-methyl 3-(3-(N-((4'-(dimethylamino)-3-fluoro-[1,1'-biphenyl]-4-yl)methyl)cyclohexanecarboxamido)phenyl)acrylate |

TABLE 1-continued

| Cmpd | Structure | Name |
| --- | --- | --- |
| 52 | 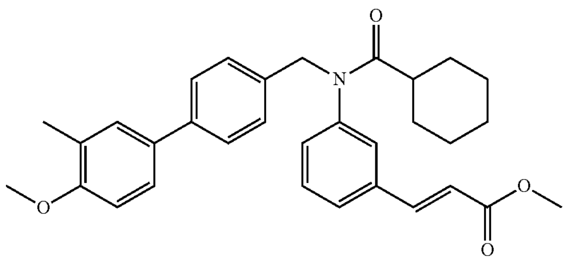 | (E)-Methyl 3-(3-(N-((4'-methoxy-3'-methyl-[1,1'-biphenyl]-4-yl)methyl)cyclohexanecarboxamido)phenyl)acrylate |
| 53 | 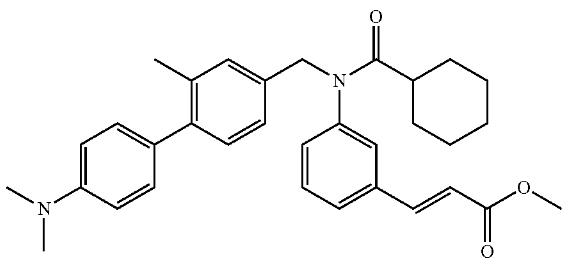 | (E)-Methyl 3-(3-(N-((4'-(dimethylamino)-2-methyl-[1,1'-biphenyl]-4-yl)methyl)cyclohexanecarboxamido)phenyl)acrylate |
| 54 | 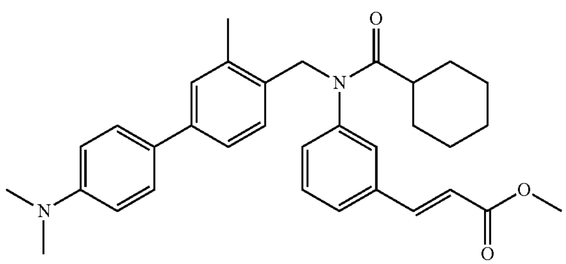 | (E)-Methyl 3-(3-(N-((4'-(dimethylamino)-3-methyl-[1,1'-biphenyl]-4-yl)methyl)cyclohexanecarboxamido)phenyl)acrylate |
| 55 | 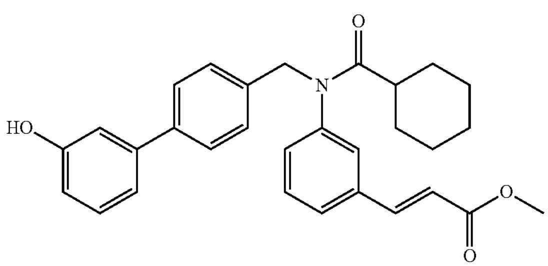 [SMILES: COC(=O)/C=C/c1cccc(N(Cc2ccc(-c3cccc(O)c3)cc2)C(=O)C2CCCCC2)c1] | (E)-Methyl 3-(3-(N-((3'-hydroxy-[1,1'-biphenyl]-4-yl)methyl)cyclohexanecarboxamido)phenyl)acrylate |
| 56 | 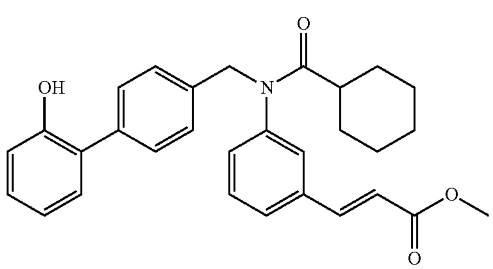 [SMILES: COC(=O)/C=C/c1cccc(N(Cc2ccc(-c3ccccc3O)cc2)C(=O)C2CCCCC2)c1] | (E)-Methyl 3-(3-(N-((2'-hydroxy-[1,1'-biphenyl]-4-yl)methyl)cyclohexanecarboxamido)phenyl)acrylate |
| 57 | 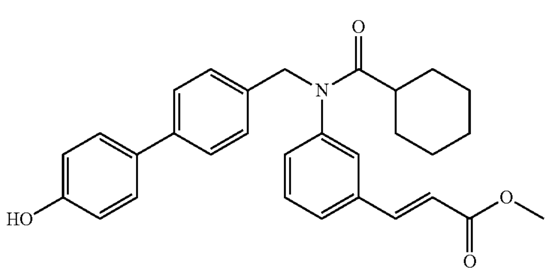 [SMILES: COC(=O)/C=C/c1cccc(N(Cc2ccc(-c3ccc(O)cc3)cc2)C(=O)C2CCCCC2)c1] | (E)-Methyl 3-(3-(N-((4'-hydroxy-[1,1'-biphenyl]-4-yl)methyl)cyclohexanecarboxamido)phenyl)acrylate |

TABLE 1-continued

| Cmpd | Structure | Name |
| --- | --- | --- |
| 58 | 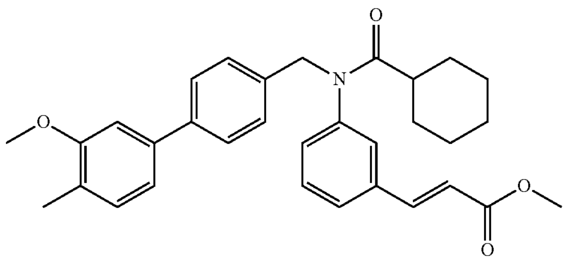 | (E)-Methyl 3-(3-(N-((3'-methoxy-4'-methyl-[1,1'-biphenyl]-4-yl)methyl)cyclohexanecarboxamido)phenyl)acrylate |
| 59 | 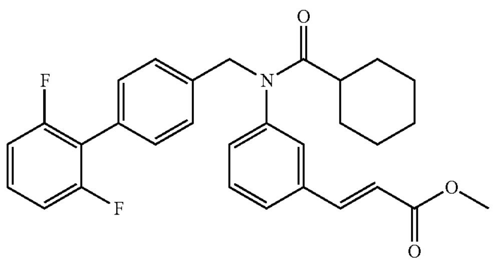 [SMILES: COC(=O)/C=C/c1cccc(N(Cc2ccc(-c3c(F)cccc3F)cc2)C(=O)C2CCCCC2)c1] | (E)-Methyl 3-(3-(N-((2',6'-difluoro-[1,1'-biphenyl]-4-yl)methyl)cyclohexanecarboxamido)phenyl)acrylate |
| 60 | 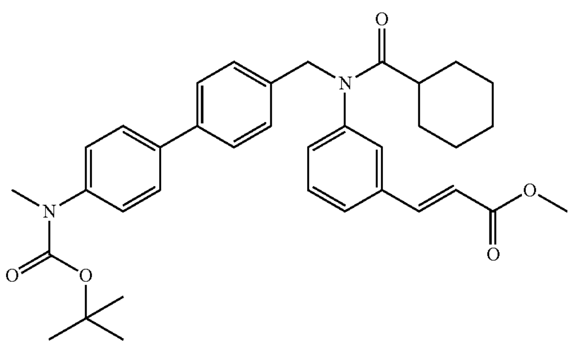 | (E)-Methyl 3-(3-(N-((4'-((tert-butoxycarbonyl)(methyl)amino)-[1,1'-biphenyl]-4-yl)methyl)cyclohexanecarboxamido)phenyl)acrylate |
| 61 | 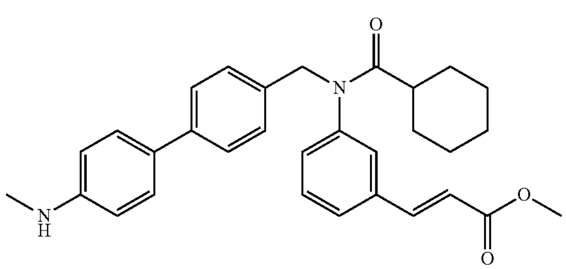 | (E)-Methyl 3-(3-(N-((4'-(methylamino)-[1,1'-biphenyl]-4-yl)methyl)cyclohexanecarboxamido)phenyl)acrylate |
| 62 | 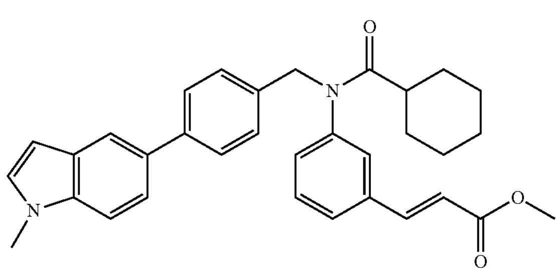 [SMILES: COC(=O)/C=C/c1cccc(N(Cc2ccc(-c3ccc4c(ccn4C)c3)cc2)C(=O)C2CCCCC2)c1] | (E)-Methyl 3-(3-(N-(4-(1-methyl-1H-indol-5-yl)benzyl)cyclohexanecarboxamido)phenyl)acrylate |

TABLE 1-continued

| Cmpd | Structure | Name |
|---|---|---|
| 62.1 | 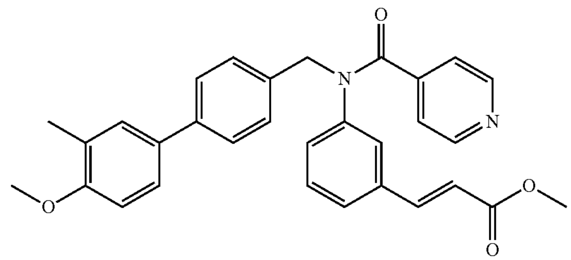 | (E)-Methyl 3-(3-(N-((4'-methoxy-3'-methyl-[1,1'-biphenyl]-4-yl)methyl)isonicotinamido)phenyl)acrylate |
| 62.2 | 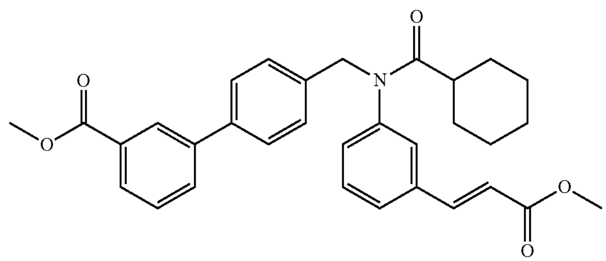 | (E)-Methyl 4'-((N-(3-(3-methoxy-3-oxoprop-1-en-1-yl)phenyl)cyclohexanecarboxamido)methyl)-[1,1'-biphenyl]-3-carboxylate |
| 62.3 | 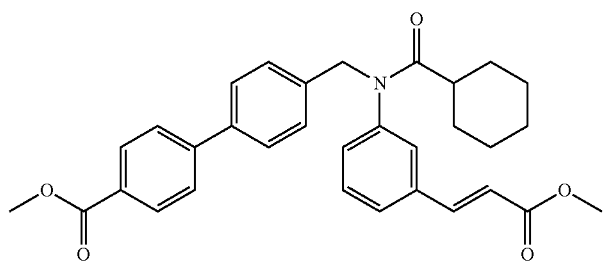 | (E)-Methyl 4'-((N-(3-(3-methoxy-3-oxoprop-1-en-1-yl)phenyl)cyclohexanecarboxamido)methyl)-[1,1'-biphenyl]-4-carboxylate |
| 62.4 | 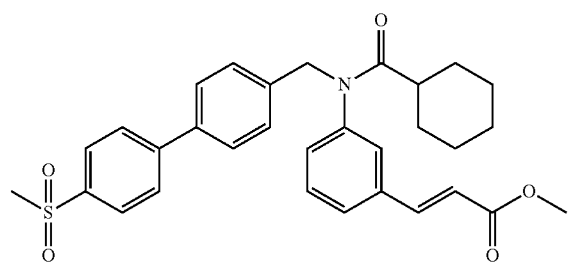 | (E)-Methyl 3-(3-(N-((4'-(methylsulfonyl)-[1,1'-biphenyl]-4-yl)methyl)cyclohexanecarboxamido)phenyl)acrylate |
| 62.5 | 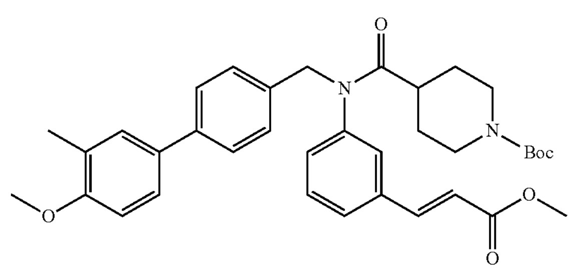 | (E)-tert-Butyl 4-(((4'-methoxy-3'-methyl-[1,1'-biphenyl]-4-yl)methyl)(3-(3-methoxy-3-oxoprop-1-en-1-yl)phenyl)carbamoyl)piperidine-1-carboxylate |
| 62.6 | 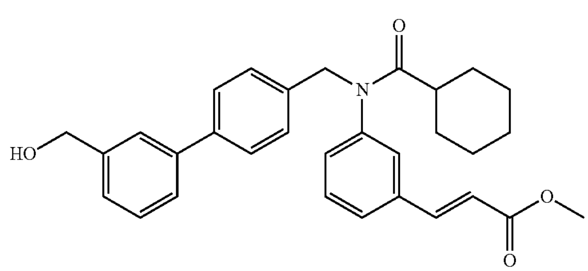 [SMILES: COC(=O)/C=C/c1cccc(N(Cc2ccc(-c3cccc(CO)c3)cc2)C(=O)C2CCCCC2)c1] | (E)-Methyl 3-(3-(N-((3'-(hydroxymethyl)-[1,1'-biphenyl]-4-yl)methyl)cyclohexanecarboxamido)phenyl)acrylate |

TABLE 1-continued

| Cmpd | Structure | Name |
|---|---|---|
| 62.7 | 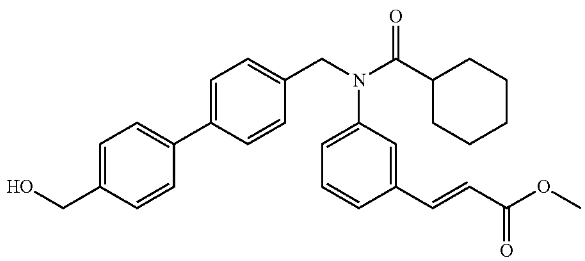 [SMILES: COC(=O)/C=C/c1cccc(N(Cc2ccc(-c3ccc(CO)cc3)cc2)C(=O)C2CCCCC2)c1] | (E)-Methyl 3-(3-(N-((4'-(hydroxymethyl)-[1,1'-biphenyl]-4-yl)methyl)cyclohexanecarboxamido)phenyl)acrylate |
| 62.8 | 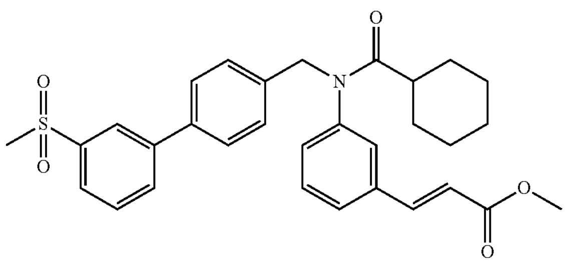 | (E)-Methyl 3-(3-(N-((3'-(methylsulfonyl)-[1,1'-biphenyl]-4-yl)methyl)cyclohexanecarboxamido)phenyl)acrylate |
| 62.9 | 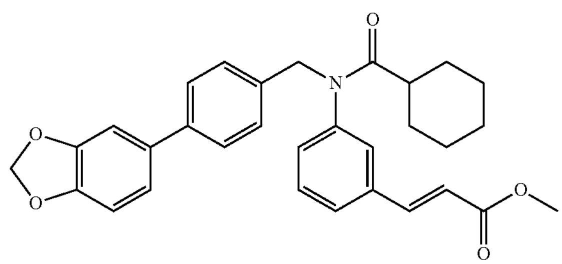 [SMILES: COC(=O)/C=C/c1cccc(N(Cc2ccc(-c3ccc4c(c3)OCO4)cc2)C(=O)C2CCCCC2)c1] | (E)-Methyl 3-(3-(N-(4-(benzo[d][1,3]dioxol-5-yl)benzyl)cyclohexanecarboxamido)phenyl)acrylate |
| 62.10 | 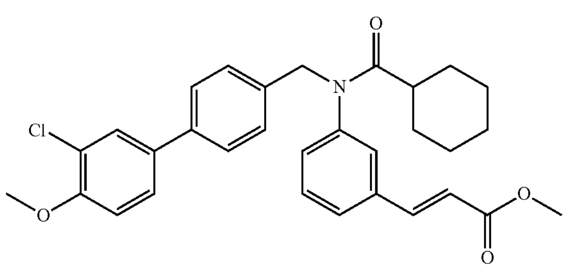 | (E)-Methyl 3-(3-(N-((3'-chloro-4'-methoxy-[1,1'-biphenyl]-4-yl)methyl)cyclohexanecarboxamido)phenyl)acrylate |
| 62.11 | 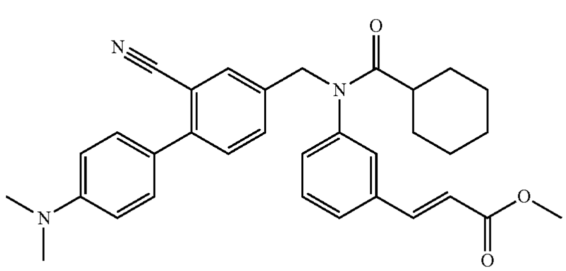 | (E)-Methyl 3-(3-(N-((2-cyano-4'-(dimethylamino)-[1,1'-biphenyl]-4-yl)methyl)cyclohexanecarboxamido)phenyl)acrylate |

| Cmpd | Structure | Name |
|---|---|---|
| 62.12 | 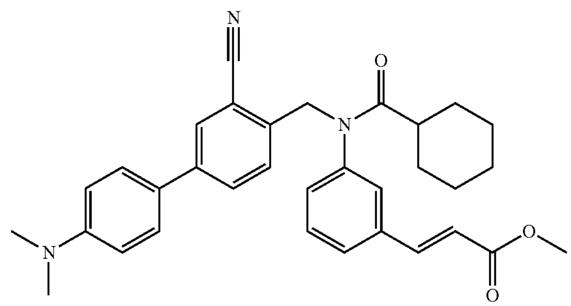 | (E)-Methyl 3-(3-(N-((3-cyano-4'-(dimethylamino)-[1,1'-biphenyl]-4-yl)methyl)cyclohexanecarboxamido)phenyl)acrylate |
| 62.13 | 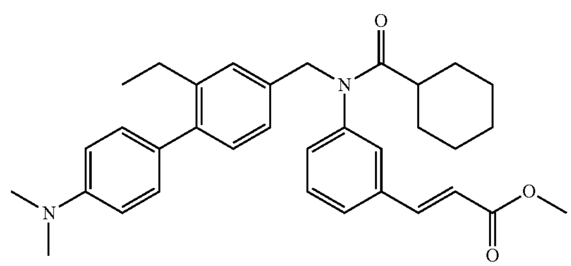 | (E)-Methyl 3-(3-(N-((4'-(dimethylamino)-2-ethyl-[1,1'-biphenyl]-4-yl)methyl)cyclohexanecarboxamido)phenyl)acrylate |
| 62.14 | 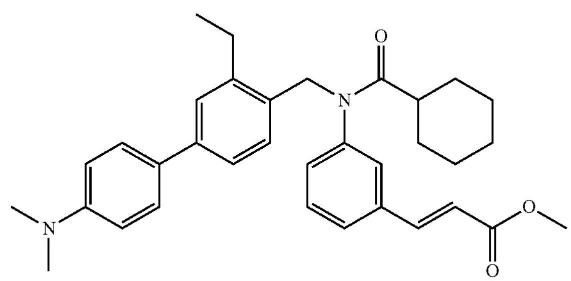 | (E)-Methyl 3-(3-(N-((4'-(dimethylamino)-3-ethyl-[1,1'-biphenyl]-4-yl)methyl)cyclohexanecarboxamido)phenyl)acrylate |
| 62.15 | 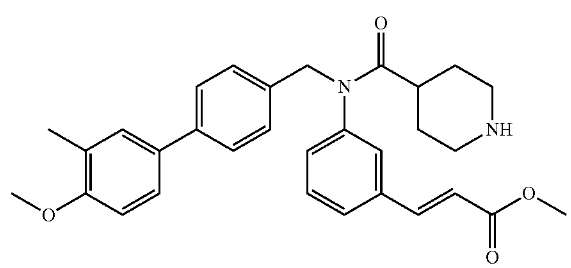 | (E)-Methyl 3-(3-(N-((4'-methoxy-3'-methyl-[1,1'-biphenyl]-4-yl)methyl)piperidine-4-carboxamido)phenyl)acrylate |
| 62.16 | 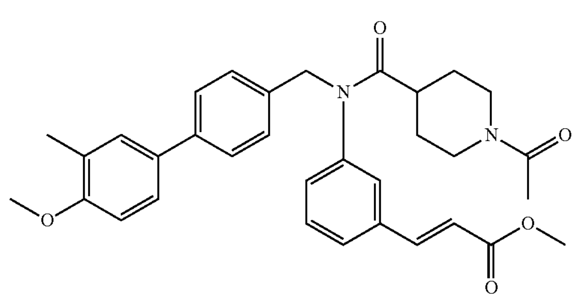 [SMILES: COC(=O)/C=C/c1cccc(N(Cc2ccc(-c3ccc(OC)c(C)c3)cc2)C(=O)C2CCN(C(C)=O)CC2)c1] | (E)-Methyl 3-(3-(1-acetyl-N-((4'-methoxy-3'-methyl-[1,1'-biphenyl]-4-yl)methyl)piperidine-4-carboxamido)phenyl)acrylate |

TABLE 1-continued

| Cmpd | Structure | Name |
|---|---|---|
| 62.17 | 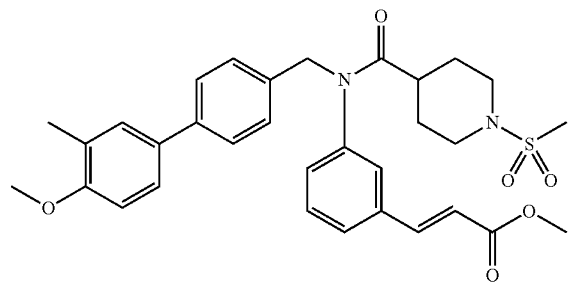 | (E)-Methyl 3-(3-(N-((4'-methoxy-3'-methyl-[1,1'-biphenyl]-4-yl)methyl)-1-(methylsulfonyl)piperidine-4-carboxamido)phenyl)acrylate |
| 63 | 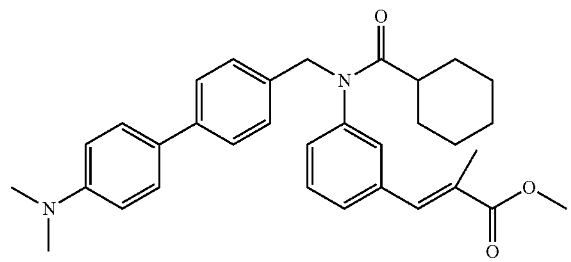 | (E)-Methyl 3-(3-(N-((4'-(dimethylamino)-[1,1'-biphenyl]-4-yl)methyl)cyclohexanecarboxamido)phenyl)-2-methylacrylate |
| 64 | 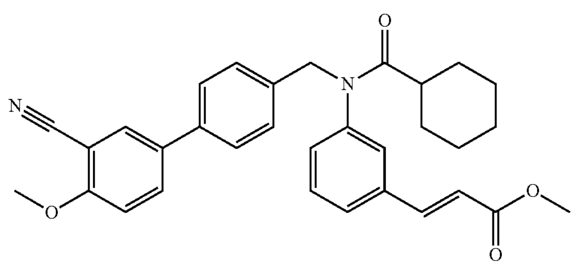 | (E)-Methyl 3-(3-(N-((3'-cyano-4'-methoxy-[1,1'-biphenyl]-4-yl)methyl)cyclohexanecarboxamido)phenyl)acrylate |
| 65 | 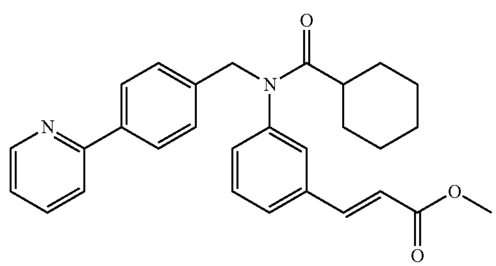 [SMILES: COC(=O)/C=C/c1cccc(N(Cc2ccc(-c3ccccn3)cc2)C(=O)C2CCCCC2)c1] | (E)-Methyl 3-(3-(N-(4-(pyridin-2-yl)benzyl)cyclohexanecarboxamido)phenyl)acrylate |
| 66 | 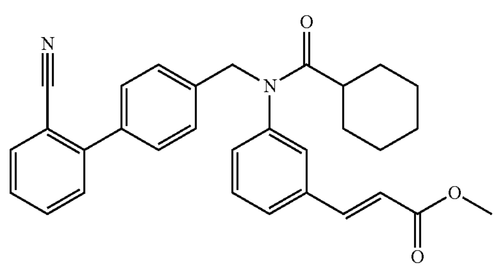 [SMILES: COC(=O)/C=C/c1cccc(N(Cc2ccc(-c3ccccc3C#N)cc2)C(=O)C2CCCCC2)c1] | (E)-Methyl 3-(3-(N-((2'-cyano-[1,1'-biphenyl]-4-yl)methyl)cyclohexanecarboxamido)phenyl)acrylate |
| 67 | 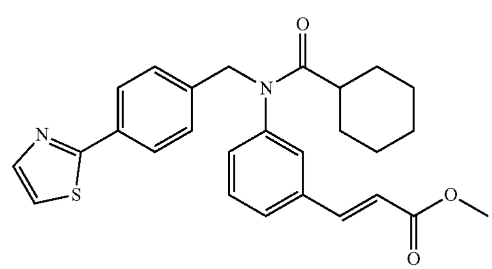 [SMILES: COC(=O)/C=C/c1cccc(N(Cc2ccc(-c3nccs3)cc2)C(=O)C2CCCCC2)c1] | (E)-Methyl 3-(3-(N-(4-(thiazol-2-yl)benzyl)cyclohexanecarboxamido)phenyl)acrylate |

TABLE 1-continued

| Cmpd | Structure | Name |
|---|---|---|
| 68 | 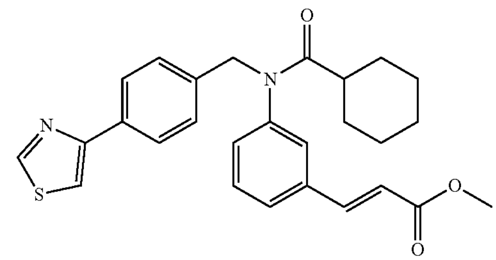 [SMILES: COC(=O)/C=C/c1cccc(N(Cc2ccc(-c3cscn3)cc2)C(=O)C2CCCCC2)c1] | (E)-Methyl 3-(3-(N-(4-(thiazol-4-yl)benzyl)cyclohexanecarboxamido)phenyl)acrylate |
| 69 | 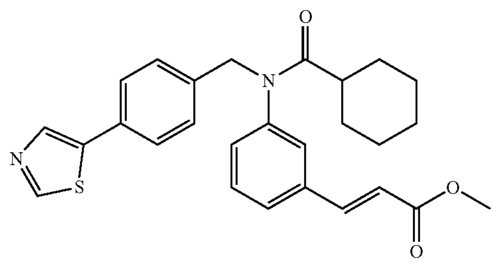 [SMILES: COC(=O)/C=C/c1cccc(N(Cc2ccc(-c3cncs3)cc2)C(=O)C2CCCCC2)c1] | (E)-Methyl 3-(3-(N-(4-(thiazol-5-yl)benzyl)cyclohexanecarboxamido)phenyl)acrylate |
| 70 | 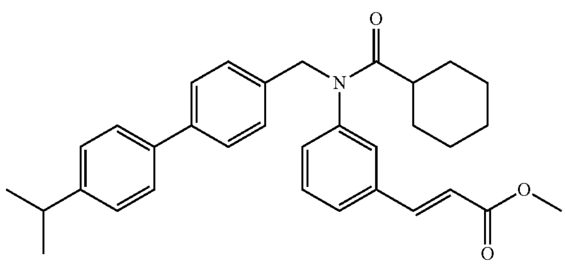 | (E)-Methyl 3-(3-(N-((4'-isopropyl-[1,1'-biphenyl]-4-yl)methyl)cyclohexanecarboxamido)phenyl)acrylate |
| 71 | 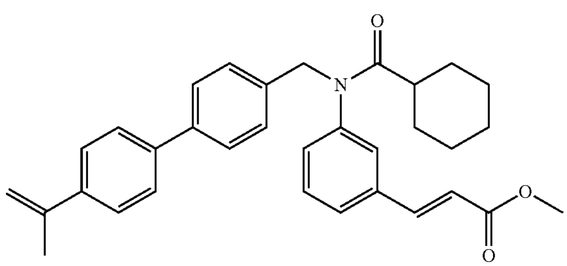 [SMILES: C=C(C)c1ccc(-c2ccc(CN(C(=O)C3CCCCC3)c3cccc(/C=C/C(=O)OC)c3)cc2)cc1] | (E)-Methyl 3-(3-(N-((4'-(prop-1-en-2-yl)-[1,1'-biphenyl]-4-yl)methyl)cyclohexanecarboxamido)phenyl)acrylate |
| 72 | 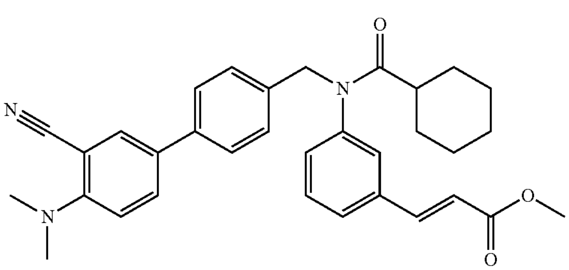 | (E)-Methyl 3-(3-(N-((3'-cyano-4'-(dimethylamino)-[1,1'-biphenyl]-4-yl)methyl)cyclohexanecarboxamido)phenyl)acrylate |
| 73 | 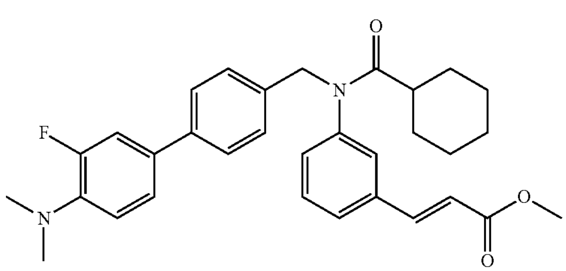 | (E)-Methyl 3-(3-(N-((4'-(dimethylamino)-3'-fluoro-[1,1'-biphenyl]-4-yl)methyl)cyclohexanecarboxamido)phenyl)acrylate |

TABLE 1-continued

| Cmpd | Structure | Name |
| --- | --- | --- |
| 74 | 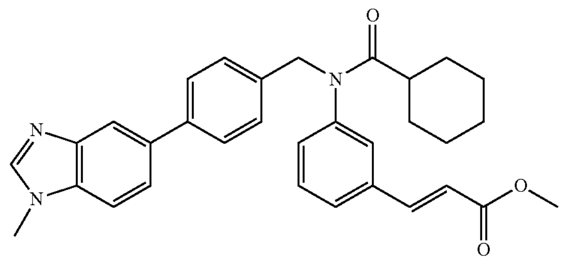 [SMILES: COC(=O)/C=C/c1cccc(N(Cc2ccc(-c3ccc4c(c3)ncn4C)cc2)C(=O)C2CCCCC2)c1] | (E)-Methyl 3-(3-(N-(4-(1-methyl-1H-benzo[d]imidazol-5-yl)benzyl)cyclohexanecarboxamido)phenyl)acrylate |
| 75 | 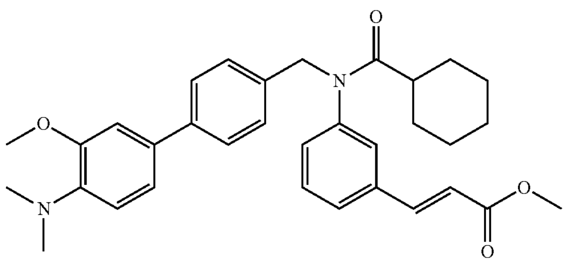 | (E)-methyl 3-(3-(N-((4'-(dimethylamino)-3'-methoxy-[1,1'-biphenyl]-4-yl)methyl)cyclohexanecarboxamido)phenyl)acrylate |
| 75.1 | 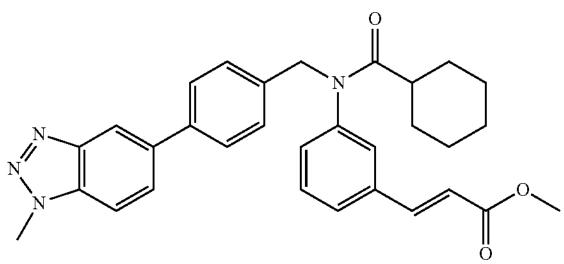 [SMILES: COC(=O)/C=C/c1cccc(N(Cc2ccc(-c3ccc4c(c3)nnn4C)cc2)C(=O)C2CCCCC2)c1] | (E)-Methyl 3-(3-(N-(4-(1-methyl-1H-benzo[d][1,2,3]triazol-5-yl)benzyl)cyclohexanecarboxamido)phenyl)acrylate |
| 75.2 | 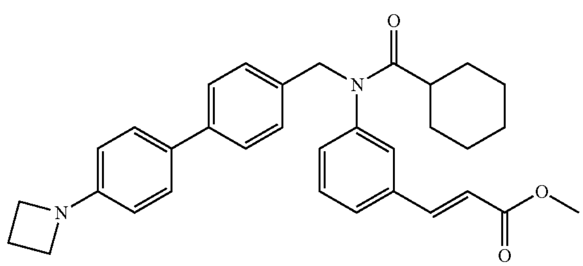 [SMILES: COC(=O)/C=C/c1cccc(N(Cc2ccc(-c3ccc(N4CCC4)cc3)cc2)C(=O)C2CCCCC2)c1] | (E)-Methyl 3-(3-(N-((4'-(azetidin-1-yl)-[1,1'-biphenyl]-4-yl)methyl)cyclohexanecarboxamido)phenyl)acrylate |
| 75.3 | 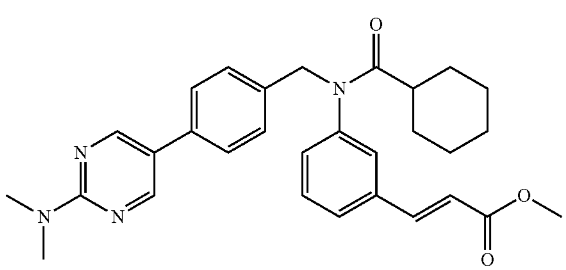 | (E)-Methyl 3-(3-(N-(4-(2-(dimethylamino)pyrimidin-5-yl)benzyl)cyclohexanecarboxamido)phenyl)acrylate |
| 75.4 | 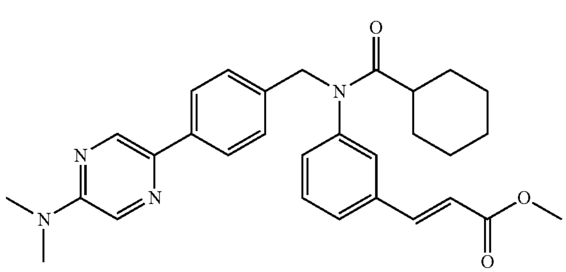 | (E)-Methyl 3-(3-(N-(4-(5-(dimethylamino)pyrazin-2-yl)benzyl)cyclohexanecarboxamido)phenyl)acrylate |

TABLE 1-continued

| Cmpd | Structure | Name |
|---|---|---|
| 75.5 | 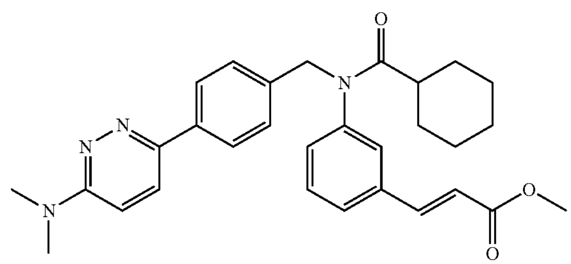 | (E)-Methyl 3-(3-(N-(4-(6-(dimethylamino)pyridazin-3-yl)benzyl)cyclohexanecarboxamido)phenyl)acrylate |
| 75.6 | 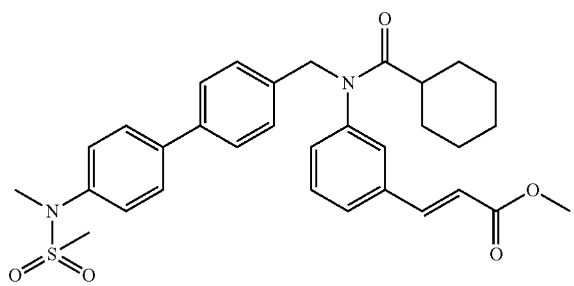 | (E)-Methyl 3-(3-(N-((4'-(N-methylmethylsulfonamido)-[1,1'-biphenyl]-4-yl)methyl)cyclohexanecarboxamido)phenyl)acrylate |
| 75.7 | 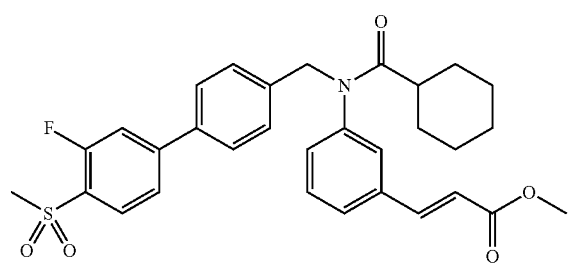 | (E)-Methyl 3-(3-(N-((3'-fluoro-4'-(methylsulfonyl)-[1,1'-biphenyl]-4-yl)methyl)cyclohexanecarboxamido)phenyl)acrylate |
| 75.8 | 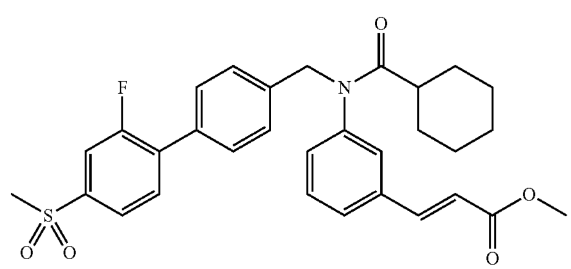 | (E)-Methyl 3-(3-(N-((2'-fluoro-4'-(methylsulfonyl)-[1,1'-biphenyl]-4-yl)methyl)cyclohexanecarboxamido)phenyl)acrylate |
| 75.9 | 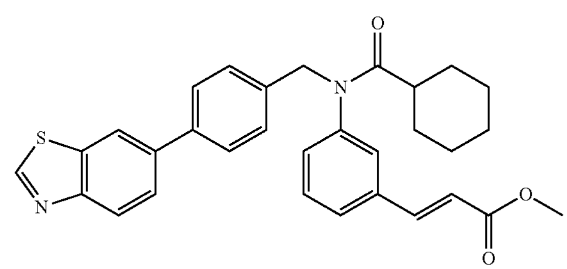 | (E)-Methyl 3-(3-(N-(4-(benzo[d]thiazol-6-yl)benzyl)cyclohexanecarboxamido)phenyl)acrylate |

TABLE 1-continued

| Cmpd | Structure | Name |
|---|---|---|
| 75.10 | 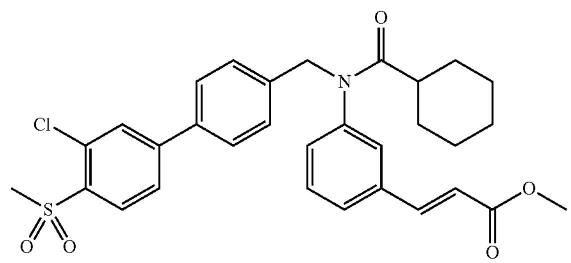 | (E)-Methyl 3-(3-(N-((3'-chloro-4'-(methylsulfonyl)-[1,1'-biphenyl]-4-yl)methyl)cyclohexanecarboxamido)phenyl)acrylate |
| 75.11 | 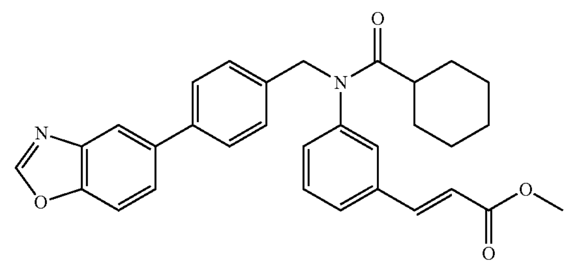 [SMILES: COC(=O)/C=C/c1cccc(N(Cc2ccc(-c3ccc4ocnc4c3)cc2)C(=O)C2CCCCC2)c1] | (E)-Methyl 3-(3-(N-(4-(benzo[d]oxazol-5-yl)benzyl)cyclohexanecarboxamido)phenyl)acrylate |
| 75.12 | 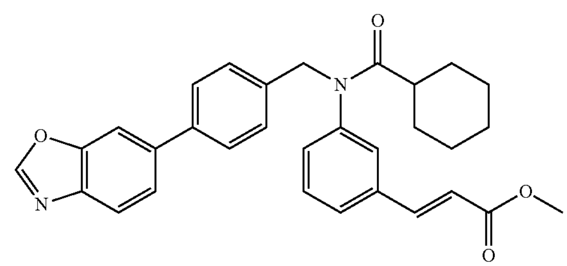 | (E)-Methyl 3-(3-(N-(4-(benzo[d]oxazol-6-yl)benzyl)cyclohexanecarboxamido)phenyl)acrylate |
| 75.13 | 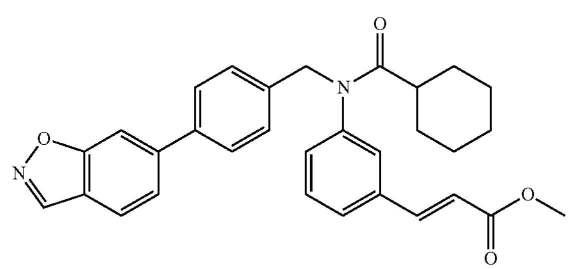 [SMILES: COC(=O)/C=C/c1cccc(N(Cc2ccc(-c3ccc4cnoc4c3)cc2)C(=O)C2CCCCC2)c1] | (E)-Methyl 3-(3-(N-(4-(benzo[d]isoxazol-6-yl)benzyl)cyclohexanecarboxamido)phenyl)acrylate |
| 75.14 | 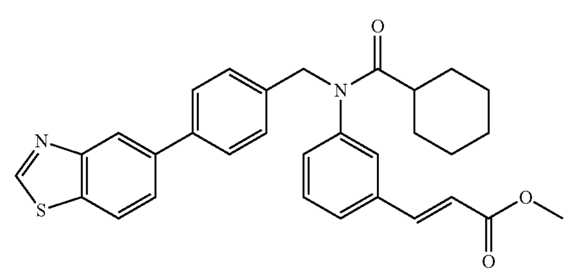 | (E)-Methyl 3-(3-(N-(4-(benzo[d]thiazol-5-yl)benzyl)cyclohexanecarboxamido)phenyl)acrylate |
| 75.15 | 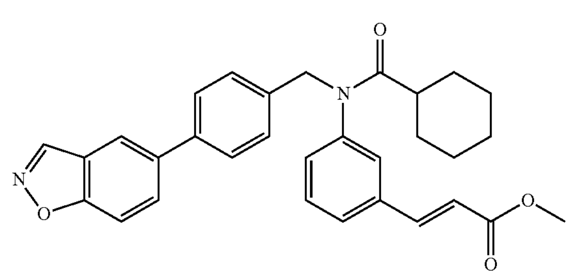 [SMILES: COC(=O)/C=C/c1cccc(N(Cc2ccc(-c3ccc4oncc4c3)cc2)C(=O)C2CCCCC2)c1] | (E)-Methyl 3-(3-(N-(4-(benzo[d]isoxazol-5-yl)benzyl)cyclohexanecarboxamido)phenyl)acrylate |

TABLE 1-continued

| Cmpd | Structure | Name |
| --- | --- | --- |
| 75.16 | 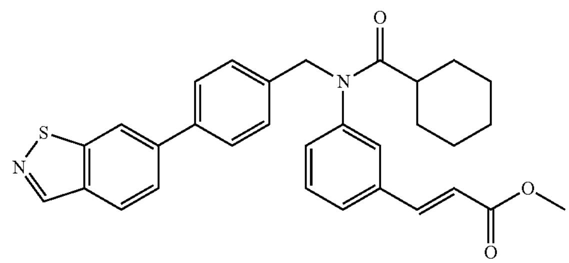 [SMILES: COC(=O)/C=C/c1cccc(N(Cc2ccc(-c3ccc4cnsc4c3)cc2)C(=O)C2CCCCC2)c1] | (E)-Methyl 3-(3-(N-(4-(benzo[d]isothiazol-6-yl)benzyl)cyclohexanecarboxamido)phenyl)acrylate |
| 75.17 | 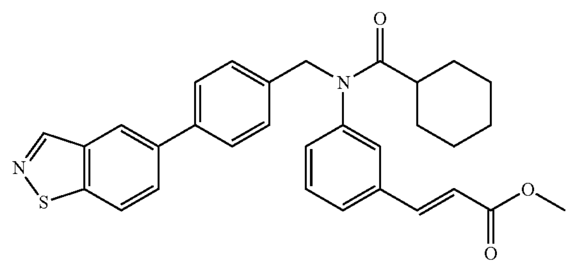 [SMILES: COC(=O)/C=C/c1cccc(N(Cc2ccc(-c3ccc4sncc4c3)cc2)C(=O)C2CCCCC2)c1] | (E)-Methyl 3-(3-(N-(4-(benzo[d]isothiazol-5-yl)benzyl)cyclohexanecarboxamido)phenyl)acrylate |
| 75.18 | 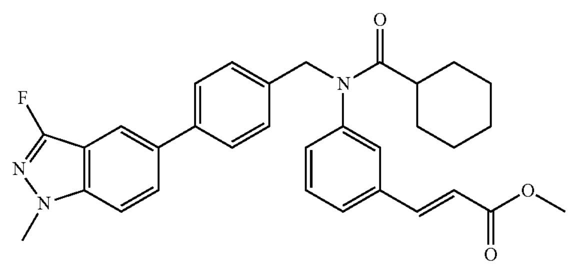 [SMILES: COC(=O)/C=C/c1cccc(N(Cc2ccc(-c3ccc4c(c3)c(F)nn4C)cc2)C(=O)C2CCCCC2)c1] | (E)-Methyl 3-(3-(N-(4-(3-fluoro-1-methyl-1H-indazol-5-yl)benzyl)cyclohexanecarboxamido)phenyl)acrylate |
| 75.19 | 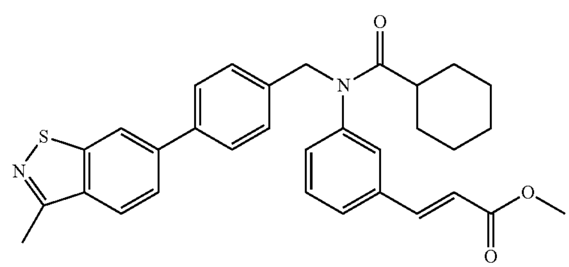 [SMILES: COC(=O)/C=C/c1cccc(N(Cc2ccc(-c3ccc4c(C)nsc4c3)cc2)C(=O)C2CCCCC2)c1] | (E)-Methyl 3-(3-(N-(4-(3-methylbenzo[d]isothiazol-6-yl)benzyl)cyclohexanecarboxamido)phenyl)acrylate |
| 76 | 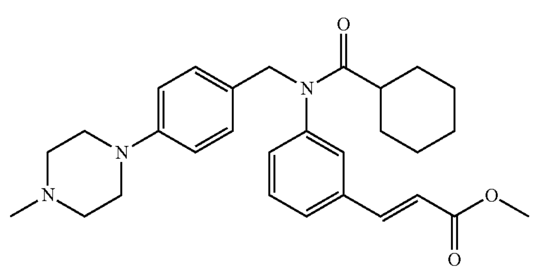 | (E)-Methyl 3-(3-(N-(4-(4-methylpiperazin-1-yl)benzyl)cyclohexanecarboxamido)phenyl)acrylate |
| 77 | 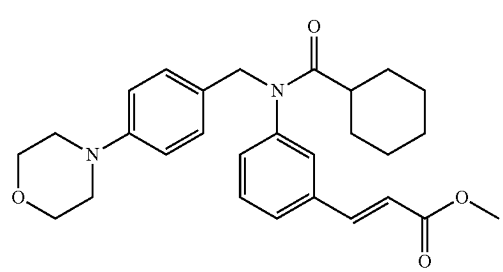 [SMILES: COC(=O)/C=C/c1cccc(N(Cc2ccc(N3CCOCC3)cc2)C(=O)C2CCCCC2)c1] | (E)-Methyl 3-(3-(N-(4-morpholinobenzyl)cyclohexanecarboxamido)phenyl)acrylate |

TABLE 1-continued

| Cmpd | Structure | Name |
|---|---|---|
| 78 | 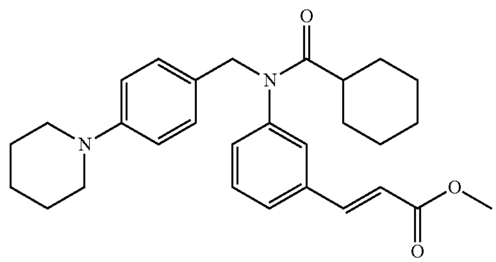 [SMILES: COC(=O)/C=C/c1cccc(N(Cc2ccc(N3CCCCC3)cc2)C(=O)C2CCCCC2)c1] | (E)-Methyl 3-(3-(N-(4-(piperidin-1-yl)benzyl)cyclohexanecarboxamido)phenyl)acrylate |
| 79 | 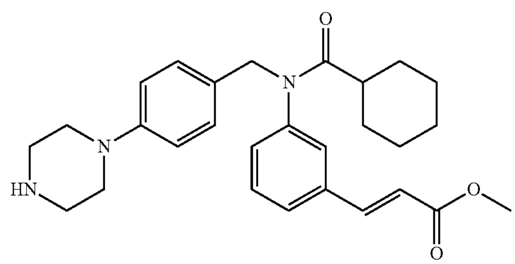 [SMILES: COC(=O)/C=C/c1cccc(N(Cc2ccc(N3CCNCC3)cc2)C(=O)C2CCCCC2)c1] | (E)-Methyl 3-(3-(N-(4-(piperazin-1-yl)benzyl)cyclohexanecarboxamido)phenyl)acrylate |
| 80 | 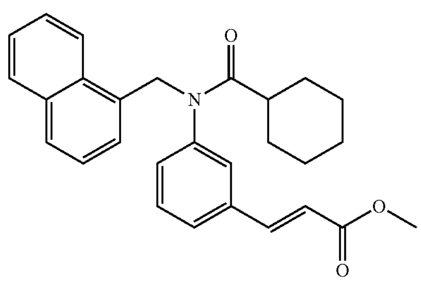 [SMILES: COC(=O)/C=C/c1cccc(N(Cc2cccc3ccccc23)C(=O)C2CCCCC2)c1] | (E)-Methyl 3-(3-(N-(naphthalen-1-ylmethyl)cyclohexanecarboxamido)phenyl)acrylate |
| 81 | 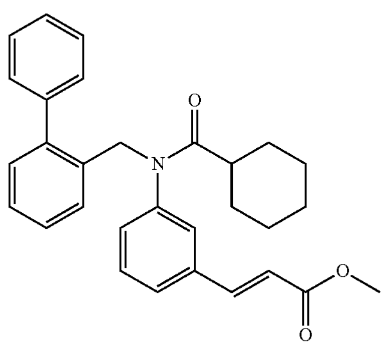 [SMILES: COC(=O)/C=C/c1cccc(N(Cc2ccccc2-c2ccccc2)C(=O)C2CCCCC2)c1] | (E)-Methyl 3-(3-(N-([1,1'-biphenyl]-2-ylmethyl)cyclohexanecarboxamido)phenyl)acrylate |
| 82 | 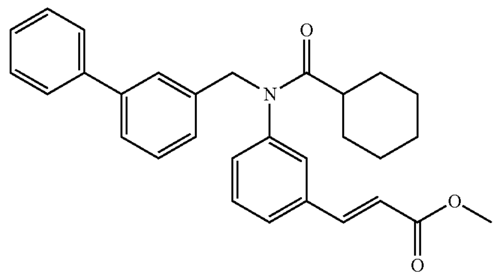 [SMILES: COC(=O)/C=C/c1cccc(N(Cc2cccc(-c3ccccc3)c2)C(=O)C2CCCCC2)c1] | (E)-Methyl 3-(3-(N-([1,1'-biphenyl]-3-ylmethyl)cyclohexanecarboxamido)phenyl)acrylate |

TABLE 1-continued

| Cmpd | Structure | Name |
|---|---|---|
| 83 | 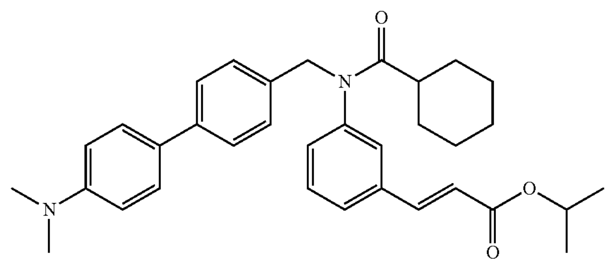 [SMILES: CC(C)OC(=O)/C=C/c1cccc(N(Cc2ccc(-c3ccc(N(C)C)cc3)cc2)C(=O)C2CCCCC2)c1] | (E)-iso-Propyl 3-(3-(N-((4'-(dimethylamino)-[1,1'-biphenyl]-4-yl)methyl)cyclohexanecarboxamido)phenyl)acrylate |
| 84 | 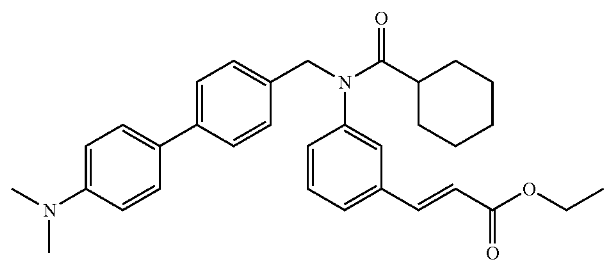 [SMILES: CCOC(=O)/C=C/c1cccc(N(Cc2ccc(-c3ccc(N(C)C)cc3)cc2)C(=O)C2CCCCC2)c1] | (E)-Ethyl 3-(3-(N-((4'-(dimethylamino)-[1,1'-biphenyl]-4-yl)methyl)cyclohexanecarboxamido)phenyl)acrylate |
| 85 | 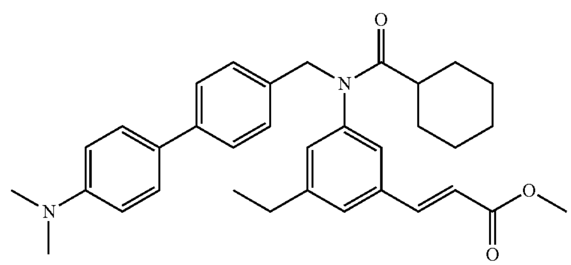 | (E)-Methyl 3-(3-(N-((4'-(dimethylamino)-[1,1'-biphenyl]-4-yl)methyl)cyclohexanecarboxamido)-5-ethylphenyl)acrylate |
| 86 | 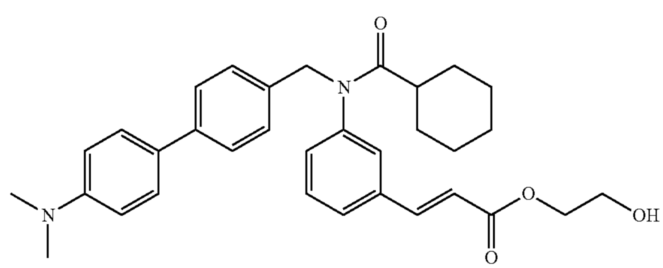 [SMILES: CN(C)c1ccc(-c2ccc(CN(C(=O)C3CCCCC3)c3cccc(/C=C/C(=O)OCCO)c3)cc2)cc1] | (E)-2-Hydroxyethyl 3-(3-(N-((4'-(dimethylamino)-[1,1'-biphenyl]-4-yl)methyl)cyclohexanecarboxamido)phenyl)acrylate |
| 86.1 | 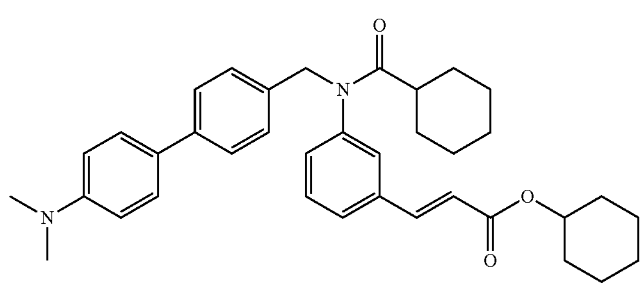 [SMILES: CN(C)c1ccc(-c2ccc(CN(C(=O)C3CCCCC3)c3cccc(/C=C/C(=O)OC4CCCCC4)c3)cc2)cc1] | (E)-Cyclohexyl 3-(3-(N-((4'-(dimethylamino)-[1,1'-biphenyl]-4-yl)methyl)cyclohexanecarboxamido)phenyl)acrylate |
| 86.2 | 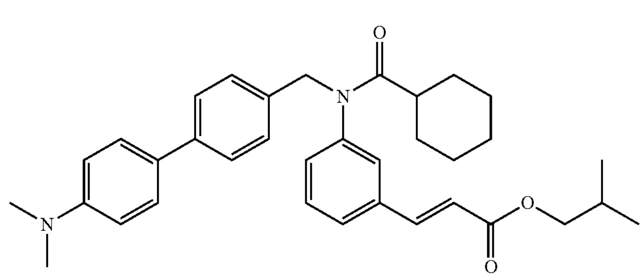 [SMILES: CC(C)COC(=O)/C=C/c1cccc(N(Cc2ccc(-c3ccc(N(C)C)cc3)cc2)C(=O)C2CCCCC2)c1] | (E)-Isobutyl 3-(3-(N-((4'-(dimethylamino)-[1,1'-biphenyl]-4-yl)methyl)cyclohexanecarboxamido)phenyl)acrylate |

TABLE 1-continued

| Cmpd | Structure | Name |
|---|---|---|
| 86.3 | 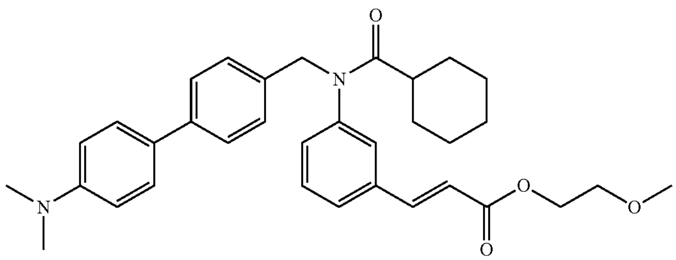 | (E)-2-Methoxyethyl 3-(3-(N-((4'-(dimethylamino)-[1,1'-biphenyl]-4-yl)methyl)cyclohexanecarboxamido)phenyl)acrylate |
| 86.4 | 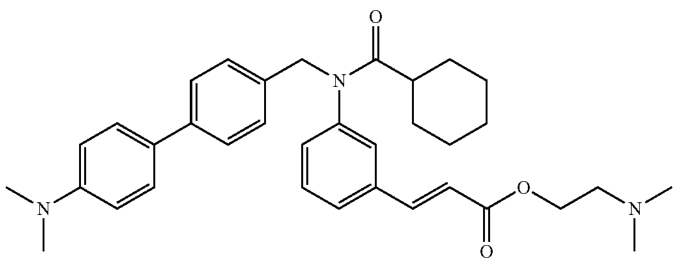 | (E)-2-(Dimethylamino)ethyl 3-(3-(N-((4'-(dimethylamino)-[1,1'-biphenyl]-4-yl)methyl)cyclohexanecarboxamido)phenyl)acrylate |
| 86.5 | 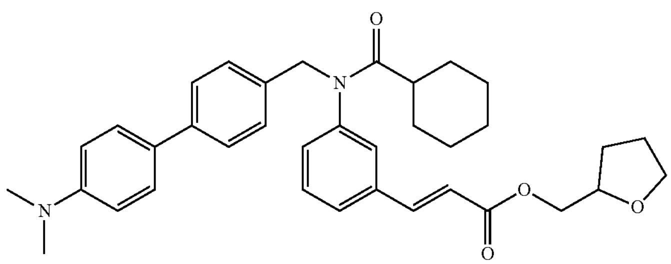 [SMILES: CN(C)c1ccc(-c2ccc(CN(C(=O)C3CCCCC3)c3cccc(/C=C/C(=O)OCC4CCCO4)c3)cc2)cc1] | (E)-(Tetrahydrofuran-2-yl)methyl 3-(3-(N-((4'-(dimethylamino)-[1,1'-biphenyl]-4-yl)methyl)cyclohexanecarboxamido)phenyl)acrylate |
| 86.6 | 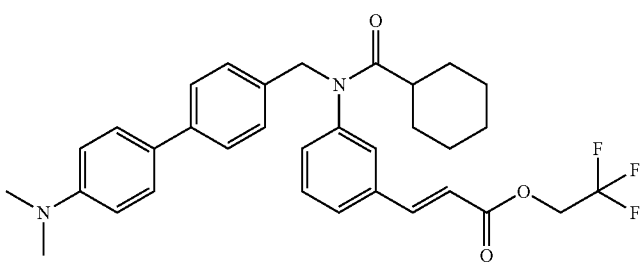 [SMILES: CN(C)c1ccc(-c2ccc(CN(C(=O)C3CCCCC3)c3cccc(/C=C/C(=O)OCC(F)(F)F)c3)cc2)cc1] | (E)-2,2,2-Trifluoroethyl 3-(3-(N-((4'-(dimethylamino)-[1,1'-biphenyl]-4-yl)methyl)cyclohexanecarboxamido)phenyl)acrylate |
| 86.7 | 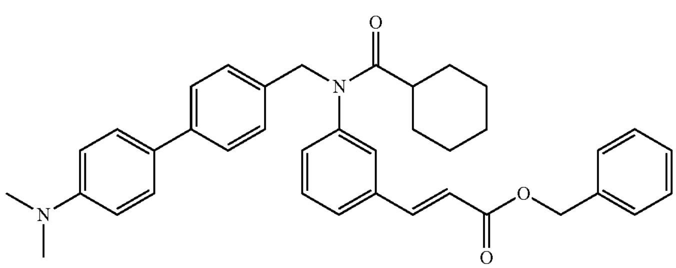 [SMILES: CN(C)c1ccc(-c2ccc(CN(C(=O)C3CCCCC3)c3cccc(/C=C/C(=O)OCc4ccccc4)c3)cc2)cc1] | (E)-Benzyl 3-(3-(N-((4'-(dimethylamino)-[1,1'-biphenyl]-4-yl)methyl)cyclohexanecarboxamido)phenyl)acrylate |
| 86.8 | 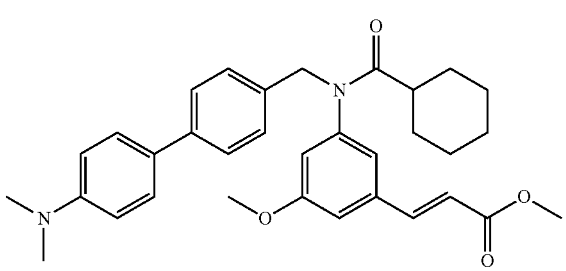 | (E)-Methyl 3-(3-(N-((4'-(dimethylamino)-[1,1'-biphenyl]-4-yl)methyl)cyclohexanecarboxamido)-5-methoxyphenyl)acrylate |

TABLE 1-continued

| Cmpd | Structure | Name |
|---|---|---|
| 86.9 | 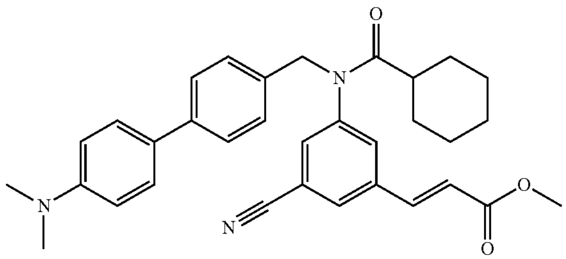 | (E)-Methyl 3-(3-cyano-5-(N-((4'-(dimethylamino)-[1,1'-biphenyl]-4-yl)methyl)cyclohexanecarboxamido)phenyl)acrylate |
| 86.10 | 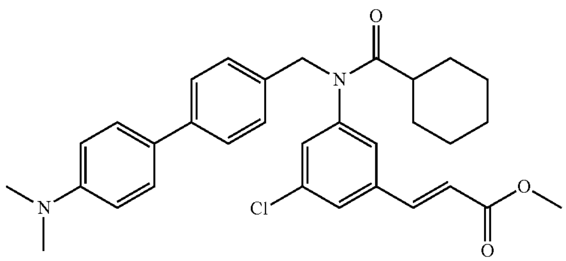 | (E)-Methyl 3-(3-chloro-5-(N-((4'-(dimethylamino)-[1,1'-biphenyl]-4-yl)methyl)cyclohexanecarboxamido)phenyl)acrylate |
| 86.11 | 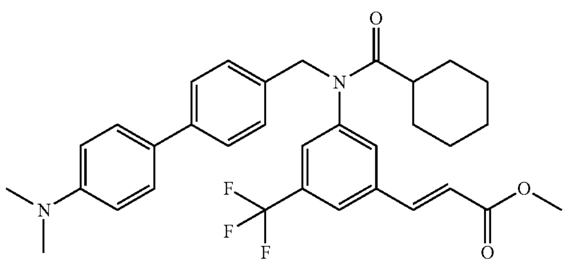 | (E)-Methyl 3-(3-(N-((4'-(dimethylamino)-[1,1'-biphenyl]-4-yl)methyl)cyclohexanecarboxamido)-5-(trifluoromethyl)phenyl)acrylate |
| 87 | 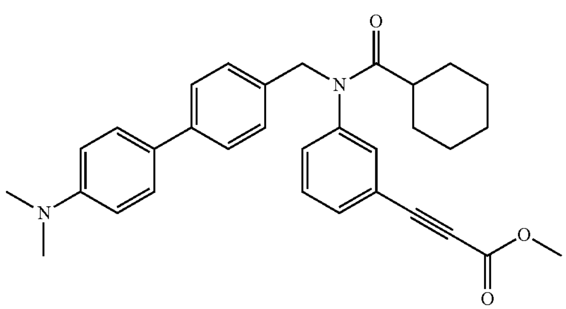 | Methyl 3-(3-(N-((4'-(Dimethylamino)-[1,1'-biphenyl]-4-yl)methyl)cyclohexanecarboxamido)phenyl)propiolate |
| 88 | 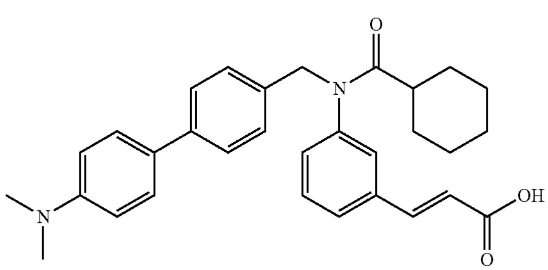 [SMILES: CN(C)c1ccc(-c2ccc(CN(C(=O)C3CCCCC3)c3cccc(/C=C/C(=O)O)c3)cc2)cc1] | (E)-3-(3-(N-((4'-(dimethylamino)-[1,1'-biphenyl]-4-yl)methyl)cyclohexanecarboxamido)phenyl)acrylic acid |

TABLE 1-continued

| Cmpd | Structure | Name |
|---|---|---|
| 89 | 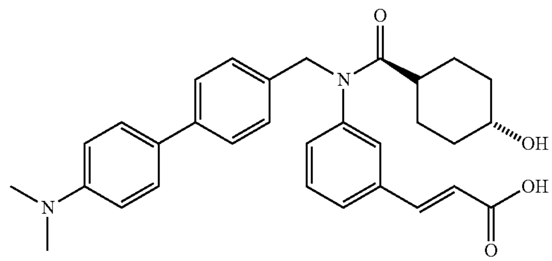 | (E)-3-(3-((1s,4s)-N-((4'-(Dimethylamino)-[1,1'-biphenyl]-4-yl)methyl)-4-hydroxycyclohexanecarboxamido)phenyl)acrylic acid |
| 90 | 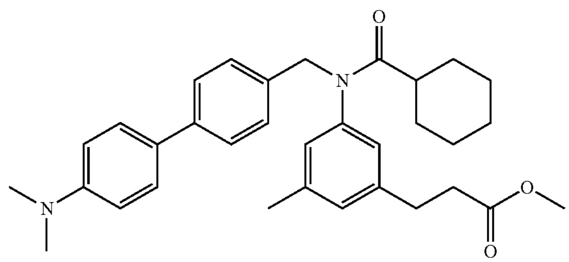 | Methyl 3-(3-(N-((4'-(dimethylamino)-[1,1'-biphenyl]-4-yl)methyl)cyclohexanecarboxamido)-5-methylphenyl)propanoate |
| 91 | 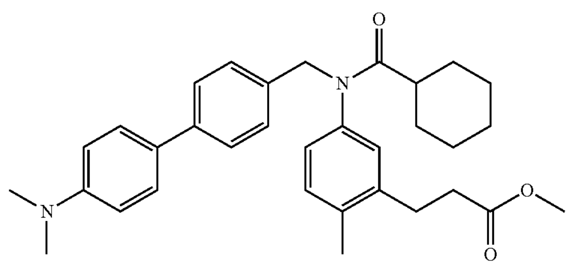 | Methyl 3-(5-(N-((4'-(dimethylamino)-[1,1'-biphenyl]-4-yl)methyl)cyclohexanecarboxamido)-2-methylphenyl)propanoate |
| 92 | 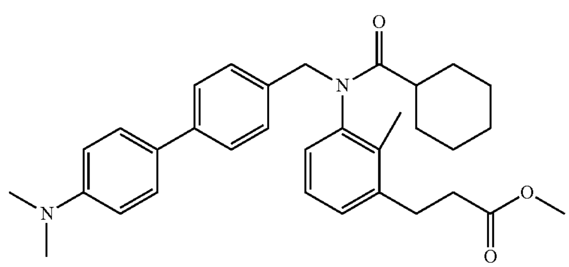 | Methyl 3-(3-(N-((4'-(dimethylamino)-[1,1'-biphenyl]-4-yl)methyl)cyclohexanecarboxamido)-2-methylphenyl)propanoate |
| 93 | 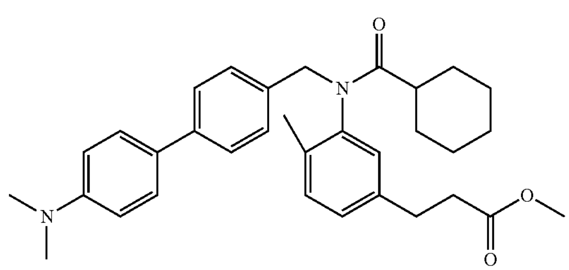 | Methyl 3-(3-(N-((4'-(dimethylamino)-[1,1'-biphenyl]-4-yl)methyl)cyclohexanecarboxamido)-4-methylphenyl)propanoate |
| 94 | 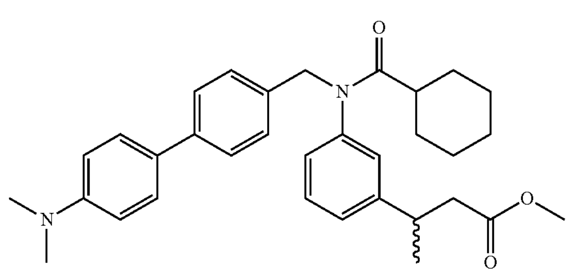 | Methyl 3-(3-(N-((4'-(dimethylamino)-[1,1'-biphenyl]-4-yl)methyl)cyclohexanecarboxamido)phenyl)butanoate |

TABLE 1-continued

| Cmpd | Structure | Name |
|---|---|---|
| 95 | 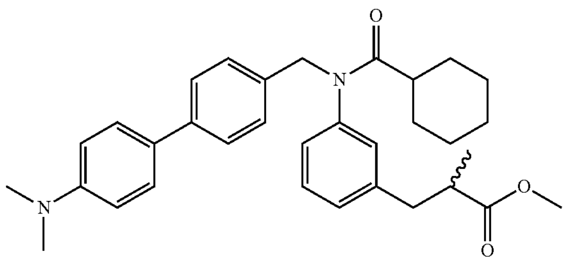 | Methyl 3-(3-(N-((4'-(dimethylamino)-[1,1'-biphenyl]-4-yl)methyl)cyclohexanecarboxamido)phenyl)-2-methylpropanoate |
| 96 | 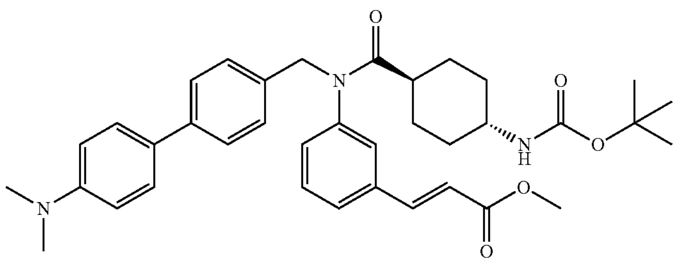 [SMILES: COC(=O)/C=C/c1cccc(N(Cc2ccc(-c3ccc(N(C)C)cc3)cc2)C(=O)[C@H]2CC[C@H](NC(=O)OC(C)(C)C)CC2)c1] | (E)-Methyl 3-(3-(trans-4-((tert-butoxycarbonyl)amino)-N-((4'-(dimethylamino)-[1,1'-biphenyl]-4-yl)methyl)cyclohexanecarboxamido)phenyl)acrylate |
| 97 | 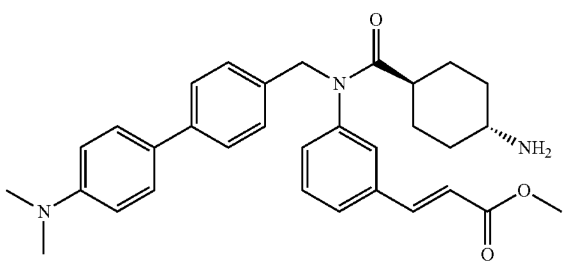 | (E)-Methyl 3-(3-(trans-4-amino-N-((4'-(dimethylamino)-[1,1'-biphenyl]-4-yl)methyl)cyclohexanecarboxamido)phenyl)acrylate |
| 98 | 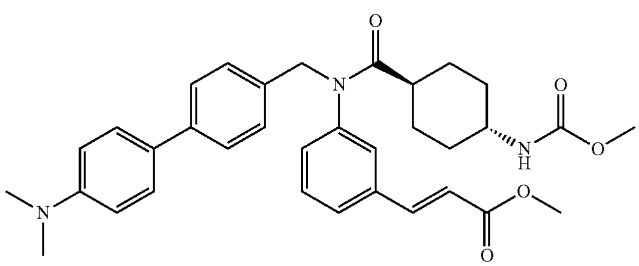 | (E)-Methyl 3-(3-(trans-N-((4'-(dimethylamino)-[1,1'-biphenyl]-4-yl)methyl)-4-((methoxycarbonyl)amino)cyclohexanecarboxamido)phenyl)acrylate |
| 98.1 | 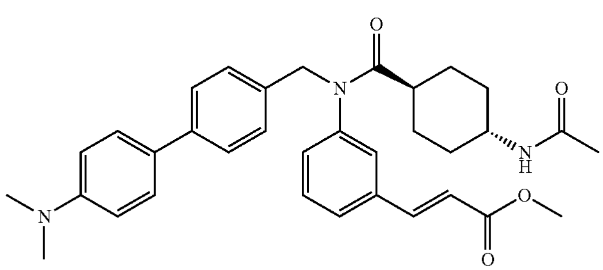 [SMILES: COC(=O)/C=C/c1cccc(N(Cc2ccc(-c3ccc(N(C)C)cc3)cc2)C(=O)[C@H]2CC[C@H](NC(C)=O)CC2)c1] | trans-(E)-Methyl 3-(3-(4-acetamido-N-((4'-(dimethylamino)-[1,1'-biphenyl]-4-yl)methyl)cyclohexanecarboxamido)phenyl)acrylate |
| 98.2 | 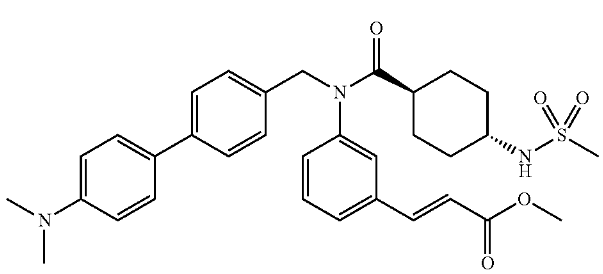 | trans-(E)-Methyl 3-(3-(N-((4'-(dimethylamino)-[1,1'-biphenyl]-4-yl)methyl)-4-(methylsulfonamido)cyclohexanecarboxamido)phenyl)acrylate |

TABLE 1-continued

| Cmpd | Structure | Name |
| --- | --- | --- |
| 99 | 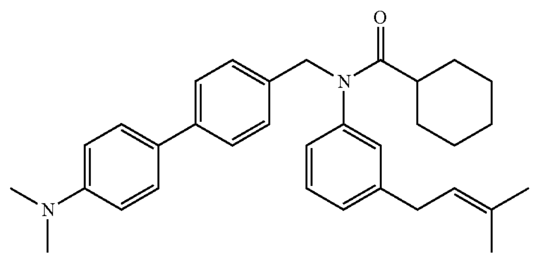 [SMILES: CC(C)=CCc1cccc(N(Cc2ccc(-c3ccc(N(C)C)cc3)cc2)C(=O)C2CCCCC2)c1] | N-((4'-(Dimethylamino)-[1,1'-biphenyl]-4-yl)methyl)-N-(3-(3-methylbut-2-en-1-yl)phenyl)cyclohexanecarboxamide |
| 100 | 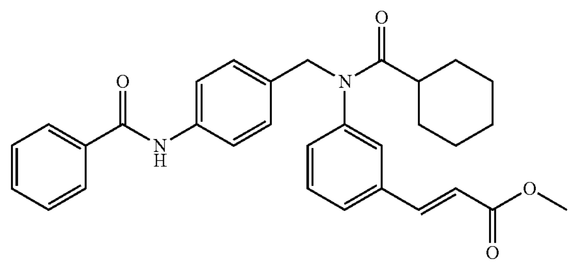 | (E)-Methyl 3-(3-(N-(4-benzamidobenzyl)cyclohexanecarboxamido)phenyl)acrylate |
| 101 | 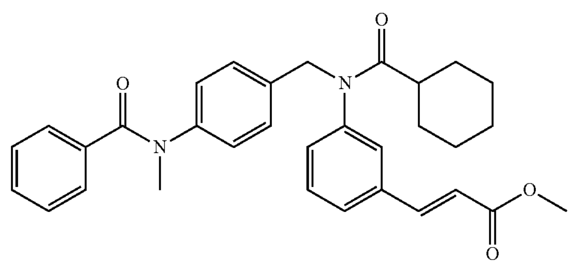 [SMILES: COC(=O)/C=C/c1cccc(N(Cc2ccc(N(C)C(=O)c3ccccc3)cc2)C(=O)C2CCCCC2)c1] | (E)-Methyl 3-(3-(N-(4-(N-methylbenzamido)benzyl)cyclohexane-carboxamido)phenyl)acrylate |
| 102 | 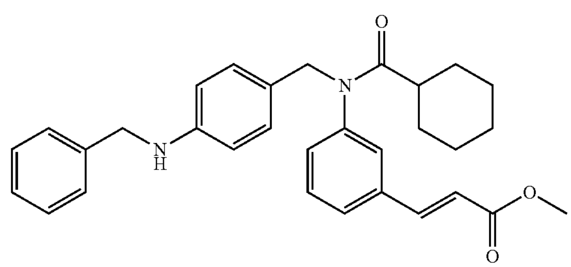 [SMILES: COC(=O)/C=C/c1cccc(N(Cc2ccc(NCc3ccccc3)cc2)C(=O)C2CCCCC2)c1] | (E)-Methyl 3-(3-(N-(4-(benzylamino)benzyl)cyclohexane-carboxamido)phenyl)acrylate |
| 103 | 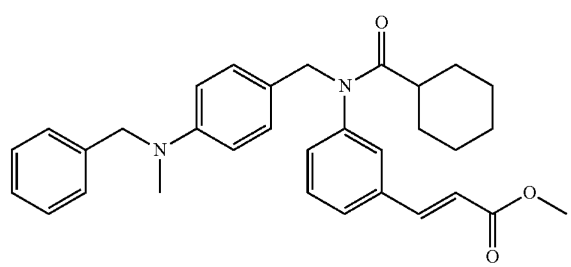 [SMILES: COC(=O)/C=C/c1cccc(N(Cc2ccc(N(C)Cc3ccccc3)cc2)C(=O)C2CCCCC2)c1] | (E)-Methyl 3-(3-(N-(4-(benzyl(methyl)amino)benzyl)cyclo-hexanecarboxamido)phenyl)acrylate |

TABLE 2

| Structure | Name |
| --- | --- |
| 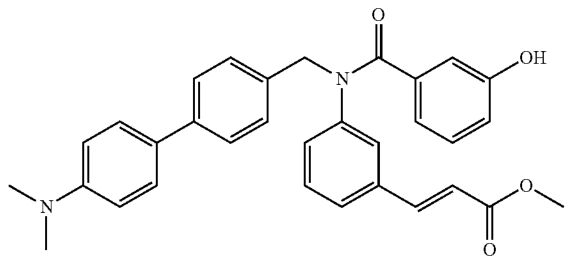 | (E)-Methyl 3-(3-(N-((4'-(dimethylamino)-[1,1'-biphenyl]-4-yl)methyl)-3-hydroxybenzamido)phenyl)acrylate |
| 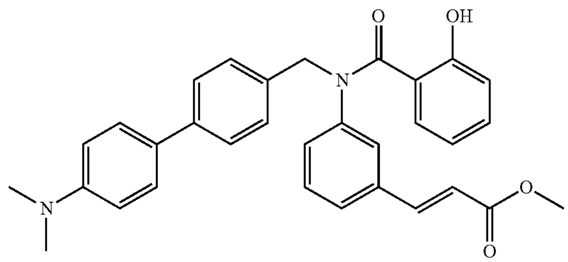 | (E)-Methyl 3-(3-(N-((4'-(dimethylamino)-[1,1'-biphenyl]-4-yl)methyl)-2-hydroxybenzamido)phenyl)acrylate |
| 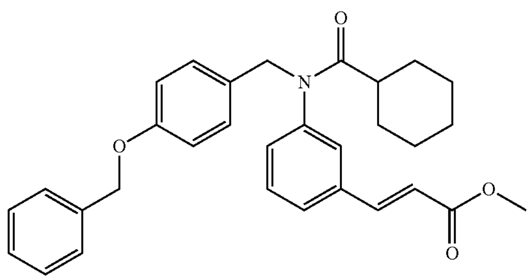 [SMILES: COC(=O)/C=C/c1cccc(N(Cc2ccc(OCc3ccccc3)cc2)C(=O)C2CCCCC2)c1] | (E)-Methyl 3-(3-(N-(4-(benzyloxy)benzyl)cyclohexanecarboxamido)phenyl)acrylate |
| 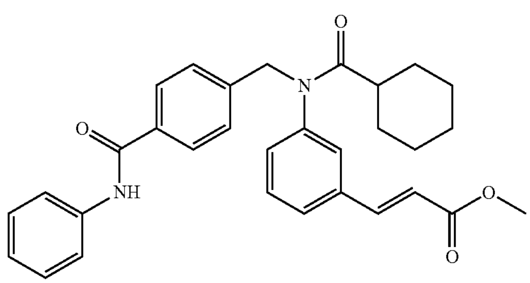 [SMILES: COC(=O)/C=C/c1cccc(N(Cc2ccc(C(=O)Nc3ccccc3)cc2)C(=O)C2CCCCC2)c1] | (E)-Methyl 3-(3-(N-(4-(phenylcarbamoyl)benzyl)cyclohexanecarboxamido)phenyl)acrylate |
| 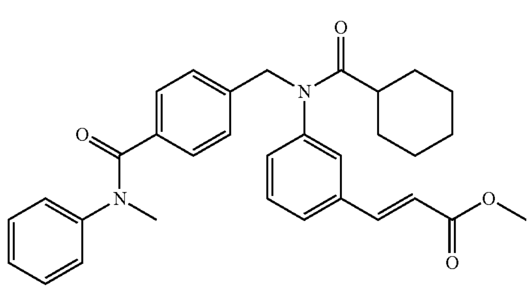 [SMILES: COC(=O)/C=C/c1cccc(N(Cc2ccc(C(=O)N(C)c3ccccc3)cc2)C(=O)C2CCCCC2)c1] | (E)-Methyl 3-(3-(N-(4-(methyl(phenyl)carbamoyl)benzyl)cyclohexanecarboxamido)phenyl)acrylate |

TABLE 2-continued

| Structure | Name |
|---|---|
| 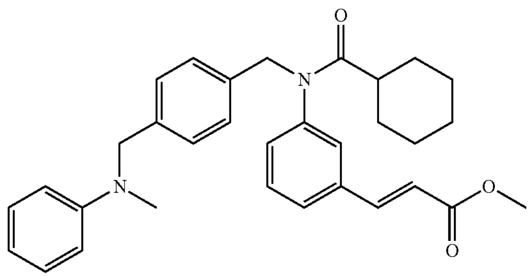 [SMILES: COC(=O)/C=C/c1cccc(N(Cc2ccc(CN(C)c3ccccc3)cc2)C(=O)C2CCCCC2)c1] | (E)-Methyl 3-(3-(N-(4-((methyl(phenyl)amino)methyl)benzyl)cyclohexane-carboxamido)phenyl)acrylate |
| 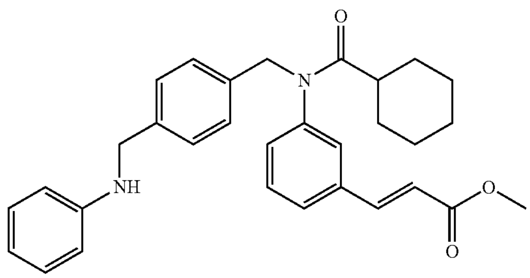 [SMILES: COC(=O)/C=C/c1cccc(N(Cc2ccc(CNc3ccccc3)cc2)C(=O)C2CCCCC2)c1] | (E)-Methyl 3-(3-(N-(4-((phenylamino)methyl)benzyl)cyclohexanecarbox-amido)phenyl)acrylate |
| 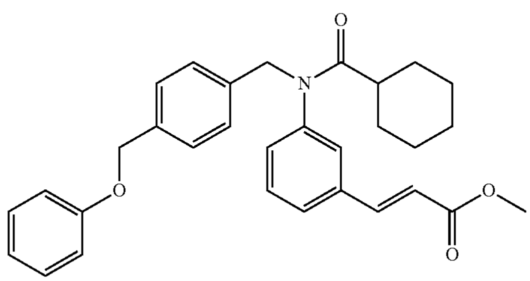 [SMILES: COC(=O)/C=C/c1cccc(N(Cc2ccc(COc3ccccc3)cc2)C(=O)C2CCCCC2)c1] | (E)-Methyl 3-(3-(N-(4-(phenoxymethyl)benzyl)cyclohexanecarboxamido)phenyl)acrylate |
| 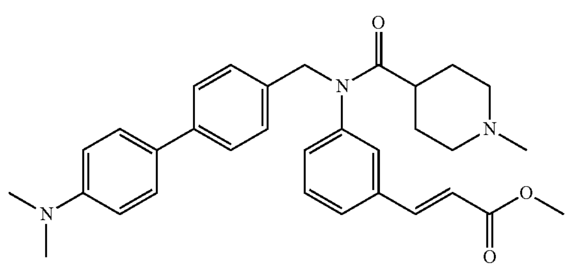 | (E)-Methyl 3-(3-(N-((4'-(dimethylamino)-[1,1'-biphenyl]-4-yl)methyl)-1-methylpiperidine-4-carboxamido)phenyl)acrylate |
| 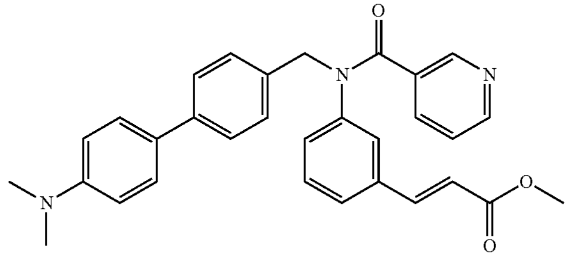 | (E)-Methyl 3-(3-(N-((4'-(dimethylamino)-[1,1'-biphenyl]-4-yl)methyl)nicotinamido)phenyl)acrylate |

TABLE 2-continued

| Structure | Name |
|---|---|
| 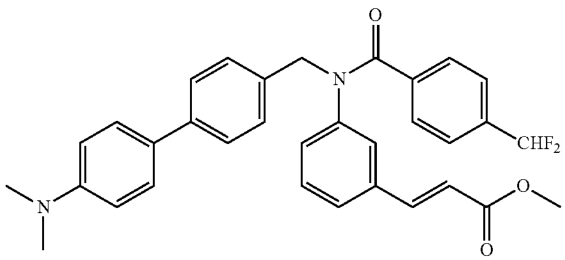 | (E)-Methyl 3-(3-(4-(difluoromethyl)-N-((4'-(dimethylamino)-[1,1'-biphenyl]-4-yl)methyl)benzamido)phenyl)acrylate |
| 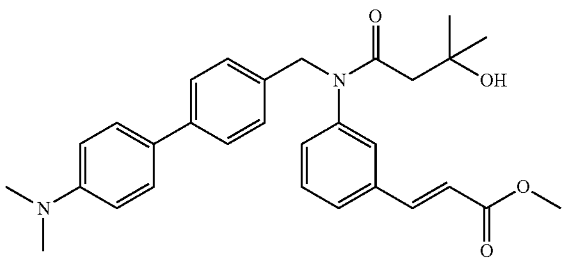 | (E)-Methyl 3-(3-(N-((4'-(dimethylamino)-[1,1'-biphenyl]-4-yl)methyl)-3-hydroxy-3-methylbutanamido)phenyl)acrylate |
| 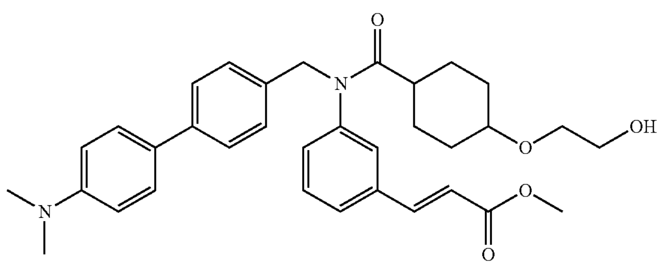 [SMILES: COC(=O)/C=C/c1cccc(N(Cc2ccc(-c3ccc(N(C)C)cc3)cc2)C(=O)C2CCC(OCCO)CC2)c1] | (E)-Methyl 3-(3-(N-((4'-(dimethylamino)-[1,1'-biphenyl]-4-yl)methyl)-4-(2-hydroxyethoxy)cyclohexanecarboxamido)phenyl)acrylate |
| 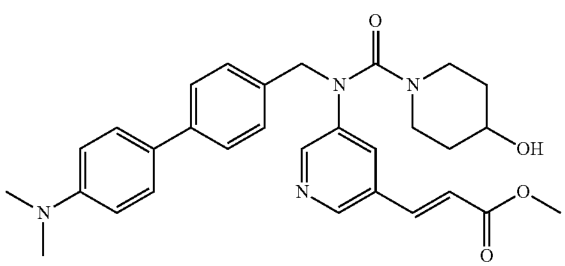 | (E)-Methyl 3-(5-(N-((4'-(dimethylamino)-[1,1'-biphenyl]-4-yl)methyl)-4-hydroxypiperidine-1-carboxamido)pyridin-3-yl)acrylate |
| 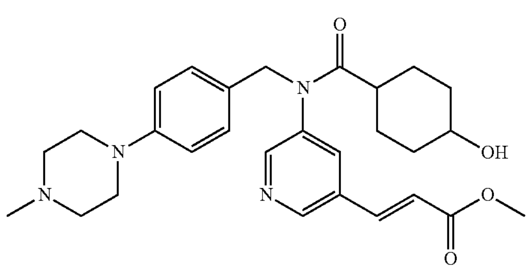 | (E)-Methyl 3-(5-(4-hydroxy-N-(4-(4-methylpiperazin-1-yl)benzyl)cyclohexanecarboxamido)pyridin-3-yl)acrylate |
| 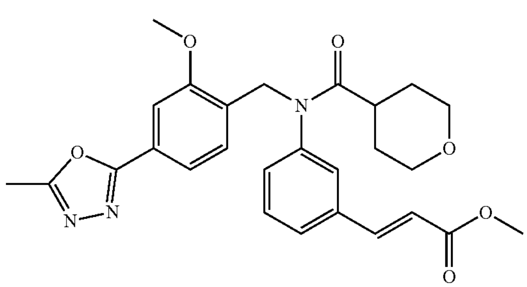 | (E)-Methyl 3-(3-(N-(2-methoxy-4-(5-methyl-1,3,4-oxadiazol-2-yl)benzyl)tetrahydro-2H-pyran-4-carboxamido)phenyl)acrylate |

TABLE 2-continued

| Structure | Name |
|---|---|
| 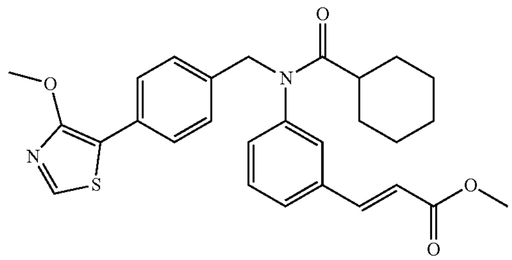 | (E)-Methyl 3-(3-(N-(4-(4-methoxythiazol-5-yl)benzyl)cyclohexanecarboxamido)phenyl)acrylate |
| 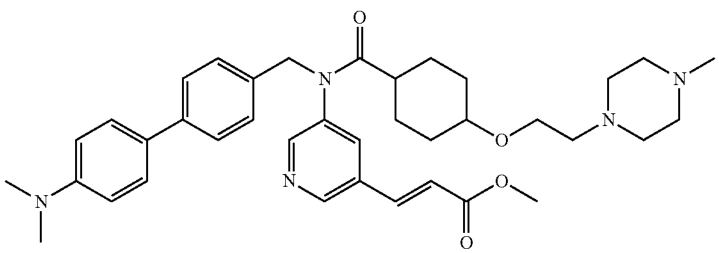 | (E)-Methyl 3-(5-(N-((4'-(dimethylamino)-[1,1'-biphenyl]-4-yl)methyl)-4-(2-(4-methylpiperazin-1-yl)ethoxy)cyclohexanecarboxamido)pyridin-3-yl)acrylate |
| 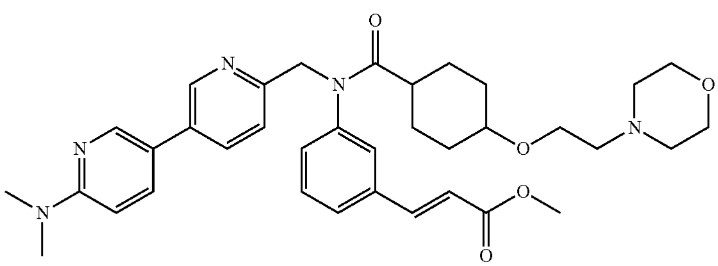 [SMILES: COC(=O)/C=C/c1cccc(N(Cc2ccc(-c3ccc(N(C)C)nc3)cn2)C(=O)C2CCC(OCCN3CCOCC3)CC2)c1] | (E)-Methyl 3-(3-(N-((6'-(dimethylamino)-[3,3'-bipyridin]-6-yl)methyl)-4-(2-morpholinoethoxy)cyclohexanecarboxamido)phenyl)acrylate |
| 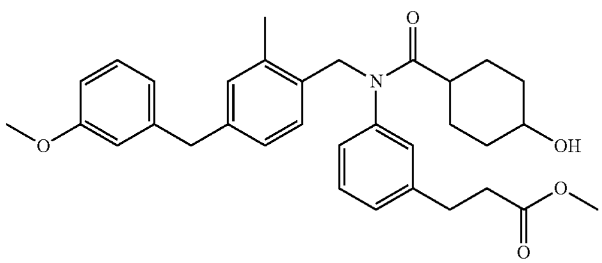 | Methyl 3-(3-(4-hydroxy-N-(4-(3-methoxybenzyl)-2-methylbenzyl)cyclohexanecarboxamido)phenyl)propanoate |
| 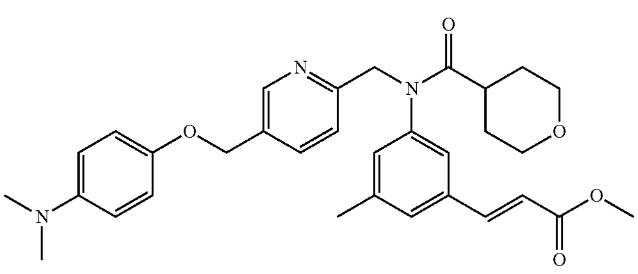 | (E)-Methyl 3-(3-(N-((5-((4-(dimethylamino)phenoxy)methyl)pyridin-2-yl)methyl)tetrahydro-2H-pyran-4-carboxamido)-5-methylphenyl)acrylate |
| 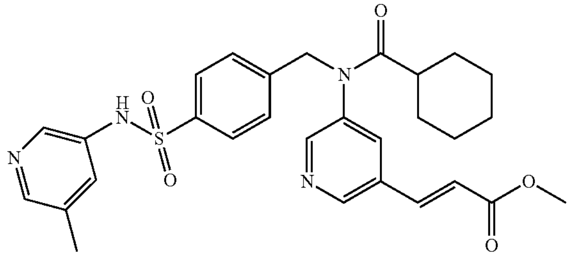 [SMILES: COC(=O)/C=C/c1cncc(N(Cc2ccc(S(=O)(=O)Nc3cncc(C)c3)cc2)C(=O)C2CCCCC2)c1] | (E)-Methyl 3-(5-(N-(4-(N-(5-methylpyridin-3-yl)sulfamoyl)benzyl)cyclohexanecarboxamido)pyridin-3-yl)acrylate |

TABLE 2-continued

| Structure | Name |
|---|---|
| 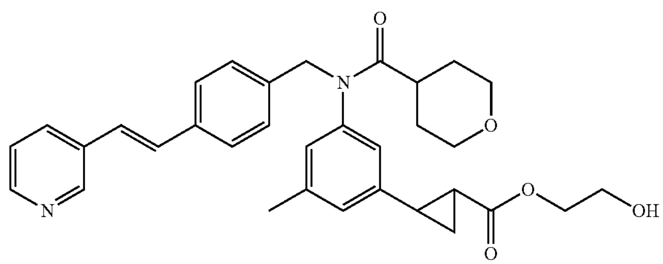 [SMILES: Cc1cc(C2CC2C(=O)OCCO)cc(N(Cc2ccc(/C=C/c3cccnc3)cc2)C(=O)C2CCOCC2)c1] | (E)-2-Hydroxyethyl 2-(3-methyl-5-(N-(4-(2-(pyridin-3-yl)vinyl)benzyl)tetrahydro-2H-pyran-4-carboxamido)phenyl)cyclopropanecarboxylate |
| 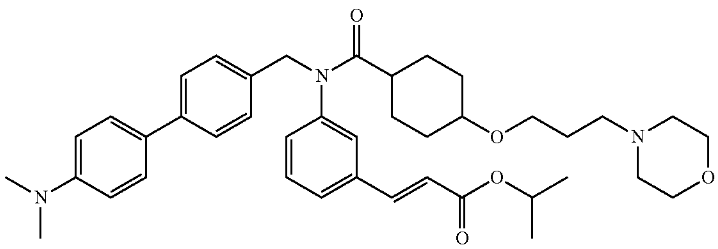 [SMILES: CC(C)OC(=O)/C=C/c1cccc(N(Cc2ccc(-c3ccc(N(C)C)cc3)cc2)C(=O)C2CCC(OCCCN3CCOCC3)CC2)c1] | (E)-Isopropyl 3-(3-(N-((4'-(dimethylamino)-[1,1'-biphenyl]-4-yl)methyl)-4-(3-morpholinopropoxy)cyclohexanecarboxamido)phenyl)acrylate |
| 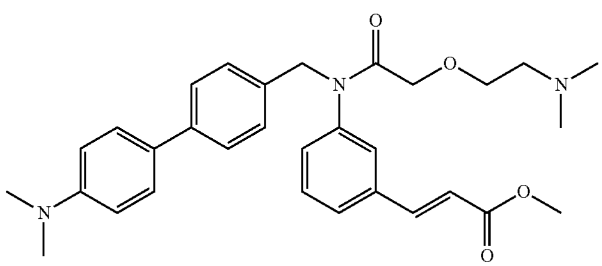 | (E)-Methyl 3-(3-(N-((4'-(dimethylamino)-[1,1'-biphenyl]-4-yl)methyl)-2-(2-(dimethylamino)ethoxy)acetamido)phenyl)acrylate |
| 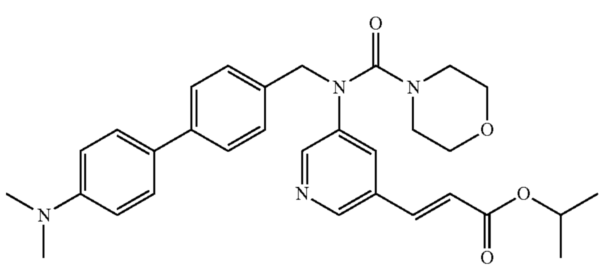 [SMILES: CC(C)OC(=O)/C=C/c1cncc(N(Cc2ccc(-c3ccc(N(C)C)cc3)cc2)C(=O)N2CCOCC2)c1] | (E)-Isopropyl 3-(5-(N-((4'-(dimethylamino)-[1,1'-biphenyl]-4-yl)methyl)morpholine-4-carboxamido)pyridin-3-yl)acrylate |
| 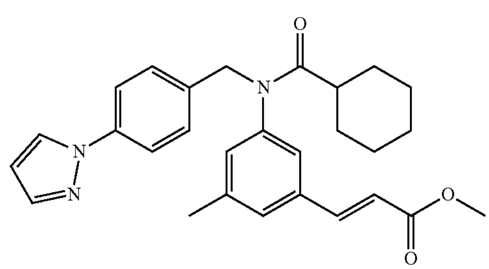 [SMILES: COC(=O)/C=C/c1cc(C)cc(N(Cc2ccc(-n3cccn3)cc2)C(=O)C2CCCCC2)c1] | (E)-Methyl 3-(3-(N-(4-(1H-pyrazol-1-yl)benzyl)cyclohexanecarboxamido)-5-methylphenyl)acrylate |
| 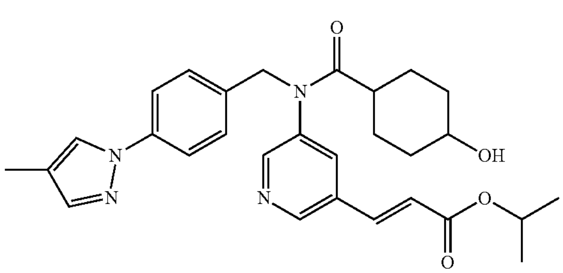 [SMILES: Cc1cnn(-c2ccc(CN(C(=O)C3CCC(O)CC3)c3cncc(/C=C/C(=O)OC(C)C)c3)cc2)c1] | (E)-Isopropyl 3-(5-(4-hydroxy-N-(4-(4-methyl-1H-pyrazol-1-yl)benzyl)cyclohexanecarboxamido)pyridin-3-yl)acrylate |

TABLE 2-continued

| Structure | Name |
|---|---|
| 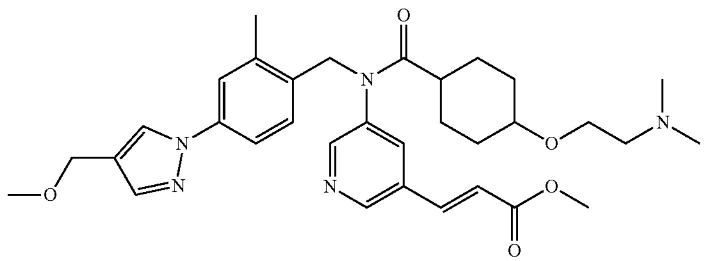 | (E)-Methyl 3-(5-(4-(2-(dimethylamino)ethoxy)-N-(4-(4-(methoxymethyl)-1H-pyrazol-1-yl)-2-methylbenzyl)cyclohexanecarboxamido)pyridin-3-yl)acrylate |
| | (E)-Isopropyl 3-(5-(N-(4-(((1H-indazol-7-yl)carbamoyl)benzyl)-4-hydroxycyclohexanecarboxamido)pyridin-3-yl)acrylate |
| 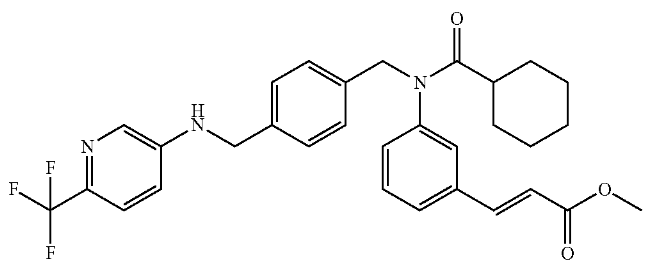 [SMILES: COC(=O)/C=C/c1cccc(N(Cc2ccc(CNc3ccc(C(F)(F)F)nc3)cc2)C(=O)C2CCCCC2)c1] | (E)-Methyl 3-(3-(N-(4-(((6-(trifluoromethyl)pyridin-3-yl)amino)methyl)benzyl)cyclohexanecarboxamido)phenyl)acrylate |
| 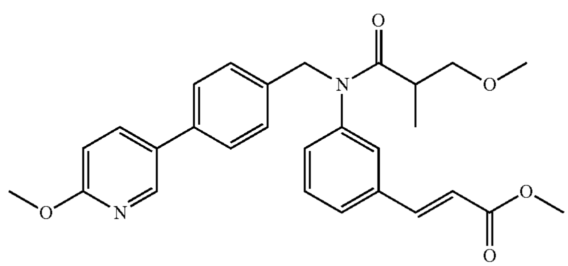 | (E)-Methyl 3-(3-(3-methoxy-N-(4-(6-methoxypyridin-3-yl)benzyl)-2-methylpropanamido)phenyl)acrylate |
| 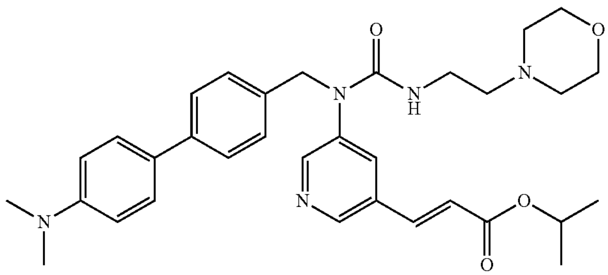 [SMILES: CC(C)OC(=O)/C=C/c1cncc(N(Cc2ccc(-c3ccc(N(C)C)cc3)cc2)C(=O)NCCN2CCOCC2)c1] | (E)-Isopropyl 3-(5-(1-((4'-(dimethylamino)-[1,1'-biphenyl]-4-yl)methyl)-3-(2-morpholinoethyl)ureido)pyridin-3-yl)acrylate |

TABLE 2-continued

| Structure | Name |
|---|---|
| 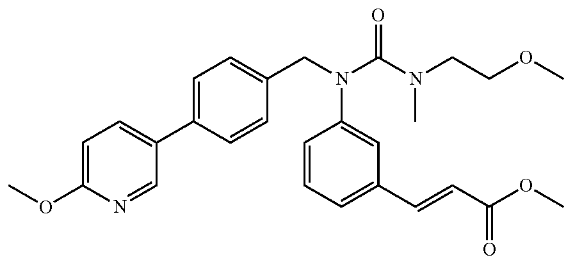 | (E)-Methyl 3-(3-(3-(2-methoxyethyl)-1-(4-(6-methoxypyridin-3-yl)benzyl)-3-methylureido)phenyl)acrylate |
| 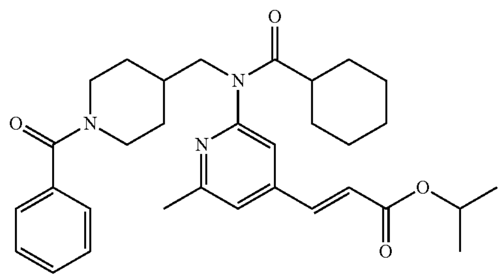 [SMILES: Cc1cc(/C=C/C(=O)OC(C)C)cc(N(CC2CCN(C(=O)c3ccccc3)CC2)C(=O)C2CCCCC2)n1] | (E)-Isopropyl 3-(2-(N-((1-benzoylpiperidin-4-yl)methyl)cyclohexanecarboxamido)-6-methylpyridin-4-yl)acrylate |
| 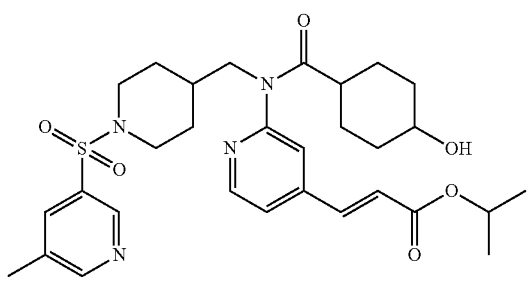 [SMILES: Cc1cncc(S(=O)(=O)N2CCC(CN(C(=O)C3CCC(O)CC3)c3cc(/C=C/C(=O)OC(C)C)ccn3)CC2)c1] | (E)-Isopropyl 3-(2-(4-hydroxy-N-((1-((5-methylpyridin-3-yl)sulfonyl)piperidin-4-yl)methyl)cyclohexanecarboxamido)pyridin-4-yl)acrylate |
| 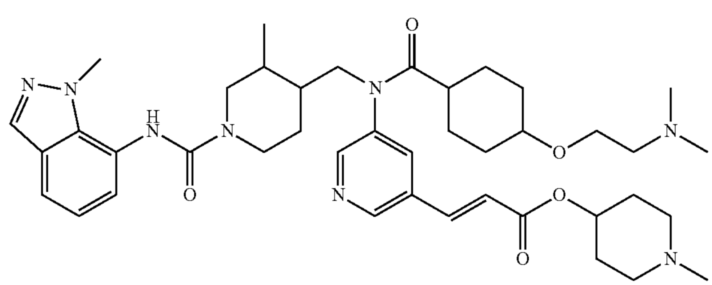 [SMILES: CC1CN(C(=O)Nc2cccc3cnn(C)c23)CCC1CN(C(=O)C1CCC(OCCN(C)C)CC1)c1cncc(/C=C/C(=O)OC2CCN(C)CC2)c1] | (E)-1-Methylpiperidin-4-yl 3-(5-(4-(2-(dimethylamino)ethoxy)-N-((3-methyl-1-((1-methyl-1H-indazol-7-yl)carbamoyl)piperidin-4-yl)methyl)cyclohexanecarboxamido)pyridin-3-yl)acrylate |
| 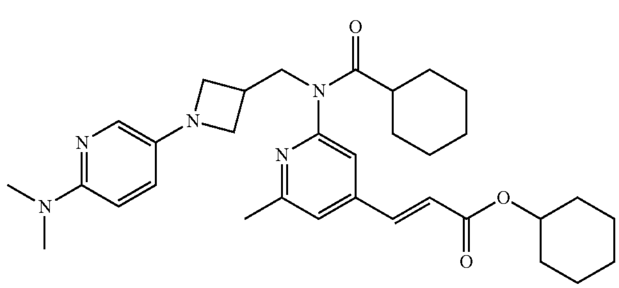 [SMILES: Cc1cc(/C=C/C(=O)OC2CCCCC2)cc(N(CC2CN(c3ccc(N(C)C)nc3)C2)C(=O)C2CCCCC2)n1] | (E)-Cyclohexyl 3-(2-(N-((1-(6-(dimethylamino)pyridin-3-yl)azetidin-3-yl)methyl)cyclohexanecarboxamido)-6-methylpyridin-4-yl)acrylate |

TABLE 2-continued

| Structure | Name |
|---|---|
| 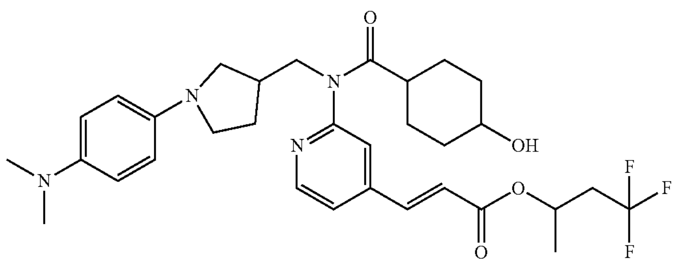 [SMILES: CC(CC(F)(F)F)OC(=O)/C=C/c1ccnc(N(CC2CCN(c3ccc(N(C)C)cc3)C2)C(=O)C2CCC(O)CC2)c1] | (E)-4,4,4-Trifluorobutan-2-yl 3-(2-(N-((1-(4-(dimethylamino)phenyl)pyrrolidin-3-yl)methyl)-4-hydroxycyclohexanecarboxamido)pyridin-4-yl)acrylate |
| 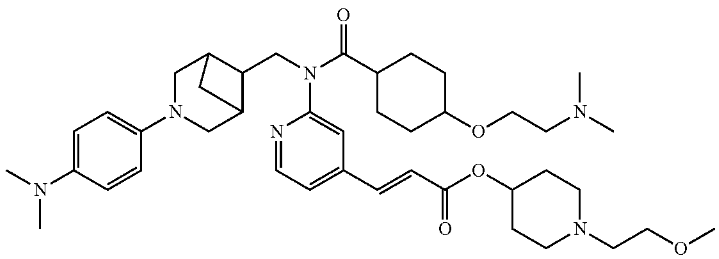 | (E)-1-(2-Methoxyethyl)piperidin-4-yl 3-(2-(4-(2-(dimethylamino)ethoxy)-N-((3-(4-(dimethylamino)phenyl)-3-azabicyclo[3.1.1]heptan-6-yl)methyl)cyclohexanecarboxamido)pyridin-4-yl)acrylate |
| 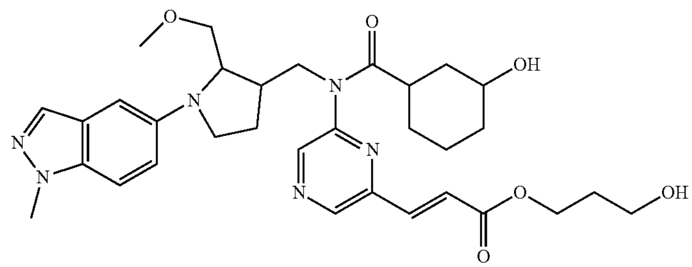 [SMILES: COCC1C(CN(C(=O)C2CCCC(O)C2)c2cncc(/C=C/C(=O)OCCCO)n2)CCN1c1ccc2c(cnn2C)c1] | (E)-3-Hydroxypropyl 3-(6-(3-hydroxy-N-((2-(methoxymethyl)-1-(1-methyl-1H-indazol-5-yl)pyrrolidin-3-yl)methyl)cyclohexanecarboxamido)pyrazin-2-yl)acrylate |
| 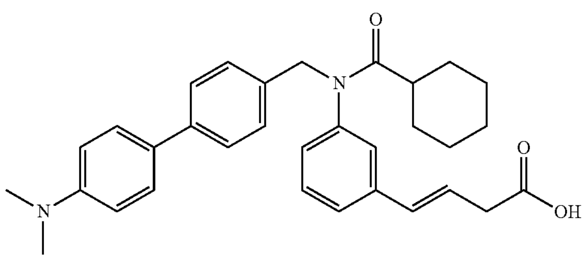 [SMILES: CN(C)c1ccc(-c2ccc(CN(C(=O)C3CCCCC3)c3cccc(/C=C/CC(=O)O)c3)cc2)cc1] | (E)-4-(3-(N-((4'-(Dimethylamino)-[1,1'-biphenyl]-4-yl)methyl)cyclohexanecarboxamido)phenyl)but-3-enoic acid |

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt."

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elsevier, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, the compounds described herein are rapidly metabolized following absorption from the gastro-intestinal tract to metabolites that have greatly reduced FXR agonist activity.

In additional or further embodiments, the compounds are rapidly metabolized in plasma.

In additional or further embodiments, the compounds are rapidly metabolized by the intestines.

In additional or further embodiments, the compounds are rapidly metabolized by the liver.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

The compounds described herein are prepared by the general synthetic routes described below in Schemes 1-8.

temperature for an appropriate amount of time. In some instances, the suitable base is TEA. In some instances, the suitable solvent is DMF. In some instances, the appropriate temperature is about 90° C. In some instances, the appropriate reaction time is about 5 h to about 24 h. In some instances, I-3 is subjected under transition-metal reduction conditions to provide amine I-4. Suitable reaction conditions for transition-metal reduction include but are not limited to Fe, NH$_4$Cl in a suitable solvent mixture at an appropriate temperature for an appropriate amount of time. In some embodiments, the suitable solvent is EtOH and H$_2$O. In some embodiments, the appropriate temperature is about 105° C. and the appropriate time is about 1 h. In other instances, the appropriate temperature is about 90° C. and the appropriate time is about 12 h. In some embodiments, compound I-6 is obtained from subjecting aldehyde I-5 and amine I-4 under reductive amination conditions. In some embodiments, aldehyde I-5 and amine I-4 are first subjected under acidic conditions, such as AcOH in MeOH at rt for about 2 h, before treatment with an appropriate reducing Scheme 1

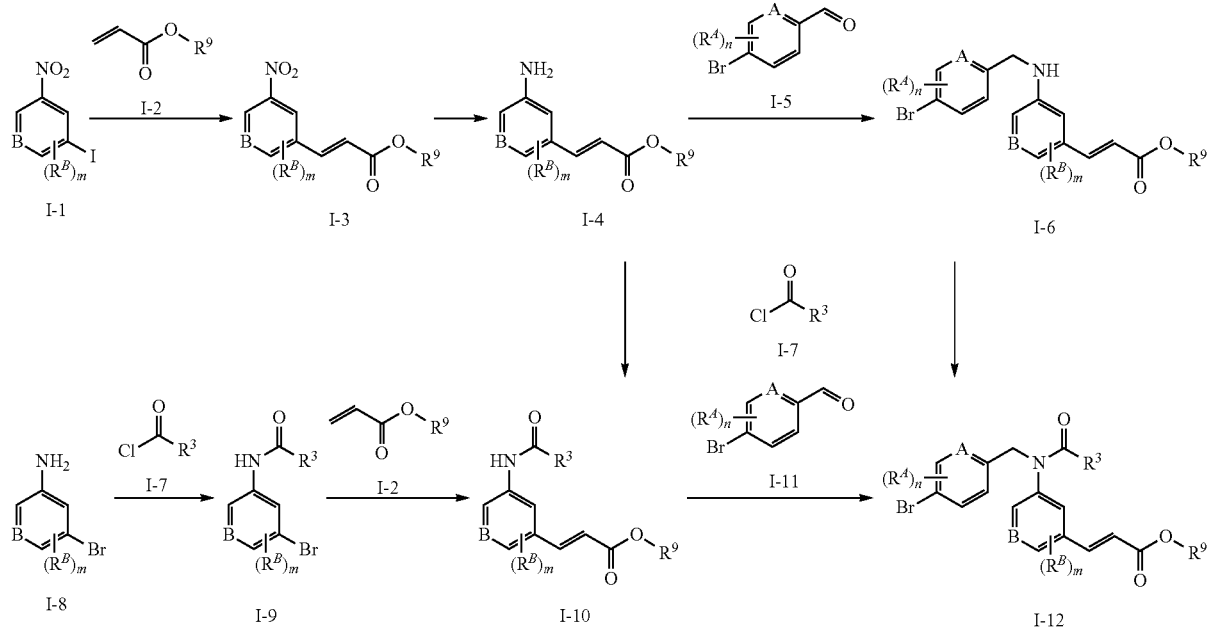

In Scheme 1, B is —CH or C-Me in some embodiments. In some embodiments, A is —CH. In some embodiments, R$^3$ is cyclohexyl. In some embodiments, R$^9$ is methyl. In some embodiments, m is 0 or 1. In some embodiments, m is 0 and B is —CH for compound I-1. In some embodiments, R$^B$ is methyl and m is 1. In some embodiments, R$^B$ is methyl and m is 1 for compound I-8. In some embodiments, m is 0 and B is —CMe for compound I-8. In some embodiments, n is 0. In some embodiments, n is 0 for compound I-5. In some embodiments, R$^4$ is methyl or fluoro and n is 1. In some embodiments, R$^4$ is methyl or fluoro and n is 1 for compound I-11.

In some embodiments, a compound of general structure I-3 is prepared from the palladium-catalyzed Heck reaction of iodide I-1 with acrylate I-2. Suitable conditions for palladium-catalyzed Heck reaction include Pd$_2$dba$_3$ and P(o-tolyl)$_3$ with a suitable base and solvent at an appropriate agent, such as NaBH$_3$CN, for a suitable time at an appropriate temperature, such as rt for about 12 h.

In some embodiments, reaction of I-4 with acyl chloride I-7 under N-acylation conditions provides compound I-10. Suitable N-acylation conditions include but are not limited to TEA in a suitable solvent, such as DCM or ACN, at an appropriate time and temperature. In some embodiments, the appropriate time and temperature is about 1 h to about 16 h and about 0° C. In some embodiments, the appropriate time and temperature is about 2 h to about 16 h and about 0° C. Other suitable conditions include the addition of a catalytic amount of DMAP.

In some embodiments, I-10 is obtained from compound I-8. In some embodiments, reaction of I-8 with acyl chloride I-7 under N-acylation conditions provides compound I-9. Suitable N-acylation conditions include but are not limited to TEA in a suitable solvent, such as DCM or ACN, at an appropriate time and temperature. In some embodiments, the appropriate time and temperature is about 1 h to about 16 h and about 0° C. In some embodiments, the appropriate time and temperature is about 2 h to about 16 h and about 0° C. to rt. Other suitable conditions include the addition of a catalytic amount of DMAP. In some embodiments, a compound I-10 is prepared from the palladium-catalyzed Heck reaction of bromide I-9 with acrylate I-2. Suitable conditions in a suitable solvent, such as THF or DMF, at an appropriate time and temperature. In some embodiments, compound I-10 is pre-treated with NaH for an appropriate time and temperature prior to addition of benzyl bromide I-11. In some embodiments, the appropriate time and temperature prior to addition of benzyl bromide I-11 is about 0.5 h to about 1 hour at 0° C. In some embodiments, the reaction is allowed to proceed for about 5 h to about 14 h at about 0° C. to rt after the addition of the benzyl bromide I-11.

Scheme 2

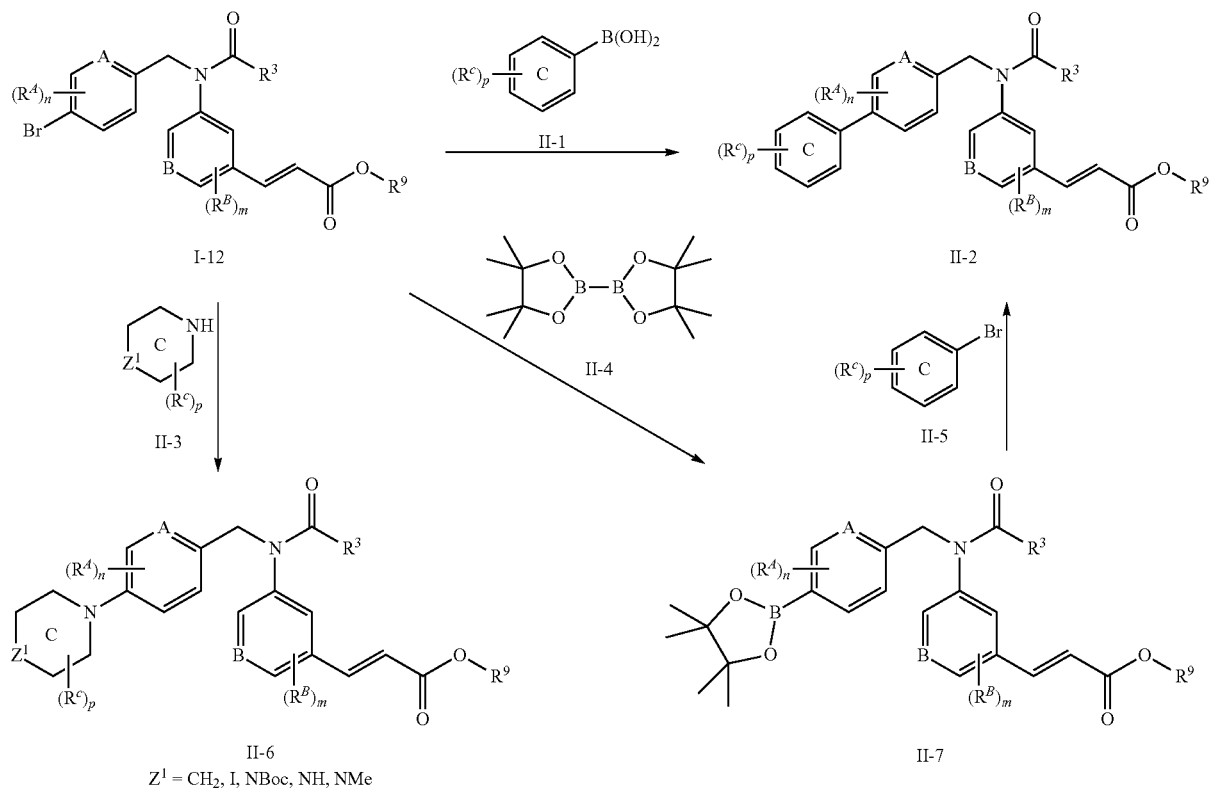

$Z^1$ = CH$_2$, I, NBoc, NH, NMe for palladium-catalyzed Heck reaction include Pd$_2$dba$_3$ and P(o-tolyl)$_3$ with a suitable base and solvent at an appropriate temperature for an appropriate amount of time. In some instances, the suitable base is TEA. In some instances, the suitable solvent is DMF. In some instances, the appropriate temperature is about 90° C. In some cases, the appropriate reaction time is about 5 h to about 24 h. In some embodiments, acrylate I-2 and amine I-8 are coupled under palladium-catalyzed Heck reaction conditions as described above to provide amine I-4.

In some embodiments, compound I-12 is obtained from subjecting I-6 under N-acylation conditions with acyl chloride I-7. Suitable N-acylation conditions include but are not limited to TEA in a suitable solvent, such as DCM or ACN, at an appropriate time and temperature. In some embodiments, the appropriate time and temperature is about 1 h to about 16 h and about 0° C. In some embodiments, the appropriate time and temperature is about 2 h to about 16 h and about 0° C. to rt. Other suitable conditions include the addition of a catalytic amount of DMAP. In some instances, compound I-12 is obtained from subjecting I-10 under N-alkylation conditions with benzyl bromide I-11. Suitable N-alkylation conditions include but are not limited to NaH In Scheme 2, B is —CH in some embodiments. In some embodiments, A is —CH. In some embodiments, other C rings contemplated for use include the C rings described herein. In some embodiments, $R^3$ is cyclohexyl. In some embodiments, $R^9$ is methyl. In some embodiments, m is 0. In some embodiments, n is 0. In some embodiments, $R^C$ is H, F, Cl, Me, CF$_3$, iPr, alkenyl, CN, OH, OMe, OiPr, OCF$_3$, NMe$_2$, N(Me)Boc, or N(Me)H, and p is 1 or 2.

In some embodiments, compound II-2 is prepared from the palladium-catalyzed cross coupling of bromide I-12 with boronic acid II-1. Suitable palladium catalysts for cross coupling include but are not limited to Pd(PPh$_3$)$_4$, Pd(PPh$_3$)$_2$Cl$_2$ and Pd(dppf)Cl$_2$ in a suitable solvent, such as THF, DMF, or DME, with an appropriate base at the suitable temperature for an appropriate amount of time. In some embodiments, the appropriate base is CsF, K$_2$CO$_3$ or Cs$_2$CO$_3$. In some embodiments, the suitable temperature is about 90° C. In some embodiments, the appropriate amount of time is about 5 h. In some embodiments, the appropriate amount of time is about 5 h to about 24 h. In some embodiments, the suitable temperature is about 80° C. In some embodiments, the appropriate amount of time is about 1 h to about 17 h. For some embodiments, wherein compound II-1 is NH-indazole-B(OH)$_2$, the suitable conditions for palladium-catalyzed cross-coupling includes Pd(PPh$_3$)$_4$ with a suitable base and solvent at an appropriate temperature for an appropriate amount of time, such as about 80° C. for about 46 h. In some embodiments, the suitable base is K$_2$CO$_3$. In some embodiments, the suitable base is an aqueous solution of base. In some embodiments, the suitable solvent is DME. In some embodiments, wherein R$^C$ is N(Me)Boc and p is 1 or 2, compound II-2 is further subjected under acidic conditions, such as TFA in DCM, to afford a compound, wherein R$^C$ is N(Me)H.

Alternatively, bromide I-12 is reacted with amine II-3 under palladium-catalyzed cross-coupling conditions to provide II-6. Suitable palladium catalysts for cross-coupling include but are not limited to Pd(OAc)$_2$ with a suitable ligand in a suitable solvent, such as PhMe, with an appropriate base at the suitable temperature for an appropriate amount of time. In some embodiments, the suitable ligand is BINAP. In some embodiments, the appropriate base is Cs$_2$CO$_3$. In some embodiments, the suitable temperature and appropriate amount of time is about 100° C. and about 12 h.

In some embodiments, bromide I-12 is reacted with bis(pinacolato)diboron (II-4) under palladium-catalyzed cross-coupling conditions to provide pinacol boronate ester II-7. Suitable palladium catalysts for cross-coupling include but are not limited to Pd(dppf)Cl$_2$ in a suitable solvent, such as DMF, with an appropriate base at the suitable temperature for an appropriate amount of time. In some embodiments, the appropriate base is KOAc. In some embodiments, the suitable temperature and appropriate amount of time is about 90° C. and about 24 h. In some embodiments, pinacol boronate ester II-7 is reacted with aryl bromide II-5 under palladium-catalyzed cross-coupling conditions to provide compound II-2. Suitable palladium catalysts for cross-coupling include but are not limited to Pd(PPh$_3$)$_4$ in a suitable solvent, such as DMF, with an appropriate base at the suitable temperature for an appropriate amount of time. In some embodiments, the appropriate base is Cs$_2$CO$_3$. In some embodiments, the suitable temperature and appropriate amount of time is about 90° C. and about 12 h. In some embodiments, the suitable temperature and appropriate amount of time is about 80° C. and about 5 h.

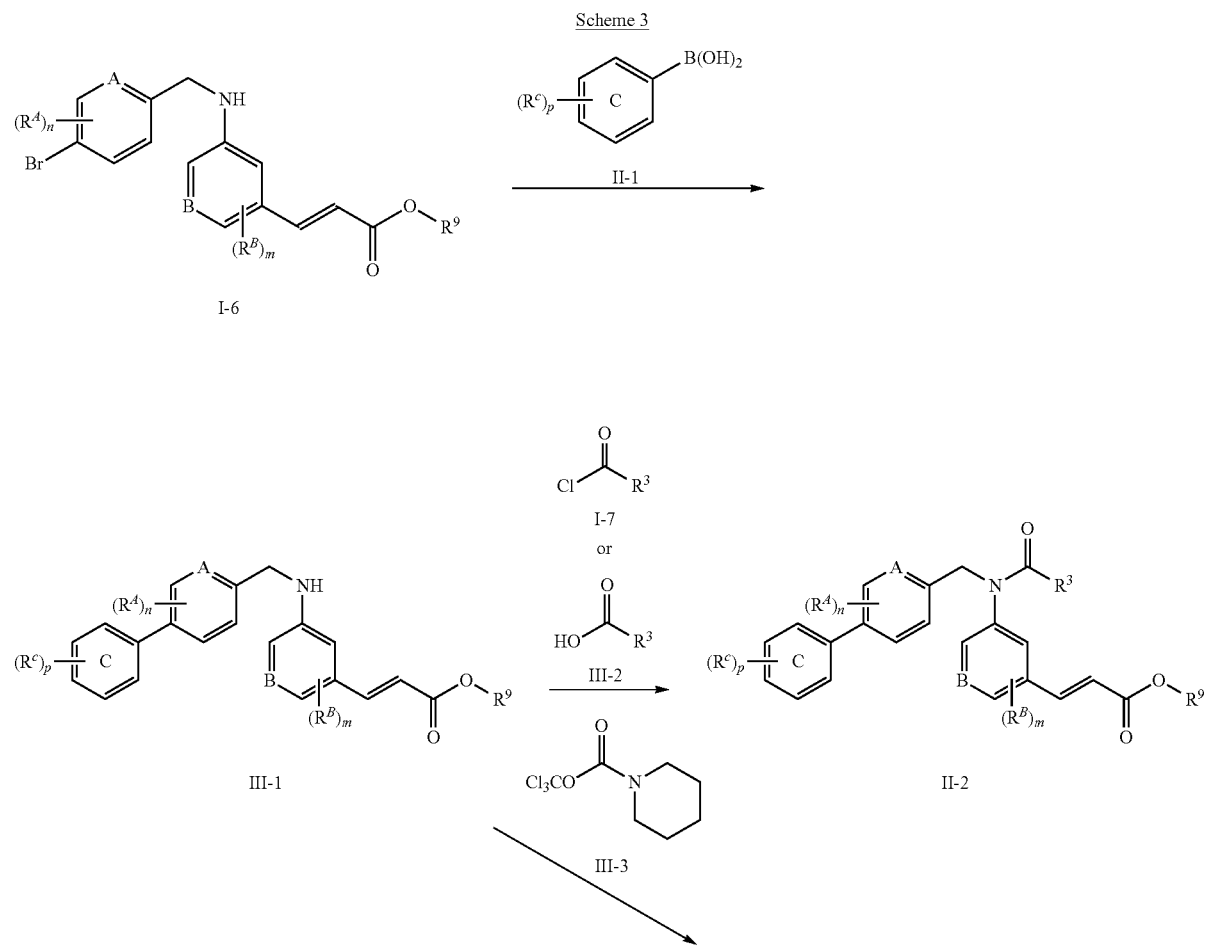

Scheme 3

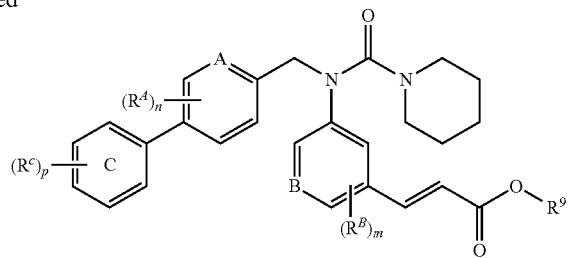

III-4

In Scheme 3, B is —CH in some embodiments. In some embodiments, A is —CH. In some embodiments, other C rings contemplated for use include the C rings described herein. In some embodiments, $R^3$ is iPr, nPr, tBu, $CH_2tBu$, cHept, 1-adamantyl, 4-CNPh, 4-MeOPh, 4-MeO-cHex, OEt, THP, or oxetane. In some embodiments, $R^3$ is iPr, nPr, tBu, $CH_2tBu$, cHept, 1-adamantyl, 4-CNPh, 4-MeOPh, 4-MeO-cHex, OEt, THP, or oxetane in compound I-7. In some embodiments, $R^3$ is cPent, cBu, or cyclohexanone for compound III-2. In some embodiments, $R^9$ is methyl. In some embodiments, m is 0. In some embodiments, n is 0. In some embodiments, $R^C$ is —$N(R^{10})_2$ and p is 1. In some embodiments, $R^{10}$ is methyl.

In some embodiments, compound III-1 is prepared from the palladium-catalyzed cross-coupling of bromide I-6 with boronic acid II-1. Suitable palladium catalysts for cross coupling include but are not limited to $Pd(PPh_3)_4$ in a suitable solvent, such as DMF, with an appropriate base at the suitable temperature for an appropriate amount of time. In some embodiments, the appropriate base is $Cs_2CO_3$. In some embodiments, the suitable temperature is about 90° C. In some embodiments, the appropriate amount of time is about 12 h.

Compound II-2 may be obtained from reacting compound III-1 with either acyl chloride I-7 or acid III-2. In some embodiments, reaction of III-1 with acyl chloride I-7 under N-acylation conditions provides compound II-2. Suitable N-acylation conditions include but are not limited to TEA in a suitable solvent, such as DCM, at an appropriate time and temperature. In some embodiments, the appropriate time and temperature is about 1 h to about 18 h and about 0° C. to rt.

In some embodiments, the appropriate time and temperature is about 0.5 h to about 1.5 h and about 0° C. In some embodiments, reaction of III-1 with acid III-2 with a coupling agent provides compound II-2. In some embodiments, suitable coupling conditions include but are not limited to EDCI, HOBt and TEA in a suitable solvent, such as DCM, for an appropriate time and at the appropriate temperature. In some embodiments, wherein $R^3$ is cPent, cBu, or cyclohexanone, suitable coupling conditions include but are not limited to EDCI, HOBt and TEA in a suitable solvent, such as DCM, for an appropriate time and at the appropriate temperature, such as for about 36 h at about 60° C. In some embodiments, suitable coupling conditions include but are not limited to EEDQ in a suitable solvent, such as PhMe, for an appropriate time and at an appropriate temperature. In some embodiments, wherein $R^3$ is cyclohexanone, suitable coupling conditions include but are not limited to EEDQ in a suitable solvent, such as PhMe, for an appropriate time and at an appropriate temperature, such as for about 36 h at about 110° C.

Alternatively, compound III-1 provides compound III-4 under suitable conditions. In some embodiments, III-3 is generated in situ from the reaction of piperidine with triphosgene in the presence of a suitable base and a suitable solvent, such as DCM, at an appropriate temperature for an appropriate amount of time, such as at about 0° C. for about 2 h. In some embodiments, the suitable base is TEA. In some embodiments, compound III-1 is added after about 2 h, and the reaction is allowed to proceed at an appropriate temperature for an appropriate amount of time, such as at about 0° C. for about 2 h followed by at rt for about 8 h, to provide compound III-4.

Scheme 4

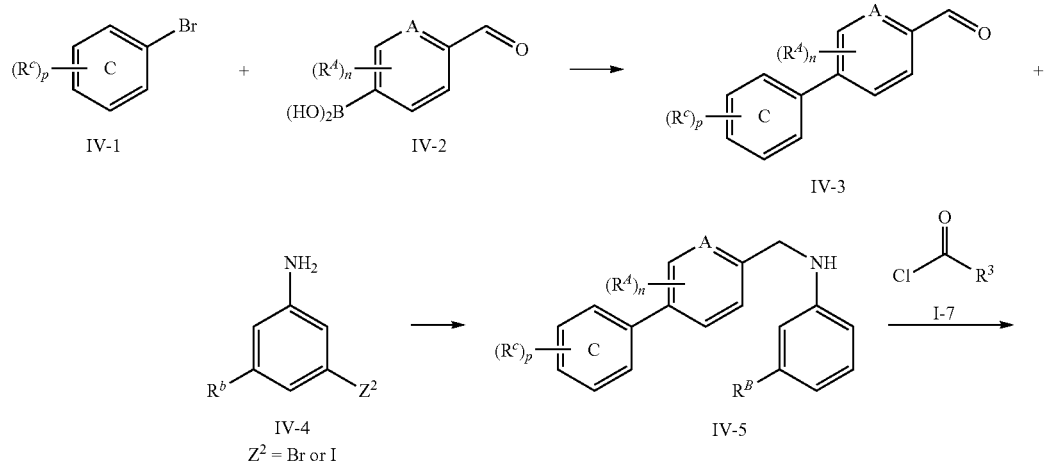

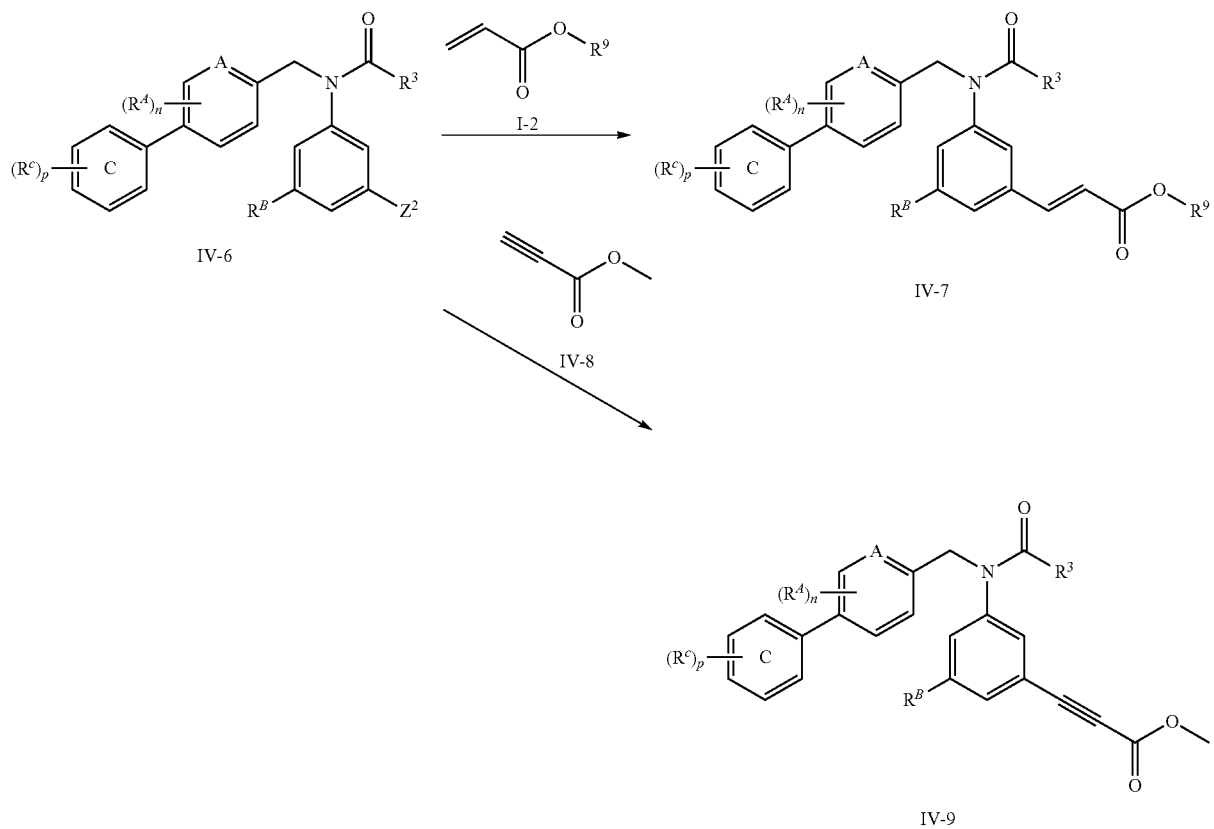

In Scheme 4, $R^B$ is H or ethyl in some embodiments. In some embodiments, A is —CH. In some embodiments, other C rings contemplated for use include the C rings described herein. In some embodiments, $R^3$ is cyclohexyl. In some embodiments, $R^9$ is Me, Et, iPr, or $CH_2CH_2OH$. In some embodiments, $R^9$ is Me, Et, iPr, or $CH_2CH_2OH$ in compound I-2. In some embodiments, m is 0. In some embodiments, n is 0. In some embodiments, $R^C$ is —$N(R^{10})_2$ and p is 1. In some embodiments, $R^{10}$ is methyl.

In some embodiments, aldehyde IV-3 is prepared from the palladium-catalyzed cross-coupling of bromide IV-1 with boronic acid IV-2. Suitable palladium catalysts for cross-coupling include but are not limited to $Pd(OAc)_2$ with a suitable ligand in a suitable solvent, such as PhMe, iPr-OH, $H_2O$ or a mixture thereof, with an appropriate base at an suitable temperature for an appropriate amount of time. In some embodiments, the suitable ligand is S-Phos. In some embodiments, the appropriate base is $K_3PO_4$. In some embodiments, the suitable temperature is rt. In some embodiments, the appropriate amount of time is 3 h. In some embodiments, compound IV-5 is obtained from subjecting aldehyde IV-3 and amine IV-4 under reductive amination conditions. In some embodiments, treatment of aldehyde IV-3 and amine IV-4 under appropriate reducing conditions, such as $NaBH(OAc)_3$ in AcOH and DCE, to provide amine IV-5 at a suitable temperature and appropriate amount of time. In some embodiments, the suitable temperature and appropriate amount of time is rt at about 0.5 to about 1.5 h. In some embodiments, aldehyde IV-3 and amine IV-4 is pre-mixed with AcOH for an appropriate amount of time at an appropriate temperature, such as for about 5 min at rt, prior to the addition of $NaBH(OAc)_3$. In some embodiments, the acylation of amino IV-5 with acyl chloride I-7 affords compound IV-6. Suitable acylation conditions include but are not limited to TEA in a suitable solvent, such as DCM, for an appropriate time and at an appropriate temperature, such as at about 0° C. to rt for about 1 h to about 1.5 h. In some embodiments, IV-7 is prepared from the palladium-catalyzed Heck reaction of halide IV-6 with acrylate I-2. Suitable conditions for palladium-catalyzed Heck reaction include $Pd(OAc)_2$ and $P(o\text{-tolyl})_3$ with a suitable base and solvent at an appropriate temperature for an appropriate amount of time. In some embodiments, $Pd(dppf)Cl_2$ is used in place of $Pd(OAc)_2$. In some instances, the suitable base is TEA. In some instances, the suitable solvent is DMF. In some instances, the appropriate temperature is about 80° C. In some instances, the appropriate reaction time is about 1 h to about 4 h. In some instances, the appropriate reaction time is about 3.5 h to about 5.5 h.

In some embodiments, IV-9 is prepared from the palladium-catalyzed Sonogashira reaction of halide IV-6 with alkyne IV-8. Suitable conditions for palladium-catalyzed Sonogashira reaction include $Pd(PPh_3)_4$ and CuI with a suitable base and solvent at an appropriate temperature for an appropriate amount of time. In some instances, the suitable base is $K_2CO_3$. In some instances, the suitable solvent is THF. In some instances, the appropriate temperature and appropriate amount of time is about rt for about 2 h followed by 60° C. for about 1 h.

Scheme 5

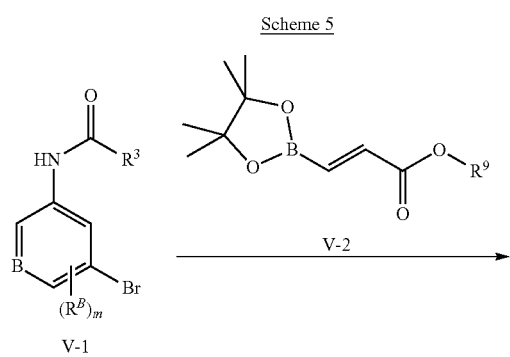

In Scheme 5, B is —CH. In some embodiments, $R^3$ is cyclohexyl. In some embodiments, $R^9$ is Me. In some embodiments, $R^9$ is Me in compound V-2. In some embodiments, m is 0.

In some embodiments, compound V-3 is prepared from the palladium-catalyzed cross-coupling of bromide V-1 with boronic ester V-2. Suitable palladium catalysts for cross-coupling include but are not limited to $Pd(PPh_3)_4$ in a suitable solvent, such as nPr-OH, with an appropriate base at a suitable temperature for an appropriate amount of time. In some embodiments, the appropriate base is $Na_2CO_3$. In some embodiments, the suitable temperature is 80° C. In some embodiments, the appropriate amount of time is 12 h. In some embodiments, compound V-3 is further reacted with the appropriate components to install the A and C rings according to the procedures as described for compound I-10 to I-12 of Scheme 1 and in Scheme 2.

Scheme 6

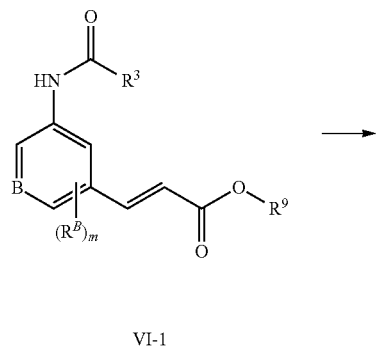

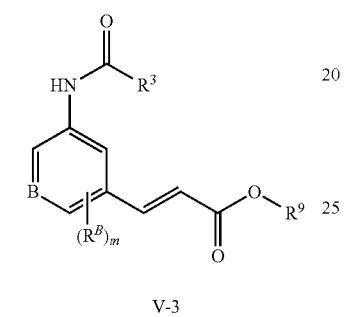

In Scheme 6, B is —CH. In some embodiments, $R^3$ is cyclohexyl. In some embodiments, $R^9$ is Me. In some embodiments, m is 0.

In some embodiments, compound VI-2 is prepared from the reduction of VI-1. Suitable reaction conditions for reduction include but are not limited to $H_2$ (1 atm) with Pd/C in a suitable solvent, such as MeOH, at a suitable temperature for an appropriate amount of time. In some embodiments, the suitable temperature is rt. In some embodiments, the appropriate amount of time is 14 h. In some embodiments, compound VI-2 is further reacted with the appropriate components to install the A and C rings according to the procedures as described for compound I-10 to I-12 of Scheme 1 and in Scheme 2.

Scheme 7

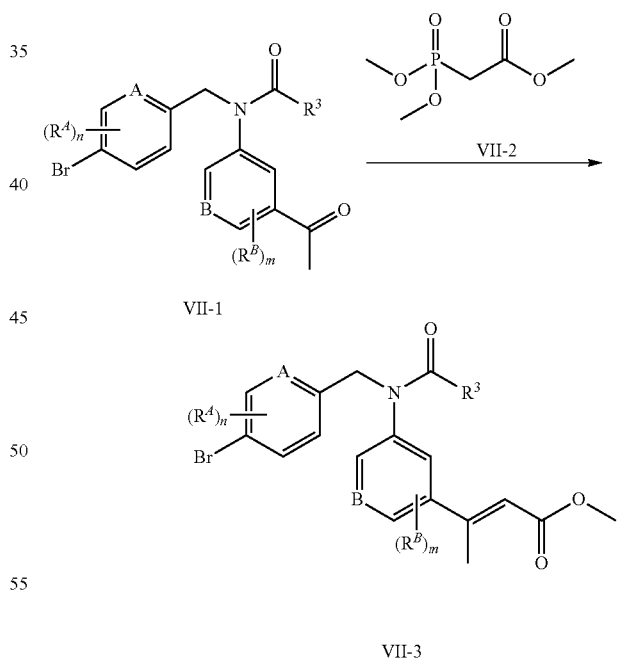

In Scheme 7, A is —CH for some embodiments. In some embodiments, B is —CH. In some embodiments, $R^3$ is cyclohexyl. In some embodiments, m is 0. In some embodiments, n is 0.

In some embodiments, compound VII-3 is prepared from the HWE reaction of VII-1 with VII-2. Suitable reaction conditions for the HWE reaction include but are not limited to a suitable base in a suitable solvent, such as THF, at a suitable temperature for an appropriate amount of time. In some embodiments, the suitable base is NaH. In some embodiments, VII-2 with pre-treated with the base for an appropriate amount of time at an appropriate temperature prior to the addition of ketone VII-1. In some embodiments, VII-2 is pre-treated with the base for about 0.5 h at about 0° C. prior to the addition of ketone VII-1. In some embodiments, after the addition of the ketone, the reaction is allowed to proceed for about 2 h at about 0° C. to rt. In some embodiments, compound VII-3 is further reacted with the appropriate components to install the C ring according to the procedures as described in Scheme 2.

of time. In some embodiments, the suitable temperature for an appropriate amount of time is rt for about 0.5 h to about 14 h. In some embodiments, compound VIII-4 is prepared from hydrolysis of VIII-3 with an appropriate base. Suitable reaction conditions for hydrolysis include but are not limited to a suitable base in a suitable solvent, such as THF and MeOH or a mixture thereof, at a suitable temperature for an appropriate amount of time. In some embodiments, the suitable base is NaOH (1M). In some embodiments, the suitable temperature for an appropriate amount of time is rt for about 2 h.

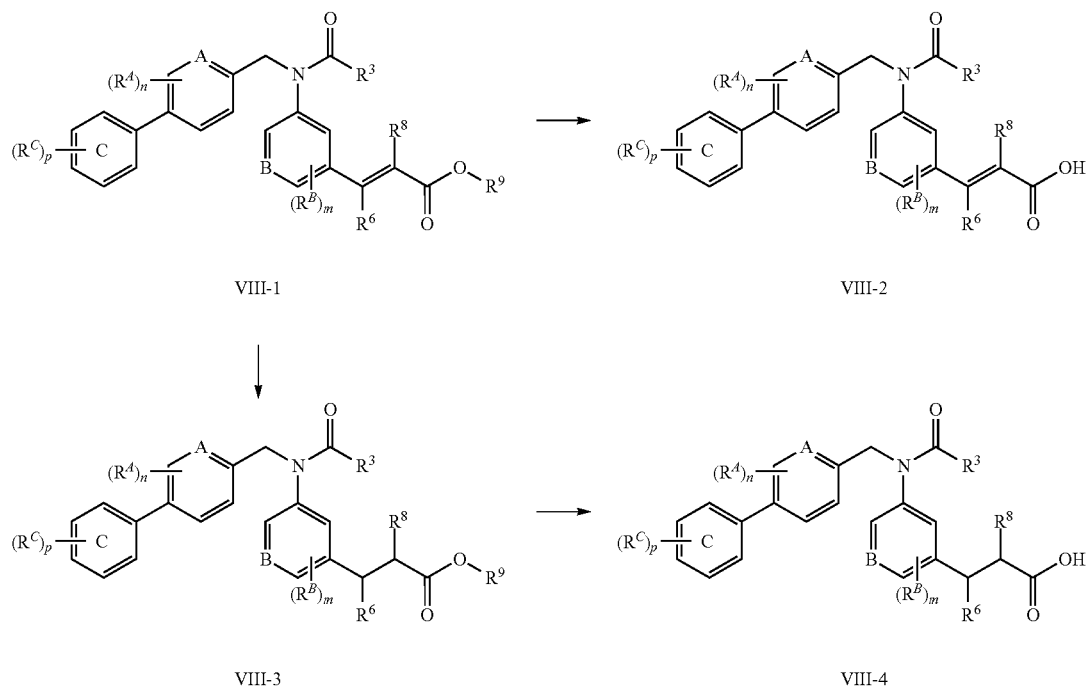

In Scheme 8, A is —CH for some embodiments. In some embodiments, B is —CH or —C-Me. In some embodiments, $R^3$ is cyclohexyl. In some embodiments, m is 0 or 1. In some embodiments, $R^B$ is H or Me. In some embodiments, B is —C-Me and m is 0. In some embodiments, n is 0. In some embodiments, $R^6$ is H or Me. In some embodiments, $R^8$ is H or Me. In some embodiments, $R^9$ is methyl. In some embodiments, $R^C$ is —N($R^{10}$)$_2$ and p is 1. In some embodiments, $R^{10}$ is methyl.

In some embodiments, compound VIII-2 is prepared from hydrolysis of VIII-1 with an appropriate base. Suitable reaction conditions for hydrolysis include but are not limited to a suitable base in a suitable solvent, such as THF and MeOH or a mixture thereof, at a suitable temperature for an appropriate amount of time. In some embodiments, the suitable base is NaOH (1M). In some embodiments, the suitable temperature for an appropriate amount of time is rt for about 2 h.

Alternatively, VIII-1 is subjected under reduction conditions to provide VIII-3. Suitable reaction conditions for reduction include but are not limited to H$_2$ (1 atm) with Pd/C (10%) in a suitable solvent, such as MeOH or MeOH/EtOAc, at a suitable temperature for an appropriate amount In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C(CH_3)=$CH_2$, —CH=$CHCH_3$, —C(CH_3)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$—C≡$CCH_2CH_3$, —$CH_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π C electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1] pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$fluoroalkyl.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of a FXR agonist. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

Disclosed herein, are methods of administering a FXR agonist in combination with an additional therapeutic agent. In some embodiments, the additional therapeutic agent comprises a therapeutic agent for treatment of diabetes or diabetes related disorder or conditions, alcoholic or non-alcoholic liver disease, inflammation related intestinal conditions, or cell proliferative disorders.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours;

(v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a FXR agonist is administered in combination with an additional therapeutic agent for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anagliptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or a combination thereof. In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In some instances, nicotinamide ribonucleoside or its analogs thereof, which promote NAD$^+$ production, a substrate for many enzymatic reactions including p450s which is a target for FXR (e.g., see Yang et al., *J. Med. Chem.* 50:6458-61, 2007).

In some embodiments, a FXR agonist is administered in combination with an additional therapeutic agent such as a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anaglptin, teneligliptin, alogliptin, gemiglptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or combinations thereof, for the treatment of diabetes or diabetes related disorder or conditions. In some embodiments, a FXR agonist is administered in combination with an additional therapeutic agent such as fish oil, fibrate, vitamins such as niacin, retinoic acid (e.g., 9 cis-retinoic acid), nicotinamide ribonucleoside or its analogs thereof, or combinations thereof, for the treatment of diabetes or diabetes related disorder or conditions.

In some embodiments, a FXR agonist is administered in combination with a statin such as a HMG-CoA reductase inhibitor, fish oil, fibrate, niacin or a combination thereof, for the treatment of dyslipidemia.

In additional embodiments, a FXR agonist is administered in combination with a vitamin such as retinoic acid for the treatment of diabetes and diabetes related disorder or condition such as lowering elevated body weight and/or lowering elevated blood glucose from food intake.

In some embodiments, the farnesoid X receptor agonist is administered with at least one additional therapy. In some embodiments, the at least one additional therapy is a glucose-lowering agent. In some embodiments, the at least one additional therapy is an anti-obesity agent. In some embodiments, the at least one additional therapy is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the at least one additional therapy is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the at least one additional therapy is a lipid-lowering agent. In certain embodiments, the at least one additional therapy is administered at the same time as the farnesoid X receptor agonist. In certain embodiments, the at least one additional therapy is administered less frequently than the farnesoid X receptor agonist. In certain embodiments, the at least one additional therapy is administered more frequently than the farnesoid X receptor agonist. In certain embodiments, the at least one additional therapy is administered prior to administration of the farnesoid X receptor agonist. In certain embodiments, the at least one additional therapy is administered after administration of the farnesoid X receptor agonist.

In some embodiments, a compound described herein, or a pharmaceutically acceptable salt thereof, is administered in combination with chemotherapy, anti-inflammatory agents, radiation therapy, monoclonal antibodies, or combinations thereof.

In some embodiments, a FXR agonist is administered in combination with an additional therapeutic agent for the treatment of alcoholic or non-alcoholic liver disease. In some embodiments, the additional therapeutic agent includes antioxidant, corticosteroid, anti-tumor necrosis factor (TNF) or a combination thereof.

In some embodiments, a FXR agonist is administered in combination with an additional therapeutic agent such as antioxidant, corticosteroid, anti-tumor necrosis factor (TNF), or a combination thereof, for the treatment of alcoholic or non-alcoholic liver disease. In some embodiments, a FXR agonist is administered in combination with an antioxidant, a vitamin precursor, a corticosteroid, an anti-tumor necrosis factor (TNF), or a combination thereof, for the treatment of alcoholic or non-alcoholic liver disease.

In some embodiments, a FXR agonist is administered in combination with an additional therapeutic agent for the treatment of inflammation related intestinal conditions. In some instances, the additional therapeutic agent comprises an antibiotic (such as metronidazole, vancomycin, and/or fidaxomicin), a corticosteroid, or an additional anti-inflammatory or immuno-modulatory therapy.

In some instances, a FXR agonist is administered in combination with an additional therapeutic agent such as an antibiotic, a corticosteroid, or an additional anti-inflammatory or immuno-modulatory therapy, for the treatment of inflammation related intestinal conditions. In some cases, a FXR agonist is administered in combination with metronidazole, vancomycin, fidaxomicin, corticosteroid, or combinations thereof, for the treatment of inflammation related intestinal conditions.

As discussed above, inflammation is sometimes associated with pseudomembranous colitis. In some instances, pseudomembranous colitis is associated with bacterial overgrowth (such as C. dificile overgrowth). In some embodiments, a FXR agonist is administered in combination with an antibiotic such as metronidazole, vancomycin, fidaxomicin, or a combination thereof, for the treatment of inflammation associated with bacterial overgrowth (e.g., pseudomembranous colitis).

In some embodiments, the FXR agonist is administered in combination with an additional therapeutic agent for the treatment of cell proliferative disorders. In some embodiments, the additional therapeutic agent includes a chemotherapeutic, a biologic (e.g., antibody, for example bevacizumab, cetuximab, or panitumumab), a radiotherapeutic (e.g., FOLFOX, FOLFIRI, CapeOX, 5-FU, leucovorin, regorafenib, irinotecan, or oxaliplatin), or combinations thereof.

In some embodiments, the FXR agonist is administered in combination with an additional therapeutic agent for the treatment of primary biliary cirrhosis. In some embodiments, the additional therapeutic agent includes ursodeoxycholic acid (UDCA).

In some embodiments, a FXR agonist is administered in combination with an additional therapeutic agent such as a chemotherapeutic, a biologic, a radiotherapeutic, or combinations thereof, for the treatment of a cell proliferative disorder. In some instances, a FXR agonist is administered in combination with an antibody (e.g., bevacizumab, cetuximab, or panitumumab), chemotherapeutic, FOLFOX, FOLFIRI, CapeOX, 5-FU, leucovorin, regorafenib, irinotecan, oxaliplatin, or combinations thereof, for the treatment of a cell proliferative disorder.

EXAMPLES

The following examples are provided for illustrative purposes only and not to limit the scope of the claims provided herein.

As used above, and throughout the description of the invention, the following abbreviations, unless otherwise indicated, shall be understood to have the following meanings:

ACN or MeCN acetonitrile
AcOH acetic acid
BINAP 2,2'-bis(diphenylphosphino)-1,1'-binaphthalene
Bn benzyl
BOC or Boc tert-butyl carbamate
t-Bu tert-butyl
Cy cyclohexyl
DBA or dba dibenzylideneacetone
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
EEDQ 2-ethoxy-1-ethoxycarbonyl-1,2-dihydroquinoline
eq equivalent(s)
Et ethyl
$Et_2O$ diethyl ether
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum anhydride
LCMS liquid chromatography mass spectrometry
Me methyl
MeOH methanol
MS mass spectroscopy
NMM N-methyl-morpholine
NMP N-methyl-pyrrolidin-2-one
NMR nuclear magnetic resonance
PCC pyridinium chlorochromate
RP-HPLC reverse phase-high pressure liquid chromatography
TFA trifluoroacetic acid
TEA triethylamine
THF tetrahydrofuran
TLC thin layer chromatography Intermediate 1

4'-(Dimethylamino)-[1,1'-biphenyl]-4-carbaldehyde

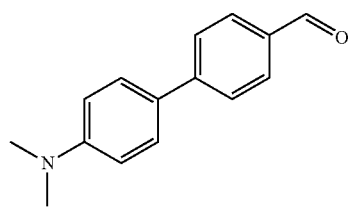 [SMILES: CN(C)c1ccc(-c2ccc(C=O)cc2)cc1]

A mixture of 4-bromo-N,N-dimethylaniline (21.28 g, 106.4 mmol), (4-formylphenyl)boronic acid (19.09 g, 127.4 mmol), potassium phosphate tribasic (67.77 g, 319.3 mmol), 2-dicyclohexylphosphino-2',6'-dimethoxybiphenyl (4.38 g, 10.7 mmol), toluene (100 mL), iso-propanol (100 mL), and water (100 mL) was degassed with vacuum/nitrogen cycles (3×). Palladium acetate (1.22 g, 5.42 mmol) was added, and the mixture was stirred at room temperature for 3 h. The reaction mixture was diluted with DCM (800 mL) and water (500 mL), and then filtered through Celite. The Celite was washed with DCM (200 mL). The layers were separated, and the organic layer was washed (500 mL water). The combined aqueous layers were extracted with DCM (200 mL). The organic extracts were combined, dried ($Na_2SO_4$), and concentrated under reduced pressure. The resulting solid was stirred in 1:1 hexanes/ethyl acetate (400 mL) for 15 min and filtered to give 4'-(dimethylamino)-[1,1'-biphenyl]-4-carbaldehyde (21.17 g, 88%) as a yellow solid. The filtrate was concentrated, stirred in 1:1 hexanes/ethyl acetate (200 mL) for 15 min and filtered to afford additional material (2.30 g, ~90% pure, 8%). $^1$H NMR (400 MHz, DMSO-$d_6$): δ 9.98 (s, 1H), 7.93 (d, J=8.5 Hz, 2H), 7.83 (d, J=8.5 Hz, 2H), 7.66 (d, J=8.9 Hz, 2H), 6.82 (d, J=8.9 Hz, 2H), 2.96 (s, 6H).

Intermediate 2

(E)-Methyl 3-(3-aminophenyl)acrylate

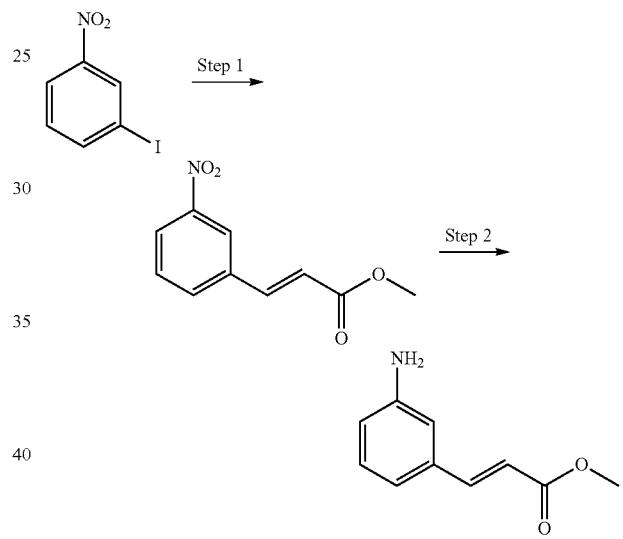

Step 1: (E)-Methyl 3-(3-nitrophenyl)acrylate

A mixture of 1-iodo-3-nitro-benzene (30 g, 120 mmol), methyl prop-2-enoate (43 mL, 482 mmol), $Pd_2(dba)_3$ (5.52 g, 6.02 mmol), P(o-tolyl)$_3$ (9.17 g, 30.1 mmol) and TEA (84 mL, 602 mmol) in DMF (300 mL) was degassed with vacuum/nitrogen cycles (3×) and then stirred at 90° C. for 12 h. The reaction mixture was filtered, diluted with water (800 mL), and extracted with ethyl acetate (3×400 mL). The combined organic layers were washed with water (3×800 mL), dried over anhydrous $Na_2SO_4$, filtered, and concentrated. Methyl tert-butyl ether (50 mL) was added, and the mixture was stirred for 2 h. The resulting solid was filtered and dried in vacuo to give methyl (E)-methyl 3-(3-nitrophenyl)acrylate (20 g, 74%) as a light yellow solid. $^1$H NMR (CDCl$_3$): δ 8.39 (s, 1H), 8.25 (dd, 1H), 7.84 (d, 1H), 7.74 (d, 1H), 7.61 (t, 1H), 6.58 (d, 1H), 3.85 (s, 3H); MS: 208.0 [M+H]$^+$.

Step 2: (E)-Methyl 3-(3-aminophenyl)acrylate

A suspension of (E)-methyl 3-(3-nitrophenyl)acrylate (1.95 g, 9.40 mmol), tin (II) chloride dihydrate (7.20 g, 31.9 mmol), and methanol (27 mL) was heated at 65° C. for 2 h, cooled to room temperature, and poured into ice water (100 mL). The reaction mixture was diluted with saturated NaHCO₃ (200 mL) and extracted with ethyl acetate (3×400 mL). The organic extracts were washed (200 mL brine), dried (Na₂SO₄), and concentrated under reduced pressure to give (E)-methyl 3-(3-aminophenyl)acrylate (1.68 g, 100%) as yellow solid. ¹H NMR (400 MHz, DMSO-d₆): δ 7.48 (d, J=15.8 Hz, 1H), 7.06 (t, J=7.8 Hz, 1H), 6.85-6.79 (m, 2H), 6.65-6.61 (m, 1H), 6.41 (d, J=15.8 Hz, 1H), 5.19 (s, 2H), 3.71 (s, 3H).

Intermediate 3

(E)-Methyl 3-(3-(((4'-(dimethylamino)-[1,1'-biphenyl]-4-yl)methyl)amino)phenyl)acrylate

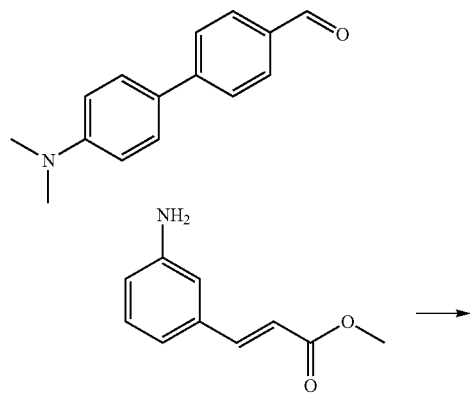

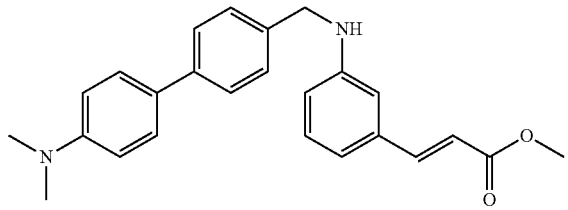

Intermediate 1 (994 mg, 4.41 mmol) and Intermediate 2 (829 mg, 4.68 mmol) were combined in dichloroethane (18 mL). Acetic acid (0.5 mL, 8.73 mmol) and sodium triacetoxyborohydride (1.51 g, 7.11 mmol) were added, and the reaction mixture was stirred at room temperature for 40 min. The reaction was diluted with ethyl acetate (30 mL). The organic layer was washed with saturated NaHCO₃ (40 mL), washed with brine (40 mL), dried (Na₂SO₄), filtered and concentrated to give (E)-methyl 3-(3-(((4'-(dimethylamino)-[1,1'-biphenyl]-4-yl)methyl)amino)phenyl)acrylate (1.69 g, 99%) as a yellow solid. ¹H NMR (400 MHz, DMSO-d₆): δ 7.55-7.47 (m, 5H), 7.39 (d, 2H), 7.09 (t, 1H), 6.89-6.84 (m, 2H), 6.78 (d, 2H), 6.68 (d, 1H), 6.46 (d, 1H), 6.40 (t, 1H), 4.30 (d, 2H), 3.70 (s, 3H), 2.91 (s, 6H); LCMS: 387.6 [M+H]⁺.

The Intermediates below were synthesized from the appropriate amines following the procedure described for Intermediate 3.

| Int | Structure | Name | [M + H]⁺ |
|---|---|---|---|
| 3.1 | 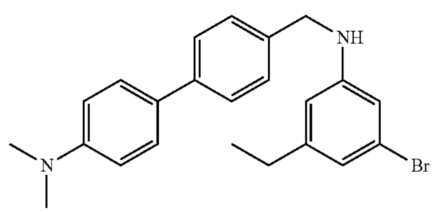 [SMILES: CCc1cc(Br)cc(NCc2ccc(-c3ccc(N(C)C)cc3)cc2)c1] | 4'-(((3-Bromo-5-ethylphenyl)amino)methyl)-N,N-dimethyl-[1,1'-biphenyl]-4-amine | 411.6 |
| 3.2 | 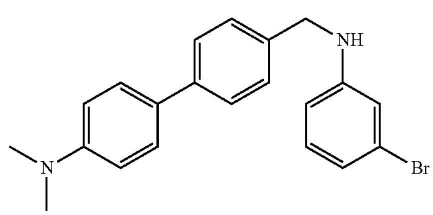 [SMILES: CN(C)c1ccc(-c2ccc(CNc3cccc(Br)c3)cc2)cc1] | 4'-(((3-Bromophenyl)amino)methyl)-N,N-dimethyl-[1,1'-biphenyl]-4-amine | 381.3 |
| 3.3 | 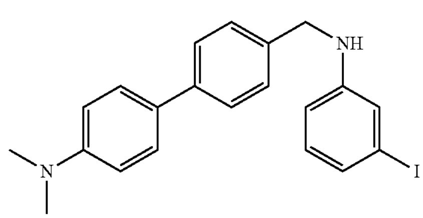 [SMILES: CN(C)c1ccc(-c2ccc(CNc3cccc(I)c3)cc2)cc1] | 4'-(((3-Iodophenyl)amino)methyl)-N,N-dimethyl-[1,1'-biphenyl]-4-amine | 429.5 |

Intermediate 4

4-Methoxycyclohexanecarbonyl chloride

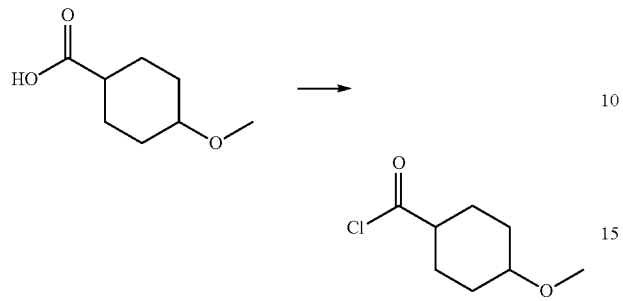

A mixture of 4-methoxycyclohexanecarboxylic acid (500 mg, 3.16 mmol), DMF (24 uL, 0.32 mmol) in $SOCl_2$ (10 mL) was degassed with vacuum/nitrogen cycles (3×), stirred at 80° C. for 1 h, filtered, and concentrated to give 4-methoxycyclohexanecarbonyl chloride (558 mg, 100%) as a colorless oil.

The Intermediate below was synthesized from oxetane-3-carboxylic acid following the procedure described for Intermediate 4.

| Int | Structure | Name | $[M + H]^+$ |
|---|---|---|---|
| 4.1 | 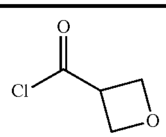 | Oxetane-3-carbonyl chloride | |

Intermediate 5

N-(3-Bromophenyl)cyclohexanecarboxamide

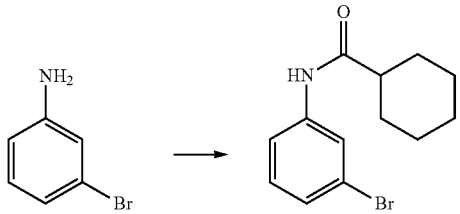 [SMILES: Nc1cccc(Br)c1 ; O=C(Nc1cccc(Br)c1)C1CCCCC1]

Cyclohexanecarbonyl chloride (61.4 g, 419 mmol) was added to a solution of 3-bromoaniline (60 g, 349 mmol), DMAP (4.26 g, 34.9 mmol), TEA (70.6 g, 698 mmol) in DCM (400 mL) at 0° C. The mixture was slowly warmed to 15° C. and stirred for 14 h. Water (200 mL) was added, and the mixture was extracted with DCM (3×300 mL). The combined organic phases were washed with brine (2×300 mL), dried over anhydrous $Na_2SO_4$, filtered and concentrated. The residue was purified by recrystallization from MTBE (200 mL) to give N-(3-bromophenyl)cyclohexanecarboxamide (90 g, 85%) as a red brown solid. MS: 282.1 $[M+H]^+$.

The Intermediates below were synthesized from the appropriate amines following the procedure described for Intermediate 5.

| Int | Structure | Name | $[M + H]^+$ |
|---|---|---|---|
| 5.1 | 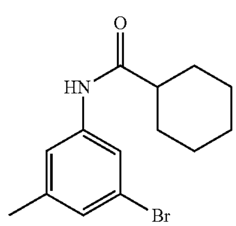 [SMILES: Cc1cc(Br)cc(NC(=O)C2CCCCC2)c1] | N-(3-Bromo-5-methylphenyl)cyclohexanecarboxamide | 296.0 |
| 5.2* | 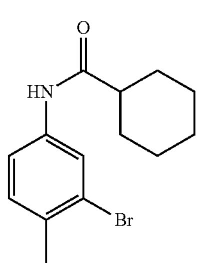 [SMILES: Cc1ccc(NC(=O)C2CCCCC2)cc1Br] | N-(3-Bromo-4-methylphenyl)cyclohexanecarboxamide | 296.1 |

-continued

| Int | Structure | Name | [M + H]+ |
|---|---|---|---|
| 5.3* | 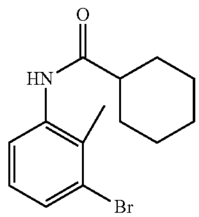 [SMILES: Cc1c(Br)cccc1NC(=O)C1CCCCC1] | N-(3-Bromo-2-methylphenyl)cyclohexanecarboxamide | 296.1 |
| 5.4 | 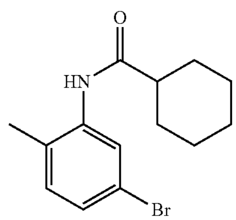 [SMILES: Cc1ccc(Br)cc1NC(=O)C1CCCCC1] | N-(5-Bromo-2-methylphenyl)cyclohexanecarboxamide | 296.1 |
| 5.5 | 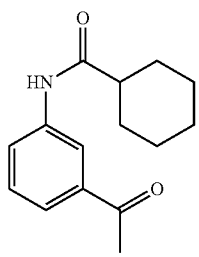 [SMILES: CC(=O)c1cccc(NC(=O)C2CCCCC2)c1] | N-(3-Acetylphenyl)cyclohexanecarboxamide | |
| 5.6 | 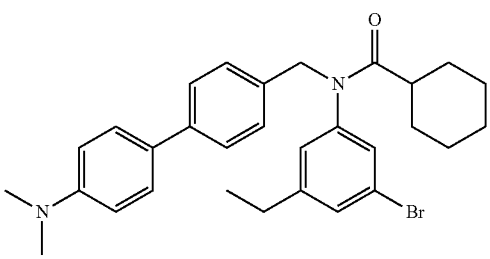 [SMILES: CCc1cc(Br)cc(N(Cc2ccc(-c3ccc(N(C)C)cc3)cc2)C(=O)C2CCCCC2)c1] | N-(3-Bromo-5-ethylphenyl)-N-((4'-(dimethylamino)-[1,1'-biphenyl]-4-yl)methyl)cyclohexanecarboxamide | 521.7 |
| 5.7 | 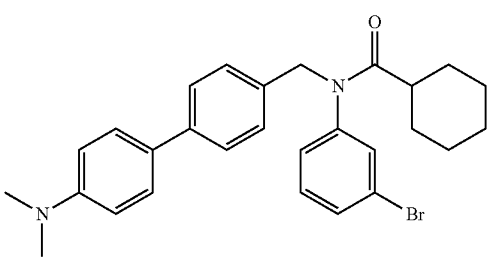 [SMILES: CN(C)c1ccc(-c2ccc(CN(C(=O)C3CCCCC3)c3cccc(Br)c3)cc2)cc1] | N-(3-Bromophenyl)-N-((4'-(dimethylamino)-[1,1'-biphenyl]-4-yl)methyl)cyclohexanecarboxamide | 491.2 |
| 5.8 | 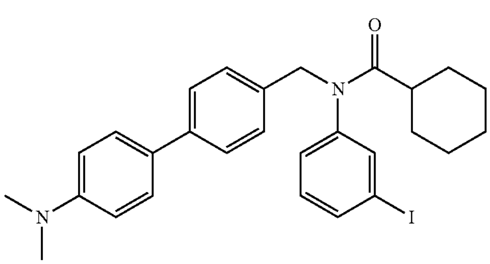 [SMILES: CN(C)c1ccc(-c2ccc(CN(C(=O)C3CCCCC3)c3cccc(I)c3)cc2)cc1] | N-(3-Iodophenyl)-N-((4'-(dimethylamino)-[1,1'-biphenyl]-4-yl)methyl)cyclohexanecarboxamide | 539.7 |

Note:
DMAP was not used for the above Intermediates; reaction time: 2-16 h.
*Acetonitrile was used as a solvent instead of DCM.

Intermediate 6

(E)-N-(3-(3-Methoxyprop-1-en-1-yl)phenyl)cyclohexanecarboxamide

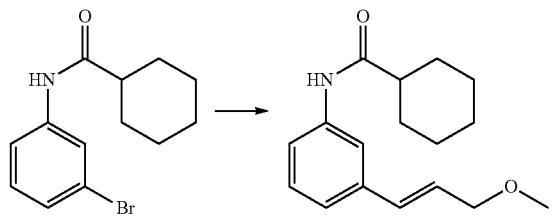 [SMILES: O=C(Nc1cccc(Br)c1)C1CCCCC1 ; COC/C=C/c1cccc(NC(=O)C2CCCCC2)c1]

A solution of (E)-2-(3-methoxyprop-1-en-1-yl)-4,4,5,5-tetramethyl-1,3,2-dioxaborolane (2.28 g, 11.5 mmol), Intermediate 5 (2.50 g, 8.86 mmol), Na$_2$CO$_3$ (2 M, 8.9 mL), Pd(PPh$_3$)$_4$ (2.05 g, 1.77 mmol) in n-PrOH (30 mL) was stirred at 80° C. for 12 h. The reaction mixture was quenched with water (100 mL), filtered, and extracted with DCM (2×100 mL). The combined organic layers were washed with brine (200 mL), dried over Na$_2$SO$_4$, filtered, and concentrated. The residue was purified by column chromatography (SiO$_2$, petroleum ether/ethyl acetate; 20/1 to 3/1) to give (E)-N-(3-(3-methoxyprop-1-en-1-yl)phenyl)cyclohexanecarboxamide (1.20 g, 40%) as a yellow oil. MS: 274.2 [M+H]$^+$.

Intermediate 7

4-Cyclohexylbenzaldehyde

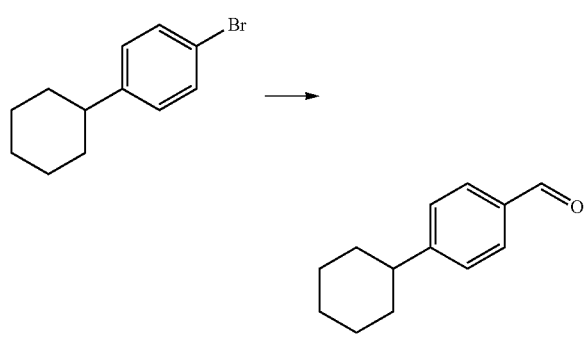

n-Butyllithium (2.5 M, 3.16 mL) was added dropwise to a solution of 1-bromo-4-cyclohexylbenzene (1.50 g, 6.27 mmol) in THF (15 mL) at −78° C. The reaction mixture was stirred at −78° C. for 1 h, and DMF (6.0 mL, 78 mmol) was added dropwise over 2 h. The mixture was allowed to warm to 0° C., quenched with saturated NH$_4$Cl (20 mL), and extracted with ethyl acetate (2×50 mL). The combined organic phases were concentrated and purified by column chromatography (100% petroleum ether) to give 4-cyclohexylbenzaldehyde (201 mg, 17%) as a colorless oil. $^1$H NMR (CDCl$_3$): δ 9.66-9.75 (m, 1H), 7.26-7.32 (m, 2H), 7.15 (d, 2H), 2.46-2.57 (m, 1H), 2.31 (t, 1H), 2.15 (d, 2H), 2.03 (d, 2H), 1.65-1.72 (m, 1H), 1.43-1.53 (m, 4H); MS: 189.2 [M+H]$^+$.

Intermediate 8

(E)-Methyl 3-(3-((1-(4-bromophenyl)ethyl)amino)phenyl)acrylate

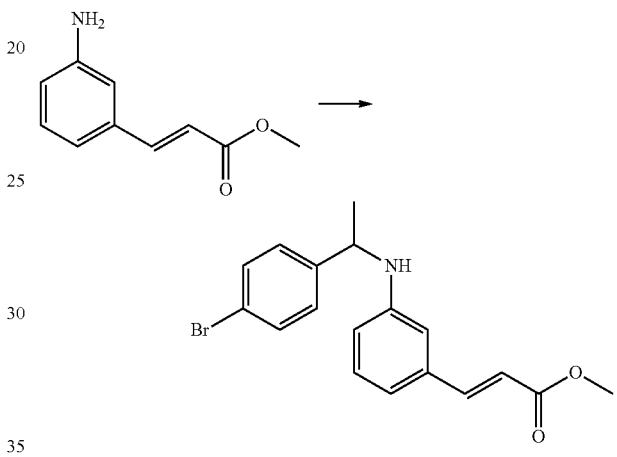

A solution of Intermediate 2 (1.50 g, 8.47 mmol) and 1-(4-bromophenyl)ethanone (2.02 g, 10.2 mmol) in acetic acid (80 mL) was stirred at 25° C. for 3 h. Sodium triacetoxyborohydride (3.59 g, 16.9 mmol) was added, and the mixture was stirred for 12 h. Water (80 mL) was added, and the mixture was extracted with ethyl acetate (2×200 mL). The organic layers were washed with NaHCO$_3$ (2×100 mL), dried over Na$_2$SO$_4$, filtered, and concentrated. The residue was purified by column chromatography (petroleum ether/ethyl acetate; 50/1) to give (E)-methyl 3-(3-((1-(4-bromophenyl)ethyl)amino)phenyl)acrylate (1.26 g, 23%) as a yellow oil. $^1$H NMR (CDCl$_3$): δ 7.46 (d, 1H), 7.31-7.40 (m, 2H), 7.11-7.22 (m, 2H), 6.96-7.07 (m, 1H), 6.72-6.84 (m, 1H), 6.48-6.56 (m, 1H), 6.36-6.46 (m, 1H), 6.16-6.26 (m, 1H), 4.37 (q, 1H), 3.63-3.74 (m, 3H), 1.42 (dd, 3H); MS: 360.0 [M+H]$^+$.

The Intermediate below was synthesized from Intermediate 7 following the procedure for Intermediate 8.

| Int | Structure | Name | [M + H]$^+$ |
|---|---|---|---|
| 8.1 | 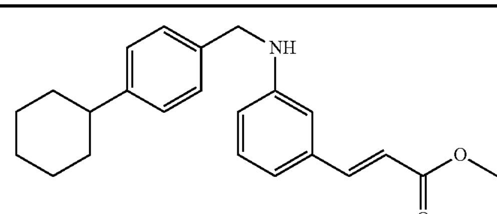 | (E)-Methyl 3-(3-((4-cyclohexylbenzyl)amino)phenyl)acrylate | 350.3 |

Intermediate 9

(E)-Methyl 3-(3-(cyclohexanecarboxamido)phenyl)acrylate

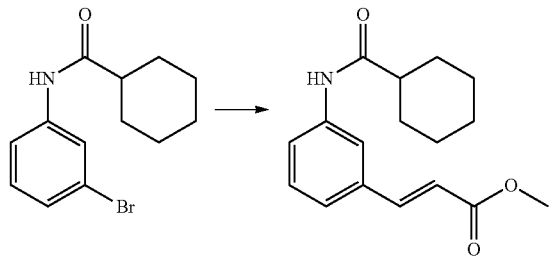 [SMILES: O=C(Nc1cccc(Br)c1)C1CCCCC1 ; COC(=O)/C=C/c1cccc(NC(=O)C2CCCCC2)c1]

A mixture of Intermediate 5 (75 g, 266 mmol), methyl acrylate (91.5 g, 1.06 mol), Pd$_2$(dba)$_3$ (24.3 g, 26.6 mmol), P(o-tolyl)$_3$ (24.3 g, 79.7 mmol) and TEA (134 g, 1.33 mol) in DMF (1.00 L) was degassed with vacuum/nitrogen cycles (3×), stirred at 90° C. for 24 h, and then filtered. Water (500 mL) was added, and the mixture was extracted with ethyl acetate (3×1 L). The combined organic layers were washed with water (3×1 L) and brine (2×800 mL), dried over anhydrous Na$_2$SO$_4$, filtered and concentrated. The residue was purified by re-crystallization from petroleum ether (1 L) to give (E)-methyl 3-(3-(cyclohexanecarboxamido)phenyl) acrylate (65 g, 82%) as a white solid. $^1$H NMR (DMSO-d$_6$): δ 7.77 (s, 1H), 7.62-7.66 (d, 1H), 7.50-7.52 (d, 1H), 7.30-7.33 (m, 1H), 7.23-7.25 (m, 2H), 6.42-6.46 (d, 1H), 3.79 (s, 3H), 2.23-2.24 (m, 1H), 1.94-1.97 (m, 2H), 1.83-1.85 (m, 2H), 1.70-1.72 (m, 1H), 1.56-1.59 (m, 2H), 1.27-1.33 (m, 3H); MS: 288.2 [M+H]$^+$. Note: this compound was also synthesized by acylation of Intermediate 2 with cyclohexanecarbonyl chloride in the presence of triethylamine.

The Intermediates below were synthesized from the respective bromide Intermediates following the procedure described for Intermediate 9.

| Int | Structure | Name | [M + H]$^+$ |
| --- | --- | --- | --- |
| 9.1 | 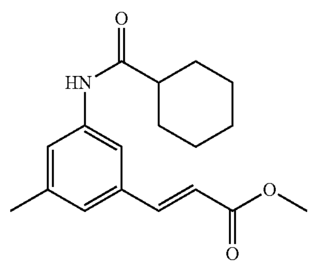 | (E)-Methyl 3-(3-(cyclohexanecarboxamido)-5-methylphenyl)acrylate | 302.3 |
| 9.2 | 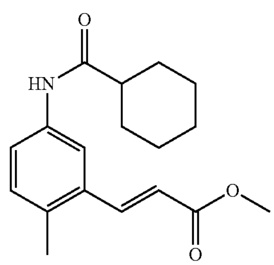 [SMILES: COC(=O)/C=C/c1cc(NC(=O)C2CCCCC2)ccc1C] | (E)-Methyl 3-(5-(cyclohexanecarboxamido)-2-methylphenyl)acrylate | 302.2 |
| 9.3 | 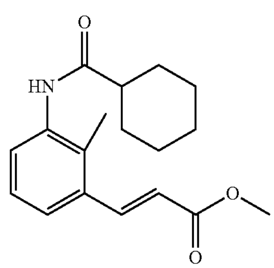 [SMILES: COC(=O)/C=C/c1cccc(NC(=O)C2CCCCC2)c1C] | (E)-Methyl 3-(3-(cyclohexanecarboxamido)-2-methylphenyl)acrylate | 302.2 |
| 9.4 | 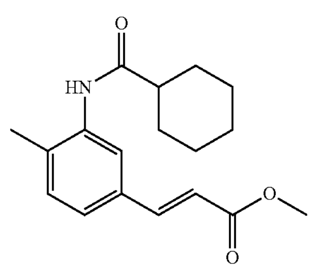 | (E)-Methyl 3-(3-(cyclohexanecarboxamido)-4-methylphenyl)acrylate | 302.3 |

-continued

| Int | Structure | Name | [M + H]⁺ |
|---|---|---|---|
| 9.5* | 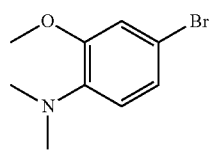 | (E)-Methyl 3-(3-(cyclohexanecarboxamido)phenyl)-2-methylacrylate | 302.2 |

Note:
The reaction time: 5-24 h.
*Methyl methacrylate was used in place of methyl acrylate.

Intermediate 10

4-Bromo-2-methoxy-N,N-dimethylaniline

Formaldehyde (3.7 mL, 49 mmol, 37% aqueous) and acetic acid (57 uL, 1 mmol) were added to a solution of 4-bromo-2-methoxyaniline (2.0 g, 9.9 mmol) in methanol (10 mL) at 25° C. The mixture was stirred for 2 h, and then sodium cyanoborohydride (3.11 g, 49.5 mmol) was added in portions. The resulting mixture was stirred for 12 h, poured into a saturated NaHCO₃ solution (40 mL), and then extracted with ethyl acetate (3×20 mL). The combined organic phases were washed with brine (2×20 mL), dried over anhydrous Na₂SO₄, filtered and concentrated. The residue was purified by column chromatography (SiO₂, petroleum ether/ethyl acetate; 15/1) to give 4-bromo-2-methoxy-N,N-dimethylaniline (2.0 g, 80%) as a brown oil. ¹H NMR (CDCl₃): δ 7.02 (dd, 1H), 6.95 (d, 1H), 6.78 (d, 1H), 3.87 (s, 3H), 2.76 (s, 6H); MS: 230.0 [M+H]⁺.

Intermediate 11

Methyl 3-(3-(cyclohexanecarboxamido)phenyl)propanoate

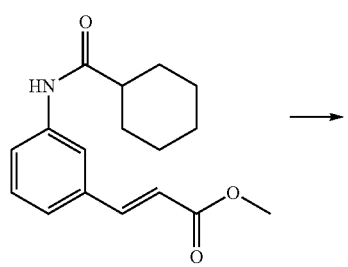

Palladium on carbon (10%, 0.2 g) was added to a solution of Intermediate 9 (1.0 g, 3.5 mmol) in methanol (10 mL). The suspension was degassed under vacuum and purged with H₂ several times. The mixture was stirred under atmosphere of H₂ (15 psi) at 15° C. for 14 h, filtered and concentrated to give methyl 3-(3-(cyclohexanecarboxamido)phenyl)propanoate (1.0 g, 95%) as a white solid. MS: 290.2 [M+H]⁺.

Intermediate 12

(E)-Methyl 3-(3-(N-(4-bromobenzyl)cyclohexanecarboxamido)phenyl)acrylate

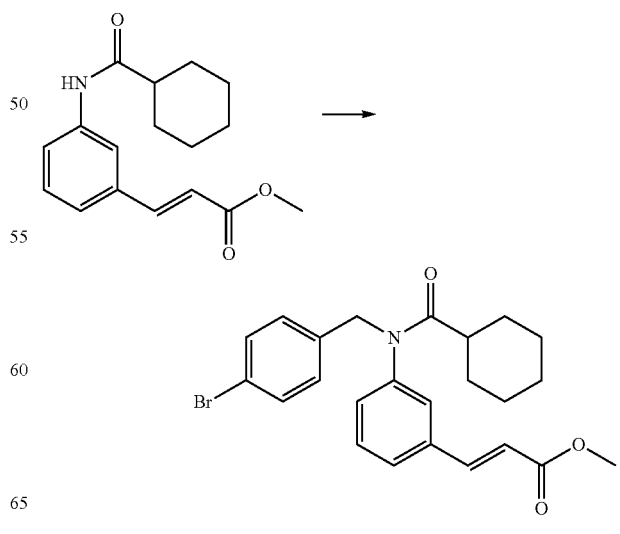

Sodium hydride (5.43 g, 136 mmol) was added in portions to a solution of Intermediate 9 (30 g, 104 mmol) in THF (800 mL) at 0° C. The mixture was stirred for 30 min, and then 1-bromo-4-(bromomethyl)benzene (31.3 g, 125 mmol) was added in portions at 0° C. The resulting mixture was slowly warmed to 15° C. and stirred for 14 h. Water (400 mL) was added, and the mixture was extracted with ethyl acetate (3×500 mL). The combined organic layers were washed with brine (2×500 mL), dried over anhydrous $Na_2SO_4$, filtered and concentrated. The residue was purified by column chromatography ($SiO_2$, petroleum ether/ethyl acetate; 3/1) to give (E)-methyl 3-(3-(N-(4-bromobenzyl)cyclohexanecarboxamido)phenyl)acrylate (35 g, 66%) as a white solid. $^1$H NMR (DMSO-$d_6$): δ 7.58-7.72 (m, 3H), 7.37-7.50 (m, 3H), 7.06-7.18 (m, 3H), 6.67 (d, 1H), 4.82 (br s, 2H), 3.73 (s, 3H), 2.16 (br s, 1H), 1.56-1.72 (m, 4H), 1.32-1.54 (m, 3H), 1.10 (q, 1H), 0.88 (d, 2H); MS: 456.2 [M+H]$^+$.

The Intermediates below were synthesized from the appropriate starting materials following the procedure described for Intermediate 12.

| Int | Structure | Name | [M + H]$^+$ |
|---|---|---|---|
| 12.1 | 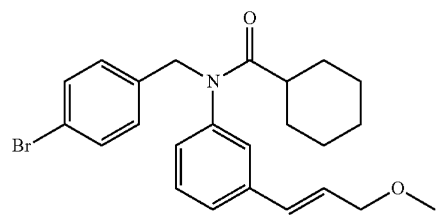 [SMILES: COC/C=C/c1cccc(N(Cc2ccc(Br)cc2)C(=O)C2CCCCC2)c1] | (E)-N-(4-Bromobenzyl)-N-(3-(3-methoxyprop-1-en-1-yl)phenyl)cyclohexanecarboxamide | |
| 12.2* | 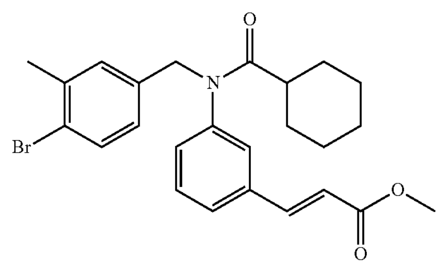 [SMILES: COC(=O)/C=C/c1cccc(N(Cc2ccc(Br)c(C)c2)C(=O)C2CCCCC2)c1] | (E)-Methyl 3-(3-(N-(4-bromo-3-methylbenzyl)cyclohexanecarboxamido)phenyl)acrylate | 470.2 |
| 12.3* | 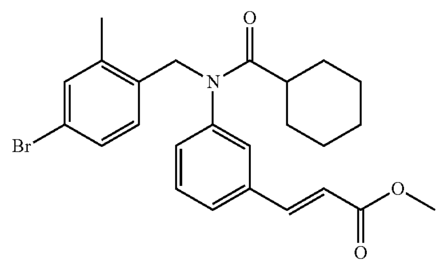 [SMILES: COC(=O)/C=C/c1cccc(N(Cc2ccc(Br)cc2C)C(=O)C2CCCCC2)c1] | (E)-Methyl 3-(3-(N-(4-bromo-2-methylbenzyl)cyclohexanecarboxamido)phenyl)acrylate | 470.1 |
| 12.4 | 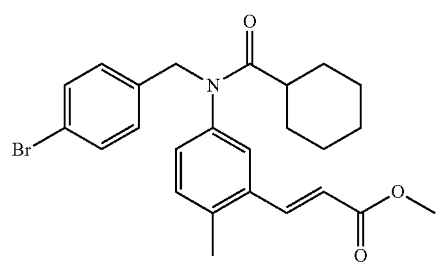 [SMILES: COC(=O)/C=C/c1cc(N(Cc2ccc(Br)cc2)C(=O)C2CCCCC2)ccc1C] | (E)-Methyl 3-(5-(N-(4-bromobenzyl)cyclohexanecarboxamido)-2-methylphenyl)acrylate | 470.0 |
| 12.5 | 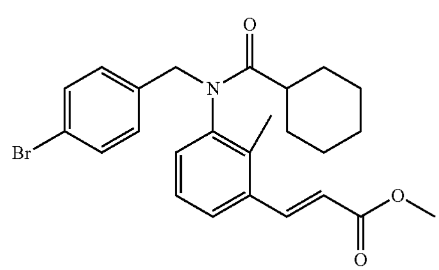 [SMILES: COC(=O)/C=C/c1cccc(N(Cc2ccc(Br)cc2)C(=O)C2CCCCC2)c1C] | (E)-Methyl 3-(3-(N-(4-bromobenzyl)cyclohexanecarboxamido)-2-methylphenyl)acrylate | 470.1 |

-continued

| Int | Structure | Name | [M + H]+ |
|---|---|---|---|
| 12.6* | 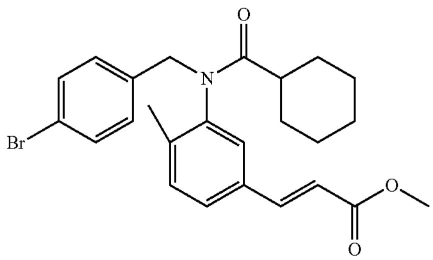 [SMILES: COC(=O)/C=C/c1ccc(C)c(N(Cc2ccc(Br)cc2)C(=O)C2CCCCC2)c1] | (E)-Methyl 3-(3-(N-(4-bromobenzyl)cyclohexanecarbox-amido)-2-methylphenyl)acrylate | 470.0 |
| 12.7 | 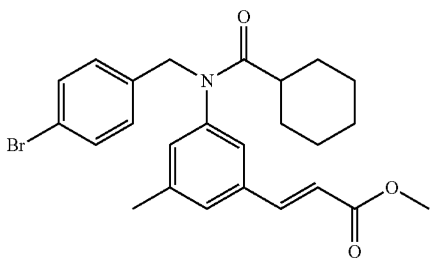 [SMILES: COC(=O)/C=C/c1cc(C)cc(N(Cc2ccc(Br)cc2)C(=O)C2CCCCC2)c1] | (E)-Methyl 3-(3-(N-(4-bromobenzyl)cyclohexanecarbox-amido)-5-methylphenyl)acrylate | 470.2 |
| 12.8 | 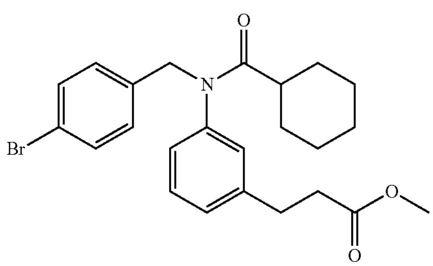 [SMILES: COC(=O)CCc1cccc(N(Cc2ccc(Br)cc2)C(=O)C2CCCCC2)c1] | Methyl 3-(3-(N-(4-bromobenzyl)cyclohexanecarbox-amido)phenyl)propanoate | 458.2 |
| 12.9* | 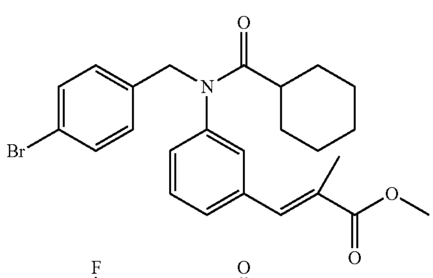 | (E)-Methyl 3-(3-(N-(4-bromobenzyl)cyclohexanecarbox-amido)phenyl)-2-methylacrylate | 470.2 |
| 12.10 | 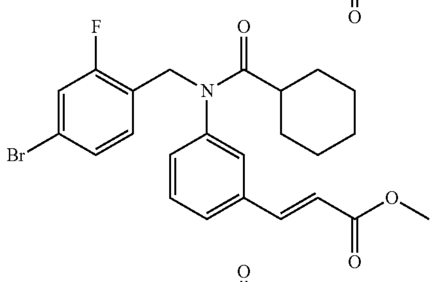 | (E)-Methyl 3-(3-(N-(4-bromo-2-fluorobenzyl)cyclohexanecarbox-amido)phenyl)acrylate | 474.0 |
| 12.11 | 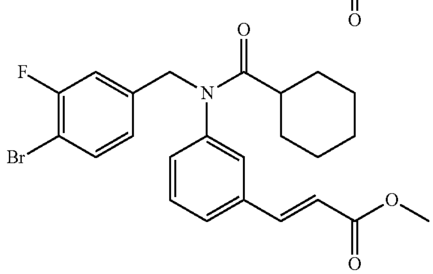 | (E)-Methyl 3-(3-(N-(4-bromo-3-fluorobenzyl)cyclohexanecarbox-amido)phenyl)acrylate | 474.1 |

Notes:
Reaction time: 2-16 h;
*DMF instead of THF; Cs$_2$CO$_3$, CH$_3$CN also utilized.

Intermediate 13

(E)-Methyl 3-(3-(N-(1-(4-bromophenyl)ethyl)cyclohexanecarboxamido)phenyl)acrylate

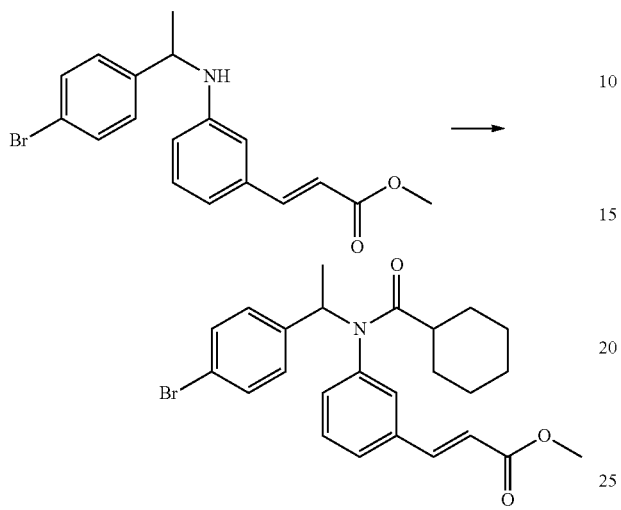

Cyclohexanecarbonyl chloride (1.10 g, 7.50 mmol) was added over 1 h to a solution of Intermediate 8 (900 mg, 2.50 mmol) and DMAP (458 mg, 3.75 mmol) in pyridine (45 mL) at 0° C. The mixture was heated at 120° C. for 11 h, concentrated, dissolved in ethyl acetate (300 mL), and washed with 1 N HCl solution (100 mL). The organic layer was dried over Na$_2$SO$_4$, filtered, and concentrated. The residue was purified by column chromatography (petroleum ether/ethyl acetate; 10/1) to give methyl (E)-methyl 3-(3-(N-(1-(4-bromophenyl)ethyl)cyclohexanecarboxamido)phenyl)acrylate (1.0 g, 77%) as a yellow oil. MS: 470.0 [M+H]$^+$.

Intermediate 14

N-(3-Acetylphenyl)-N-(4-bromobenzyl)cyclohexanecarboxamide

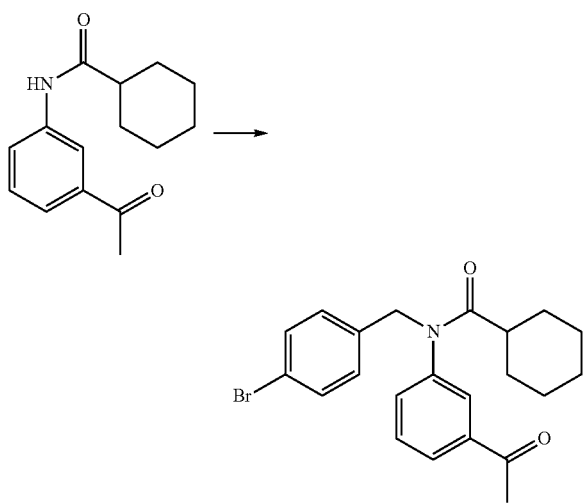

Cesium carbonate (26.6 g, 81.5 mmol) and 1-bromo-4-(bromomethyl)benzene (12.2 g, 48.9 mmol) were added to a solution of Intermediate 5.5 (10 g, 40.8 mmol) in DMF (100 mL). The mixture was stirred at 80° C. for 24 h, filtered, diluted with water (150 mL) and then extracted with ethyl acetate (3×100 mL). The combined organic layers were washed with water (3×100 mL) and brine (2×100 mL), dried over anhydrous Na$_2$SO$_4$, filtered and concentrated. The residue was purified by column chromatography (SiO$_2$, petroleum ether/ethyl acetate; 20/1) to give N-(3-acetylphenyl)-N-(4-bromobenzyl)cyclohexanecarboxamide (7.5 g, 40%) as a yellow oil. $^1$H NMR (CDCl$_3$): δ 7.89-7.91 (d, 1H), 7.58 (s, 1H), 7.46-7.49 (m, 1H), 7.37-7.39 (d, 2H), 7.34 (d, 1H), 7.03-7.05 (d, 2H), 4.82 (s, 2H), 2.55 (s, 3H), 2.07 (m, 1H), 1.55-1.67 (m, 7H), 1.17-1.20 (m, 1H), 0.88-0.97 (m, 2H); MS: 414.0 [M+H]$^+$.

Intermediate 15

(E)-Methyl 3-(3-(N-(4-bromobenzyl)cyclohexanecarboxamido)phenyl)but-2-enoate

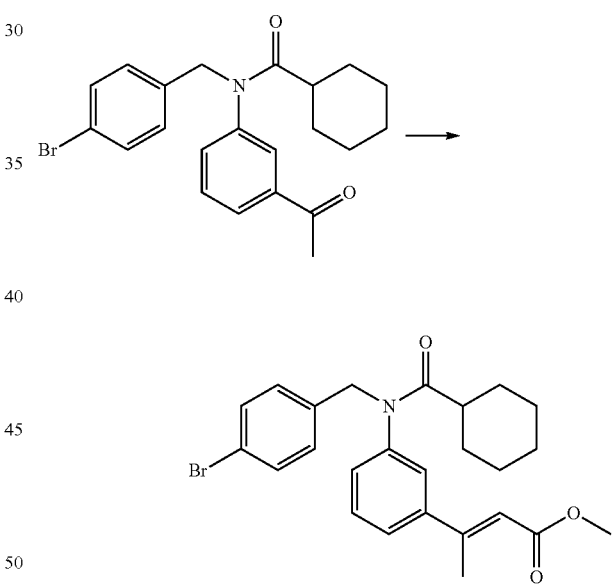

Sodium hydride (926 mg, 23.2 mmol) was added in portions to a solution of methyl 2-(dimethoxyphosphoryl)acetate (2.11 g, 11.6 mmol) in THF (20 mL) at 0° C. After stirring the mixture for 30 min, Intermediate 14 (4.0 g, 9.7 mmol) was added in portions at 0° C. The resulting mixture was slowly warmed to 20° C., stirred for 2 h, quenched with water (40 mL), and then extracted with ethyl acetate (3×50 mL). The combined organic phases were washed with brine (2×50 mL), dried over anhydrous Na$_2$SO$_4$, filtered and concentrated to give (E)-methyl 3-(3-(N-(4-bromobenzyl)cyclohexanecarboxamido)phenyl)but-2-enoate (4.5 g, crude) as a light yellow oil. MS: 472.0 [M+H]$^+$.

207
Intermediate 16

(E)-Methyl 3-(3-(N-(4-(4,4,5,5-tetramethyl-1,3,2-dioxaborolan-2-yl)benzyl)cyclohexanecarboxamido)phenyl)acrylate

208
Compound 1

(E)-Methyl 3-(3-(N-((4'-(dimethylamino)-[1,1'-biphenyl]-4-yl)methyl)pivalamido)phenyl)acrylate

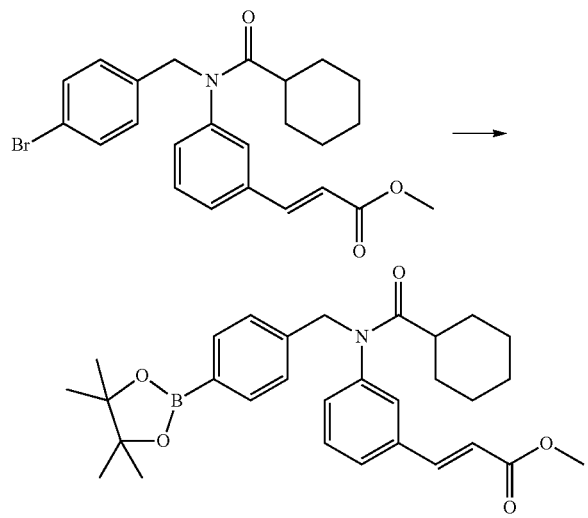

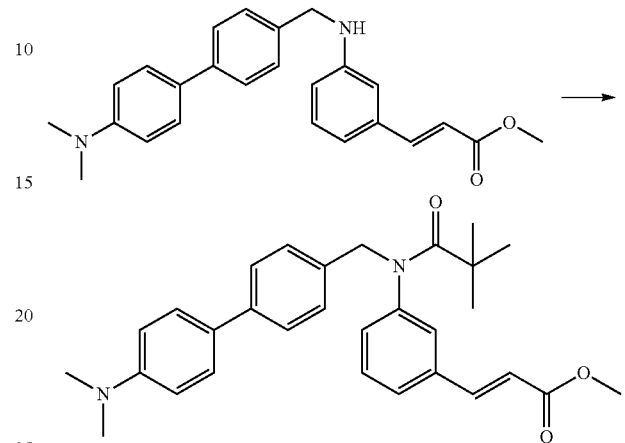

A mixture of Intermediate 12 (10 g, 21.9 mmol), 4,4,5,5-tetramethyl-2-(4,4,5,5-tetramethyl-1,3,2-dioxaborolan-2-yl)-1,3,2-dioxaborolane (27.8 g, 110 mmol), Pd(dppf)Cl$_2$ (1.60 g, 2.19 mmol) and potassium acetate (10.8 g, 110 mmol) in DMF (200 mL) was degassed with vacuum/nitrogen cycles (3×), stirred at 90° C. for 24 h, and then filtered. Water (200 mL) was added, and the mixture was extracted with ethyl acetate (3×300 mL). The combined organic layers were washed with water (3×300 mL) and brine (2×300 mL), dried over anhydrous Na$_2$SO$_4$, filtered and concentrated. The residue was purified by column chromatography (SiO$_2$, petroleum ether/ethyl acetate; 3/1) to give (E)-methyl 3-(3-(N-(4-(4,4,5,5-tetramethyl-1,3,2-dioxaborolan-2-yl)benzyl)cyclohexanecarboxamido)phenyl)acrylate (8.0 g, 69%) as a yellow oil. $^1$H NMR (CDCl$_3$): δ 7.66-7.68 (d, 2H), 7.53-7.57 (d, 1H), 7.42 (d, 1H), 7.27-7.31 (t, 1H), 7.12-7.14 (d, 2H), 7.05 (br s, 1H), 6.91 (d, 1H), 6.28-6.32 (d, 1H), 4.84 (s, 2H), 3.77 (s, 3H), 2.08-2.11 (m, 1H), 1.56-1.64 (m, 7H), 1.30 (s, 12H), 1.21-1.24 (m, 1H), 0.88-0.92 (m, 2H); MS: 504.4 [M+H]$^+$.

Pivaloyl chloride (66 μL, 0.54 mmol) was added to a solution of Intermediate 3 (157 mg, 0.41 mmol) and triethylamine (0.12 mL, 0.86 mmol) in DCM at 0° C. The reaction was stirred at 0° C. for 1 h, stirred at room temp for 5 h, and then diluted with DCM (20 mL). The organic layer was washed with saturated NaHCO$_3$ (20 mL), washed with brine (20 mL), dried (Na$_2$SO$_4$), filtered, concentrated and purified by reverse-phase HPLC (45-57% acetonitrile/water (0.1% TFA)). The residue was diluted with ethyl acetate (50 mL), washed with saturated NaHCO$_3$ (2×50 mL), washed with brine (50 mL), dried (NaSO$_4$), filtered, concentrated and dried on high vacuum overnight to give (E)-methyl 3-(3-(N-((4'-(dimethylamino)-[1,1'-biphenyl]-4-yl)methyl)pivalamido)phenyl)acrylate (65 mg, 34%) as a yellow solid. $^1$H NMR (400 MHz, DMSO-d$_6$): δ 7.69 (d, 1H), 7.66-7.59 (m, 2H), 7.52-7.46 (m, 4H), 7.38 (t, 1H), 7.19-7.12 (m, 3H), 6.78 (d, 2H), 6.62 (d, 1H), 4.80 (s, 2H), 3.89 (s, 3H), 2.93 (s, 6H), 1.00 (s, 9H); LCMS: 471.7 [M+H]$^+$.

The Compounds below were synthesized from the appropriate starting materials following the procedure described for Compound 1.

| Cmpd | Structure | Name | [M + H]$^+$ |
|---|---|---|---|
| 2 | 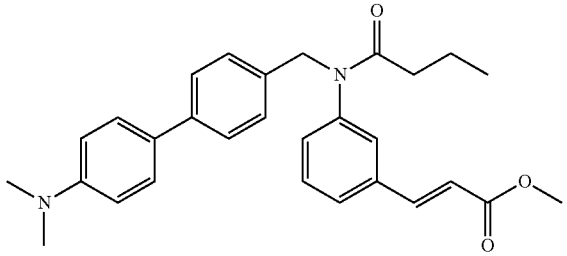 | (E)-Methyl 3-(3-(N-((4'-(dimethylamino)-[1,1'-biphenyl]-4-yl)methyl)butyramido)phenyl)acrylate | 457.3 |

-continued

| Cmpd | Structure | Name | [M + H]+ |
|---|---|---|---|
| 3 | 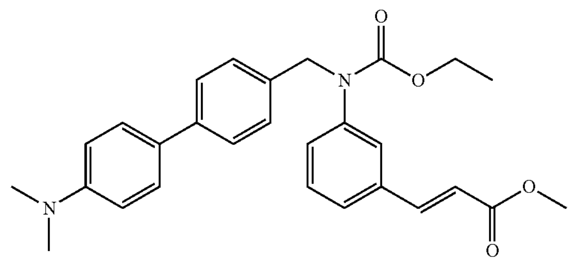 | (E)-Methyl 3-(3-(((4'-(dimethylamino)-[1,1'-biphenyl]-4-yl)methyl)(ethoxycarbonyl)amino)phenyl)acrylate | 459.3 |
| 4 | 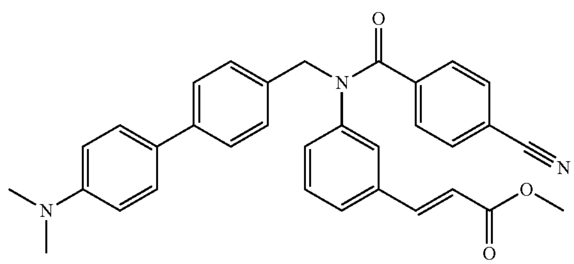 [SMILES: COC(=O)/C=C/c1cccc(N(Cc2ccc(-c3ccc(N(C)C)cc3)cc2)C(=O)c2ccc(C#N)cc2)c1] | (E)-Methyl 3-(3-(4-cyano-N-((4'-(dimethylamino)-[1,1'-biphenyl]-4-yl)methyl)benzamido)phenyl)acrylate | 516.2 |
| 5 | 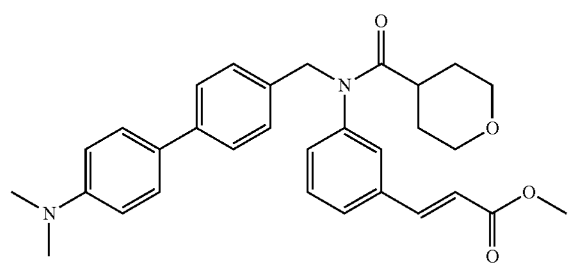 | (E)-Methyl 3-(3-(N-((4'-(dimethylamino)-[1,1'-biphenyl]-4-yl)methyl)tetrahydro-2H-pyran-4-carboxamido)phenyl)acrylate | 499.3 |
| 6 | 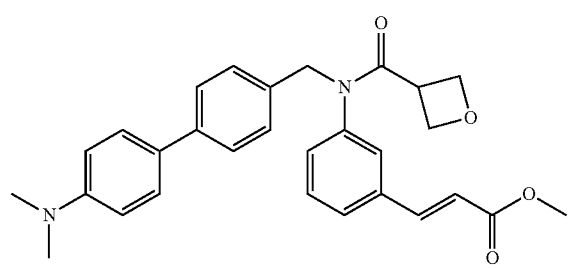 | (E)-Methyl 3-(3-(N-((4'-(dimethylamino)-[1,1'-biphenyl]-4-yl)methyl)oxetane-3-carboxamido)phenyl)acrylate | 471.3 |
| 7 | 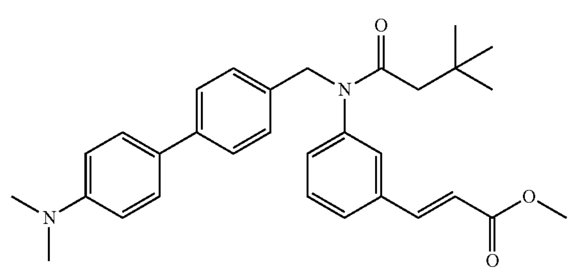 | (E)-Methyl 3-(3-(N-((4'-(dimethylamino)-[1,1'-biphenyl]-4-yl)methyl)-3,3-dimethylbutanamido)phenyl)acrylate | 485.3 |
| 8 | 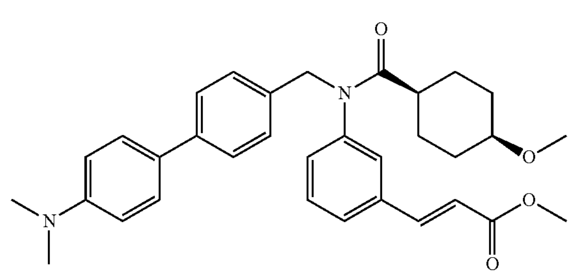 | cis-(E)-Methyl 3-(3-(N-((4'-(dimethylamino)-[1,1'-biphenyl]-4-yl)methyl)-4-methoxycyclohexanecarboxamido)phenyl)acrylate | 527.4 |

-continued

| Cmpd | Structure | Name | [M + H]+ |
|---|---|---|---|
| 9 | 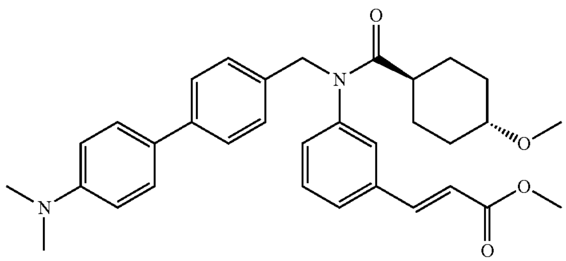 | trans-(E)-Methyl 3-(3-(N-((4'-(dimethylamino)-[1,1'-biphenyl]-4-yl)methyl)-4-methoxycyclohexanecarboxamido)phenyl)acrylate | 527.4 |
| 10 | 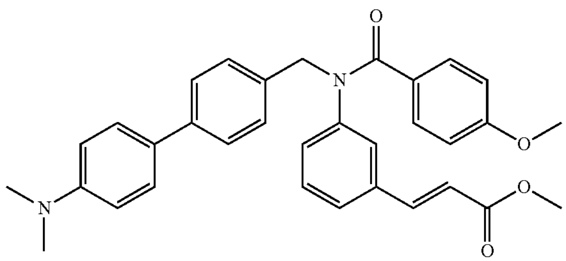 | (E)-Methyl 3-(3-(N-((4'-(dimethylamino)-[1,1'-biphenyl]-4-yl)methyl)-4-methoxybenzamido)phenyl)acrylate | 521.7 |
| 11* | 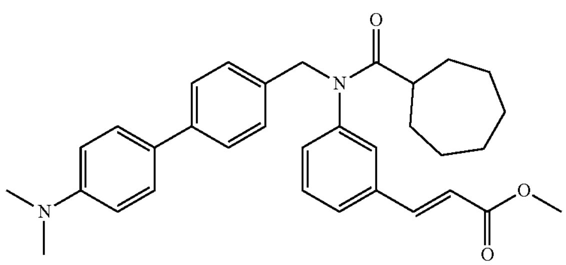 | (E)-Methyl 3-(3-(N-((4'-(dimethylamino)-[1,1'-biphenyl]-4-yl)methyl)cycloheptanecarboxamido)phenyl)acrylate | 511.8 |
| 12 | 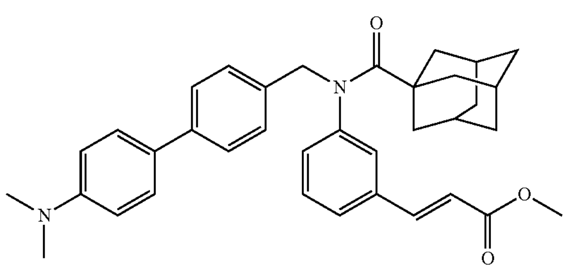 | (E)-Methyl 3-(3-(-N-((4'-(dimethylamino)-[1,1'-biphenyl]-4-yl)methyl)adamantane-1-carboxamido)phenyl)acrylate | 549.8 |
| 13 | 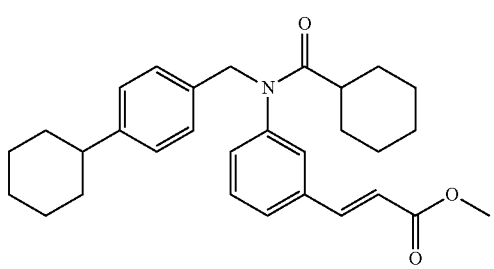 [SMILES: COC(=O)/C=C/c1cccc(N(Cc2ccc(C3CCCCC3)cc2)C(=O)C2CCCCC2)c1] | (E)-Methyl 3-(3-(N-(4-cyclohexylbenzyl)cyclohexanecarboxamido)phenyl)acrylate | 460.2 |
| 13.1 | 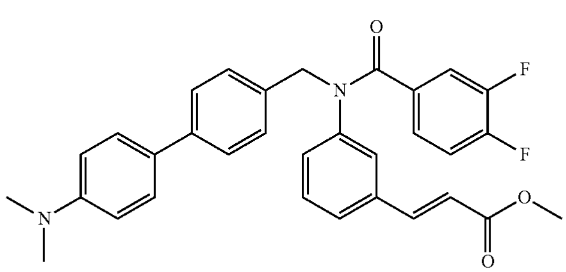 | (E)-Methyl 3-(3-(N-((4'-(dimethylamino)-[1,1'-biphenyl]-4-yl)methyl)-3,4-difluorobenzamido)phenyl)acrylate | 527.7 |

-continued

| Cmpd | Structure | Name | [M + H]+ |
|---|---|---|---|
| 13.2 | 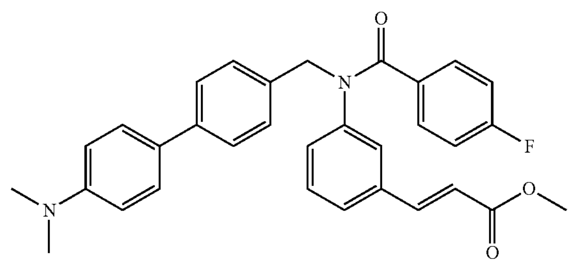 | (E)-Methyl 3-(3-(N-((4'-(dimethylamino)-[1,1'-biphenyl]-4-yl)methyl)-4-fluorobenzamido)phenyl)acrylate | 509.2 |
| 13.3 | 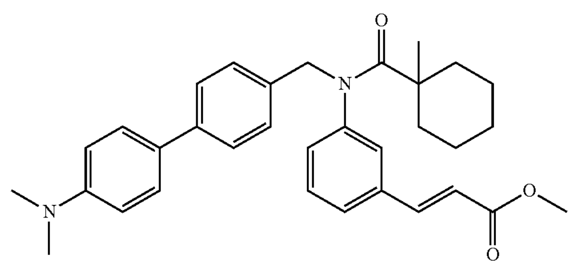 | (E)-Methyl 3-(3-(N-((4'-(dimethylamino)-[1,1'-biphenyl]-4-yl)methyl)-1-methylcyclohexanecarboxamido)phenyl)acrylate | 511.7 |
| 13.4 | 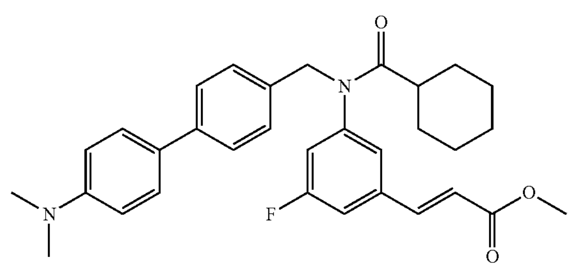 | (E)-Methyl 3-(3-(N-((4'-(dimethylamino)-[1,1'-biphenyl]-4-yl)methyl)cyclohexanecarboxamido)-5-fluorophenyl)acrylate | 515.6 |
| 13.5 | 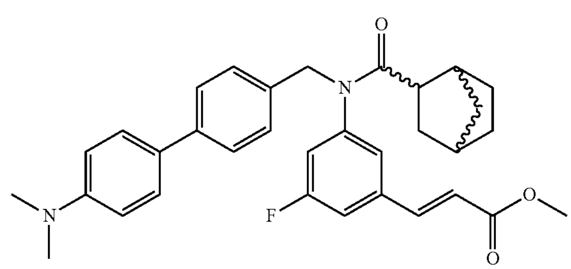 | (E)-Methyl 3-(3-(N-((4'-(dimethylamino)-[1,1'-biphenyl]-4-yl)methyl)bicyclo[2.2.1]heptane-2-carboxamido)-5-fluorophenyl)acrylate | 527.6 |
| 13.6 | 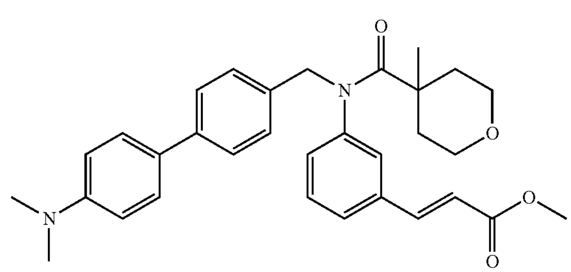 | (E)-Methyl 3-(3-(N-((4'-(dimethylamino)-[1,1'-biphenyl]-4-yl)methyl)-4-methyltetrahydro-2H-pyran-4-carboxamido)phenyl)acrylate | 513.6 |

| Cmpd | Structure | Name | [M + H]+ |
|---|---|---|---|
| 13.7 | 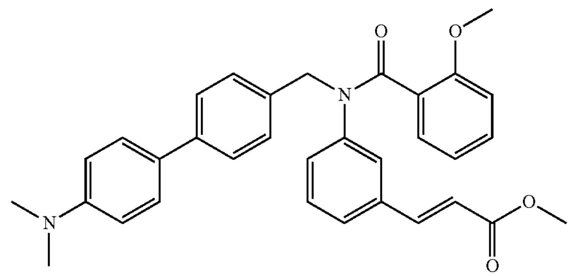 | (E)-Methyl 3-(3-(N-((4'-(dimethylamino)-[1,1'-biphenyl]-4-yl)methyl)-2-methoxybenzamido)phenyl)acrylate | 521.6 |
| 13.8 | 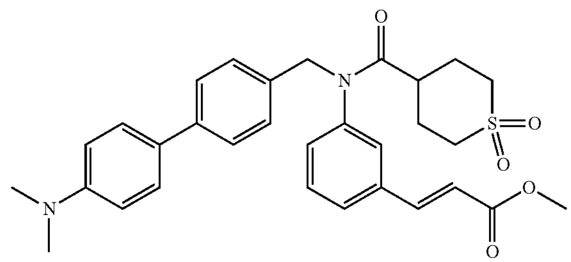 | (E)-Methyl 3-(3-(N-((4'-(dimethylamino)-[1,1'-biphenyl]-4-yl)methyl)-1,1-dioxidotetrahydro-2H-thiopyran-4-carboxamido)phenyl)acrylate | 547.5 |
| 13.9 | 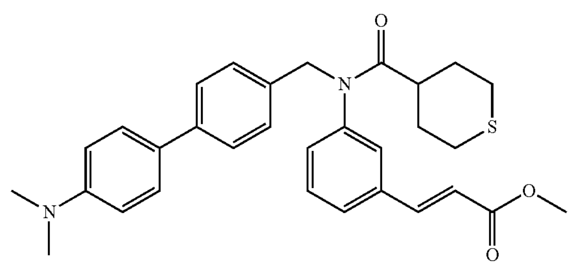 | (E)-Methyl 3-(3-(N-((4'-(dimethylamino)-[1,1'-biphenyl]-4-yl)methyl)tetrahydro-2H-thiopyran-4-carboxamido)phenyl)acrylate | 515.5 |
| 13.10 | 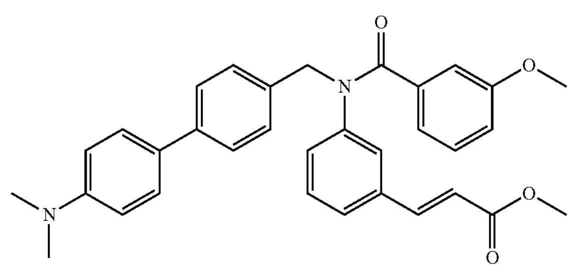 | (E)-Methyl 3-(3-(N-((4'-(dimethylamino)-[1,1'-biphenyl]-4-yl)methyl)-3-methoxybenzamido)phenyl)acrylate | 521.5 |
| 13.11 | 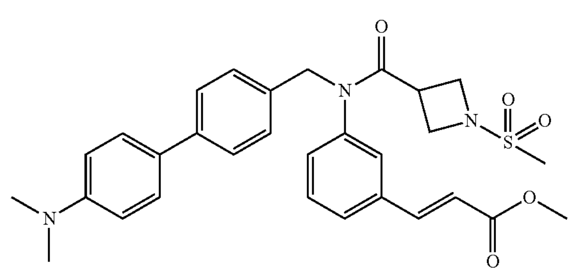 | (E)-Methyl 3-(3-(N-((4'-(dimethylamino)-[1,1'-biphenyl]-4-yl)methyl)-1-(methylsulfonyl)azetidine-3-carboxamido)phenyl)acrylate | 548.4 |
| 13.12 | 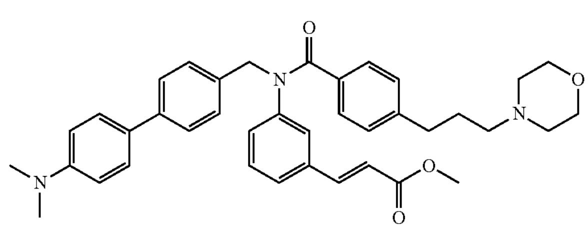 [SMILES: COC(=O)/C=C/c1cccc(N(Cc2ccc(-c3ccc(N(C)C)cc3)cc2)C(=O)c2ccc(CCCN3CCOCC3)cc2)c1] | (E)-Methyl 3-(3-(N-((4'-(dimethylamino)-[1,1'-biphenyl]-4-yl)methyl)-4-(2-morpholinoethoxy)benzamido)phenyl)acrylate | 620.4 |

| Cmpd | Structure | Name | [M + H]+ |
|---|---|---|---|
| 13.13 | 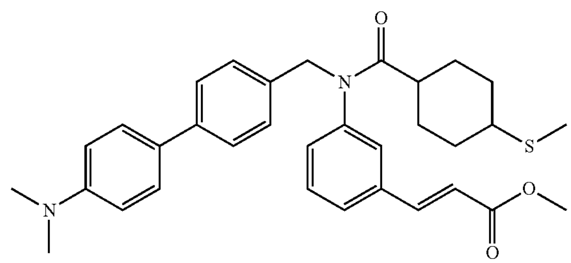 | (E)-Methyl 3-(3-(N-((4'-(dimethylamino)-[1,1'-biphenyl]-4-yl)methyl)-4-(methylthio)cyclohexanecarboxamido)phenyl)acrylate | 543.3 |
| 13.14** | 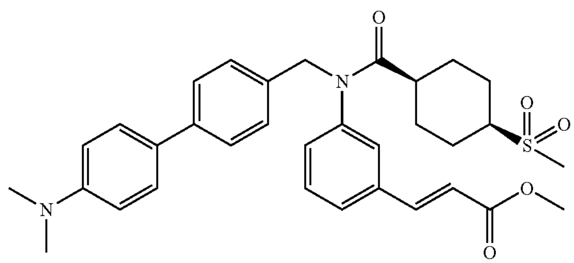 [SMILES: COC(=O)/C=C/c1cccc(N(Cc2ccc(-c3ccc(N(C)C)cc3)cc2)C(=O)[C@H]2CC[C@@H](S(C)(=O)=O)CC2)c1] | cis-(E)-Methyl 3-(3-(N-((4'-(dimethylamino)-[1,1'-biphenyl]-4-yl)methyl)-4-(methylsulfonyl)cyclohexanecarboxamido)phenyl)acrylate | 575.4 |
| 13.15** | 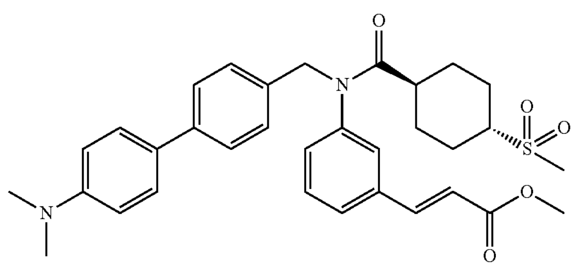 [SMILES: COC(=O)/C=C/c1cccc(N(Cc2ccc(-c3ccc(N(C)C)cc3)cc2)C(=O)[C@H]2CC[C@H](S(C)(=O)=O)CC2)c1] | trans-(E)-methyl 3-(3-(N-((4'-(dimethylamino)-[1,1'-biphenyl]-4-yl)methyl)-4-(methylsulfonyl)cyclohexanecarboxamido)phenyl)acrylate | 575.5 |
| 13.16 | 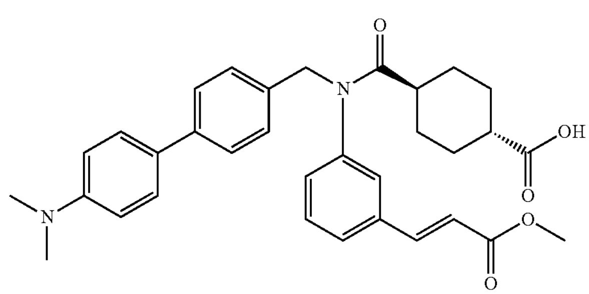 [SMILES: COC(=O)/C=C/c1cccc(N(Cc2ccc(-c3ccc(N(C)C)cc3)cc2)C(=O)[C@H]2CC[C@H](C(=O)O)CC2)c1] | trans-4-(((4'-(Dimethylamino)-[1,1'-biphenyl]-4-yl)methyl)(3-((E)-3-methoxy-3-oxoprop-1-en-1-yl)phenyl)carbamoyl)cyclohexanecarboxylic acid | 541.6 |
| 13.17 | 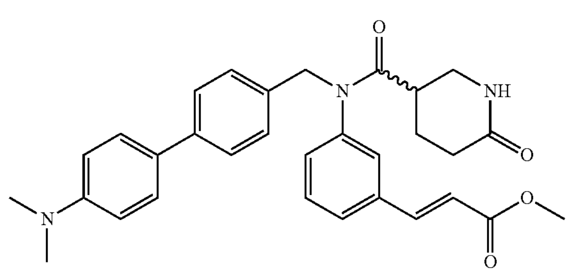 | (E)-Methyl 3-(3-(N-((4'-(dimethylamino)-[1,1'-biphenyl]-4-yl)methyl)-6-oxopiperidine-3-carboxamido)phenyl)acrylate | 512.4 |

| Cmpd | Structure | Name | [M + H]⁺ |
|---|---|---|---|
| 13.18 | 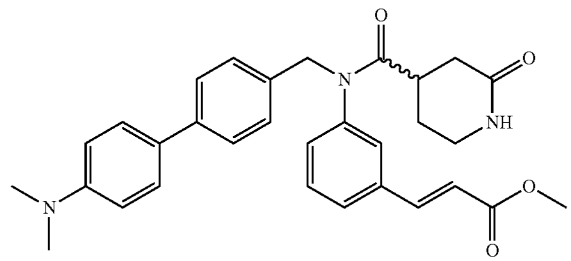 | (E)-Methyl 3-(3-(N-((4'-(dimethylamino)-[1,1'-biphenyl]-4-yl)methyl)-2-oxopiperidine-4-carboxamido)phenyl)acrylate | 512.3 |

Acylation conditions varied: 1.3-2 eq. RCOCl; 2-4 eq. Et₃N or pyridine; DCM, THF, or the base as solvent.
*Acid chloride was added as a solution in DCM.
**Stereoisomers were separated by HPLC.

The Compounds below were synthesized from the appropriate starting materials according to the procedure described for Compound 1 followed by additional transformations (sulfide oxidation, protecting group removal, ketone reduction, Mitsunobu inversion, etc.).

| Cmpd | Structure | Name | [M + H]⁺ |
|---|---|---|---|
| 13.19 | 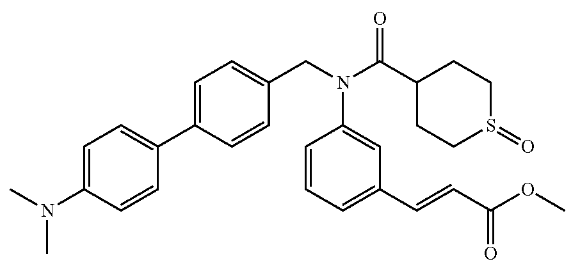 | (E)-Methyl 3-(3-(N-((4'-(dimethylamino)-[1,1'-biphenyl]-4-yl)methyl)-1-oxidotetrahydro-2H-thiopyran-4-carboxamido)phenyl)acrylate | 531.6 |
| 13.20 | 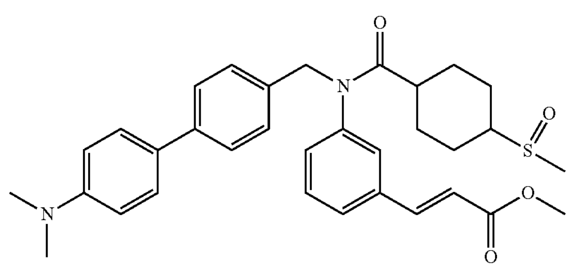 | (E)-Methyl 3-(3-(N-((4'-(dimethylamino)-[1,1'-biphenyl]-4-yl)methyl)-4-(methylsulfinyl)cyclohexanecarboxamido)phenyl)acrylate | 559.4 |
| 13.21 | 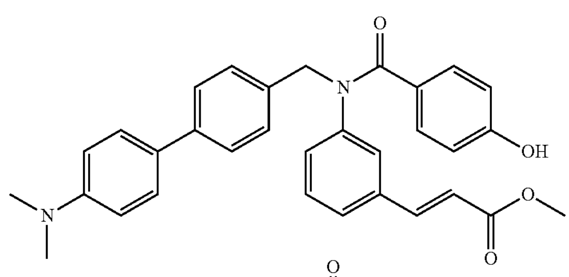 | (E)-Methyl 3-(3-(N-((4'-(dimethylamino)-[1,1'-biphenyl]-4-yl)methyl)-4-hydroxybenzamido)phenyl)acrylate | 507.5 |
| 13.22 | 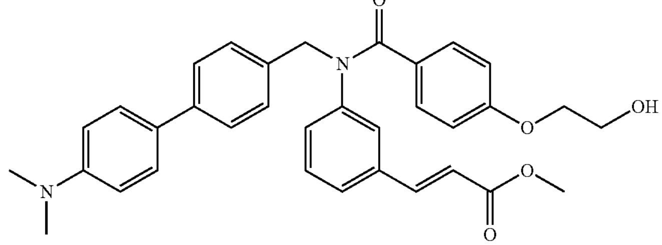 | (E)-Methyl 3-(3-(N-((4'-(dimethylamino)-[1,1'-biphenyl]-4-yl)methyl)-4-(2-hydroxyethoxy)benzamido)phenyl)acrylate | 551.3 |

-continued

| Cmpd | Structure | Name | [M + H]⁺ |
|---|---|---|---|
| 13.23 | 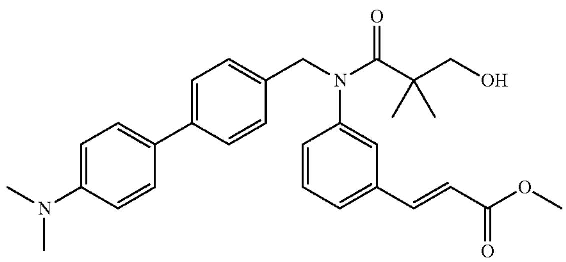 | (E)-Methyl 3-(3-(N-((4'-(dimethylamino)-[1,1'-biphenyl]-4-yl)methyl)-3-hydroxy-2,2-dimethylpropanamido)phenyl)acrylate | 487.6 |
| 13.24* | 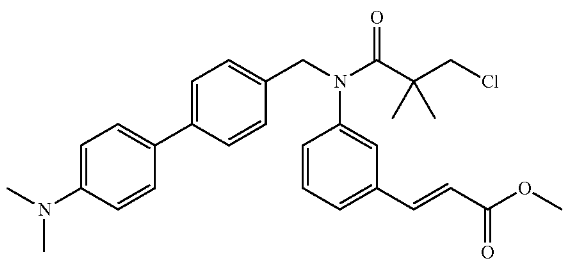 | (E)-Methyl 3-(3-(3-chloro-N-((4'-(dimethylamino)-[1,1'-biphenyl]-4-yl)methyl)-2,2-dimethylpropanamido)phenyl)acrylate | 505.6 |
| 13.25** | 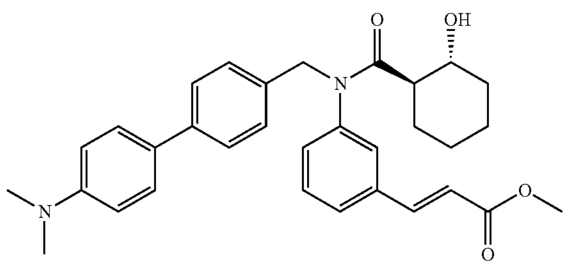 | trans-(E)-Methyl 3-(3-(N-((4'-(dimethylamino)-[1,1'-biphenyl]-4-yl)methyl)-2-hydroxycyclohexanecarboxamido)phenyl)acrylate | 513.3 |
| 13.26** | 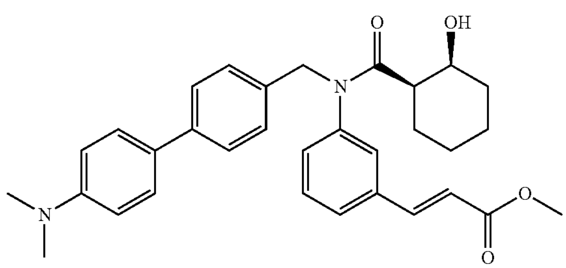 | cis-(E)-Methyl 3-(3-(N-((4'-(dimethylamino)-[1,1'-biphenyl]-4-yl)methyl)-2-hydroxycyclohexanecarboxamido)phenyl)acrylate | 513.3 |
| 13.27 | 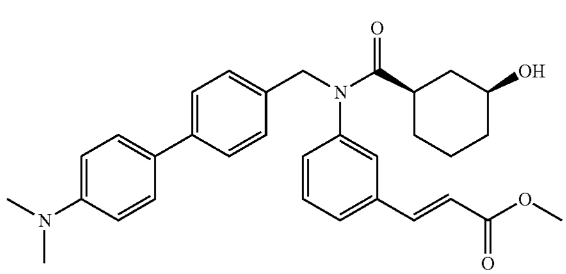 | cis-(E)-Methyl 3-(3-(N-((4'-(dimethylamino)-[1,1'-biphenyl]-4-yl)methyl)-3-hydroxycyclohexanecarboxamido)phenyl)acrylate | 513.4 |

| Cmpd | Structure | Name | [M + H]+ |
|---|---|---|---|
| 13.28 | 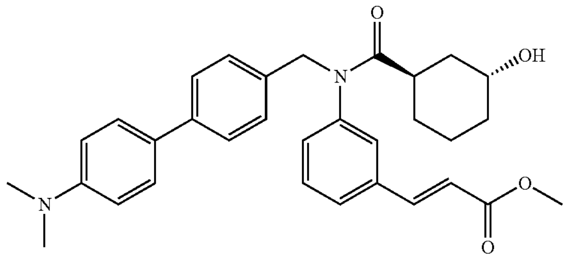 | trans-(E)-Methyl 3-(3-(N-((4'-(dimethylamino)-[1,1'-biphenyl]-4-yl)methyl)-3-hydroxycyclohexanecarboxamido)phenyl)acrylate | 513.6 |

*Isolated during the purification of Compound 13.23.
**Stereoisomers separated by HPLC.

Compound 14

(E)-Methyl 3-(3-(N-((4'-(dimethylamino)-[1,1'-biphenyl]-4-yl)methyl)cyclopentanecarboxamido)phenyl)acrylate

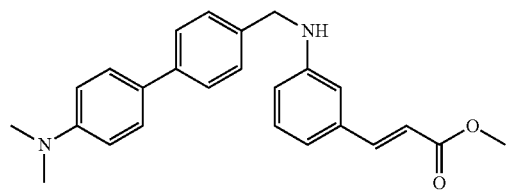

A mixture of Intermediate 3 (500 mg, 1.29 mmol), cyclopentanecarboxylic acid (280 uL, 2.58 mmol), EDCI (495 mg, 2.58 mmol), HOBt (349 mg, 2.58 mmol) and TEA (447 uL, 3.23 mmol) in DCM (6 mL) was degassed with vacuum/nitrogen cycles (3×) and stirred at 60° C. for 36 h. The reaction mixture was filtered, diluted with water (20 mL), and extracted with ethyl acetate (3×20 mL). The combined organic layers were washed with brine (2×20 mL), dried over anhydrous $Na_2SO_4$, filtered and concentrated under reduced pressure. The residue was purified by reverse-phase HPLC to give (E)-methyl 3-(3-(N-((4'-(dimethylamino)-[1,1'-biphenyl]-4-yl)methyl)cyclopentanecarboxamido)phenyl)acrylate (130 mg, 20%) as a yellow solid. $^1$H NMR (DMSO-$d_6$): δ 7.58-7.71 (m, 3H), 7.45-7.53 (m, 4H), 7.41 (t, 1H), 7.17 (d, 3H), 6.77 (d, 2H), 6.65 (d, 1H), 4.88 (br s, 2H), 3.71 (s, 3H), 2.92 (s, 6H), 2.55-2.59 (m, 1H), 1.52-1.77 (m, 6H), 1.37 (br s, 2H); MS: 483.4 [M+H]+.

The Compound below was synthesized from Intermediate 3 and cyclobutanecarboxylic acid following the procedure described for Compound 14.

| Cmpd | Structure | Name | [M + H]+ |
|---|---|---|---|
| 15 | 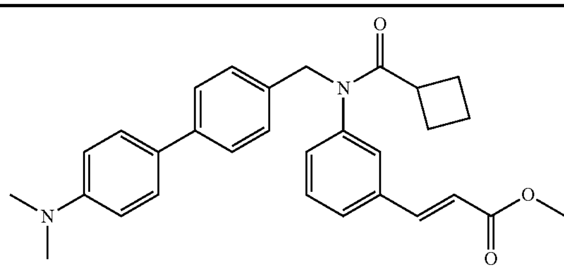 | (E)-Methyl 3-(3-(N-((4'-(dimethylamino)-[1,1'-biphenyl]-4-yl)methyl)cyclobutanecarboxamido)phenyl)acrylate | 469.3 |

-continued

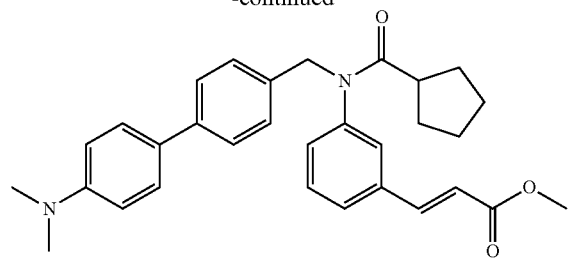

Compound 16

(E)-Methyl 3-(3-(((4'-(dimethylamino)-[1,1'-biphenyl]-4-yl)methyl)amino)phenyl)acrylate

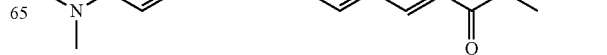

Compound 17

(E)-Methyl 3-(3-(N-((4'-(dimethylamino)-[1,1'-biphenyl]-4-yl)methyl)-4-oxocyclohexanecarboxamido)phenyl)acrylate

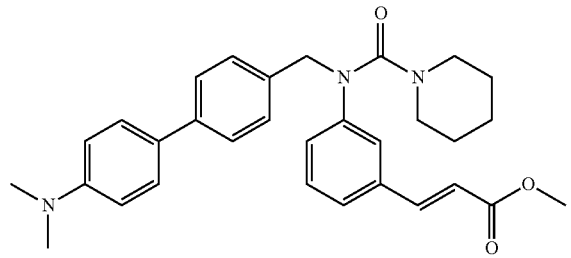

Triphosgene (296 mg, 1.0 mmol) was added to a solution of piperidine (99 uL, 1.0 mmol) and TEA (628 uL, 4.53 mmol) in DCM (10 mL) at 0° C. After stirring the mixture for 2 h, Intermediate 3 (350 mg, 0.91 mmol) was added to the reaction mixture. The stirring was continued at 0° C. for 2 h and at 25° C. for 8 h. The mixture was diluted with water (10 mL) and extracted with DCM (2×20 mL). The combined organic layers were washed with brine (10 mL), dried over Na$_2$SO$_4$, filtered, and concentrated. The residue was purified by reverse-phase HPLC to give (E)-methyl 3-(3-(N-((4'-(dimethylamino)-[1,1'-biphenyl]-4-yl)methyl)piperidine-1-carboxamido)phenyl)acrylate (200 mg, 42%) as a yellow solid. $^1$H NMR (400 MHz, DMSO-d$_6$): δ 7.57 (d, 1H), 7.41-7.52 (m, 5H), 7.26-7.39 (m, 4H), 7.10 (d, 1H), 6.74 (d, 2H), 6.59 (d, 1H), 4.83 (s, 2H), 3.69 (s, 3H), 3.13 (br s, 4H), 2.89 (s, 6H), 1.41 (br s, 2H), 1.27 (br s, 4H); MS: 498.3 [M+H]$^+$.

A mixture of Intermediate 3 (800 mg, 2.07 mmol), 4-oxocyclohexanecarboxylic acid (500 mg, crude), ethyl 2-ethoxyquinoline-1(2H)-carboxylate (768 mg, 3.10 mmol), and toluene (10 mL) was degassed with vacuum/nitrogen cycles (3×), and then stirred at 110° C. for 36 h. The reaction mixture was diluted with water (40 mL) and extracted with ethyl acetate (3×40 mL). The combined organic phases were washed with water (3×40 mL), washed with brine (2×40 mL), dried over anhydrous Na$_2$SO$_4$, filtered, and concentrated. The residue was purified by column chromatography (SiO$_2$, petroleum ether/ethyl acetate; 10/1 to 3/1) to give (E)-methyl 3-(3-(N-((4'-(dimethylamino)-[1,1'-biphenyl]-4-yl)methyl)-4-oxocyclohexanecarboxamido)phenyl)acrylate (430 mg, 38%) as a yellow oil. MS: 511.3 [M+H]$^+$.

The Compounds below were synthesized from the appropriate starting materials following the procedure described for Compound 17.

| Cmpd | Structure | Name | [M + H]$^+$ |
|---|---|---|---|
| 17.1 | 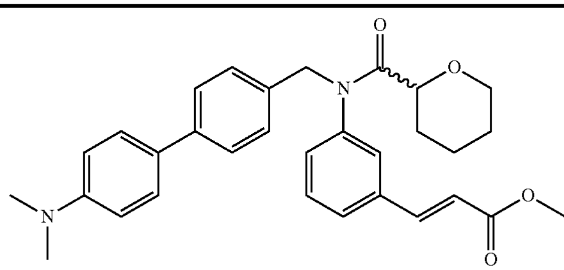 | (E)-Methyl 3-(3-(N-((4'-(dimethylamino)-[1,1'-biphenyl]-4-yl)methyl)tetrahydro-2H-pyran-2-carboxamido)phenyl)acrylate | 499.5 |
| 17.2 | 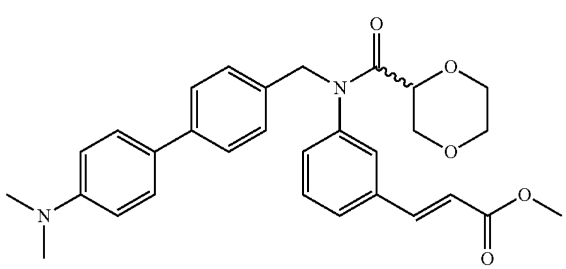 | (E)-Methyl 3-(3-(N-((4'-(dimethylamino)-[1,1'-biphenyl]-4-yl)methyl)-1,4-dioxane-2-carboxamido)phenyl)acrylate | 501.4 |

| Cmpd | Structure | Name | [M + H]+ |
|---|---|---|---|
| 17.3 | 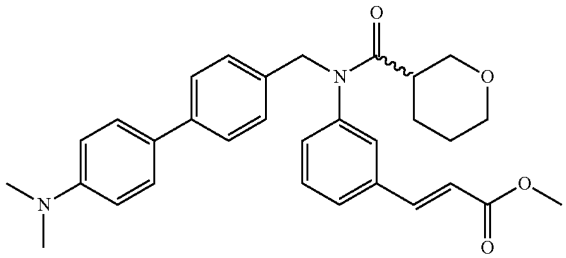 | (E)-Methyl 3-(3-(N-((4'-(dimethylamino)-[1,1'-biphenyl]-4-yl)methyltetrahydro-2H-pyran-3-carboxamido)phenyl)acrylate | 499.4 |

Compounds 18 & 19 cis-(E)-Methyl 3-(3-(N-((4'-(dimethylamino)-[1,1'-biphenyl]-4-yl)methyl)-4-hydroxycyclohexanecarboxamido)phenyl)acrylate & trans-(E)-methyl 3-(3-(N-((4'-(dimethylamino)-[1,1'-biphenyl]-4-yl)methyl)-4-hydroxycyclohexanecarboxamido)phenyl)acrylate

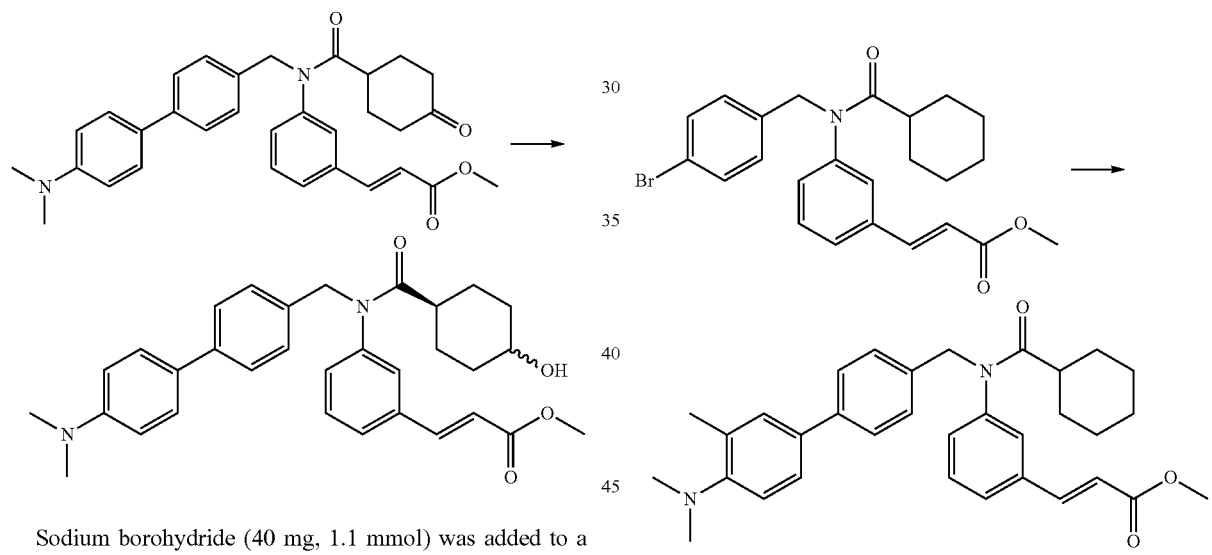

Sodium borohydride (40 mg, 1.1 mmol) was added to a solution of Compound 17 (430 mg, 0.84 mmol) in methanol (6 mL). The mixture was stirred at 25° C. for 1 h, poured into saturated ammonium chloride (60 mL), and then extracted with ethyl acetate (3×30 mL). The combined organic phases were washed with brine (2×30 mL), dried over anhydrous Na$_2$SO$_4$, filtered, and concentrated in vacuo. The residue was purified by reverse-phase HPLC to give the title compounds as yellow solids.

18: cis-(E)-Methyl 3-(3-(N-((4'-(dimethylamino)-[1,1'-biphenyl]-4-yl)methyl)-4-hydroxycyclohexanecarboxamido)phenyl)acrylate (109 mg, 25%): $^1$H NMR (DMSO-d$_6$): δ 7.60-7.72 (m, 3H), 7.39-7.51 (m, 5H), 7.16 (d, 3H), 6.77 (d, 2H), 6.65 (d, 1H), 4.85 (br s, 2H), 4.42 (d, 1H), 3.72 (s, 3H), 3.26-3.30 (m, 1H), 2.92 (s, 6H), 2.08 (d, 1H), 1.63-1.81 (m, 4H), 1.40-1.54 (m, 2H), 0.78 (d, 2H); MS: 513.3 [M+H]+.

19: trans-(E)-Methyl 3-(3-(N-((4'-(dimethylamino)-[1,1'-biphenyl]-4-yl)methyl)-4-hydroxycyclohexanecarboxamido)phenyl)acrylate (52 mg, 12%): $^1$H NMR (DMSO-d$_6$): δ 7.59-7.72 (m, 3H), 7.49 (dd, 4H), 7.40 (t, 1H), 7.17 (d, 3H), 6.77 (d, 2H), 6.65 (d, 1H), 4.86 (br s, 2H), 4.27 (d, 1H), 3.64-3.75 (m, 4H), 2.92 (s, 6H), 2.19 (br s, 1H), 1.77-1.92 (m, 2H), 1.59 (d, 2H), 1.37 (d, 2H), 1.09 (br s, 2H); MS: 513.3 [M+H]+.

Compound 20

(E)-Methyl 3-(3-(N-((4'-(dimethylamino)-3'-methyl-[1,1'-biphenyl]-4-yl)methyl)cyclohexanecarboxamido)phenyl)acrylate A mixture of Intermediate 12 (500 mg, 1.10 mmol), (4-(dimethylamino)-3-methylphenyl)boronic acid (294 mg, 1.64 mmol), Cs$_2$CO$_3$ (1.07 g, 3.29 mmol), Pd(PPh$_3$)$_4$ (127 mg, 0.11 mmol), and DMF (10 mL) was degassed with vacuum/nitrogen cycles (3×) and then stirred at 80° C. for 5 h. A saturated ammonium chloride solution (30 mL) was added, and the mixture was extracted with ethyl acetate (3×30 mL). The combined organic phases were washed with brine (2×30 mL), dried over anhydrous Na$_2$SO$_4$, filtered and concentrated. The residue was purified by reverse-phase HPLC to give (E)-methyl 3-(3-(N-((4'-(dimethylamino)-3'-methyl-[1,1'-biphenyl]-4-yl)methyl)cyclohexanecarboxamido)phenyl)acrylate (265 mg, 47%) as a white solid. $^1$H NMR (DMSO-d$_6$): δ 7.57-7.66 (m, 3H), 7.48 (d, 2H), 7.33-7.39 (m, 3H), 7.11-7.18 (m, 3H), 7.02 (d, 1H), 6.60 (d, 1H), 4.83 (br s, 2H), 3.67 (s, 3H), 2.61 (s, 6H), 2.26 (s, 3H), 2.14 (m, 1H), 1.54-1.67 (m, 4H), 1.31-1.49 (m, 3H), 1.01-1.13 (m, 1H), 0.85 (d, 2H); MS: 511.3 [M+H]+.

The Compounds below were synthesized from the appropriate starting materials following the procedure described for Compound 20.

| Cmpd | Structure | Name | [M + H⁺] |
|---|---|---|---|
| 21 | 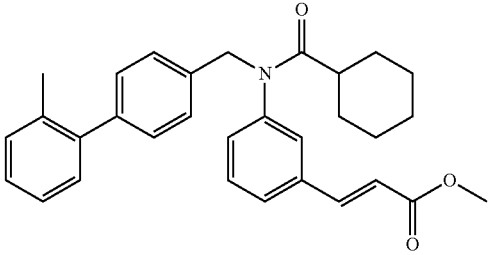 [SMILES: COC(=O)/C=C/c1cccc(N(Cc2ccc(-c3ccccc3C)cc2)C(=O)C2CCCCC2)c1] | (E)-Methyl 3-(3-(N-((2'-methyl-[1,1'-biphenyl]-4-yl)methyl)cyclohexanecarboxamido)phenyl)acrylate | 468.3 |
| 22 | 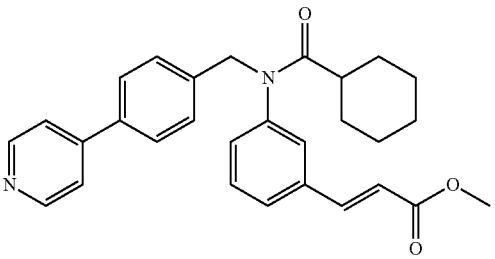 [SMILES: COC(=O)/C=C/c1cccc(N(Cc2ccc(-c3ccncc3)cc2)C(=O)C2CCCCC2)c1] | (E)-Methyl 3-(3-(N-(4-(pyridin-4-yl)benzyl)cyclohexanecarboxamido)phenyl)acrylate | 455.3 |
| 23 | 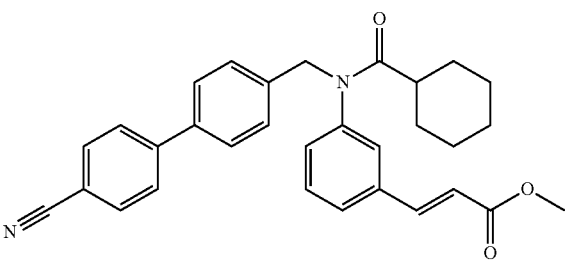 [SMILES: COC(=O)/C=C/c1cccc(N(Cc2ccc(-c3ccc(C#N)cc3)cc2)C(=O)C2CCCCC2)c1] | (E)-Methyl 3-(3-(N-((4'-cyano-[1,1'-biphenyl]-4-yl)methyl)cyclohexanecarboxamido)phenyl)acrylate | 479.3 |
| 24 | 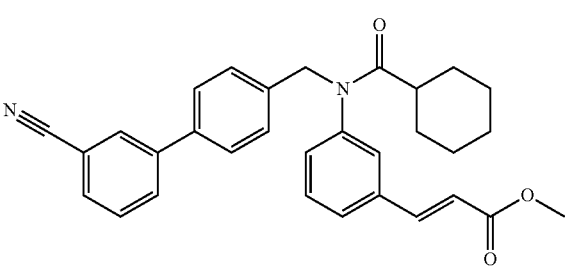 [SMILES: COC(=O)/C=C/c1cccc(N(Cc2ccc(-c3cccc(C#N)c3)cc2)C(=O)C2CCCCC2)c1] | (E)-Methyl 3-(3-(N-((3'-cyano-[1,1'-biphenyl]-4-yl)methyl)cyclohexanecarboxamido)phenyl)acrylate | 479.3 |
| 25 | 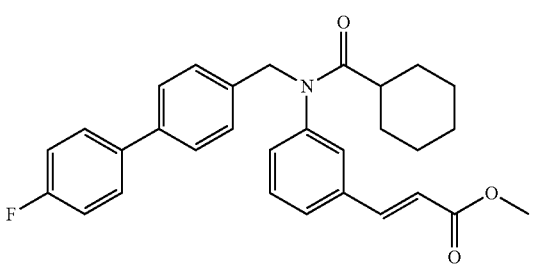 [SMILES: COC(=O)/C=C/c1cccc(N(Cc2ccc(-c3ccc(F)cc3)cc2)C(=O)C2CCCCC2)c1] | (E)-Methyl 3-(3-(N-((4'-fluoro-[1,1'-biphenyl]-4-yl)methyl)cyclohexanecarboxamido)phenyl)acrylate | 472.3 |

-continued

| Cmpd | Structure | Name | [M + H⁺] |
|---|---|---|---|
| 26 | 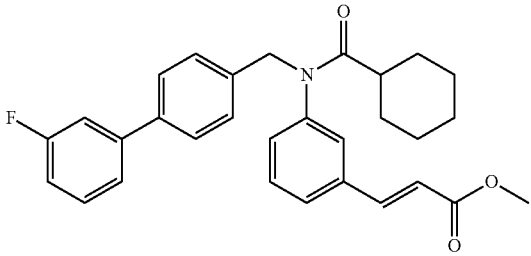 [SMILES: COC(=O)/C=C/c1cccc(N(Cc2ccc(-c3cccc(F)c3)cc2)C(=O)C2CCCCC2)c1] | (E)-Methyl 3-(3-(N-((3'-fluoro-[1,1'-biphenyl]-4-yl)methyl)cyclohexanecarboxamido)phenyl)acrylate | 472.3 |
| 27 | 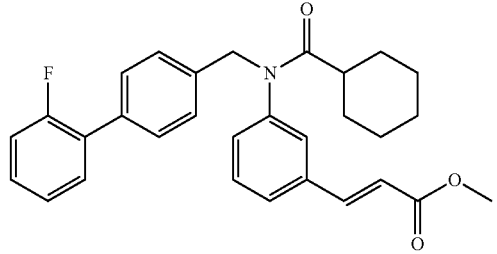 [SMILES: COC(=O)/C=C/c1cccc(N(Cc2ccc(-c3ccccc3F)cc2)C(=O)C2CCCCC2)c1] | (E)-Methyl 3-(3-(N-((2'-fluoro-[1,1'-biphenyl]-4-yl)methyl)cyclohexanecarboxamido)phenyl)acrylate | 472.3 |
| 28 | 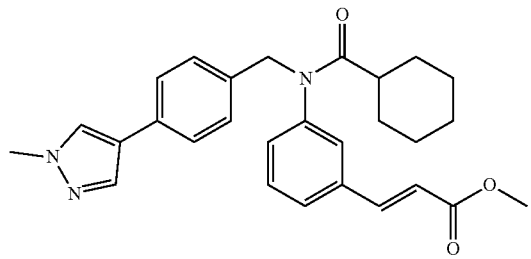 | (E)-Methyl 3-(3-(N-(4-(1-methyl-1H-pyrazol-4-yl)benzyl)cyclohexanecarboxamido)phenyl)acrylate | 458.3 |
| 29 | 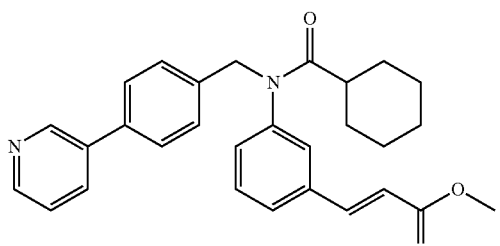 | (E)-Methyl 3-(3-(N-(4-(pyridin-3-yl)benzyl)cyclohexanecarboxmido)phenyl)acrylate | 455.3 |
| 30 | 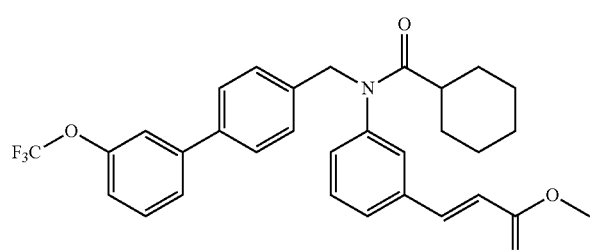 | (E)-Methyl 3-(3-(N-((3'-(trifluoromethoxy)-[1,1'-biphenyl]-4-yl)methyl)cyclohexanecarboxamido)phenyl)acrylate | 538.3 |
| 31 | 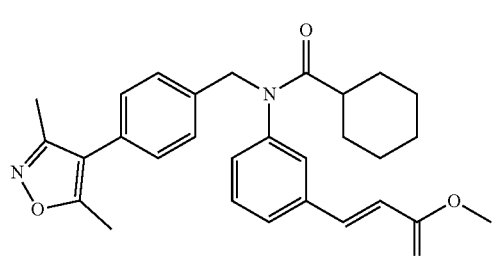 | (E)-Methyl 3-(3-(N-(4-(3,5-dimethylisoxazol-4-yl)benzyl)cyclohexanecarboxamido)phenyl)acrylate | 473.3 |

-continued

| Cmpd | Structure | Name | [M + H⁺] |
|---|---|---|---|
| 32 | 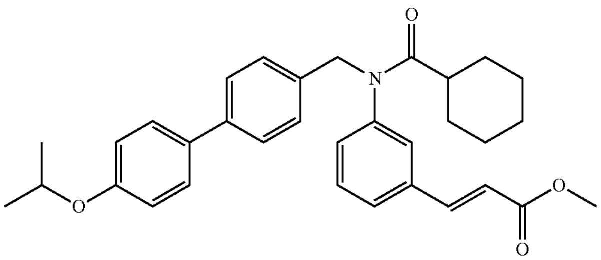 [SMILES: COC(=O)/C=C/c1cccc(N(Cc2ccc(-c3ccc(OC(C)C)cc3)cc2)C(=O)C2CCCCC2)c1] | (E)-Methyl 3-(3-(N-((4'-isopropoxy-[1,1'-biphenyl]-4-yl)methyl)cyclohexanecarboxamido)phenyl)acrylate | 512.3 |
| 33 | 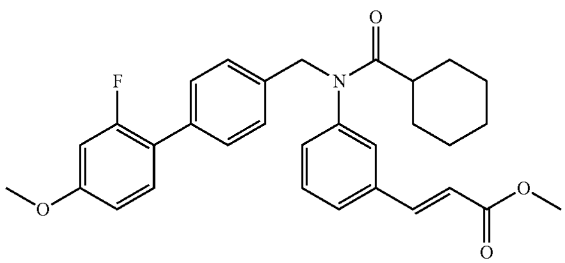 | (E)-Methyl 3-(3-(N-((2'-fluoro-4'-methoxy-[1,1'-biphenyl]-4-yl)methyl)cyclohexanecarboxamido)phenyl)acrylate | 502.3 |
| 34 | 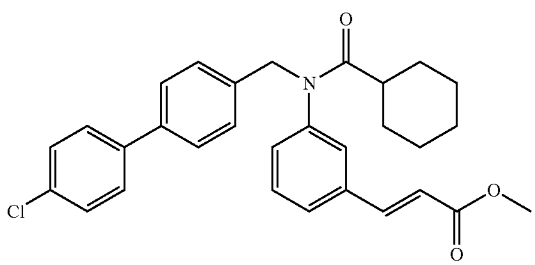 | (E)-Methyl 3-(3-(N-((4'-chloro-[1,1'-biphenyl]-4-yl)methyl)cyclohexanecarobxamido)phenyl)acrylate | 488.2 |
| 35 | 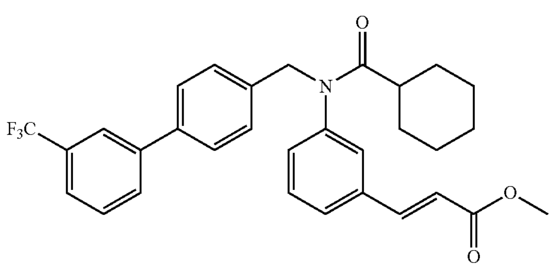 [SMILES: COC(=O)/C=C/c1cccc(N(Cc2ccc(-c3cccc(C(F)(F)F)c3)cc2)C(=O)C2CCCCC2)c1] | (E)-Methyl 3-(3-(N-((3'-(trifluoromethyl)-[1,1'-biphenyl]-4-yl)methyl)cyclohexanecarboxamido)phenyl)acrylate | 522.3 |
| 36 | 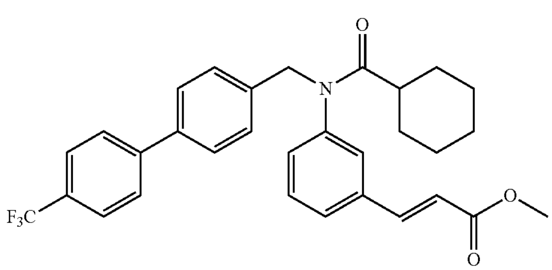 [SMILES: COC(=O)/C=C/c1cccc(N(Cc2ccc(-c3ccc(C(F)(F)F)cc3)cc2)C(=O)C2CCCCC2)c1] | (E)-Methyl 3-(3-(N-((4'-(trifluoromethyl)-[1,1'-biphenyl]-4-yl)methyl)cyclohexanecarboxamido)phenyl)acrylate | 522.3 |
| 37 | 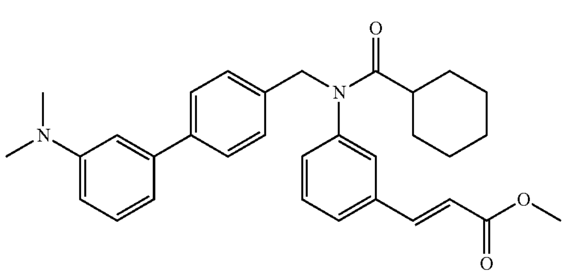 | (E)-Methyl 3-(3-(N-((3'-(dimethylamino)-[1,1'-biphenyl]-4-yl)methyl)cyclohexanecarobxamido)phenyl)acrylate | 497.3 |

-continued

| Cmpd | Structure | Name | [M + H⁺] |
|---|---|---|---|
| 38 | 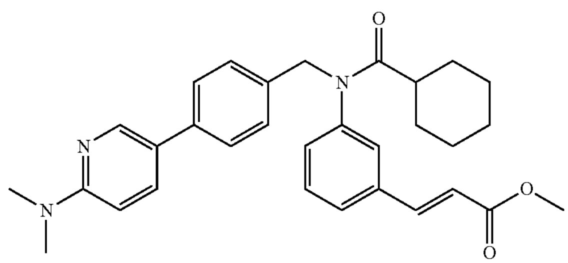 | (E)-Methyl 3-(3-(N-(4-(6-(dimethylamino)pyridin-3-yl)benzyl)cyclohexanecarboxamido)phenyl)acrylate | 498.3 |
| 39 | 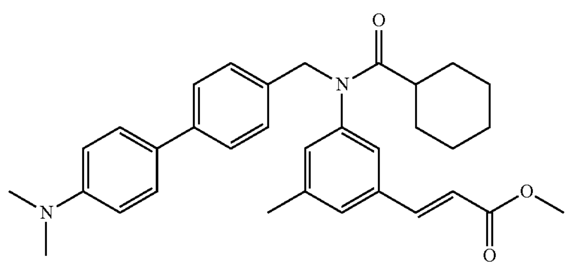 | (E)-Methyl 3-(3-(N-((4'-(dimethylamino)-[1,1'-biphenyl]-4-yl)methyl)cyclohexanecarboxamido)-5-methylphenyl)acrylate | 511.4 |
| 40 | 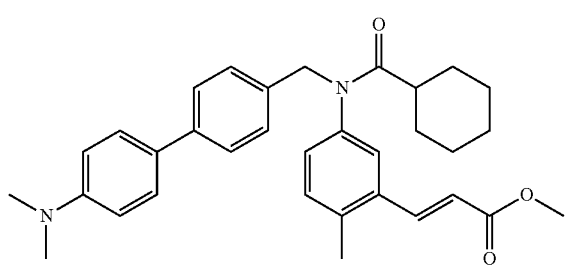 | (E)-Methyl 3-(5-(N-((4'-(dimethylamino)-[1,1'-biphenyl]-4-yl)methyl)cyclohexanecarboxamido)-2-methylphenyl)acrylate | 511.4 |
| 41 | 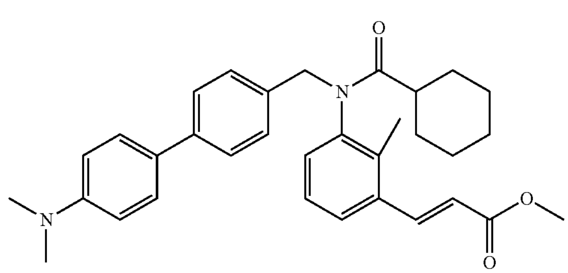 | (E)-Methyl 3-(3-(N-((4'-(dimethylamino)-[1,1'-biphenyl]-4-yl)methyl)cyclohexanecarboxamido)-2-methylphenyl)acrylate | 511.4 |
| 42 | 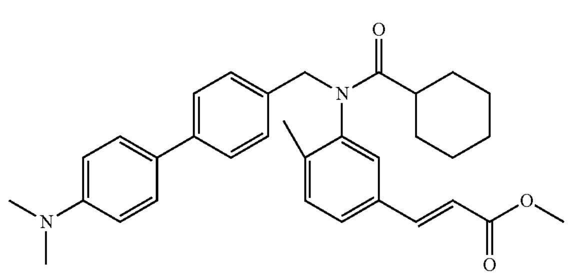 | (E)-Methyl 3-(3-(N-((4'-(dimethylamino)-[1,1'-biphenyl]-4-yl)methyl)cyclohexanecarobxamido)-4-methylphenyl)acrylate | 511.3 |
| 43 | 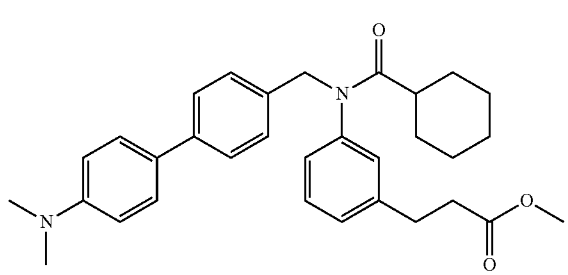 | Methyl 3-(3-(N-((4'-(dimethylamino)-[1,1'-biphenyl]-4-yl)methyl)cyclohexanecarboxamido)phenyl)propanoate | 499.4 |

-continued

| Cmpd | Structure | Name | [M + H⁺] |
|---|---|---|---|
| 44 | 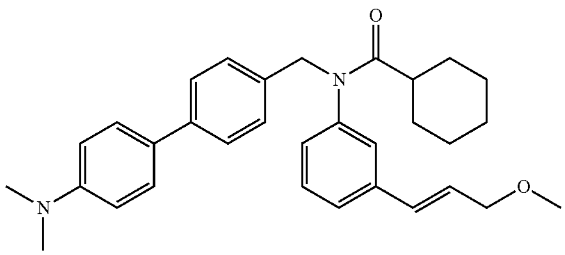 | (E)-N-((4'-(Dimethylamino)-[1,1'-biphenyl]-4-yl)methyl)-N-(3-(3-methoxyprop-1-en-1-yl)phenyl)cyclohexanecarboxamide | 483.4 |
| 45 | 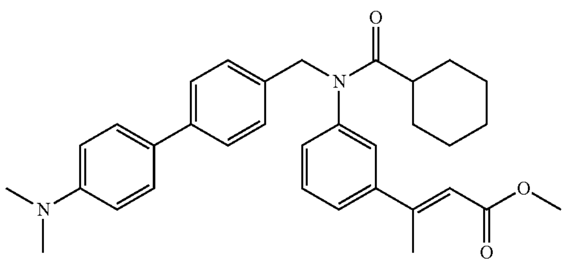 | (E)-Methyl 3-(3-(N-((4'-(dimethylamino)-[1,1'-biphenyl]-4-yl)methyl)cyclohexanecarboxamido)phenyl)but-2-enoate | 511.4 |
| 46 | 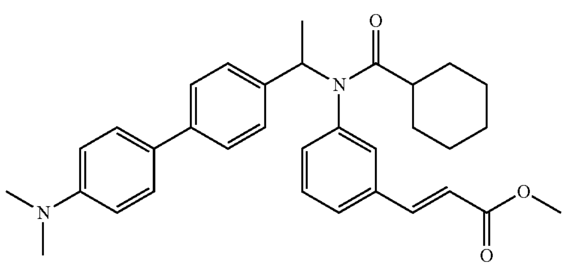 | (E)-Methyl 3-(3-(N-(1-(4'-(dimethylamino)-[1,1'-biphenyl]-4-yl)ethyl)cyclohexanecarboxamido)phenyl)acrylate | 511.4 |
| 47 | 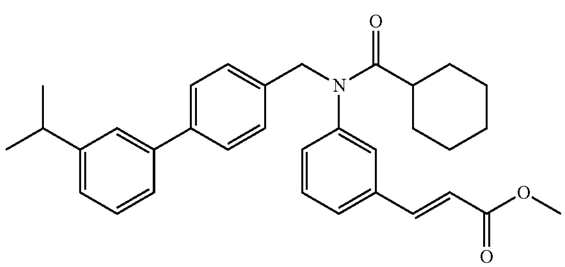 [SMILES: COC(=O)/C=C/c1cccc(N(Cc2ccc(-c3cccc(C(C)C)c3)cc2)C(=O)C2CCCCC2)c1] | (E)-Methyl 3-(3-(N-((3'-isopropyl-[1,1'-biphenyl]-4-yl)methyl)cyclohexanecarboxamido)phenyl)acrylate | 496.3 |
| 48 | 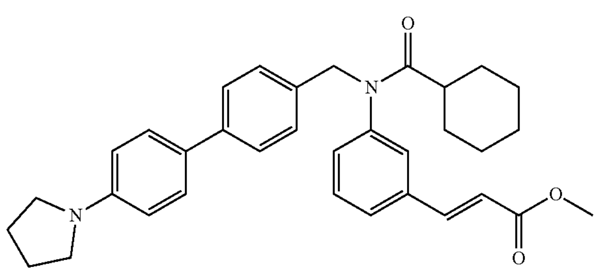 [SMILES: COC(=O)/C=C/c1cccc(N(Cc2ccc(-c3ccc(N4CCCC4)cc3)cc2)C(=O)C2CCCCC2)c1] | (E)-Methyl 3-(3-(N-((4'-(pyrrolidin-1-yl)-[1,1'-biphenyl]-4-yl)methyl)cyclohexanecarobxamido)phenyl)acrylate | 523.4 |
| 49 | 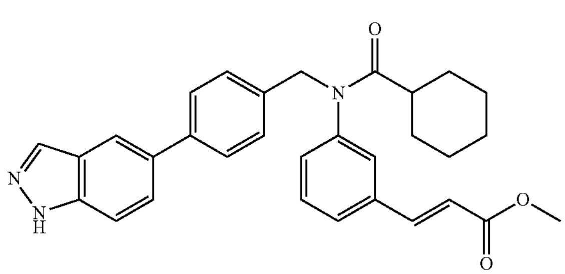 | (E)-Methyl 3-(3-(N-(4-(1H-indazol-5-yl)benzyl)cyclohexanecarboxamido)phenyl)acrylate | 494.7 |

| Cmpd | Structure | Name | [M + H⁺] |
|---|---|---|---|
| 50 | 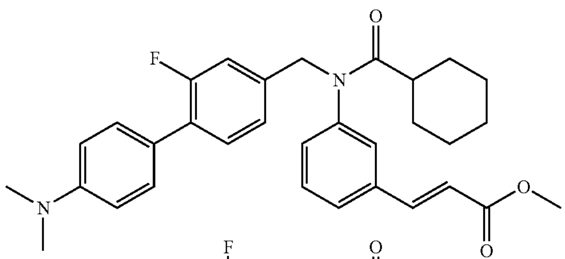 | (E)-Methyl 3-(3-(N-((4'-(dimethylamino)-2-fluoro-[1,1'-biphenyl]-4-yl)methyl)cyclohexanecarboxamido)phenyl)acrylate | 515.2 |
| 51 | 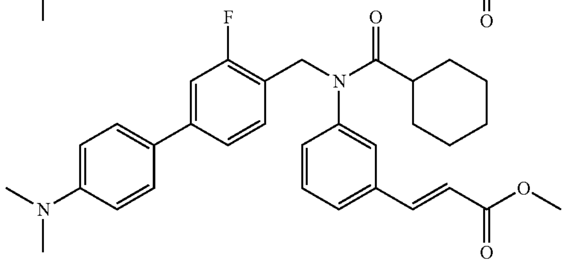 | (E)-Methyl 3-(3-(N-((4'-(dimethylamino)-3-fluoro-[1,1'-biphenyl]-4-yl)methyl)cyclohexanecarboxamido)phenyl)acrylate | 515.3 |

Note:
reaction time: 5-24 h.
*2M $K_2CO_3$/DME instead of $Cs_2CO_3$/DMF; reaction time: 46 h.

Compound 52

(E)-Methyl 3-(3-(N-((4'-methoxy-3'-methyl-[1,1'-biphenyl]-4-yl)methyl)cyclohexanecarboxamido)phenyl)acrylate

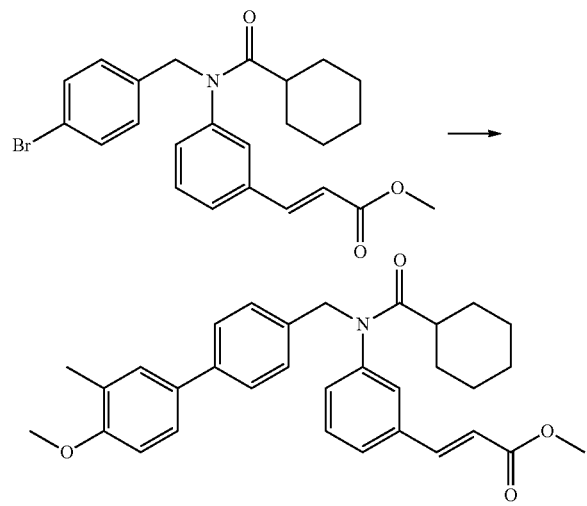

A mixture of Intermediate 12 (108 mg, 0.24 mmol), 4-methoxy-3-methyl-phenyl boronic acid (62 mg, 0.37 mmol), $Cs_2CO_3$ (243 mg, 0.75 mmol), [1,1'-bis(diphenylphosphino)ferrocene]dichloropalladium (II) (18 mg, 0.025 mmol) and DMF (3 mL) was degassed with vacuum/nitrogen cycles (3>). The reaction mixture was heated at 80° C. for 90 minutes, diluted with ethyl acetate (30 mL), washed with saturated $NaHCO_3$ (2×20 mL) and washed with brine (20 mL). The organics were dried ($Na_2SO_4$), filtered, concentrated and purified by reverse-phase HPLC (70-94% acetonitrile/water w/0.1% TFA) to give (E)-methyl 3-(3-(N-((4'-methoxy-3'-methyl-[1,1'-biphenyl]-4-yl)methyl)cyclohexanecarboxamido)phenyl)acrylate (69 mg, 58%) as a tan foam. $^1$H NMR (400 MHz, DMSO-$d_6$): δ 7.69 (d, 1H), 7.66 (s, 1H), 7.62 (d, 1H), 7.51 (d, 2H), 7.45-7.39 (m, 3H), 7.22-7.14 (m, 3H), 6.98 (d, 1H), 6.66 (d, 1H), 4.88 (s, 2H), 3.80 (s, 3H), 3.70 (s, 3H), 2.19 (s, 3H), 2.20-2.12 (m, 1H), 1.71-1.57 (m, 4H), 1.57-1.37 (m, 3H), 1.19-1.06 (m, 1H), 0.98-0.83 (m, 2H); LCMS: 498.2 [M+H]⁺.

The Compounds below were synthesized from the appropriate starting materials following the procedure described for Compound 52.

| Cmpd | Structure | Name | [M + H]⁺ |
|---|---|---|---|
| 53 | 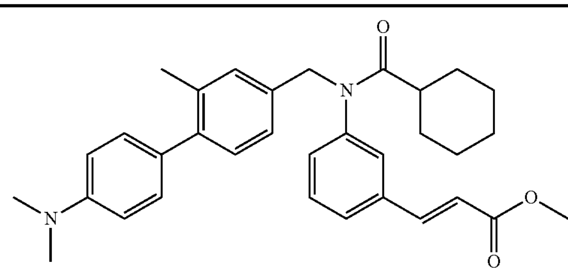 | (E)-Methyl 3-(3-(N-((4'-(dimethylamino)-2-methyl-[1,1'-biphenyl]-4-yl)methyl)cyclohexanecarboxamido)phenyl)acrylate | 511.4 |

-continued

| Cmpd | Structure | Name | [M + H]+ |
|---|---|---|---|
| 54 | 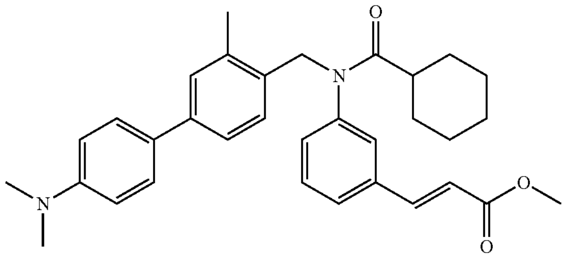 | (E)-Methyl 3-(3-(N-((4'-(dimethylamino)-3-methyl-[1,1'-biphenyl]-4-yl)methyl)cyclohexanecarboxamido)phenyl)acrylate | 511.3 |
| 55 | 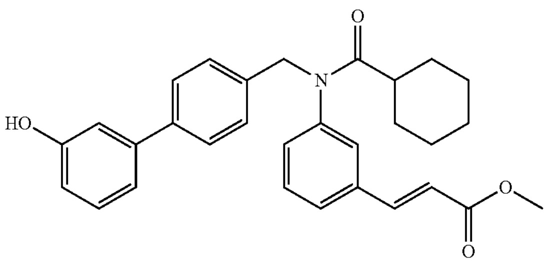 [SMILES: COC(=O)/C=C/c1cccc(N(Cc2ccc(-c3cccc(O)c3)cc2)C(=O)C2CCCCC2)c1] | (E)-Methyl 3-(3-(N-((3'-hydroxy-[1,1'-biphenyl]-4-yl)methyl)cyclohexanecarboxamido)phenyl)acrylate | 470.3 |
| 56 | 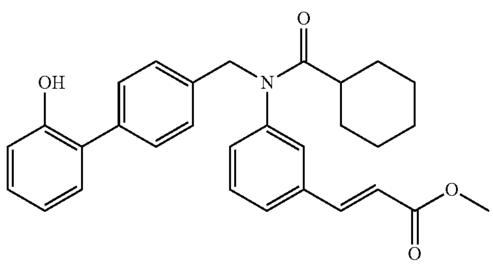 [SMILES: COC(=O)/C=C/c1cccc(N(Cc2ccc(-c3ccccc3O)cc2)C(=O)C2CCCCC2)c1] | (E)-Methyl 3-(3-(N-((2'-hydroxy-[1,1'-biphenyl]-4-yl)methyl)cyclohexanecarboxamido)phenyl)acrylate | 470.2 |
| 57 | 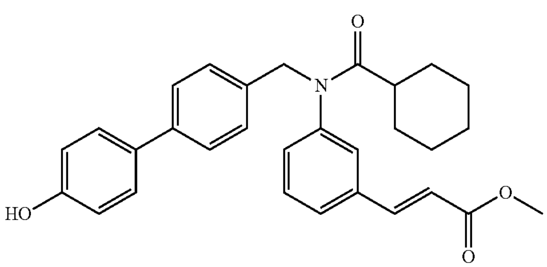 [SMILES: COC(=O)/C=C/c1cccc(N(Cc2ccc(-c3ccc(O)cc3)cc2)C(=O)C2CCCCC2)c1] | (E)-Methyl 3-(3-(N-((4'-hydroxy-[1,1'-biphenyl]-4-yl)methyl)cyclohexanecarboxamido)phenyl)acrylate | 470.2 |
| 58 | 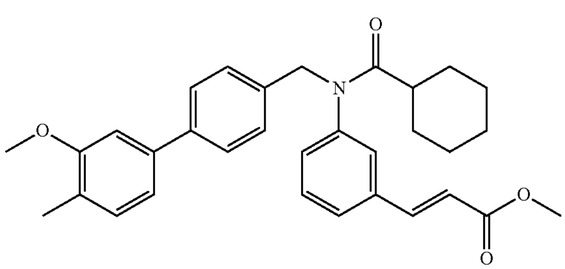 | (E)-Methyl 3-(3-(N-((3'-methoxy-4'-methyl-[1,1'-biphenyl]-4-yl)methyl)cyclohexanecarboxamido)phenyl)acrylate | 498.7 |
| 59 | 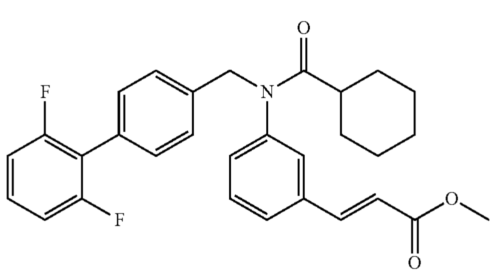 [SMILES: COC(=O)/C=C/c1cccc(N(Cc2ccc(-c3c(F)cccc3F)cc2)C(=O)C2CCCCC2)c1] | (E)-Methyl 3-(3-(N-((2',6'-difluoro-[1,1'-biphenyl]-4-yl)methyl)cyclohexanecarboxamido)phenyl)acrylate | 490.7 |

| Cmpd | Structure | Name | [M + H]+ |
|---|---|---|---|
| 60 | 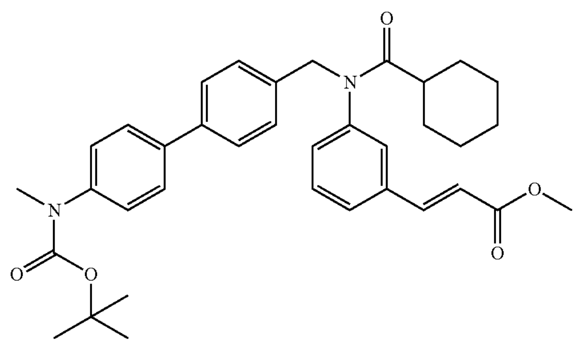 | (E)-Methyl 3-(3-(N-((4'-((tert-butoxycarbonyl)(methyl)amino)-[1,1'-biphenyl]-4-yl)methyl)cyclohexanecarboxamido)phenyl)acrylate | 583.8 |
| 61* | 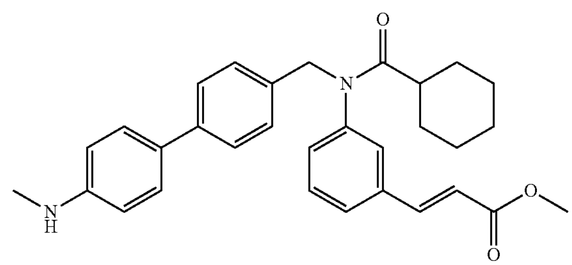 | (E)-Methyl 3-(3-(N-((4'-(methylamino)-[1,1'-biphenyl]-4-yl)methyl)cyclohexanecarboxamido)phenyl)acrylate | 483.7 |
| 62 | 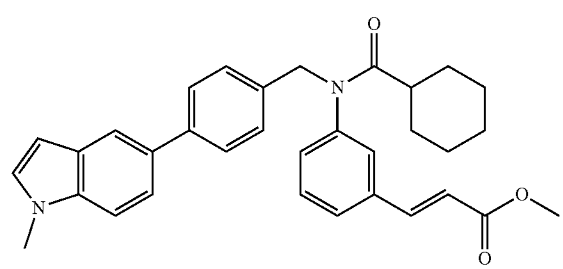 [SMILES: COC(=O)/C=C/c1cccc(N(Cc2ccc(-c3ccc4c(ccn4C)c3)cc2)C(=O)C2CCCCC2)c1] | (E)-Methyl 3-(3-(N-(4-(1-methyl-1H-indol-5-yl)benzyl)cyclohexanecarboxamido)phenyl)acrylate | 507.8 |
| 62.1 | 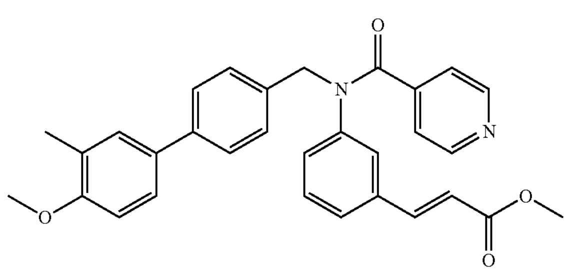 | (E)-Methyl 3-(3-(N-((4'-methoxy-3'-methyl-[1,1'-biphenyl]-4-yl)methyl)isonicotinamido)phenyl)acrylate | 493.5 |
| 62.2 | 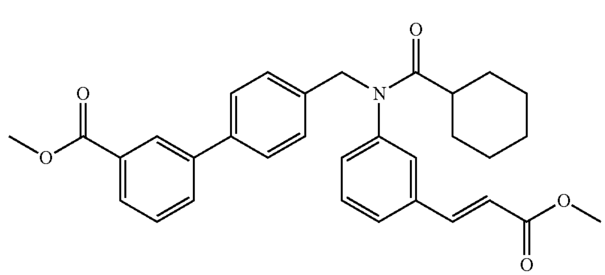 | (E)-Methyl 4'-((N-(3-(3-methoxy-3-oxoprop-1-en-1-yl)phenyl)cyclohexanecarboxamido)methyl)-[1,1'-biphenyl]-3-carboxylate | 512.5 |

-continued

| Cmpd | Structure | Name | [M + H]+ |
|---|---|---|---|
| 62.3 | 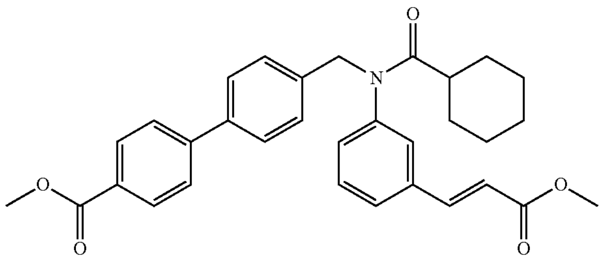 | (E)-Methyl 4'-((N-(3-(3-methoxy-3-oxoprop-1-en-1-yl)phenyl)cyclohexanecarboxamido)methyl)-[1,1'-biphenyl]-4-carboxylate | 512.5 |
| 62.4 | 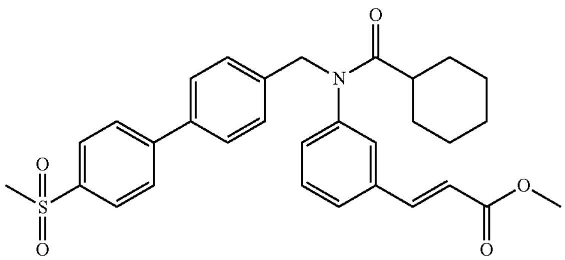 | (E)-Methyl 3-(3-(N-((4'-(methylsulfonyl)-[1,1'-biphenyl]-4-yl)methyl)cyclohexanecarboxamido)phenyl)acrylate | 532.6 |
| 62.5 | 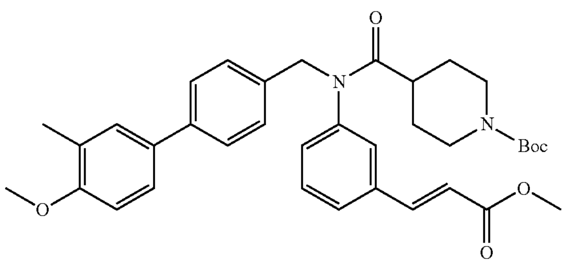 | (E)-tert-Butyl 4-(((4'-methoxy-3'-methyl-[1,1'-biphenyl]-4-yl)methyl)(3-(3-methoxy-3-oxoprop-1-en-1-yl)phenyl)carbamoyl)piperidine-1-carboxylate | 599.5 |
| 62.6 | 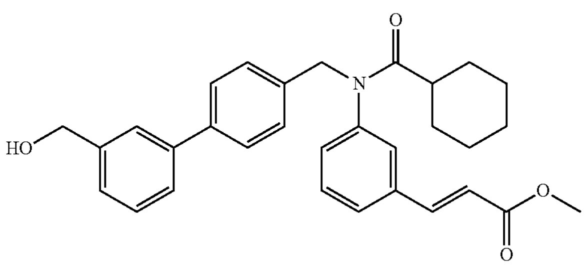 [SMILES: COC(=O)/C=C/c1cccc(N(Cc2ccc(-c3cccc(CO)c3)cc2)C(=O)C2CCCCC2)c1] | (E)-Methyl 3-(3-(N-((3'-(hydroxymethyl)-[1,1'-biphenyl]-4-yl)methyl)cyclohexanecarboxamido)phenyl)acrylate | 484.5 |
| 62.7 | 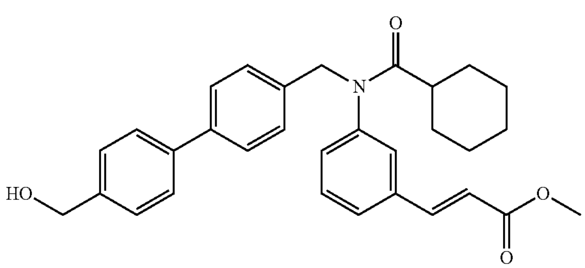 [SMILES: COC(=O)/C=C/c1cccc(N(Cc2ccc(-c3ccc(CO)cc3)cc2)C(=O)C2CCCCC2)c1] | (E)-Methyl 3-(3-(N-((4'-(hydroxymethyl)-[1,1'-biphenyl]-4-yl)methyl)cyclohexanecarboxamido)phenyl)acrylate | 484.6 |
| 62.8 | 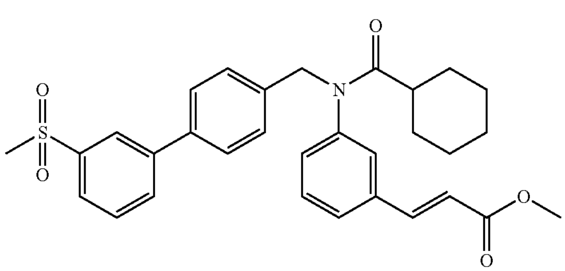 | (E)-Methyl 3-(3-(N-((3'-(methylsulfonyl)-[1,1'-biphenyl]-4-yl)methyl)cyclohexanecarboxamido)phenyl)acrylate | 532.6 |

-continued

| Cmpd | Structure | Name | [M + H]+ |
|---|---|---|---|
| 62.9 | 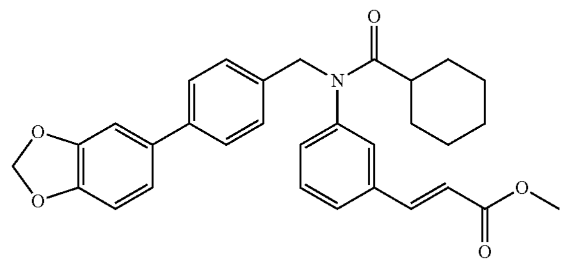 [SMILES: COC(=O)/C=C/c1cccc(N(Cc2ccc(-c3ccc4c(c3)OCO4)cc2)C(=O)C2CCCCC2)c1] | (E)-Methyl 3-(3-(N-(4-(benzo[d][1,3]dioxol-5-yl)benzyl)cyclohexanecarboxamido)phenyl)acrylate | 498.5 |
| 62.10 | 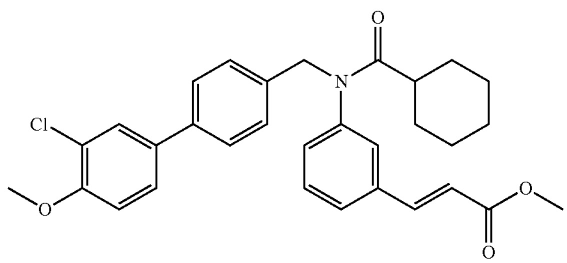 | (E)-Methyl 3-(3-(N-((3'-chloro-4'-methoxy-[1,1'-biphenyl]-4-yl)methyl)cyclohexanecarboxamido)phenyl)acrylate | 518.5 |
| 62.11 | 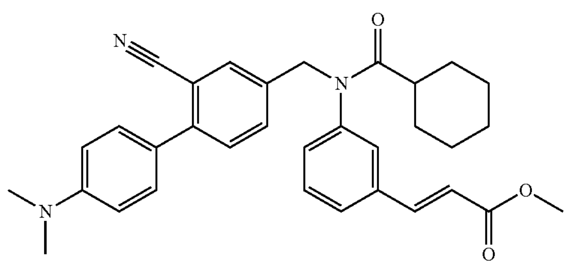 | (E)-Methyl 3-(3-(N-((2-cyano-4'-(dimethylamino)-[1,1'-biphenyl]-4-yl)methyl)cyclohexanecarboxamido)phenyl)acrylate | 522.7 |
| 62.12 | 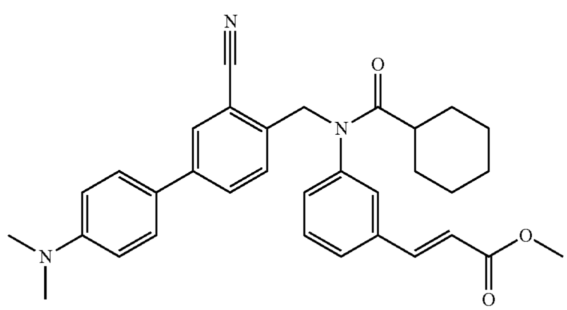 | (E)-Methyl 3-(3-(N-((3-cyano-4'-(dimethylamino)-[1,1'-biphenyl]-4-yl)methyl)cyclohexanecarboxamido)phenyl)acrylate | 522.7 |
| 62.13 | 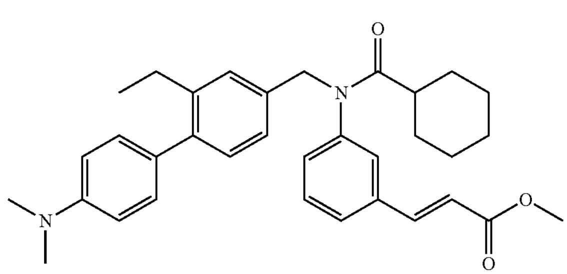 | (E)-Methyl 3-(3-(N-((4'-(dimethylamino)-2-ethyl-[1,1'-biphenyl]-4-yl)methyl)cyclohexanecarboxamido)phenyl)acrylate | 525.6 |

| Cmpd | Structure | Name | [M + H]⁺ |
|---|---|---|---|
| 62.14 | 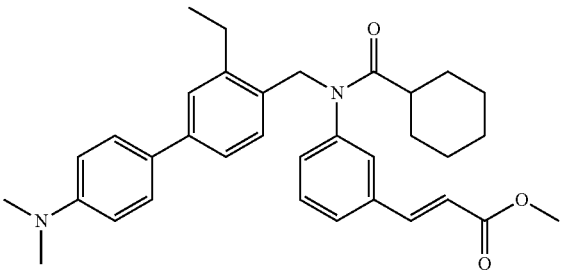 | (E)-Methyl 3-(3-(N-((4'-(dimethylamino)-3-ethyl-[1,1'-biphenyl]-4-yl)methyl)cyclohexanecarboxamido)phenyl)acrylate | 525.5 |
| 62.15* | 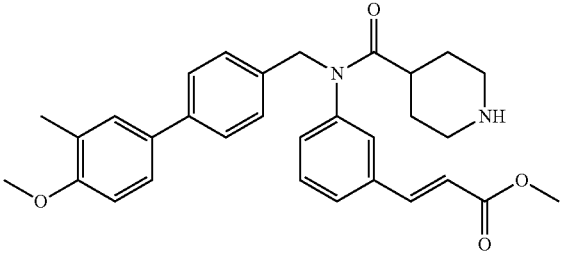 | (E)-Methyl 3-(3-(N-((4'-methoxy-3'-methyl-[1,1'-biphenyl]-4-yl)methyl)piperidine-4-carboxamido)phenyl)acrylate | 499.4 |
| 62.16* | 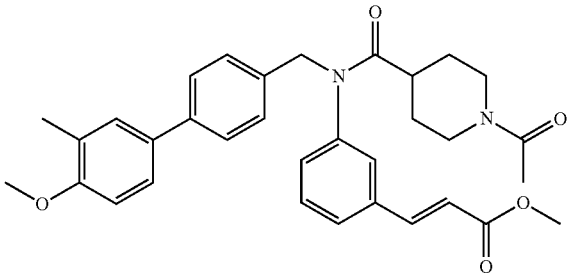 [SMILES: COC(=O)/C=C/c1cccc(N(Cc2ccc(-c3ccc(OC)c(C)c3)cc2)C(=O)C2CCN(C(C)=O)CC2)c1] | (E)-Methyl 3-(3-(1-acetyl-N-((4'-methoxy-3'-methyl-[1,1'-biphenyl]-4-yl)methyl)piperidine-4-carboxamido)phenyl)acrylate | 541.8 |
| 62.17* | 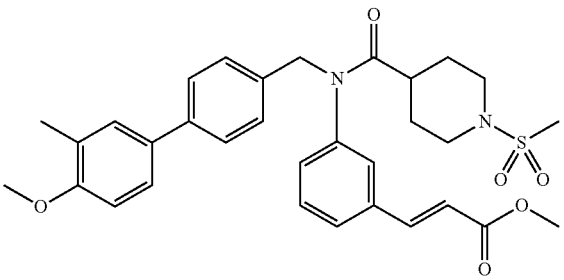 | (E)-Methyl 3-(3-(N-((4'-methoxy-3'-methyl-[1,1'-biphenyl]-4-yl)methyl)-1-(methylsulfonyl)piperidine-4-carboxamido)phenyl)acrylate | 577.6 |

*61 from 60 by Boc removal (TFA/DCM); 62.15 from 62.5 by Boc removal (HCl/Dioxane); 62.16 from 62.15 by acylation (TEA/DCM); 62.17 from 62.15 by sulfonylation (TEA/DCM).

251

Compound 63

(E)-Methyl 3-(3-(N-((4'-(dimethylamino)-[1,1'-biphenyl]-4-yl)methyl)cyclohexanecarboxamido)phenyl)-2-methylacrylate

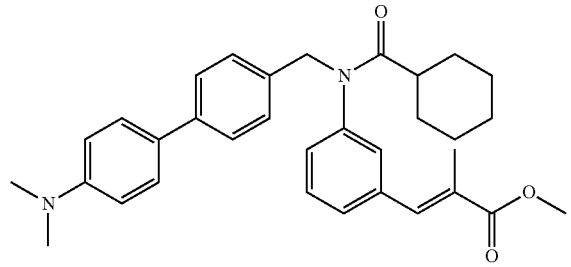

A mixture of Intermediate 12.9 (1.70 g, 3.61 mmol), (4-(dimethylamino)phenyl)boronic acid (1.19 g, 7.22 mmol), CsF (1.10 g, 7.22 mmol), Pd(PPh$_3$)$_2$Cl$_2$ (405 mg, 0.58 mmol) in THF (200 mL) was degassed with vacuum/nitrogen cycles (3×), stirred at 90° C. for 5 h and then filtered. Water (80 mL) was added, and the mixture was extracted with ethyl acetate (3×30 mL). The combined organic layers were washed with water (3×80 mL), dried over anhydrous Na$_2$SO$_4$, filtered and concentrated. The residue was purified by column chromatography (SiO$_2$, petroleum ether/ethyl acetate=30/1 to 10/1) to give (E)-methyl 3-(3-(N-((4'-(dimethylamino)-[1,1'-biphenyl]-4-yl)methyl)cyclohexanecarboxamido)phenyl)-2-methylacrylate (1.60 g, 71%) was obtained as a yellow oil. $^1$H NMR (CDCl$_3$): δ 7.57 (s, 1H), 7.44 (dd, 4H), 7.32-7.37 (m, 1H), 7.27-7.31 (m, 1H), 7.17 (d, 2H), 6.94-7.00 (m, 2H), 6.77 (d, 2H), 4.86 (s, 2H), 3.78 (s, 3H), 2.97 (s, 6H), 2.10-2.19 (m, 1H), 1.88 (s, 3H), 1.55-1.68 (m, 7H), 1.17-1.24 (m, 1H), 0.93 (d, 2H); MS: 511.3 [M+H]$^+$.

252

Compound 64

(E)-Methyl 3-(3-(N-((3'-cyano-4'-methoxy-[1,1'-biphenyl]-4-yl)methyl)cyclohexanecarboxamido)phenyl)acrylate

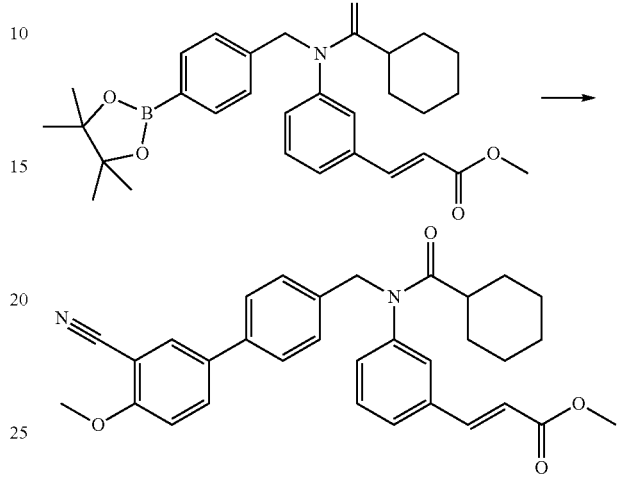

A mixture of Intermediate 16 (500 mg, 0.99 mmol), 5-bromo-2-methoxy-benzonitrile (316 mg, 1.49 mmol), Cs$_2$CO$_3$ (647 mg, 1.99 mmol), Pd(PPh$_3$)$_4$ (230 mg, 199 mmol) in DMF (6 mL) was degassed with vacuum/nitrogen cycles (3×), stirred at 90° C. for 12 h, and then filtered. Saturated EDTA-2Na (20 mL) was added, and the reaction mixture was stirred for 1 h and then extracted with ethyl acetate (3×20 mL). The combined organic layers were washed with water (3×15 mL) and brine (2×20 mL), dried over anhydrous Na$_2$SO$_4$, filtered and concentrated. The residue was purified by reverse-phase HPLC to give (E)-methyl 3-(3-(N-((3'-cyano-4'-methoxy-[1,1'-biphenyl]-4-yl)methyl)cyclohexanecarboxamido)phenyl)acrylate (110 mg, 22%) as a white solid. $^1$H NMR (DMSO-d$_6$): δ 8.01 (d, 1H), 7.96 (dd, 1H), 7.58-7.70 (m, 5H), 7.42 (t, 1H), 7.31 (d, 1H), 7.24 (d, 2H), 7.17 (d, 1H), 6.64 (d, 1H), 4.89 (s., 2H), 3.95 (s, 3H), 3.71 (s, 3H), 2.19 (m, 1H), 1.58-1.72 (m, 4H), 1.36-1.54 (m, 3H), 1.05-1.18 (m, 1H), 0.89 (d, 2H); MS: 509.3 [M+H]$^+$.

The Compounds below were synthesized from the appropriate bromides following the procedure described for Compound 64.

| Cmpd | Structure | Name | [M + H]$^+$ |
|---|---|---|---|
| 65 | ![structure] | (E)-Methyl 3-(3-(N-4-(pyridin-2-yl)benzyl)cyclohexanecarboxamido)phenyl)acrylate | 455.3 |

-continued

| Cmpd | Structure | Name | [M + H]+ |
|---|---|---|---|
| 66 | 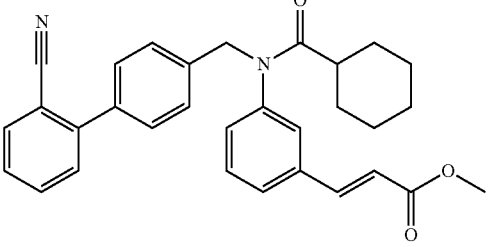 | (E)-Methyl 3-(3-(N-((2'-cyano-[1,1'-biphenyl]-4-yl)methyl)cyclohexanecarboxamido)phenyl)acrylate | 479.3 |
| 67 | 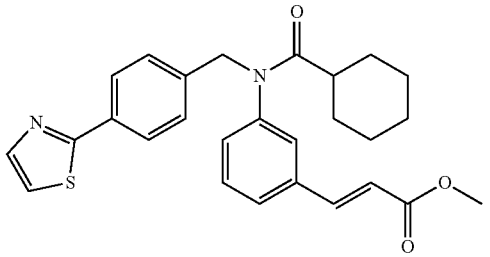 [SMILES: COC(=O)/C=C/c1cccc(N(Cc2ccc(-c3nccs3)cc2)C(=O)C2CCCCC2)c1] | (E)-Methyl 3-(3-(N-(4-(thiazol-2-yl)benzyl)cyclohexanecarboxamido)phenyl)acrylate | 461.2 |
| 68 | 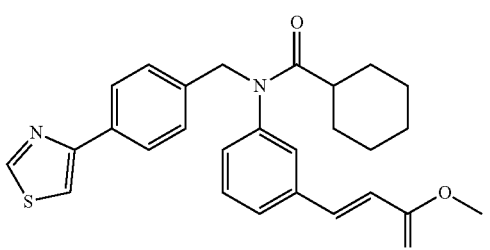 | (E)-Methyl 3-(3-(N-(4-(thiazol-4-yl)benzyl)cyclohexanecarboxamido)phenyl)acrylate | 461.3 |
| 69 | 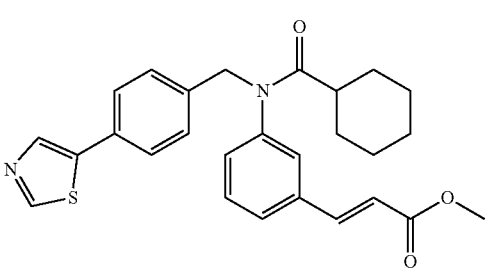 [SMILES: COC(=O)/C=C/c1cccc(N(Cc2ccc(-c3cncs3)cc2)C(=O)C2CCCCC2)c1] | (E)-Methyl 3-(3-(N-(4-(thiazol-5-yl)benzyl)cyclohexanecarboxamido)phenyl)acrylate | 461.3 |
| 70 | 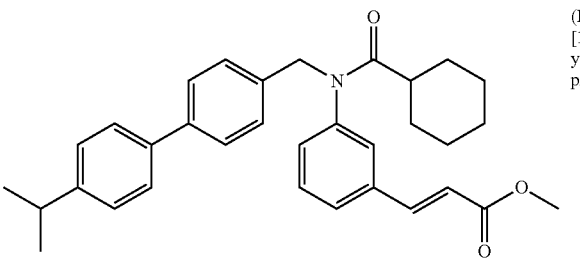 | (E)-Methyl 3-(3-(N-((4'-isopropyl-[1,1'-biphenyl]-4-yl)methyl)cyclohexanecarboxamido)phenyl)acrylate | 496.3 |
| 71 | 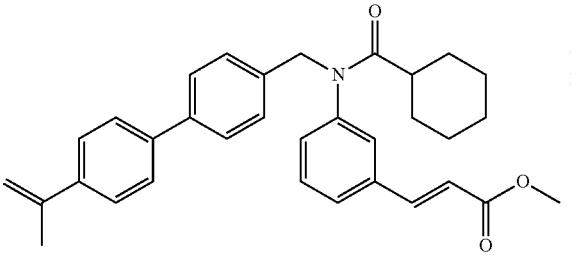 [SMILES: C=C(C)c1ccc(-c2ccc(CN(C(=O)C3CCCCC3)c3cccc(/C=C/C(=O)OC)c3)cc2)cc1] | (E)-Methyl 3-(3-(N-((4'-(prop-1-en-2-yl)-[1,1'-biphenyl]-4-yl)methyl)cyclohexanecarboxamido)phenyl)acrylate | 494.3 |

-continued

| Cmpd | Structure | Name | [M + H]+ |
|---|---|---|---|
| 72 | 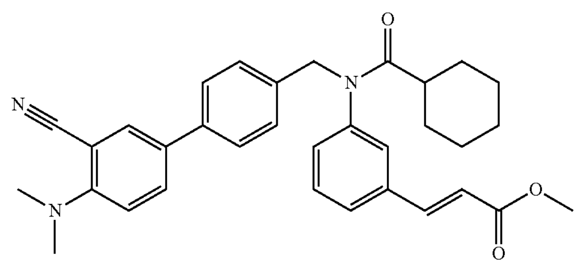 | (E)-Methyl 3-(3-(N-((3'-cyano-4'-(dimethylamino)-[1,1'-biphenyl]-4-yl)methyl)cyclohexanecarboxamido)phenyl)acrylate | 522.3 |
| 73 | 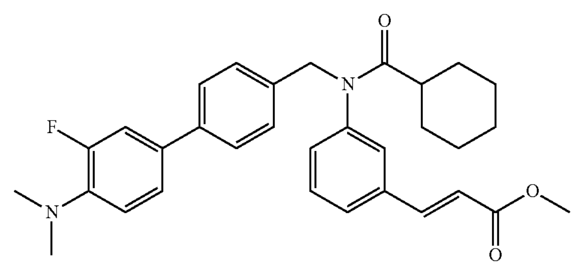 | (E)-Methyl 3-(3-(N-((4'-(dimethylamino)-3'-fluoro-[1,1'-biphenyl]-4-yl)methyl)cyclohexanecarboxamido)phenyl)acrylate | 515.3 |
| 74 | 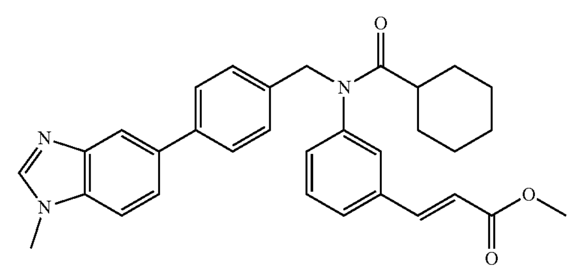 [SMILES: COC(=O)/C=C/c1cccc(N(Cc2ccc(-c3ccc4c(c3)ncn4C)cc2)C(=O)C2CCCCC2)c1] | (E)-Methyl 3-(3-(N-(4-(1-methyl-1H-benzo[d]imidazol-5-yl)benzyl)cyclohexanecarboxamido)phenyl)acrylate | 508.3 |
| 75 | 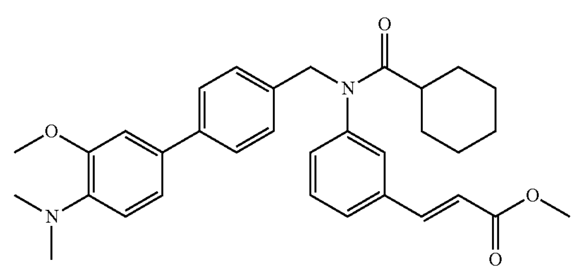 | (E)-Methyl 3-(3-(N-((4'-(dimethylamino)-3'-methoxy-[1,1'-biphenyl]-4-yl)methylcyclohexanecarboxamido)phenyl)acrylate | 527.3 |
| 75.1 | 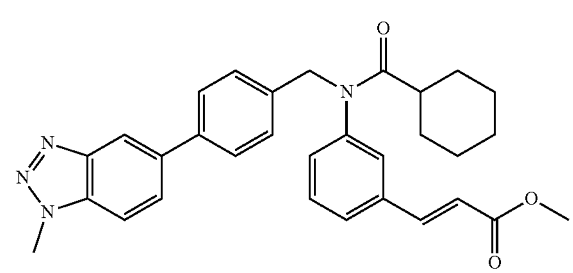 [SMILES: COC(=O)/C=C/c1cccc(N(Cc2ccc(-c3ccc4c(c3)nnn4C)cc2)C(=O)C2CCCCC2)c1] | (E)-Methyl 3-(3-(N-(4-(1-methyl-1H-benzo[d][1,2,3]triazol-5-yl)benzyl)cyclohexanecarboxamido)phenyl)acrylate | 509.7 |
| 75.2 | 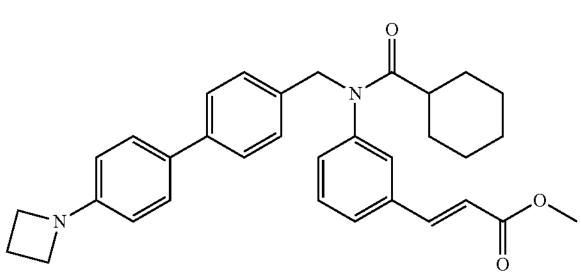 [SMILES: COC(=O)/C=C/c1cccc(N(Cc2ccc(-c3ccc(N4CCC4)cc3)cc2)C(=O)C2CCCCC2)c1] | (E)-Methyl 3-(3-(N-((4'-(azetidin-1-yl)-[1,1'-biphenyl]-4-yl)methyl)cyclohexanecarboxamido)phenyl)acrylate | 509.7 |

| Cmpd | Structure | Name | [M + H]⁺ |
|---|---|---|---|
| 75.3 | 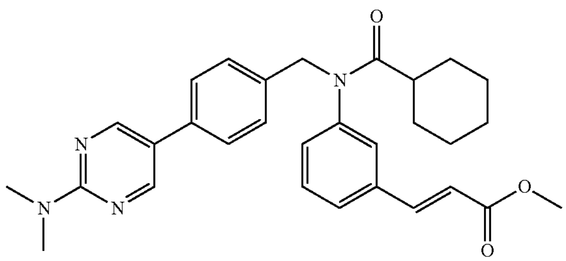 | (E)-Methyl 3-(3-(N-(4-(2-(dimethylamino)pyrimidin-5-yl)benzyl)cyclohexanecarboxamido)phenyl)acrylate | 499.5 |
| 75.4 | 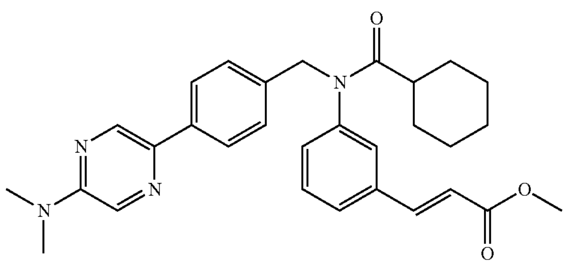 | (E)-Methyl 3-(3-(N-(4-(5-(dimethylamino)pyrazin-2-yl)benzyl)cyclohexanecarboxamido)phenyl)acrylate | 499.5 |
| 75.5 | 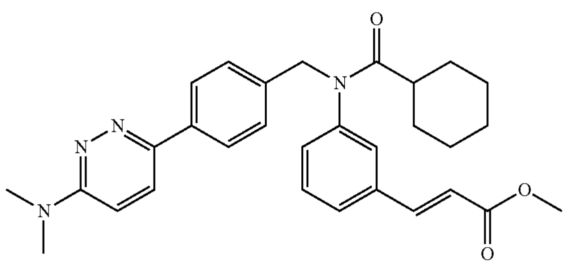 | (E)-Methyl 3-(3-(N-(4-(6-(dimethylamino)pyridazin-3-yl)benzyl)cyclohexanecarboxamido)phenyl)acrylate | 499.5 |
| 75.6 | 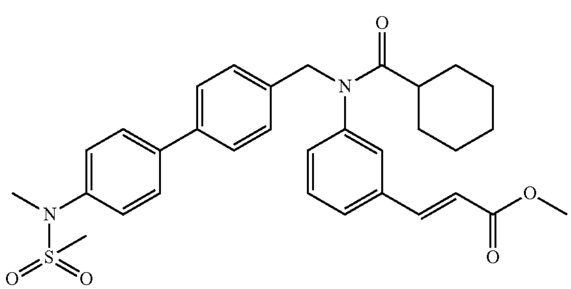 | (E)-Methyl 3-(3-(N-((4'-(N-methylmethylsulfonamido)-[1,1'-biphenyl]-4-yl)methyl)cyclohexanecarboxamido)phenyl)acrylate | 561.6 |
| 75.7 | 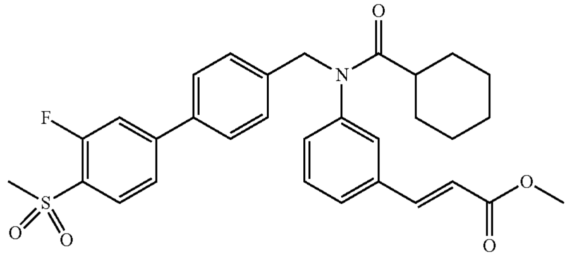 | (E)-Methyl 3-(3-(N-((3'-fluoro-4'-(methylsulfonyl)-[1,1'-biphenyl]-4-yl)methyl)cyclohexanecarboxamido)phenyl)acrylate | 550.3 |

| Cmpd | Structure | Name | [M + H]+ |
|---|---|---|---|
| 75.8 | 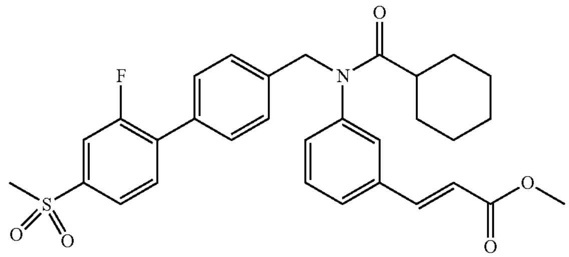 | (E)-Methyl 3-(3-(N-((2'-fluoro-4'-(methylsulfonyl)-[1,1'-biphenyl]-4-yl)methyl)cyclohexanecarboxamido)phenyl)acrylate | 550.3 |
| 75.9 | 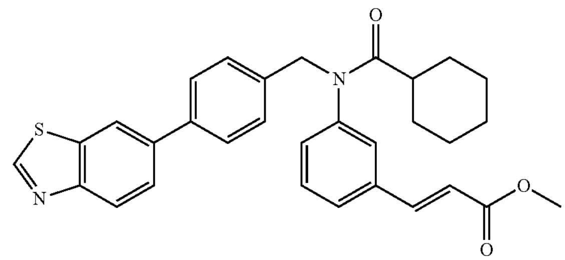 | (E)-Methyl 3-(3-(N-(4-(benzo[d]thiazol-6-yl)benzyl)cyclohexanecarboxamido)phenyl)acrylate | 511.2 |
| 75.10 | 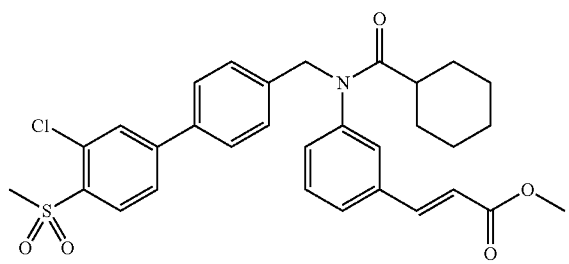 | (E)-Methyl 3-(3-(N-((3'-chloro-4'-(methylsulfonyl)-[1,1'-biphenyl]-4-yl)methyl)cyclohexanecarboxamido)phenyl)acrylate | 566.3 |
| 75.11 | 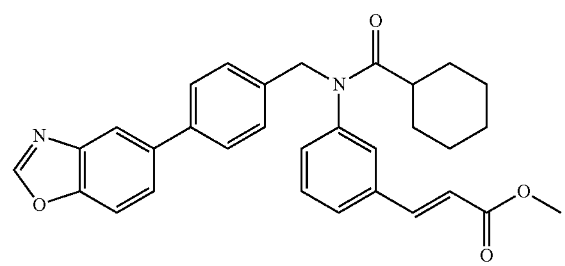 [SMILES: COC(=O)/C=C/c1cccc(N(Cc2ccc(-c3ccc4ocnc4c3)cc2)C(=O)C2CCCCC2)c1] | (E)-Methyl 3-(3-(N-(4-(benzo[d]oxazol-5-yl)benzyl)cyclohexanecarboxamido)phenyl)acrylate | 495.4 |
| 75.12 | 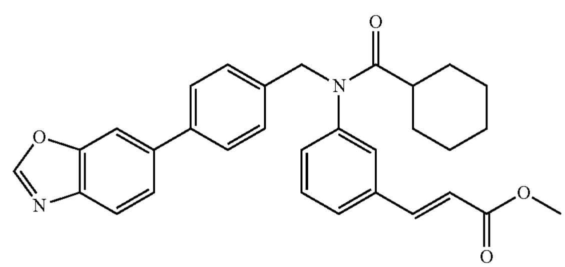 [SMILES: COC(=O)/C=C/c1cccc(N(Cc2ccc(-c3ccc4ncoc4c3)cc2)C(=O)C2CCCCC2)c1] | (E)-Methyl 3-(3-(N-(4-(benzo[d]oxazol-6-yl)benzyl)cyclohexanecarboxamido)phenyl)acrylate | 495.5 |
| 75.13 | 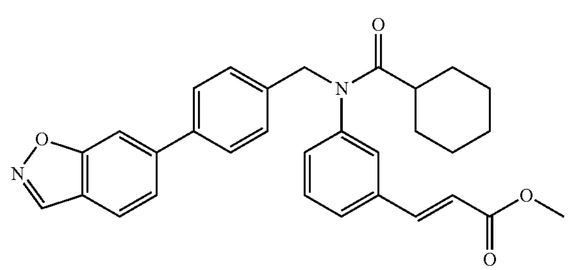 | (E)-Methyl 3-(3-(N-(4-(benzo[d]isoxazol-6-yl)benzyl)cyclohexanecarboxamido)phenyl)acrylate | 495.5 |

-continued

| Cmpd | Structure | Name | [M + H]+ |
| --- | --- | --- | --- |
| 75.14 | 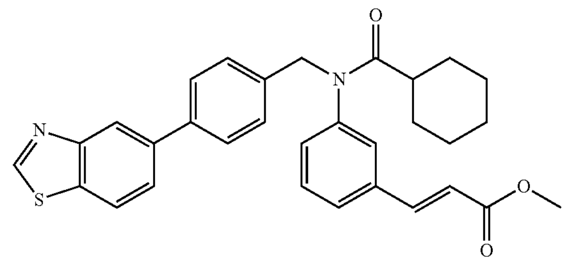 | (E)-Methyl 3-(3-(N-(4-(benzo[d]thiazol-5-yl)benzyl)cyclohexanecarboxamido)phenyl)acrylate | 511.6 |
| 75.15 | 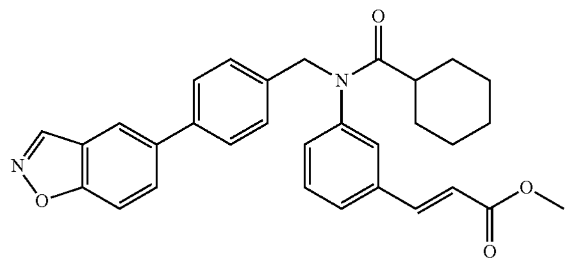 | (E)-Methyl 3-(3-(N-(4-(benzo[d]isoxazol-5-yl)benzyl)cyclohexanecarboxamido)phenyl)acrylate | 495.5 |
| 75.16 | 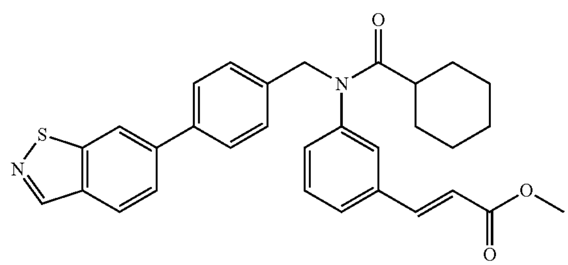 [SMILES: COC(=O)/C=C/c1cccc(N(Cc2ccc(-c3ccc4cnsc4c3)cc2)C(=O)C2CCCCC2)c1] | (E)-Methyl 3-(3-(N-(4-(benzo[d]isothiazol-6-yl)benzyl)cyclohexanecarboxamido)phenyl)acrylate | 511.6 |
| 75.17 | 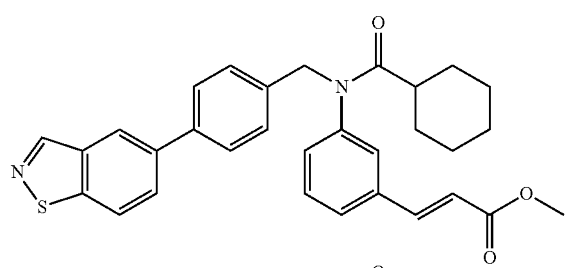 | (E)-Methyl 3-(3-(N-(4-(benzo[d]isothiazol-5-yl)benzyl)cyclohexanecarboxamido)phenyl)acrylate | 511.5 |
| 75.18 | 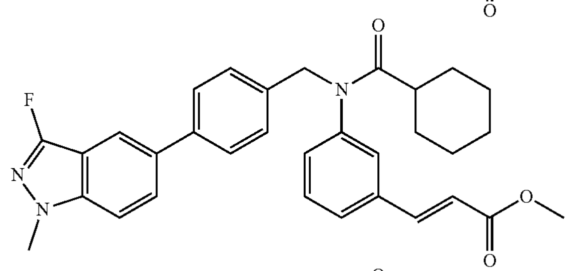 | (E)-Methyl 3-(3-(N-(4-(3-fluoro-1-methyl-1H-indazol-5-yl)benzyl)cyclohexanecarboxamido)phenyl)acrylate | 526.6 |
| 75.19 | 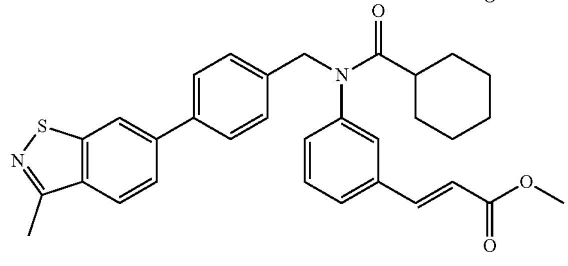 | (E)-Methyl 3-(3-(N-(4-(3-methylbenzo[d]isothiazol-6-yl)benzyl)cyclohexanecarboxamido)phenyl)acrylate | 525.5 |

Suzuki conditions varied: Pd(PPh$_3$)$_4$, Pd(dppf)Cl$_2$, or Pd(PPh$_3$)$_2$Cl$_2$; Cs$_2$CO$_3$ or K$_2$CO$_3$; DMF or dioxane; also, Pd(dppf)Cl$_2$, Et$_3$N, tBu$_3$PH$^+$BF$_4^-$; CH$_3$CN/H$_2$O.

Compound 76

(E)-Methyl 3-(3-(N-(4-(4-methylpiperazin-1-yl)benzyl)cyclohexanecarboxamido)phenyl)acrylate

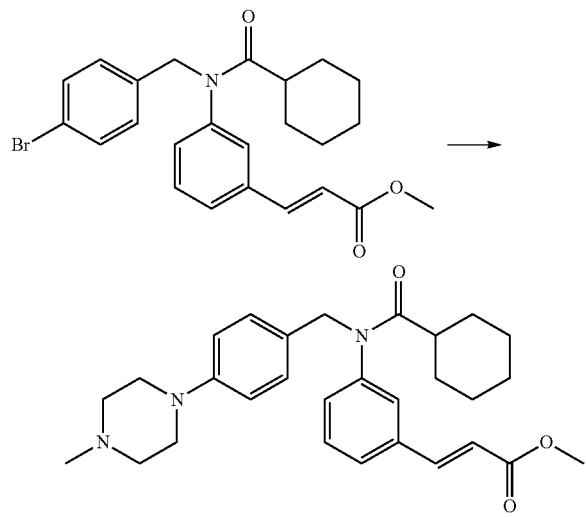

A mixture of Intermediate 12 (502 mg, 1.10 mmol), 1-methylpiperazine (132 mg, 1.32 mmol), Cs$_2$CO$_3$ (717 mg, 2.20 mmol), palladium (II) acetate (25 mg, 0.11 mmol) and BINAP (69 mg, 0.11 mmol) in toluene (6 mL) was degassed with vacuum/nitrogen cycles (3×), stirred at 100° C. for 12 h, and then filtered. The filtrate was concentrated and purified by reverse-phase HPLC to give (E)-methyl 3-(3-(N-(4-(4-methylpiperazin-1-yl)benzyl)cyclohexanecarboxamido)phenyl)acrylate (130 mg, 25%) as a light yellow solid. $^1$H NMR (DMSO-d$_6$): δ 7.54-7.70 (m, 3H), 7.40 (t, 1H), 6.99-7.08 (m, 3H), 6.90 (d, 2H), 6.64 (d, 1H), 4.75 (br s, 2H), 3.70-3.77 (m, 5H), 3.44 (d, 2H), 3.08 (d, 4H), 2.77 (d, 3H), 2.11 (br s, 1H), 1.62 (t, 4H), 1.34-1.51 (m, 3H), 1.02-1.17 (m, 1H), 0.86 (d, 2H); MS: 476.3 [M+H]$^+$.

The Compounds below were synthesized from the appropriate amines following the procedure described for Compound 76.

| Cmpd | Structure | Name | [M + H]$^+$ |
|---|---|---|---|
| 77 | 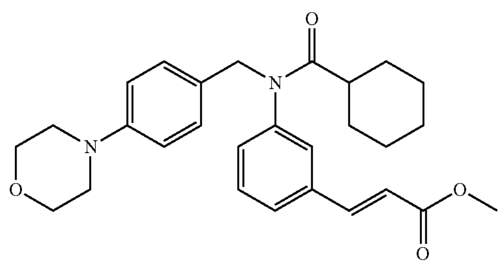 [SMILES: COC(=O)/C=C/c1cccc(N(Cc2ccc(N3CCOCC3)cc2)C(=O)C2CCCCC2)c1] | (E)-Methyl 3-(3-(N-(4-morpholinobenzyl)cyclohexanecarboxamido)phenyl)acrylate | 463.3 |
| 78 | 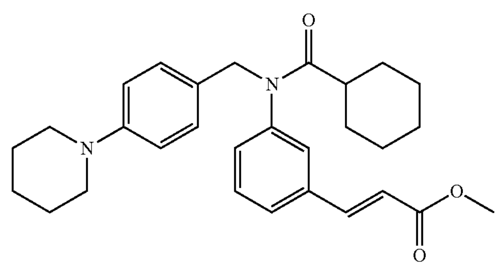 [SMILES: COC(=O)/C=C/c1cccc(N(Cc2ccc(N3CCCCC3)cc2)C(=O)C2CCCCC2)c1] | (E)-Methyl 3-(3-(N-(4-(piperidin-1-yl)benzyl)cyclohexanecarboxamido)phenyl)acrylate | 461.3 |
| 79* | 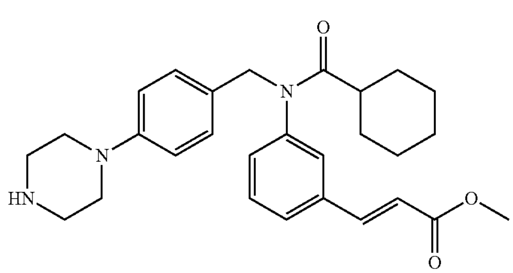 [SMILES: COC(=O)/C=C/c1cccc(N(Cc2ccc(N3CCNCC3)cc2)C(=O)C2CCCCC2)c1] | (E)-Methyl 3-(3-(N-(4-(piperazin-1-yl)benzyl)cyclohexanecarboxamido)phenyl)acrylate | 462.3 |

*Synthesized from tert-butyl piperazine-1-carboxylate followed by Boc removal (TFA/DCM).

Compound 80

(E)-Methyl 3-(3-(N-(naphthalen-1-ylmethyl)cyclohexanecarboxamido)phenyl)acrylate

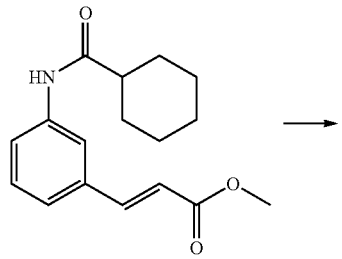

Sodium hydride (60% in dispersion in mineral oil, 17 mg, 0.43 mmol) was added to a solution of Intermediate 9 (101 mg, 0.35 mmol) and THF (2 mL) at 0° C. After stirring the mixture for 5 min, a solution of 1-(bromomethyl)naphthalene (95 mg, 0.43 mmol) and THF (1 mL) was added. The reaction mixture was stirred for 5 min at 0° C., stirred at room temperature for 4 h, and then diluted with ethyl acetate (20 mL). The organic phase was washed (2×20 mL saturated NaHCO$_3$), dried (MgSO$_4$), and concentrated. The residue was purified by silica gel chromatography to give (E)-methyl 3-(3-(N-(naphthalen-1-ylmethyl)cyclohexanecarboxamido)phenyl)acrylate (45 mg, 30%) as a white solid. $^1$H NMR (400 MHz, DMSO-d$_6$): δ 8.06-8.03 (m, 1H), 7.94-7.89 (m, 1H), 7.78 (d, 1H), 7.60 (d, 1H), 7.57-7.49 (m, 4H), 7.31 (t, 1H), 7.27 (t, 1H), 7.14 (t, 1H), 6.89 (d, 1H), 6.55 (d, 1H), 5.35 (s, 2H), 3.71 (s, 3H), 2.18-2.08 (m, 1H), 1.72-1.55 (m, 4H), 1.54-1.38 (m, 3H), 1.27-1.03 (m, 1H), 0.90-0.78 (m, 2H); LCMS: 428.6 [M+H]$^+$.

The Compounds below were synthesized from the appropriate bromides following the procedure described for Compound 80.

| Cmpd | Structure | Name | [M + H]$^+$ |
|---|---|---|---|
| 81 | 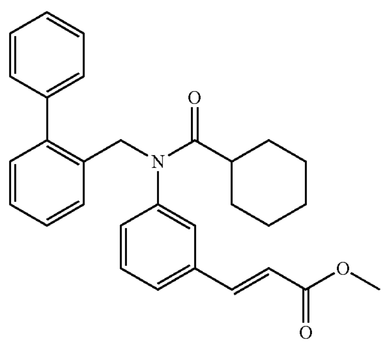 [SMILES: COC(=O)/C=C/c1cccc(N(Cc2ccccc2-c2ccccc2)C(=O)C2CCCCC2)c1] | (E)-Methyl 3-(3-(N-([1,1'-biphenyl]-2-ylmethyl)cyclohexanecarboxamido)phenyl)acrylate | 454.7 |
| 82 | 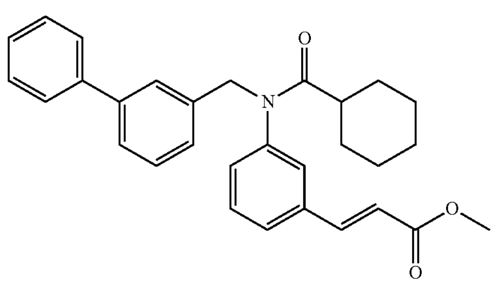 [SMILES: COC(=O)/C=C/c1cccc(N(Cc2cccc(-c3ccccc3)c2)C(=O)C2CCCCC2)c1] | (E)-Methyl 3-(3-(N-([1,1'-biphenyl]-3-ylmethyl)cyclohexanecarboxamido)phenyl)acrylate | 454.2 |

Compound 83

(E)-iso-Propyl 3-(3-(N-((4'-(dimethylamino)-[1,1'-biphenyl]-4-yl)methyl)cyclohexanecarboxamido)phenyl)acrylate

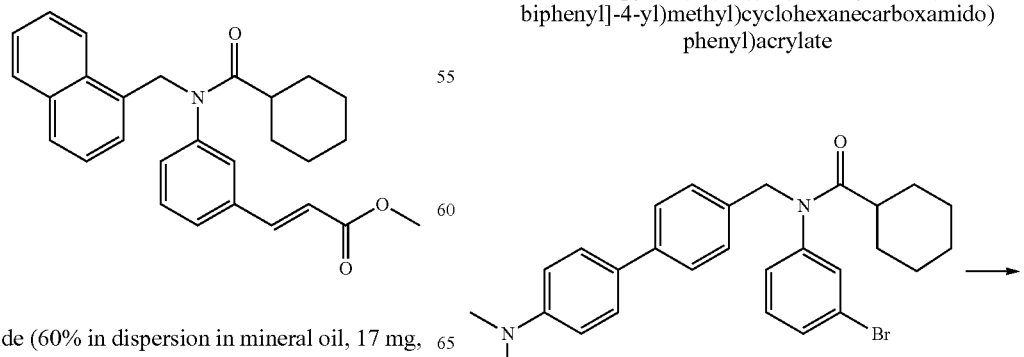

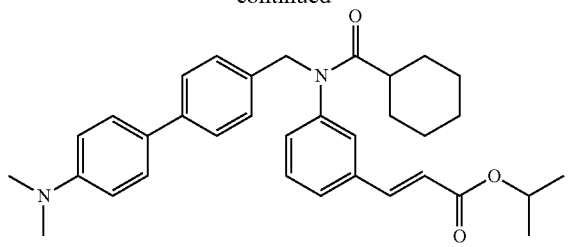

A mixture of Intermediate 5.7 (100 mg, 0.20 mmol), Pd(dppf)Cl$_2$ (15 mg, 0.021 mmol), triethylamine (0.12 mL, 0.86 mmol), and DMF (2 mL) was degassed by bubbling nitrogen for 10 min. iso-Propyl acrylate (71 mg, 0.62 mmol) was added, and the reaction mixture was heated at 80° C. for 5.5 h, cooled to room temperature, and then diluted with ethyl acetate (25 mL). The organic phase was washed (2×20 mL water), dried (Na$_2$SO$_4$), and concentrated. The residue was purified by silica gel chromatography to give (E)-iso-propyl 3-(3-(N-((4'-(dimethylamino)-[1,1'-biphenyl]-4-yl)methyl)cyclohexanecarboxamido)phenyl)acrylate (55 mg, 52%) as a yellow solid. $^1$H NMR (400 MHz, DMSO-d$_6$): δ 7.67 (d, 1H), 7.64-7.62 (m, 1H), 7.59 (d, 1H), 7.51-7.45 (m, 4H), 7.40 (t, 1H), 7.19-7.12 (m, 3H), 6.77 (d, 2H), 6.62 (d, 1H), 5.05-4.94 (m, 1H), 4.85 (s, 2H), 2.92 (s, 6H), 2.23-2.10 (m, 1H), 1.75-1.56 (m, 4H), 1.55-1.47 (m, 1H), 1.46-1.34 (m, 2H), 1.24 (d, 6H), 1.16-1.09 (m, 1H), 0.95-0.82 (m, 2H); LCMS: 525.8 [M+H]$^+$.

The Compounds below were synthesized from the appropriate starting materials following the procedure described for Compound 83.

| Cmpd | Structure | Name | [M + H]$^+$ |
|---|---|---|---|
| 84 | 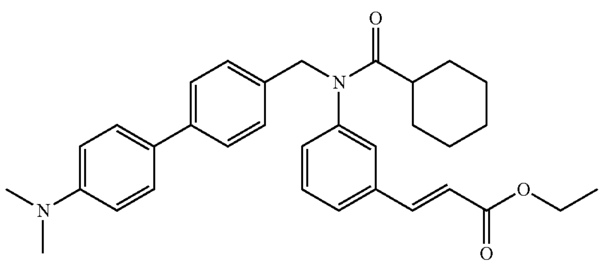 [SMILES: CCOC(=O)/C=C/c1cccc(N(Cc2ccc(-c3ccc(N(C)C)cc3)cc2)C(=O)C2CCCCC2)c1] | (E)-Ethyl 3-(3-(N-((4'-(dimethylamino)-[1,1'-biphenyl]-4-yl)methyl)cyclohexanecarboxamido)phenyl)acrylate | 511.8 |
| 85 | 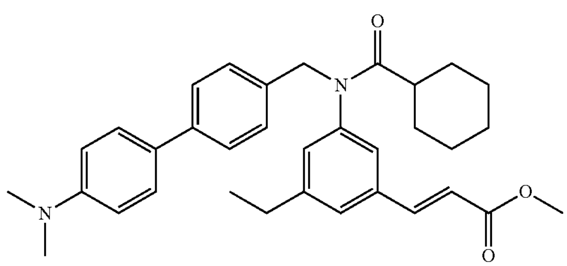 | (E)-Methyl 3-(3-(N-((4'-(dimethylamino)-[1,1'-biphenyl]-4-yl)methyl)cyclohexanecarboxamido)-5-ethylphenyl)acrylate | 525.8 |
| 86 | 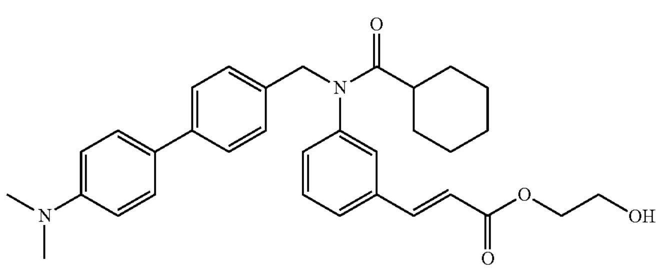 [SMILES: CN(C)c1ccc(-c2ccc(CN(C(=O)C3CCCCC3)c3cccc(/C=C/C(=O)OCCO)c3)cc2)cc1] | (E)-2-Hydroxyethyl 3-(3-(N-((4'-(dimethylamino)-[1,1'-biphenyl]-4-yl)methyl)cyclohexanecarboxamido)phenyl)acrylate | 527.8 |
| 86.1 | 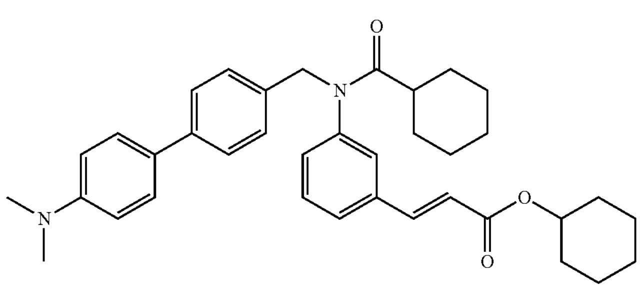 [SMILES: CN(C)c1ccc(-c2ccc(CN(C(=O)C3CCCCC3)c3cccc(/C=C/C(=O)OC4CCCCC4)c3)cc2)cc1] | (E)-Cyclohexyl 3-(3-(N-((4'-(dimethylamino)-[1,1'-biphenyl]-4-yl)methyl)cyclohexanecarboxamido)phenyl)acrylate | 565.8 |

-continued

| Cmpd | Structure | Name | [M + H]⁺ |
|---|---|---|---|
| 86.2 | 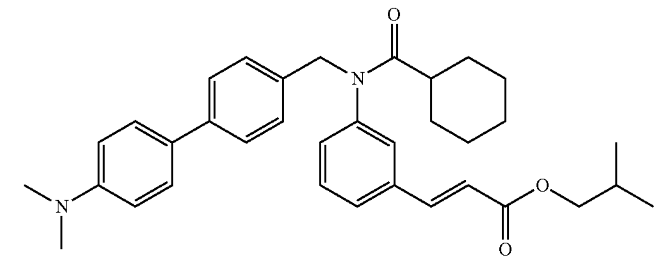 [SMILES: CC(C)COC(=O)/C=C/c1cccc(N(Cc2ccc(-c3ccc(N(C)C)cc3)cc2)C(=O)C2CCCCC2)c1] | (E)-Isobutyl 3-(3-(N-((4'-(dimethylamino)-[1,1'-biphenyl]-4-yl)methyl)cyclohexanecarboxamido)phenyl)acrylate | 539.7 |
| 86.3 | 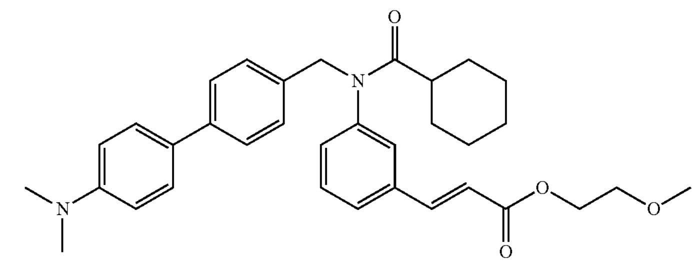 | (E)-2-Methoxyethyl 3-(3-(N-((4'-(dimethylamino)-[1,1'-biphenyl]-4-yl)methyl)cyclohexanecarboxamido)phenyl)acrylate | 541.6 |
| 86.4 | 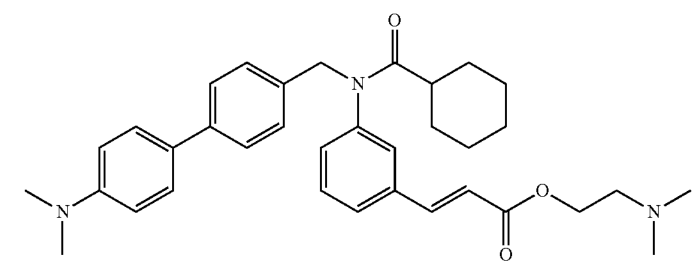 | (E)-2-(Dimethylamino)ethyl 3-(3-(N-((4'-(dimethylamino)-[1,1'-biphenyl]-4-yl)methyl)cyclohexanecarboxamido)phenyl)acrylate | 554.7 |
| 86.5 | 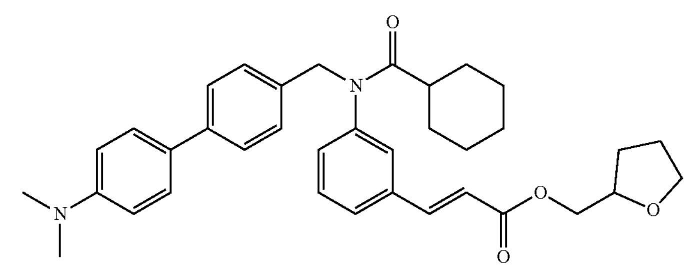 [SMILES: CN(C)c1ccc(-c2ccc(CN(C(=O)C3CCCCC3)c3cccc(/C=C/C(=O)OCC4CCCO4)c3)cc2)cc1] | (E)-(Tetrahydrofuran-2-yl)methyl 3-(3-(N-((4'-(dimethylamino)-[1,1'-biphenyl]-4-yl)methyl)cyclohexanecarboxamido)phenyl)acrylate | 567.7 |
| 86.6 | 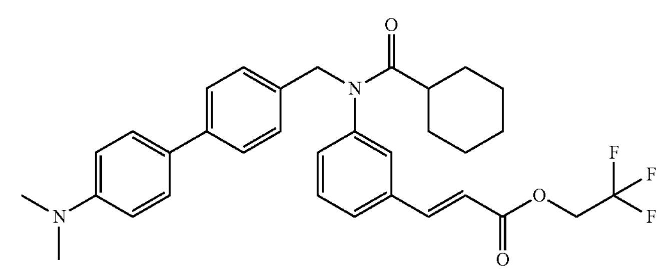 [SMILES: CN(C)c1ccc(-c2ccc(CN(C(=O)C3CCCCC3)c3cccc(/C=C/C(=O)OCC(F)(F)F)c3)cc2)cc1] | (E)-2,2,2-Trifluoroethyl 3-(3-(N-((4'-(dimethylamino)-[1,1'-biphenyl]-4-yl)methyl)cyclohexanecarboxamido)phenyl)acrylate | 565.5 |
| 86.7 | 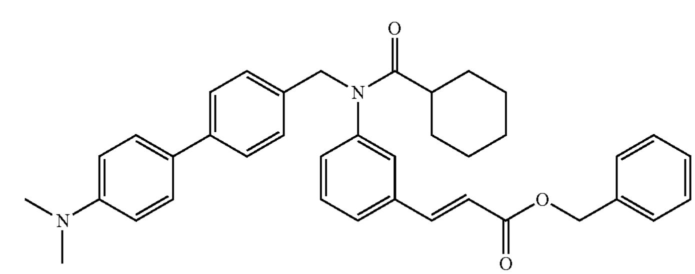 [SMILES: CN(C)c1ccc(-c2ccc(CN(C(=O)C3CCCCC3)c3cccc(/C=C/C(=O)OCc4ccccc4)c3)cc2)cc1] | (E)-Benzyl 3-(3-(N-((4'-(dimethylamino)-[1,1'-biphenyl]-4-yl)methylcyclohexanecarboxamido)phenyl)acrylate | 573.6 |

-continued

| Cmpd | Structure | Name | [M + H]+ |
|---|---|---|---|
| 86.8 | 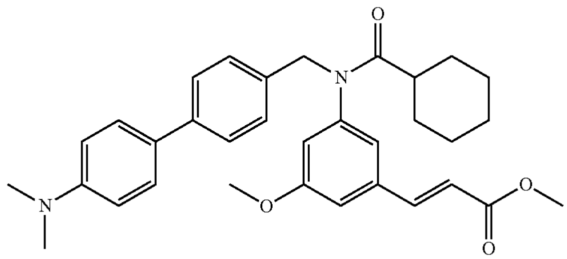 | (E)-Methyl 3-(3-(N-((4'-(dimethylamino)-[1,1'-biphenyl]-4-yl)methyl)cyclohexanecarboxamido)-5-methoxyphenyl)acrylate | 527.8 |
| 86.9 | 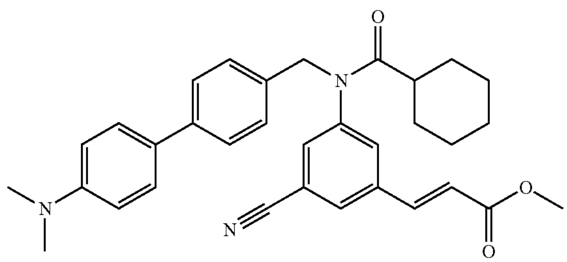 | (E)-Methyl 3-(3-cyano-5-(N-((4'-(dimethylamino)-[1,1'-biphenyl]-4-yl)methyl)cyclohexanecarboxamido)phenyl)acrylate | 522.7 |
| 86.10 | 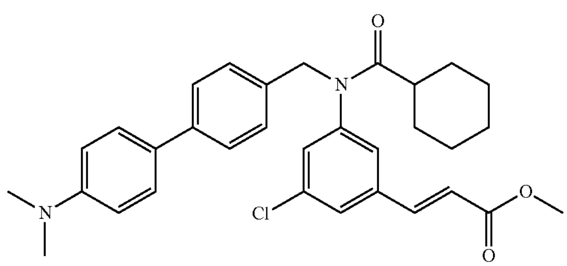 | (E)-Methyl 3-(3-chloro-5-(N-((4'-(dimethylamino)-[1,1'-biphenyl]-4-yl)methyl)cyclohexanecarboxamido)phenyl)acrylate | 531.7 |
| 86.11 | 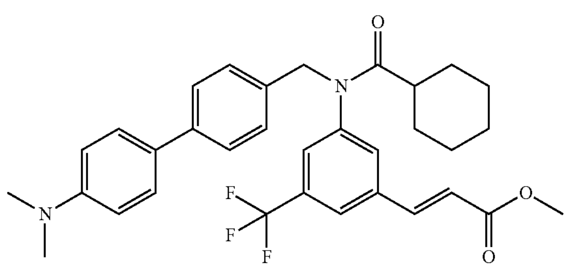 | (E)-Methyl 3-(3-(N-((4'-(dimethylamino)-[1,1'-biphenyl]-4-yl)methyl)cyclohexanecarboxamido)-5-(trifluoromethyl)phenyl)acrylate | 565.6 |

Heck conditions varied: Intermediate 5.7 or 5.8; Pd(dppf)Cl₂ or Pd₂(dba)₃ w/ P(o-tolyl)₃.

Compound 87

Methyl 3-(3-(N-((4'-(Dimethylamino)-[1,1'-biphenyl]-4-yl)methyl)cyclohexanecarboxamido)phenyl)propiolate

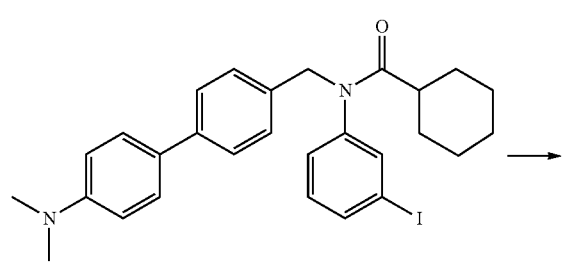

→

-continued

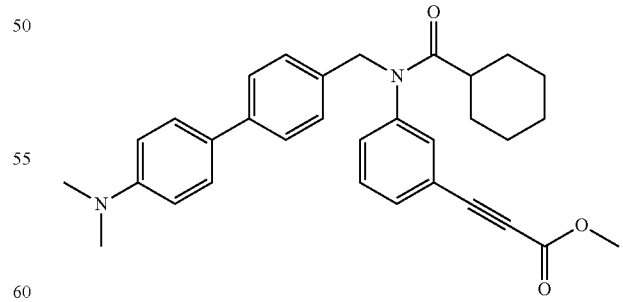

A mixture of Intermediate 5.8 (107 mg, 0.20 mmol), potassium carbonate (58 mg, 0.42 mmol), copper (I) iodide (8 mg, 0.042 mmol), tetrakis(triphenylphosphine)palladium (24 mg, 0.02 mmol), and THF (2 mL) was degassed by bubbling nitrogen for 10 min. Methyl propiolate (70 mg, 0.83 mmol) was added, and the reaction mixture was stirred at room temperature for 2 h. The reaction mixture was heated at 60° C. for 2 h, cooled to room temperature and then diluted with ethyl acetate (20 mL). The organic phase was washed (2×20 mL saturated NaHCO$_3$ and then 20 mL brine), dried (Na$_2$SO$_4$), and concentrated. The residue was purified by silica gel chromatography to give methyl 3-(3-(N-((4'-(dimethylamino)-[1,1'-biphenyl]-4-yl)methyl)cyclohexanecarboxamido)phenyl)propiolate (67 mg, 68%) as a light brown solid. $^1$H NMR (400 MHz, DMSO-d$_6$): δ 7.62 (d, 1H), 7.57-7.54 (m, 1H), 7.53-7.46 (m, 5H), 7.34 (d, 1H), 7.15 (d, 2H), 6.77 (d, 2H), 4.85 (s, 2H), 3.76 (s, 3H), 2.92 was washed (50 mL water) and dried to give (E)-3-(3-(N-((4'-(dimethylamino)-[1,1'-biphenyl]-4-yl)methyl)cyclohexanecarboxamido)phenyl)acrylic acid (2.22 g, 99%) as a yellow solid. $^1$H NMR (400 MHz, DMSO-d$_6$): δ 12.46 (br, 1H), 7.65 (d, 1H), 7.61-7.59 (m, 1H), 7.56 (d, 1H), 7.52-7.45 (m, 4H), 7.40 (t, 1H), 7.19-7.00 (m, 3H), 6.78 (d, 2H), 6.54 (d, 1H), 4.85 (s, 2H), 2.92 (s, 6H), 2.22-2.10 (m, 1H), 1.75-1.55 (m, 4H), 1.54-1.47 (m, 1H), 1.46-1.30 (m, 2H), 1.26-1.11 (m, 1H), 0.95-0.80 (m, 2H); LCMS: 483.7 [M+H]$^+$.

The Compound below was synthesized from Compound 19 following the procedure described for Compound 88.

| Cmpd | Structure | Name | [M + H]$^+$ |
|---|---|---|---|
| 89 | 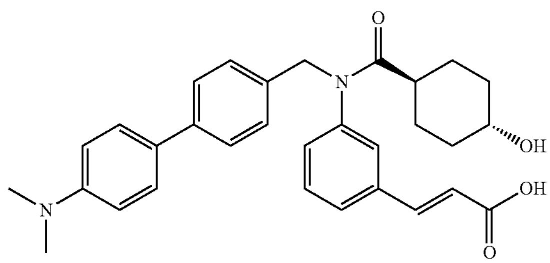 [SMILES: CN(C)c1ccc(-c2ccc(CN(c3cccc(/C=C/C(=O)O)c3)C(=O)[C@H]3CC[C@H](O)CC3)cc2)cc1] | trans-(E)-3-(3-(N-((4'-(Dimethylamino)-[1,1'-biphenyl]-4-yl)methyl)-4-hydroxycyclohexanecarboxamido)phenyl)acrylic acid | 499.7 |

(s, 6H), 2.18-2.00 (m, 1H), 1.72-1.57 (m, 4H), 1.56-1.47 (m, 1H), 1.46-1.34 (m, 2H), 1.16-1.04 (m, 1H), 0.98-0.84 (m, 2H); LCMS: 495.7 [M+H]$^+$.

Compound 88

(E)-3-(3-(N-((4'-(Dimethylamino)-[1,1'-biphenyl]-4-yl)methyl)cyclohexanecarboxamido)phenyl)acrylic acid

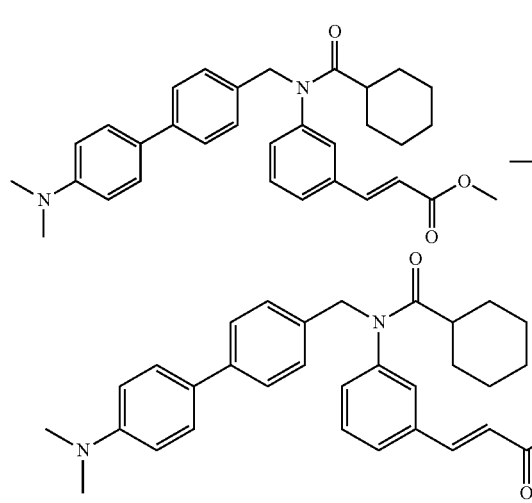

Aqueous sodium hydroxide (1N, 23 mL, 23 mmol) was added to a mixture of (E)-methyl 3-(3-(N-((4'-(dimethylamino)-[1,1'-biphenyl]-4-yl)methyl)cyclohexanecarboxamido)phenyl)acrylate (2.31 g, 4.64 mmol), THF (46 mL), and methanol (23 mL) at room temperature. The reaction mixture was stirred for 2 h, concentrated, diluted with water (100 mL), and then acidified (1N HCl, pH=4). The resulting mixture was stirred for 15 min and filtered. The filter cake Compound 90

Methyl 3-(3-(N-((4'-(dimethylamino)-[1,1'-biphenyl]-4-yl)methyl)cyclohexanecarboxamido)-5-methylphenyl)propanoate

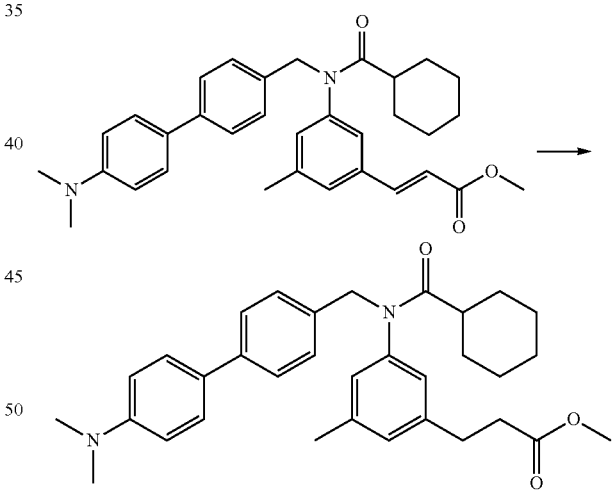

Compound 39 (192 mg, 0.38 mmol) was added to a mixture of palladium on carbon (100 mg, 10%) in methanol (20 mL). The mixture was stirred under atmosphere of hydrogen (15 psi) at 15° C. for 0.5 h, filtered, and concentrated. The residue was purified by prep-TLC (SiO$_2$, petroleum ether/ethyl acetate; 4.5/1) to give methyl 3-(3-(N-((4'-(dimethylamino)-[1,1'-biphenyl]-4-yl)methyl)cyclohexanecarboxamido)-5-methylphenyl)propanoate (150 mg, 77%) as a light yellow oil. $^1$H NMR (DMSO-d$_6$): δ 7.43-7.51 (m, 4H), 7.12 (d, 2H), 6.97 (br s, 1H), 6.72-6.82 (m, 4H), 4.75 (br s, 2H), 3.47-3.55 (m, 3H), 2.88-2.96 (m, 6H), 2.73 (s, 2H), 2.52 (d, 2H), 2.21 (s, 3H), 2.16 (br s, 1H), 1.61 (br s, 4H), 1.48 (br s, 1H), 1.38 (d, 2H), 1.09 (d, 1H), 0.89 (d, 2H); MS: 513.4 [M+H]$^+$.

The Compounds below were synthesized from the appropriate alkene Compounds following the procedure described for Compound 90.

| Cmpd | Structure | Name | [M + H]+ |
|---|---|---|---|
| 91 | 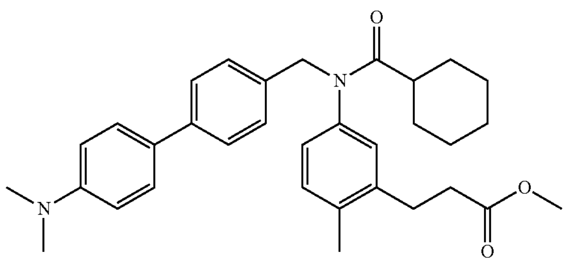 | Methyl 3-(5-(N-((4'-(dimethylamino)-[1,1'-biphenyl]-4-yl)methyl)cyclohexanecarboxamido)-2-methylphenyl)propanoate | 513.4 |
| 92 | 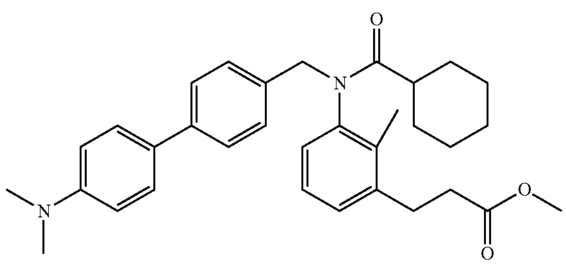 | Methyl 3-(3-(N-((4'-(dimethylamino)-[1,1'-biphenyl]-4-yl)methyl)cyclohexanecarboxamido)-2-methylphenyl)propanoate | 513.4 |
| 93 | 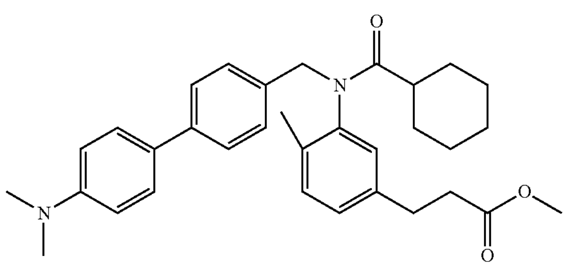 | Methyl 3-(3-(N-((4'-(dimethylamino)-[1,1'-biphenyl]-4-yl)methyl)cyclohexanecarboxamido)-4-methylphenyl)propanoate | 513.4 |
| 94 | 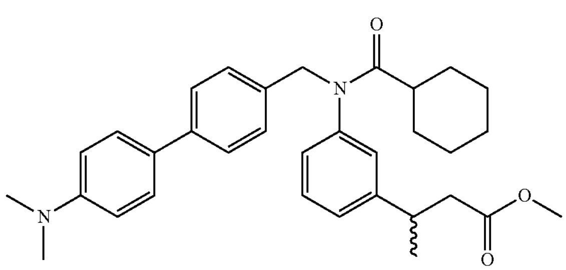 | Methyl 3-(3-(N-((4'-(dimethylamino)-[1,1'-biphenyl]-4-yl)methyl)cyclohexanecarboxamido)phenyl)butanoate | 513.4 |
| 95 | 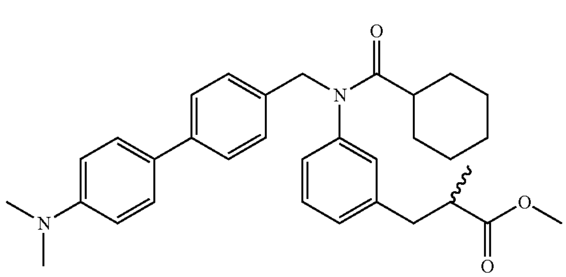 | Methyl 3-(3-(N-((4'-(dimethylamino)-[1,1'-biphenyl]-4-yl)methyl)cyclohexanecarboxamido)phenyl)-2-methylpropanoate | 513.4 |

Compound 96

(E)-Methyl 3-(3-(trans-4-((tert-butoxycarbonyl)amino)-N-((4'-(dimethylamino)-[1,1'-biphenyl]-4-yl)methyl)cyclohexanecarboxamido)phenyl)acrylate

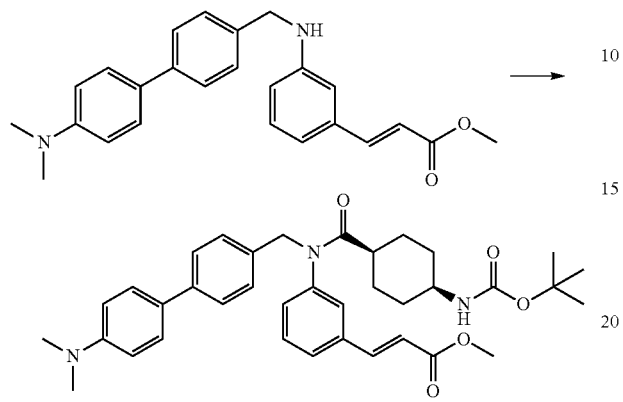

To a solution of (1r,4r)-4-((tert-butoxycarbonyl)amino)cyclohexanecarboxylic acid (102.1 mg, 419.65 umol) and Et$_3$N (270.3 mg, 2.67 mmol) in DCM (6 mL) at 0° C., SOCl$_2$ (65.5 mg, 550.56 umol) was added dropwise. The mixture was stirred for 1 hr at rt. A solution of Intermediate 3 (100 mg, 258.74 umol) in DCM (2 mL) was added, and the mixture was stirred for 2 hr at rt. The reaction was run 21 batches in parallel. The combined resulting solution was washed with aqueous citric acid (50 mL) and sat. aq. Na$_2$CO$_3$ (50 mL). The organic phase was dried over Na$_2$SO$_4$, filtered and concentrated to give a crude product, which was purified by column chromatography on silica gel (petroleum ether/EtOAc=10/1 to 3/1) to obtain (E)-methyl 3-(3-((1r,4r)-4-((tert-butoxycarbonyl)amino)-N-((4'-(dimethylamino)-[1,1'-biphenyl]-4-yl)methyl)cyclohexanecarboxamido)phenyl)acrylate (1.80 g, 2.94 mmol, 54.11% yield) as yellow oil. $^1$H NMR (400 MHz, DMSO-d$_6$) δ 7.61-7.67 (m, 3H), 7.41-7.49 (m, 5H), 7.15-7.17 (m, 3H), 6.77 (d, 2H), 6.65 (d, 1H), 6.53 (d, 1H), 4.85 (s, 2H), 3.71 (s, 3H), 3.08-3.17 (m, 1H), 2.92 (s, 6H), 1.99-2.06 (m, 1H), 1.65-1.80 (m, 4H), 1.45-1.51 (m, 2H), 1.33 (s, 9H), 0.79-0.82 (m, 2H); MS: 612.5 (M+H)$^+$.

Compound 97

(E)-Methyl 3-(3-(trans-4-amino-N-((4'-(dimethylamino)-[1,1'-biphenyl]-4-yl)methyl)cyclohexanecarboxamido)phenyl)acrylate

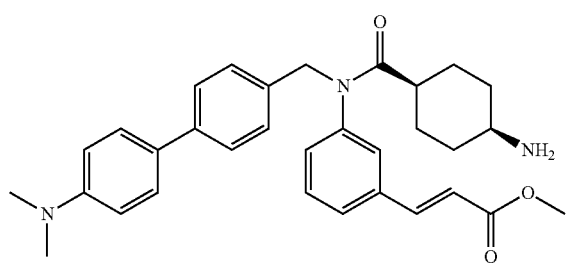

To a solution of Compound 96 (1.50 g, 2.45 mmol) in DCM (30 mL) was added TFA (5 mL) at rt. The mixture was stirred for 2 hours at rt, and the resulting solution was concentrated under reduced pressure to obtain a crude product (1.50 g, crude) as red oil. 400 mg of crude product was purified by prep-HPLC (reverse phase, water (0.04% HCl)-ACN] to obtain (E)-methyl 3-(3-((1r,4r)-4-amino-N-((4'-(dimethylamino)-[1,1'-biphenyl]-4-yl)methyl)cyclohexanecarboxamido)phenyl)acrylate (100.5 mg, purity: 99.85%) as white solid. $^1$H NMR (400 MHz, DMSO-d$_6$) δ 7.91 (br s, 3H), 7.63-7.72 (m, 5H), 7.56 (d, 2H), 7.43 (t, 1H), 7.22 (d, 4H), 6.68 (d, 1H), 4.89 (s, 2H), 3.72 (s, 3H), 2.96-3.02 (m, 7H), 2.09-2.15 (m, 1H), 1.88-1.91 (m, 2H), 1.78-1.81 (m, 2H), 1.48-1.57 (m, 2H), 0.96-1.05 (m, 2H); MS: 512.3 (M+H)$^+$.

Compound 98

(E)-Methyl 3-(3-(trans-N-((4'-(dimethylamino)-[1,1'-biphenyl]-4-yl)methyl)-4-((methoxycarbonyl)amino)cyclohexanecarboxamido)phenyl)acrylate

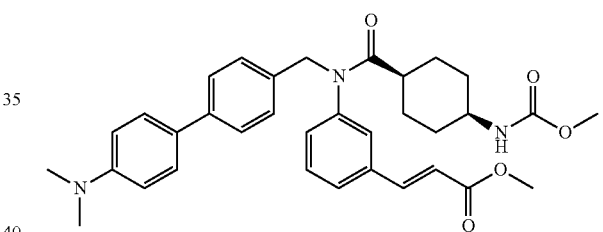

To a solution of Compound 97 (500.0 mg, 799.13 umol) and Et$_3$N (416.2 mg, 4.11 mmol) in DCM (20 mL) at 0° C. was added methyl carbonochloridate (120.6 mg, 1.28 mmol). The mixture was stirred for 1 hr at rt, and the resulting solution was washed with citric acid aqueous (10 mL) and sat. aq. NaHCO$_3$ (10 mL). The organic phase was dried over Na$_2$SO$_4$, filtered and concentrated to give a crude product, which was purified by prep-HPLC (Reverse phase; water (10 mM NH$_4$HCO$_3$)-ACN) to obtain (E)-methyl 3-(3-((1r,4r)-N-((4'-(dimethylamino)-[1,1'-biphenyl]-4-yl)methyl)-4-((methoxycarbonyl)amino)cyclohexanecarboxamido)phenyl)acrylate (135.2 mg, 225.67 umol, 28.24% yield) as light yellow solid. $^1$H NMR (400 MHz, DMSO-d$_6$): δ 7.63-7.67 (m, 3H), 7.47-7.51 (m, 4H), 7.43 (t, 1H), 7.17 (d, 3H), 6.86 (d, 1H), 6.78 (d, 2H), 6.67 (d, 1H), 4.86 (s., 2H), 3.72 (s, 3H), 3.47 (s, 3H), 3.18-3.20 (m, 1H), 2.93 (s, 6H), 2.05-2.08 (m, 1H), 1.72-1.75 (m, 4H), 1.44-1.53 (m, 2H), 0.82-0.85 (m, 2H); MS: 570.4 (M+H)$^+$.

The Compounds below were synthesized from Compound 97 following the procedure described for Compound 98 using acetyl chloride or methanesulfonyl chloride.

| Cmpd | Structure | Name | [M + H]+ |
|---|---|---|---|
| 98.1 | 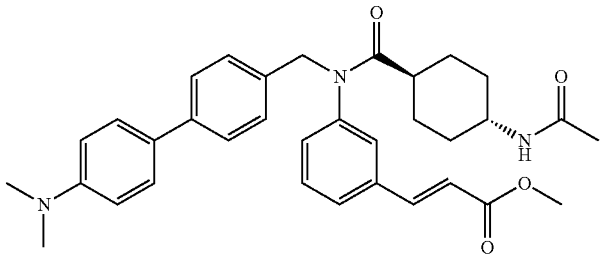 [SMILES: COC(=O)/C=C/c1cccc(N(Cc2ccc(-c3ccc(N(C)C)cc3)cc2)C(=O)[C@H]2CC[C@H](NC(C)=O)CC2)c1] | trans-(E)-Methyl 3-(3-(4-acetamido-N-((4'-(dimethylamino)-[1,1'-biphenyl]-4-yl)methyl)cyclohexanecarboxamido)phenyl)acrylate | 554.4 |
| 98.2 | 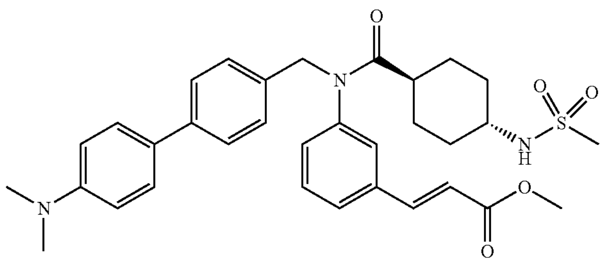 | trans-(E)-Methyl 3-(3-(N-((4'-(dimethylamino)-[1,1'-biphenyl]-4-yl)methyl)-4-(methylsulfonamido)cyclohexanecarboxamido)phenyl)acrylate | 590.5 |

Compound 99

N-((4'-(Dimethylamino)-[1,1'-biphenyl]-4-yl)methyl)-N-(3-(3-methylbut-2-en-1-yl)phenyl)cyclohexanecarboxamide

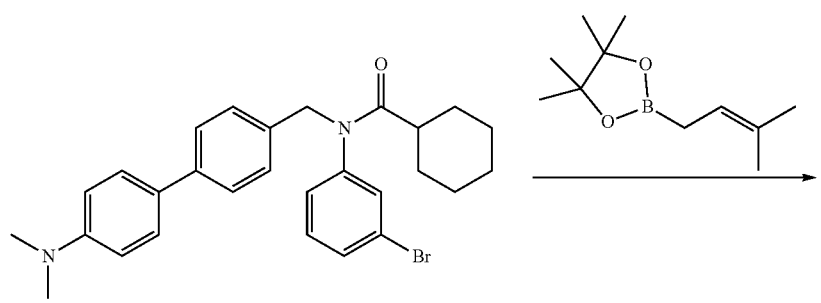

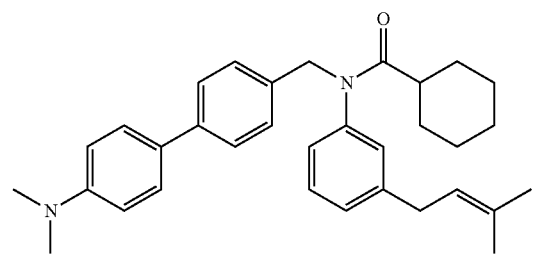

Compound 99 was made from Intermediate 5.7 and 4,4,5,5-tetramethyl-2-(3-methylbut-2-en-1-yl)-1,3,2-dioxaborolane using standard Suzuki conditions (Pd(dppf)Cl$_2$, K$_2$CO$_3$, dioxane/H$_2$O, 90° C., 12 h). MS: 481.6 (M+H)+.

Compound 100

(E)-Methyl 3-(3-(N-(4-benzamidobenzyl)cyclo-hexanecarboxamido)phenyl)acrylate

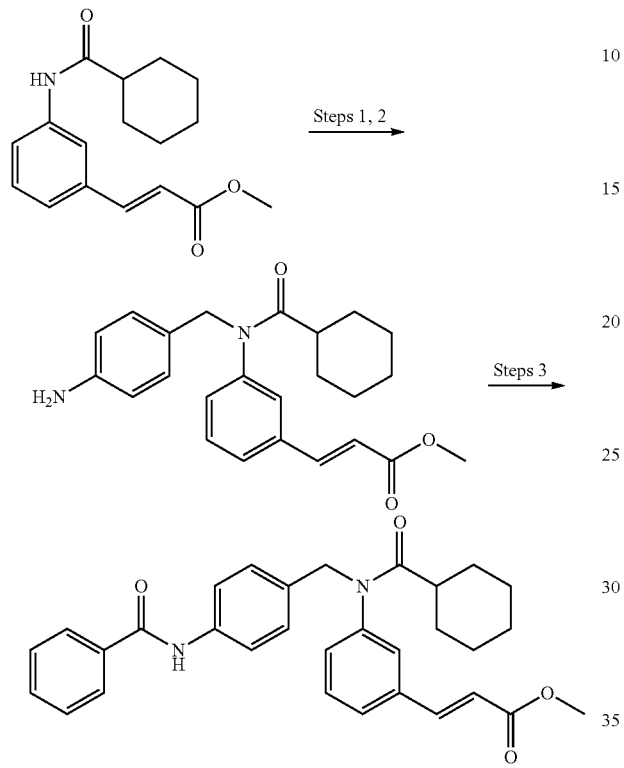

Compound 100 was made from Intermediate 9 by alkylation with 1-(bromomethyl)-4-nitrobenzene, reduction of the nitro (SnCl$_2$, 12 N HCl, EtOH, 80° C.), and then acylation with benzoyl chloride (TEA/DCM). MS: 497.7 (M+H)$^+$.

Compound 101

(E)-Methyl 3-(3-(N-(4-(N-methylbenzamido)benzyl)cyclohexanecarboxamido)phenyl)acrylate

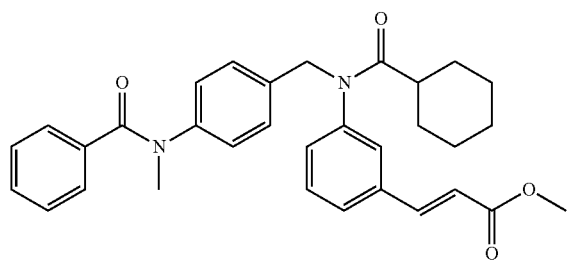 [SMILES: COC(=O)/C=C/c1cccc(N(Cc2ccc(N(C)C(=O)c3ccccc3)cc2)C(=O)C2CCCCC2)c1]

Compound 101 was made from Compound 100 using standard methylation conditions (NaH, MeI, DMF). MS: 511.7 (M+H)$^+$.

Compound 102

(E)-Methyl 3-(3-(N-(4-(benzylamino)benzyl)cyclohexanecarboxamido)phenyl)acrylate

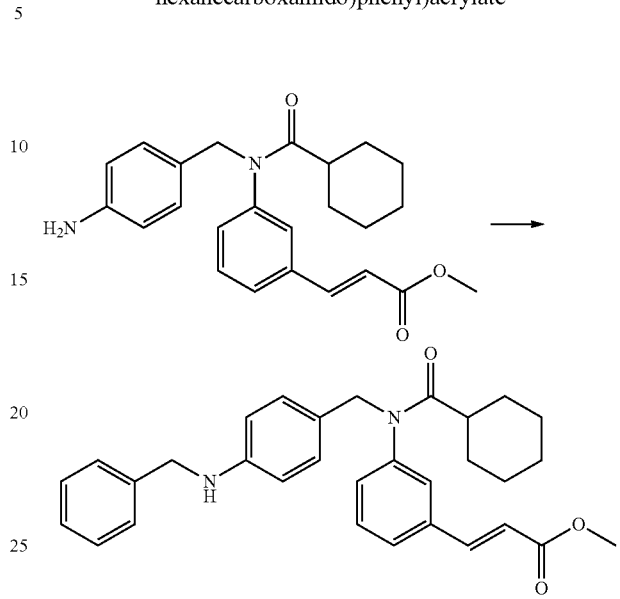

Compound 102 was made from Intermediate 9 by alkylation with 1-(bromomethyl)-4-nitrobenzene, reduction of the nitro (SnCl$_2$, 12 N HCl, EtOH, 80° C.), and then reductive amination with benzaldehyde (NaBH$_3$CN/AcOH/MeOH). MS: 483.7 (M+H)$^+$.

Compound 103

(E)-Methyl 3-(3-(N-(4-(benzyl(methyl)amino)benzyl)cyclohexanecarboxamido)phenyl)acrylate

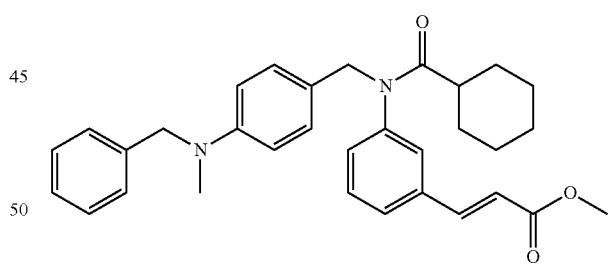

Compound 103 was made from Compound 102 and formaldehyde by reductive amination (NaBH$_3$CN/AcOH/MeOH). MS: 497.6 (M+H)$^+$.

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Example B-1: In Vitro FXR Assay (PGL3)

Seeding

CV-1 cells were seeded at a density of 2,000,000 cells in a T175 flask with DMEM+10% charcoal double-stripped FBS and incubated at 37° C. in a 5% $CO_2$ for 18 h (O/N).
Transfection After 18 h of incubation, the medium in the T175 flask was changed with fresh DMEM+10% charcoal super-stripped serum.

To prepare the transfection reaction mixture, the transfection reagent (X-tremeGENE HP from Roche, Cat #06 366 236 001) was added in to a 1.5 mL microcentrifuge tube labelled "A" at a ratio of 1:3 (DNA in transfection reagent in μL). OptiMEM medium (Life Technologies, Cat #31985-062) was added accordingly to provide a total volume of 1 mL. The transfection reaction mixture was then briefly vortexed and incubated at room temperature for 5 minutes.

In a separate 1.5 mL microcentrifuge tube labelled "B", 100 μL OptiMEM and plasmids XPD90Gal pCMXhFXRfl, pCMXhRXRfl+PGL3-ECRE*6-luc+CMX-YFP in the ratio 2 μg:2 μg:18 μg:3 μg were added. This microcentrifuge tube "B" was then briefly vortexed and incubated at room temperature for 5 minutes.

The total volume in tube labelled "A" was then transferred in to tube labelled "B." The mixture was then briefly vortexed and the transfection:DNA complex was then incubated for about 15-20 minutes at room temperature.

Following incubation, the transfection reagent/DNA mixture complex was then added to cells in the T175 flask and the cells were incubated at 8 h (O/N) at 37° C. in 5% $CO_2$.
Test Compounds In a 96 well plate, a half logarithmic serial dilution was prepared. OptiMEM was used as the diluent. Using any of one of the compounds described herein, a compound stock solution of 10 mM was prepared. An initial 1:100 dilution was made into the first well for a final concentration of 100 μM. The final concentrations in the 96-well plate was prepared by using a multichannel pipette to transfer 5 μL of the diluted compound to 384-well plate in quadruplicate.

Cells in T175 flask were trypsinized and cells were resuspended in 40 mL phenol red free DMEM+10% charcoal super-stripped FBS. Typically, one T175 flask was sufficient to seed two 384 well plates. CV-1 cells were seeded at 45 μL cell suspension/well using a multi-channel pipet or a 384 multidrop dispenser. The cells were then incubated for 18 hrs, overnight.
Reading After removing the plates from the incubator, the medium was flicked out of plate and 384 well plate was turned upside down onto paper towel. The remaining medium was gently tapped out. 15 μL lysis buffer was then added to each well using a multichannel pipet or a 384 well multi-drop dispenser. After incubation for 10 minutes at room temperature on shaker, 30 μL Luciferase buffer was added to each well. Luminescence counts were taken immediately using the Perkin Elmer Envision.

The ability of the compounds disclosed herein to inhibit FXR activity was quantified and the respective $EC_{50}$ value was determined. Table 3 provides activity of various compounds disclosed herein. Fex=fexaramine.

TABLE 3

| Compound No | Cmpd/Fex* |
|---|---|
| 1 | +++ |
| 2 | ++ |
| 3 | ++ |
| 4 | +++ |
| 5 | +++ |
| 6 | ++ |
| 7 | +++ |
| 8 | +++ |
| 9 | +++ |
| 10 | +++ |
| 11 | +++ |
| 12 | +++ |
| 13 | + |
| 14 | +++ |
| 15 | +++ |
| 16 | ++ |
| 18 | +++ |
| 19 | +++ |
| 20 | +++ |
| 21 | +++ |
| 22 | + |
| 23 | +++ |
| 24 | +++ |
| 25 | ++ |
| 26 | +++ |
| 27 | +++ |
| 28 | ++ |

TABLE 3-continued

| Compound No | Cmpd/Fex* |
|---|---|
| 29 | ++ |
| 30 | + |
| 31 | + |
| 32 | ++ |
| 33 | ++ |
| 34 | +++ |
| 35 | ++ |
| 36 | ++ |
| 37 | ++ |
| 38 | +++ |
| 39 | +++ |
| 40 | + |
| 41 | ++ |
| 42 | +++ |
| 43 | ++ |
| 44 | +++ |
| 45 | +++ |
| 46 | ++ |
| 47 | + |
| 48 | +++ |
| 49 | + |
| 50 | +++ |
| 51 | +++ |
| 52 | +++ |
| 53 | +++ |
| 54 | +++ |
| 55 | + |
| 56 | ++ |
| 57 | + |
| 58 | +++ |
| 59 | + |
| 60 | + |
| 61 | +++ |
| 62 | +++ |
| 63 | +++ |
| 64 | +++ |
| 65 | + |
| 66 | + |
| 67 | + |
| 68 | + |
| 69 | + |
| 70 | +++ |
| 71 | +++ |
| 72 | +++ |
| 73 | +++ |
| 74 | + |
| 75 | ++ |
| 76 | + |
| 77 | + |
| 78 | ++ |
| 79 | + |
| 80 | + |
| 81 | + |
| 82 | + |
| 83 | +++ |
| 84 | +++ |
| 85 | +++ |
| 86 | +++ |
| 87 | +++ |
| 88 | + |
| 89 | + |
| 90 | +++ |
| 91 | + |
| 92 | + |
| 93 | ++ |
| 94 | ++ |
| 95 | ++ |

*Where 'Cmpd/Fex' denotes the ratio of the $EC_{50}$ for the test compound relative to the $EC_{50}$ of the Fexaramine control.
'+++' means Cmpd/Fex < 10;
'++' means Cmpd/Fex > 10 & < 100;
'+' means Cmpd/Fex > 100.

Example B-2: In Vitro FXR Assay (TK)

Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 μL OptiMEM (Life Technologies, Cat #31985-062) was combined with expression plasmids for hFXR, hRXR, TK-ECRE-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Representative data for exemplary compounds disclosed herein is presented in the following table.

TABLE 4

| Cmpd | TK hFXR: EC50 (μM) |
|---|---|
| 1 | ++ |
| 2 | ++ |
| 3 | ++ |
| 4 | ++ |
| 5 | +++ |
| 6 | ++ |
| 7 | +++ |
| 8 | +++ |
| 9 | +++ |
| 10 | ++ |
| 11 | +++ |
| 12 | ++ |
| 13 | + |
| 13.1 | ++ |
| 13.2 | ++ |
| 13.3 | ++ |
| 13.4 | +++ |
| 13.5 | +++ |
| 13.6 | ++ |
| 13.7 | +++ |
| 13.8 | + |
| 13.9 | +++ |
| 13.10 | ++ |
| 13.11 | ++ |
| 13.12 | ++ |
| 13.13 | ++ |
| 13.14 | ++ |
| 13.15 | ++ |
| 13.16 | +++ |
| 13.17 | ++ |
| 13.18 | ++ |
| 13.19 | ++ |
| 13.20 | ++ |
| 13.21 | +++ |
| 13.22 | +++ |
| 13.23 | ++ |
| 13.24 | +++ |
| 13.25 | ++ |
| 13.26 | ++ |
| 13.27 | +++ |
| 13.28 | + |
| 14 | +++ |
| 15 | ++ |

TABLE 4-continued

| Cmpd | TK hFXR: EC50 (μM) |
| --- | --- |
| 16 | ++ |
| 17 | +++ |
| 17.1 | +++ |
| 17.2 | ++ |
| 17.3 | ++ |
| 18 | +++ |
| 19 | +++ |
| 20 | +++ |
| 21 | ++ |
| 22 | ++ |
| 23 | ++ |
| 24 | +++ |
| 25 | ++ |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | ++ |
| 36 | ++ |
| 37 | ++ |
| 38 | +++ |
| 39 | ++ |
| 40 | + |
| 41 | ++ |
| 42 | ++ |
| 43 | ++ |
| 44 | ++ |
| 45 | ++ |
| 46 | ++ |
| 47 | + |
| 48 | ++ |
| 49 | ++ |
| 50 | +++ |
| 51 | +++ |
| 52 | +++ |
| 53 | ++ |
| 54 | +++ |
| 55 | + |
| 56 | ++ |
| 57 | + |
| 58 | ++ |
| 59 | ++ |
| 60 | + |
| 61 | ++ |
| 62 | +++ |
| 62.1 | ++ |
| 62.2 | ++ |
| 62.3 | ++ |
| 62.4 | ++ |
| 62.5 | ++ |
| 62.6 | ++ |
| 62.7 | + |
| 62.8 | + |
| 62.9 | +++ |
| 62.10 | +++ |
| 62.11 | +++ |
| 62.12 | ++ |
| 62.13 | ++ |
| 62.14 | +++ |
| 62.15 | + |
| 62.16 | ++ |
| 62.17 | ++ |
| 63 | ++ |
| 64 | +++ |
| 65 | ++ |
| 66 | ++ |
| 67 | ++ |
| 68 | ++ |
| 69 | ++ |
| 70 | ++ |
| 71 | ++ |
| 72 | +++ |
| 73 | +++ |
| 74 | ++ |
| 75 | ++ |
| 75.1 | ++ |
| 75.2 | ++ |
| 75.3 | +++ |
| 75.4 | ++ |
| 75.5 | ++ |
| 75.6 | ++ |
| 75.7 | + |
| 75.8 | ++ |
| 75.9 | ++ |
| 75.10 | + |
| 75.11 | ++ |
| 75.12 | ++ |
| 75.13 | + |
| 75.14 | +++ |
| 75.15 | + |
| 75.16 | ++ |
| 75.17 | ++ |
| 75.18 | +++ |
| 75.19 | +++ |
| 76 | − |
| 77 | ++ |
| 78 | ++ |
| 79 | − |
| 80 | + |
| 81 | + |
| 82 | + |
| 83 | ++ |
| 84 | +++ |
| 85 | ++ |
| 86 | ++ |
| 86.1 | + |
| 86.2 | + |
| 86.3 | ++ |
| 86.4 | + |
| 86.5 | + |
| 86.6 | ++ |
| 86.7 | + |
| 86.8 | ++ |
| 86.9 | ++ |
| 86.10 | +++ |
| 86.11 | ++ |
| 87 | +++ |
| 88 | + |
| 89 | + |
| 90 | ++ |
| 91 | + |
| 92 | ++ |
| 93 | + |
| 94 | ++ |
| 95 | ++ |
| 96 | +++ |
| 97 | + |
| 98 | +++ |
| 98.1 | +++ |
| 98.2 | +++ |
| 99 | + |
| 100 | ++ |
| 101 | + |
| 102 | ++ |
| 103 | + |

Where '+++' means $EC_{50} \leq 1$;
'++' means $EC_{50} > 1$ & $< 10$;
'+' means $EC_{50} \geq 10$. Compounds with a maximum efficacy of <25% of the Fexarmine control were classified as '+'

Example B-3: NASH Activity Study (STZ Model)

NASH is induced in male C57BL/6 mice by diet-induction with AMLN diet (DIO-NASH) (D09100301, Research Diet, USA) (40% fat (18% transfat), 40% carbohydrates (20% fructose) and 2% cholesterol). The animals are kept on the diet for 29 weeks. After 26 weeks of diet induction, liver biopsies are performed for base line histological assessment of disease progression (hepatosteatosis and fibrosis), stratified and randomized into treatment groups according to liver fibrosis stage, steatosis score, and body weight. Three weeks after biopsy the mice are stratified into treatment groups and dosed daily by oral gavage with FXR agonists for 8 weeks. At the end of the study liver biopsies are performed to assess hepatic steatosis and fibrosis by examining tissue sections stained with H&E and Sirius Red, respectively. Total collagen content in the liver is measured by colorimetric determination of hydroxyproline residues by acid hydrolysis of collagen. Triglycerides and total cholesterol content in liver homogenates are measured in single determinations using autoanalyzer Cobas C-111 with commercial kit (Roche Diagnostics, Germany) according to manufacturer's instructions.

Example B-4: NASH Activity Study (AMLN Model)

NASH was induced in male C57BL/6 mice by diet-induction with AMLN diet (DIO-NASH) (D09100301, Research Diet, USA) (40% fat (18% transfat), 40% carbohydrates (20% fructose) and 2% cholesterol). The animals were kept on the diet for 29 weeks. After 26 weeks of diet induction, liver biopsies were performed for base line histological assessment of disease progression (hepatosteatosis and fibrosis), stratified and randomized into treatment groups according to liver fibrosis stage, steatosis score, and body weight. Three weeks after biopsy the mice were stratified into treatment groups and dosed daily by oral gavage with FXR agonists for 8 weeks. At the end of the study liver biopsies were performed to assess hepatic steatosis and fibrosis by examining tissue sections stained with H&E and Sirius Red, respectively. Total collagen content in the liver was measured by colorimetric determination of hydroxyproline residues by acid hydrolysis of collagen. Triglycerides and total cholesterol content in liver homogenates were measured in single determinations using autoanalyzer Cobas C-111 with commercial kit (Roche Diagnostics, Germany) according to manufacturer's instructions.

Example B-5: Intrahepatic Cholestasis Model

Experimental intrahepatic cholestasis induced by 17a-ethynylestradiol (EE2) treatment in rodents is a widely used in vivo model to examine the mechanisms involved in estrogen-induced cholestasis. Intrahepatic cholestasis can be induced in adult male mice by subcutaneous injection of 10 mg/kg 17a-ethynylestradiol (E2) daily for 5 days. Testing of FXR ligands can be performed by administration of compounds during E2 induction of cholestasis. Cholestatic effects can be quantitated by assessing liver/body weight ratio and measuring serum total bile acids and alkaline phosphatase levels can be measured using reagents and controls from Diagnostic Chemicals Ltd. and the Cobas Mira plus CC analyzer (Roche Diagnostics). For histology and mitosis measurements, liver samples from each mouse can be fixed in 10% neutral buffered formalin. Slides are stained with hematoxylin and eosin using standard protocols and examined microscopically for structural changes. Hepatocyte proliferation is evaluated by immunohistochemical staining for Ki67.

Example B-6: Direct Target Gene Regulation

Direct target gene regulation by FXR ligands can be assessed by dosing mice either acutely or chronically with compounds and collecting tissues at various time points after dosing. RNA can be isolated from tissues such as the ileum and liver, and reverse transcribed to cDNA for quantitative PCR analysis of genes known in the literature to be directly and indirectly regulated by FXR such as SHP, BSEP, IBABP, FGF15, Cyp7a1, Cyp8b1 and C3.

Example B-7: Mouse PK Study

The plasma pharmacokinetics of any one of the compounds disclosed herein as a test article test article is measured following a single bolus intravenous and oral administration to mice (CD-1, C57BL, and diet induced obesity mice). Test article is formulated for intravenous administration in a vehicle solution of DMSO, PEG400, hydroxypropyl-β-cyclodextrin (HPβCD) and is administered at a dose volume of 3 mL/kg at selected dose levels. An oral dosing formulation is prepared in appropriate oral dosing vehicles (vegetable oils, PEG400, Solutol, citrate buffer, or carboxymethyl cellulose) and is administered at a dose volume of 5~10 mL/kg at selected dose levels. Blood samples (approximately 0.15 mL) are collected by cheek pouch method at pre-determined time intervals post intravenous or oral doses into tubes containing EDTA. Plasma is isolated by centrifugation of blood at 10,000 g for 5 minutes, and aliquots are transferred into a 96-well plate and stored at −60° C. or below until analysis.

Calibration standards of test article are prepared by diluting DMSO stock solution with DMSO in a concentration range. Aliquots of calibration standards in DMSO are combined with plasma from naïve mouse so that the final concentrations of calibration standards in plasma are 10-fold lower than the calibration standards in DMSO. PK plasma samples are combined with blank DMSO to match the matrix. The calibration standards and PK samples are combined with ice-cold acetonitrile containing an analytical internal standard and centrifuged at 1850 g for 30 minutes at 4° C. The supernatant fractions are analyzed by LC/MS/MS and quantitated against the calibration curve. Pharmacokinetic parameters (area under the curve (AUC), $C_{max}$, $T_{max}$, elimination half-life ($T_{1/2}$), clearance (CL), steady state volume of distribution ($V_{dss}$), and mean residence time (MRT)) are calculated via non-compartmental analysis using Microsoft Excel (version 2013).

Example B-8: Rat ANIT Model

A compound described herein is evaluated in a chronic treatment model of cholestasis over a range of doses from 0.01 to 10 mg/kg. This model is used to evaluate the suitability of the use of FXR agonists, e.g. a compound described herein, for the treatment of cholestatic liver disorders such as bile acid malabsorption (e.g., primary or secondary bile acid diarrhea), bile reflux gastritis, collagenous colitis, lymphocytic colitis, diversion colitis, indeterminate colitis, Alagille syndrome, biliary atresia, ductopenic liver transplant rejection, bone marrow or stem cell transplant associated graft versus host disease, cystic fibrosis liver disease, and parenteral nutrition-associated liver disease.

Rats are treated with alpha-naphthylisothiocyanate (ANIT) (0.1% w/w) in food for 3 days prior to treatment with a compound described herein at doses from 0.01 to 10 mg/kg ("Veh"). A noncholestatic control group is fed standard chow diet without ANIT, and serves as the noncholestatic control animals ("Control"). After 14 days of oral dosing, rat serum is analyzed for levels of analytes. LLQ, lower limit of quantitation. Mean±SEM; n=5.

Levels of hepatobiliary injury indicators are measured in rat serum, such as elevated levels of circulating aspartate aminotransferase (AST), alanine aminotransferase (ALT), bilirubin and bile acids. ANIT exposure induces profound cholestasis and hepatocellular damage. A compound that improves many of these indicators is useful in the treatment of the aforementioned diseases or conditions.

Reductions in the accumulation of bile acids in the liver, enhancements in bile acid excretion in the biliary tract and inhibition of bile acid synthesis is consistent with the pharmacological action of a FXR agonist. An improvement in the serum conjugated bilirubin (a direct indicator for hepatic function) implies recovery from cholestasis with improved bile excretion.

Furthermore, an analysis is made to ascertain the effects of the compound described herein on serum FGF15 fibroblast growth factor 15 (FGF15 in rodent; FGF19 in human) expression, a hormone that is secreted in the portal blood and signals to the liver to repress Cyp7a1 expression synergistically with SHP. The direct FXR-dependent induction of FGF15/19 along with FGF15/19's anti-cholestatic properties makes it a convenient serum biomarker for detecting target engagement of FXR agonists.

Serum FGF15 levels are quantified using an FGF15 Meso Scale Discovery (MSD) assay. For example, Mouse FGF15 antibody from R&D Systems (AF6755) is used both as capture and detection antibody in the assay. MSD SULFO-TAG NETS-Ester is used to label the FGF15 antibody. MSD standard 96-well plates are coated with the FGF15 capture antibody and the plates are blocked with MSD Blocker A (R93AA-2). After washing the plate with PBS+0.05% Tween 20, MSD diluent 4 is dispensed into each well and incubated for 30 min. 25 pi of calibrator dilutions or samples (serum or EDTA plasma) are dispensed into each well and incubated with shaking at RT.

After washing, detection antibody is added and incubated with shaking for 1 h at RT. After washing and the addition of MSD Read buffer (R92TC-2), the plate is read on an MSD SECTOR Imager 6000. Plots of the standard curve and unknown samples are calculated using MSD data analysis software.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (II), or a pharmaceutically acceptable salt or solvate thereof:

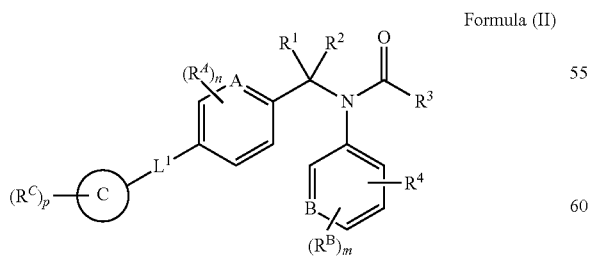

Formula (II)

wherein
$R^1$ and $R^2$ are each independently selected from H, D, F, $CH_3$, and $CF_3$;
$R^3$ is cyclohexyl that is substituted with $R^{12}$;

$R^{12}$ is selected from D, halogen, —CN, —$NO_2$, —$OR^{10}$, —$SR^{10}$, —S(=O)$R^{11}$, —S(=O)$_2R^{11}$, —S(=O)$_2N(R^{10})_2$, —$NR^{10}$S(=O)$_2R^{11}$, —C(=O)$R^{11}$, —OC(=O)$R^{11}$, —$CO_2R^{10}$, —$OCO_2R^{11}$, —$N(R^{10})_2$, —C(=O)$N(R^{10})_2$, —OC(=O)$N(R^{10})_2$, —$NR^{10}$C(=O)$R^{11}$, —$NR^{10}$C(=O)$OR^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -$L^4$-$L^5$-$R^{13}$;

$L^4$ is absent, —O—, —S—, —S(=O)—, —S(=O)$_2$—, —$NR^{10}$—, —C(=O)—, —C(=O)NH—, —NHC(=O)—, —C(=O)O—, —OC(=O)—, —OC(=O)NH—, —NHC(=O)NH—, —NHC(=O)O—, —$(CH_2)_r$—, or —$(OCH_2CH_2)_r$—, and r is 1, 2, 3, or 4;

$L^5$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;

$R^{13}$ is H, halogen, —$N(R^{10})_2$, unsubstituted or substituted $C_1$-$C_{10}$alkyl, unsubstituted or substituted $C_1$-$C_{10}$alkenyl, unsubstituted or substituted $C_1$-$C_{10}$alkynyl, unsubstituted or substituted $C_1$-$C_{10}$cycloalkyl, unsubstituted or substituted $C_1$-$C_{10}$heterocycloalkyl, unsubstituted or substituted aryl, or unsubstituted or substituted heteroaryl;

$R^4$ is -$L^3$-Y;
$L^3$ is —C($R^5$)($R^6$)—, —C($R^6$)=C($R^8$)—, —C≡C—, —O—C($R^7$)($R^8$)—, or —C($R^5$)($R^6$)—O—;
$R^5$ and $R^7$ are each independently selected from H, D, $C_1$-$C_4$alkyl, and $C_3$-$C_6$cycloalkyl;
$R^6$ and $R^8$ are each independently selected from H, D, $C_1$-$C_4$alkyl, or $C_3$-$C_6$cycloalkyl;
Y is —$CH_2OR^9$, —C(=O)$OR^9$,

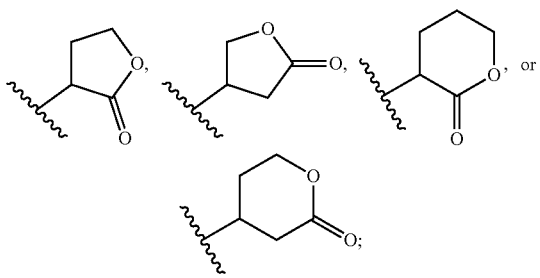

$R^9$ is selected from H, substituted or unsubstituted $C_1$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted phenyl, and substituted or unsubstituted heterocycle;
$L^1$ is absent, —O—, —S—, —S—$CH_2$—, —$CH_2$—S—, —$CH_2$—, —CH=CH—, —C≡C—, —$NR^{10}$, —$NR^{10}$—$CH_2$—, or —$CH_2$—$NR^{10}$—;

A is CR$^A$, or N;
each R$^A$ is independently selected from H, D, halogen, —CN, —OH, —OR$^{10}$, C$_1$-C$_6$alkyl, or C$_1$-C$_6$fluoroalkyl;
B is CR$^B$, or N;
each R$^B$ is independently selected from H, D, halogen, —CN, —OH, —OR$^{10}$, C$_1$-C$_6$alkyl, or C$_1$-C$_6$fluoroalkyl;
ring C is phenyl;
or ring C is a monocyclic heteroaryl selected from furanyl, thienyl, pyrrolyl, oxazolyl, thiazolyl, imidazolyl, pyrazolyl, triazolylene, tetrazolyl, isoxazolyl, isothiazolyl, oxadiazolyl, thiadiazolyl, pyridinyl, pyrimidinyl, pyrazinyl, pyridazinyl, or triazinyl;
or ring C is a bicyclic heteroaryl selected from indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, and purinyl;
each R$^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;
each R$^{10}$ is independently selected from H, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;
or two R$^{10}$ on the same N atom are taken together with the N atom to which they are attached to form a N-containing heterocycle;
each R$^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;
m is 0, 1, or 2;
n is 0, 1, or 2; and
p is 0, 1, 2, 3, or 4.

2. The compound of claim 1, or a pharmaceutically acceptable salt or solvate thereof, wherein:
A is C(H) and B is C(H).

3. The compound of claim 2, or a pharmaceutically acceptable salt or solvate thereof, wherein:
L$^1$ is absent.

4. The compound of claim 3, or a pharmaceutically acceptable salt or solvate thereof, wherein:
R$^1$ and R$^2$ are each H.

5. The compound of claim 4, or a pharmaceutically acceptable salt or solvate thereof, wherein:

R$^4$ is

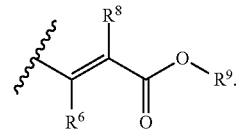

6. The compound of claim 5, or a pharmaceutically acceptable salt or solvate thereof, wherein:
ring C is phenyl.

7. The compound of claim 6, or a pharmaceutically acceptable salt or solvate thereof, wherein:
m is 0 and n is 0.

8. A compound that has the structure of Formula (VI), or a pharmaceutically acceptable salt or solvate thereof:

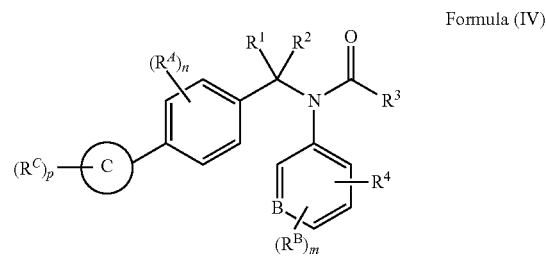

Formula (IV)

wherein
R$^1$ and R$^2$ are each independently selected from H, D, F, CH$_3$, and CF$_3$;
R$^3$ is cyclohexyl that is substituted with R$^{12}$;
each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^5$-L$^6$-R$^{13}$;
L$^5$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, and r is 1, 2, 3, or 4;
L$^6$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;
R$^{13}$ is H, halogen, —N(R$^{10}$)$_2$, unsubstituted or substituted C$_1$-C$_{10}$alkyl, unsubstituted or substituted C$_1$-C$_{10}$alkenyl, unsubstituted or substituted C$_1$-C$_{10}$alkynyl, unsubstituted or substituted C$_1$-C$_{10}$cycloalkyl, unsubstituted or substituted $C_1$-$C_{10}$heterocycloalkyl, unsubstituted or substituted aryl, or unsubstituted or substituted heteroaryl;

ring A is phenyl, cyclohexyl, pyridinyl, pyrimidinyl, pyrazinyl, or pyridazinyl;

each $R^A$ is independently selected from H, D, halogen, —CN, —OH, —OR$^{10}$, $C_1$-$C_6$alkyl, and $C_1$-$C_6$fluoroalkyl;

$L^1$ is absent, —O—, —S—, —S—CH$_2$—, —CH$_2$—S—, —CH$_2$—, —CH=CH—, —C≡C—, —NR$^{10}$—, —NR$^{10}$—CH$_2$—, or —CH$_2$—NR$^{10}$—;

ring C is phenyl, pyridinyl, pyrimidinyl, pyrazinyl, pyridazinyl, or triazinyl;

each $R^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;

ring B is phenyl, pyridinyl, pyrimidinyl, pyrazinyl, or pyridazinyl;

each $R^B$ is independently selected from H, D, halogen, —CN, —OH, —OR$^{10}$, $C_1$-$C_6$alkyl, and $C_1$-$C_6$fluoroalkyl;

$R^5$ and $R^7$ are each independently selected from H, D, $C_1$-$C_4$alkyl and $C_3$-$C_6$cycloalkyl;

or $R^5$ and $R^7$ are taken together with the intervening atoms to form a double bond;

$R^6$ and $R^8$ are each independently selected from H, D, $C_1$-$C_4$alkyl, and $C_3$-$C_6$cycloalkyl;

Y is —CH$_2$OR$^9$, —C(=O)OR$^9$, —CH$_2$C(=O)OR$^9$,

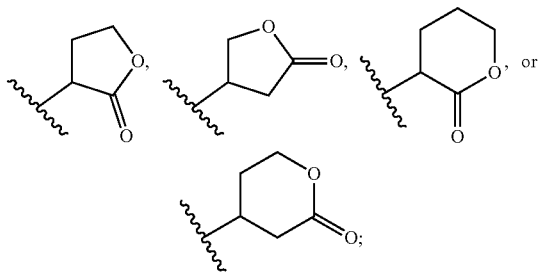

each $R^9$ is independently selected from H, substituted or unsubstituted $C_2$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted phenyl, and substituted or unsubstituted heterocycle;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;
n is 0, 1, or 2; and
p is 0, 1, 2, 3, or 4.

9. The compound of claim 8, or a pharmaceutically acceptable salt or solvate thereof, wherein:
ring B is phenyl.

10. The compound of claim 9, or a pharmaceutically acceptable salt or solvate thereof, wherein:

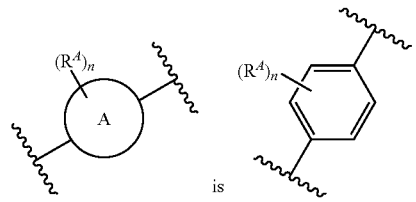

is .

11. The compound of claim 10, or a pharmaceutically acceptable salt or solvate thereof, wherein:
$L^1$ is absent.

12. The compound of claim 11, or a pharmaceutically acceptable salt or solvate thereof, wherein:
ring C is phenyl.

13. The compound of claim 12, or a pharmaceutically acceptable salt or solvate thereof, wherein:
$R^3$ is selected from substituted or unsubstituted $C_3$-$C_{10}$cycloalkyl, wherein if $R^3$ is substituted then $R^3$ is substituted with one or more $R^{t2}$ groups.

14. The compound of claim 12, or a pharmaceutically acceptable salt or solvate thereof, wherein:
$R^5$ and $R^7$ are taken together with the intervening atoms to form a double bond;
Y is —CH$_2$OR$^9$ or —C(=O)OR$^9$, and $R^9$ is selected from H, ethyl, propyl, iso-propyl, n-butyl, iso-butyl, tert-butyl, substituted or unsubstituted cyclopropyl, substituted or unsubstituted cyclobutyl, substituted or unsubstituted cyclopentyl, or substituted or unsubstituted cyclohexyl.

15. A compound selected from the group consisting of:
(E)-Methyl 3-(3-(N-((4'-(dimethylamino)-[1,1'-biphenyl]-4-yl)methyl)pivalamido)-phenyl)acrylate;
(E)-Methyl 3-(3-(N-((4'-(dimethylamino)-[1,1'-biphenyl]-4-yl)methyl)butyramido)-phenyl)acrylate;
(E)-Methyl 3-(3-(((4'-(dimethylamino)-[1,1'-biphenyl]-4-yl)methyl)(ethoxycarbonyl)amino)phenyl)acrylate;
(E)-Methyl 3-(3-(4-cyano-N-((4'-(dimethylamino)-[1,1'-biphenyl]-4-yl)methyl)benzamido)phenyl)acrylate;
(E)-Methyl 3-(3-(N-((4'-(dimethylamino)-[1,1'-biphenyl]-4-yl)methyl)tetrahydro-2H-pyran-4-carboxamido)phenyl)acrylate;
(E)-Methyl 3-(3-(N-((4'-(dimethylamino)-[1,1'-biphenyl]-4-yl)methyl)oxetane-3-carboxamido)phenyl)acrylate;
(E)-Methyl 3-(3-(N-((4'-(dimethylamino)-[1,1'-biphenyl]-4-yl)methyl)-3,3-dimethylbutanamido)phenyl) acrylate;

(E)-Methyl 3-(3-((1r,4r)-N-((4'-(dimethylamino)-[1,1'-biphenyl]-4-yl)methyl)-4-methoxycyclohexanecarboxamido)phenyl)acrylate;
(E)-Methyl 3-(3-((1s,4s)-N-((4'-(dimethylamino)-[1,1'-biphenyl]-4-yl)methyl)-4-methoxycyclohexanecarboxamido)phenyl)acrylate;
(E)-Methyl 3-(3-(N-((4'-(dimethylamino)-[1,1'-biphenyl]-4-yl)methyl)-4-methoxybenzamido)phenyl)acrylate;
(E)-Methyl 3-(3-(N-((4'-(dimethylamino)-[1,1'-biphenyl]-4-yl)methyl)cycloheptanecarboxamido)phenyl)acrylate;
(E)-Methyl 3-(3-(-N-((4'-(dimethylamino)-[1,1'-biphenyl]-4-yl)methyl)adamantane-1-carboxamido)phenyl)acrylate;
(E)-methyl 3-(3-(N-(4-cyclohexylbenzyl)cyclohexanecarboxamido)phenyl)acrylate;
(E)-Methyl 3-(3-(N-((4'-(dimethylamino)-[1,1'-biphenyl]-4-yl)methyl)-3,4-difluorobenzamido)phenyl)acrylate;
(E)-Methyl 3-(3-(N-((4'-(dimethylamino)-[1,1'-biphenyl]-4-yl)methyl)-4-fluorobenzamido)phenyl)acrylate;
(E)-Methyl 3-(3-(N-((4'-(dimethylamino)-[1,1'-biphenyl]-4-yl)methyl)-1-methylcyclohexanecarboxamido)phenyl)acrylate;
(E)-Methyl 3-(3-(N-((4'-(dimethylamino)-[1,1'-biphenyl]-4-yl)methyl)cyclohexanecarboxamido)-5-fluorophenyl)acrylate;
(E)-Methyl 3-(3-(N-((4'-(dimethylamino)-[1,1'-biphenyl]-4-yl)methyl)bicyclo[2.2.1]heptane-2-carboxamido)-5-fluorophenyl)acrylate;
(E)-Methyl 3-(3-(N-((4'-(dimethylamino)-[1,1'-biphenyl]-4-yl)methyl)-4-methyltetrahydro-2H-pyran-4-carboxamido)phenyl)acrylate;
(E)-Methyl 3-(3-(N-((4'-(dimethylamino)-[1,1'-biphenyl]-4-yl)methyl)-2-methoxybenzamido)phenyl)acrylate;
(E)-Methyl 3-(3-(N-((4'-(dimethylamino)-[1,1'-biphenyl]-4-yl)methyl)-1,1-dioxidotetrahydro-2H-thiopyran-4-carboxamido)phenyl)acrylate;
(E)-Methyl 3-(3-(N-((4'-(dimethylamino)-[1,1'-biphenyl]-4-yl)methyl)tetrahydro-2H-thiopyran-4-carboxamido)phenyl)acrylate;
(E)-Methyl 3-(3-(N-((4'-(dimethylamino)-[1,1'-biphenyl]-4-yl)methyl)-3-methoxybenzamido)phenyl)acrylate;
(E)-Methyl 3-(3-(N-((4'-(dimethylamino)-[1,1'-biphenyl]-4-yl)methyl)-1-(methylsulfonyl)azetidine-3-carboxamido)phenyl)acrylate;
(E)-Methyl 3-(3-(N-((4'-(dimethylamino)-[1,1'-biphenyl]-4-yl)methyl)-4-(2-morpholinoethoxy)benzamido)phenyl)acrylate;
(E)-Methyl 3-(3-(N-((4'-(dimethylamino)-[1,1'-biphenyl]-4-yl)methyl)-4-(methylthio)cyclohexanecarboxamido)phenyl)acrylate;
cis-(E)-Methyl 3-(3-(N-((4'-(dimethylamino)-[1,1'-biphenyl]-4-yl)methyl)-4-(methylsulfonyl)cyclohexanecarboxamido)phenyl)acrylate;
trans-(E)-methyl 3-(3-(N-((4'-(dimethylamino)-[1,1'-biphenyl]-4-yl)methyl)-4-(methylsulfonyl)cyclohexanecarboxamido)phenyl)acrylate;
trans-4-(((4'-(Dimethylamino)-[1,1'-biphenyl]-4-yl)methyl)(3-((E)-3-methoxy-3-oxoprop-1-en-1-yl)phenyl)carbamoyl)cyclohexanecarboxylic acid;
(E)-Methyl 3-(3-(N-((4'-(dimethylamino)-[1,1'-biphenyl]-4-yl)methyl)-6-oxopiperidine-3-carboxamido)phenyl)acrylate;
(E)-Methyl 3-(3-(N-((4'-(dimethylamino)-[1,1'-biphenyl]-4-yl)methyl)-2-oxopiperidine-4-carboxamido)phenyl)acrylate;
(E)-Methyl 3-(3-(N-((4'-(dimethylamino)-[1,1'-biphenyl]-4-yl)methyl)-1-oxidotetrahydro-2H-thiopyran-4-carboxamido)phenyl)acrylate;
(E)-Methyl 3-(3-(N-((4'-(dimethylamino)-[1,1'-biphenyl]-4-yl)methyl)-4-(methylsulfinyl)cyclohexanecarboxamido)phenyl)acrylate;
(E)-Methyl 3-(3-(N-((4'-(dimethylamino)-[1,1'-biphenyl]-4-yl)methyl)-4-hydroxybenzamido)phenyl)acrylate;
(E)-Methyl 3-(3-(N-((4'-(dimethylamino)-[1,1'-biphenyl]-4-yl)methyl)-4-(2-hydroxyethoxy)benzamido)phenyl)acrylate;
(E)-Methyl 3-(3-(N-((4'-(dimethylamino)-[1,1'-biphenyl]-4-yl)methyl)-3-hydroxy-2,2-dimethylpropanamido)phenyl)acrylate;
(E)-Methyl 3-(3-(3-chloro-N-((4'-(dimethylamino)-[1,1'-biphenyl]-4-yl)methyl)-2,2-dimethylpropanamido)phenyl)acrylate;
trans-(E)-Methyl 3-(3-(N-((4'-(dimethylamino)-[1,1'-biphenyl]-4-yl)methyl)-2-hydroxycyclohexanecarboxamido)phenyl)acrylate;
cis-(E)-Methyl 3-(3-(N-((4'-(dimethylamino)-[1,1'-biphenyl]-4-yl)methyl)-2-hydroxycyclohexanecarboxamido)phenyl)acrylate;
cis-(E)-Methyl 3-(3-(N-((4'-(dimethylamino)-[1,1'-biphenyl]-4-yl)methyl)-3-hydroxycyclohexanecarboxamido)phenyl)acrylate;
trans-(E)-Methyl 3-(3-(N-((4'-(dimethylamino)-[1,1'-biphenyl]-4-yl)methyl)-3-hydroxycyclohexanecarboxamido)phenyl)acrylate;
(E)-Methyl 3-(3-(N-((4'-(dimethylamino)-[1,1'-biphenyl]-4-yl)methyl)cyclopentanecarboxamido)phenyl)acrylate;
(E)-Methyl 3-(3-(N-((4'-(dimethylamino)-[1,1'-biphenyl]-4-yl)methyl)cyclobutanecarboxamido)phenyl)acrylate;
(E)-Methyl 3-(3-(((4'-(dimethylamino)-[1,1'-biphenyl]-4-yl)methyl)amino)phenyl)acrylate;
(E)-Methyl 3-(3-(N-((4'-(dimethylamino)-[1,1'-biphenyl]-4-yl)methyl)-4-oxocyclohexanecarboxamido)phenyl)acrylate;
(E)-Methyl 3-(3-(N-((4'-(dimethylamino)-[1,1'-biphenyl]-4-yl)methyl)tetrahydro-2H-pyran-2-carboxamido)phenyl)acrylate;
(E)-Methyl 3-(3-(N-((4'-(dimethylamino)-[1,1'-biphenyl]-4-yl)methyl)-1,4-dioxane-2-carboxamido)phenyl)acrylate;
(E)-Methyl 3-(3-(N-((4'-(dimethylamino)-[1,1'-biphenyl]-4-yl)methyl)tetrahydro-2H-pyran-3-carboxamido)phenyl)acrylate;
cis-(E)-Methyl 3-(3-(N-((4'-(dimethylamino)-[1,1'-biphenyl]-4-yl)methyl)-4-hydroxycyclohexane carboxamido)phenyl)acrylate;
trans-(E)-Methyl 3-(3-(N-((4'-(dimethylamino)-[1,1'-biphenyl]-4-yl)methyl)-4-hydroxycyclohexanecarboxamido)phenyl)acrylate;
(E)-Methyl 3-(3-(N-((4'-(dimethylamino)-3'-methyl-[1,1'-biphenyl]-4-yl)methyl)cyclohexanecarboxamido)phenyl)acrylate;
(E)-Methyl 3-(3-(N-((2'-methyl-[1,1'-biphenyl]-4-yl)methyl)cyclohexanecarboxamido)phenyl)acrylate;
(E)-Methyl 3-(3-(N-(4-(pyridin-4-yl)benzyl)cyclohexanecarboxamido)phenyl)acrylate;

(E)-Methyl 3-(3-(N-((4'-cyano-[1,1'-biphenyl]-4-yl)methyl)cyclohexanecarboxamido)-phenyl)acrylate;
(E)-Methyl 3-(3-(N-((3'-cyano-[1,1'-biphenyl]-4-yl)methyl)cyclohexanecarboxamido)-phenyl)acrylate;
(E)-Methyl 3-(3-(N-((4'-fluoro-[1,1'-biphenyl]-4-yl)methyl)cyclohexanecarboxamido)-phenyl)acrylate;
(E)-Methyl 3-(3-(N-((3'-fluoro-[1,1'-biphenyl]-4-yl)methyl)cyclohexanecarboxamido)-phenyl)acrylate;
(E)-Methyl 3-(3-(N-((2'-fluoro-[1,1'-biphenyl]-4-yl)methyl)cyclohexanecarboxamido)-phenyl)acrylate;
(E)-Methyl 3-(3-(N-(4-(1-methyl-1H-pyrazol-4-yl)benzyl)cyclohexanecarboxamido)-phenyl)acrylate;
(E)-Methyl 3-(3-(N-(4-(pyridin-3-yl)benzyl)cyclohexanecarboxamido)phenyl)acrylate;
(E)-Methyl 3-(3-(N-((3'-(trifluoromethoxy)-[1,1'-biphenyl]-4-yl)methyl)cyclohexanecarboxamido)phenyl)acrylate;
(E)-Methyl 3-(3-(N-(4-(3,5-dimethylisoxazol-4-yl)benzyl)cyclohexanecarboxamido)-phenyl)acrylate;
(E)-Methyl 3-(3-(N-((4'-isopropoxy-[1,1'-biphenyl]-4-yl)methyl)cyclohexanecarboxamido)phenyl)acrylate;
(E)-Methyl 3-(3-(N-((2'-fluoro-4'-methoxy-[1,1'-biphenyl]-4-yl)methyl)cyclohexanecarboxamido)phenyl)acrylate;
(E)-Methyl 3-(3-(N-((4'-chloro-[1,1'-biphenyl]-4-yl)methyl)cyclohexanecarboxamido)phenyl)acrylate;
(E)-Methyl 3-(3-(N-((3'-(trifluoromethyl)-[1,1'-biphenyl]-4-yl)methyl)cyclohexanecarboxamido)phenyl)acrylate;
(E)-Methyl 3-(3-(N-((4'-(trifluoromethyl)-[1,1'-biphenyl]-4-yl)methyl)cyclohexanecarboxamido)phenyl)acrylate;
(E)-Methyl 3-(3-(N-((3'-(dimethylamino)-[1,1'-biphenyl]-4-yl)methyl)cyclohexanecarboxamido)phenyl)acrylate;
(E)-Methyl 3-(3-(N-(4-(6-(dimethylamino)pyridin-3-yl)benzyl)cyclohexanecarboxamido)phenyl)acrylate;
(E)-Methyl 3-(3-(N-((4'-(dimethylamino)-[1,1'-biphenyl]-4-yl)methyl)cyclohexanecarboxamido)-5-methylphenyl)acrylate;
(E)-Methyl 3-(5-(N-((4'-(dimethylamino)-[1,1'-biphenyl]-4-yl)methyl)cyclohexanecarboxamido)-2-methylphenyl)acrylate;
(E)-Methyl 3-(3-(N-((4'-(dimethylamino)-[1,1'-biphenyl]-4-yl)methyl)cyclohexanecarboxamido)-2-methylphenyl)acrylate;
(E)-Methyl 3-(3-(N-((4'-(dimethylamino)-[1,1'-biphenyl]-4-yl)methyl)cyclohexanecarboxamido)-4-methylphenyl)acrylate;
Methyl 3-(3-(N-((4'-(dimethylamino)-[1,1'-biphenyl]-4-yl)methyl)cyclohexanecarboxamido)phenyl)propanoate;
(E)-N-((4'-(Dimethylamino)-[1,1'-biphenyl]-4-yl)methyl)-N-(3-(3-methoxyprop-1-en-1-yl)phenyl)cyclohexanecarboxamide;
(E)-Methyl 3-(3-(N-((4'-(dimethylamino)-[1,1'-biphenyl]-4-yl)methyl)cyclohexanecarboxamido)phenyl)but-2-enoate;
(E)-Methyl 3-(3-(N-(1-(4'-(dimethylamino)-[1,1'-biphenyl]-4-yl)ethyl)cyclohexanecarboxamido)phenyl)acrylate;
(E)-Methyl 3-(3-(N-((3'-isopropyl-[1,1'-biphenyl]-4-yl)methyl)cyclohexanecarboxamido)phenyl)acrylate;
(E)-Methyl 3-(3-(N-((4'-(pyrrolidin-1-yl)-[1,1'-biphenyl]-4-yl)methyl)cyclohexanecarboxamido)phenyl)acrylate;
(E)-Methyl 3-(3-(N-(4-(1H-indazol-5-yl)benzyl)cyclohexanecarboxamido)phenyl)acrylate;
(E)-methyl 3-(3-(N-((4'-(dimethylamino)-2-fluoro-[1,1'-biphenyl]-4-yl)methyl)cyclohexanecarboxamido)phenyl)acrylate;
(E)-methyl 3-(3-(N-((4'-(dimethylamino)-3-fluoro-[1,1'-biphenyl]-4-yl)methyl)cyclohexanecarboxamido)phenyl)acrylate;
(E)-Methyl 3-(3-(N-((4'-methoxy-3'-methyl-[1,1'-biphenyl]-4-yl)methyl)cyclohexanecarboxamido)phenyl)acrylate;
(E)-Methyl 3-(3-(N-((4'-(dimethylamino)-2-methyl-[1,1'-biphenyl]-4-yl)methyl)cyclohexanecarboxamido)phenyl)acrylate;
(E)-Methyl 3-(3-(N-((4'-(dimethylamino)-3-methyl-[1,1'-biphenyl]-4-yl)methyl)cyclohexanecarboxamido)phenyl)acrylate;
(E)-Methyl 3-(3-(N-((3'-hydroxy-[1,1'-biphenyl]-4-yl)methyl)cyclohexanecarboxamido)phenyl)acrylate;
(E)-Methyl 3-(3-(N-((2'-hydroxy-[1,1'-biphenyl]-4-yl)methyl)cyclohexanecarboxamido)phenyl)acrylate;
(E)-Methyl 3-(3-(N-((4'-hydroxy-[1,1'-biphenyl]-4-yl)methyl)cyclohexanecarboxamido)phenyl)acrylate;
(E)-Methyl 3-(3-(N-((3'-methoxy-4'-methyl-[1,1'-biphenyl]-4-yl)methyl)cyclohexanecarboxamido)phenyl)acrylate;
(E)-Methyl 3-(3-(N-((2',6'-difluoro-[1,1'-biphenyl]-4-yl)methyl)cyclohexanecarboxamido)phenyl)acrylate;
(E)-Methyl 3-(3-(N-((4'-((tert-butoxycarbonyl)(methyl)amino)-[1,1'-biphenyl]-4-yl)methyl)cyclohexanecarboxamido)phenyl)acrylate;
(E)-Methyl 3-(3-(N-((4'-(methylamino)-[1,1'-biphenyl]-4-yl)methyl)cyclohexanecarboxamido)phenyl)acrylate;
(E)-Methyl 3-(3-(N-(4-(1-methyl-1H-indol-5-yl)benzyl)cyclohexanecarboxamido)phenyl)acrylate;
(E)-Methyl 3-(3-(N-((4'-methoxy-3'-methyl-[1,1'-biphenyl]-4-yl)methyl)isonicotinamido)phenyl)acrylate;
(E)-Methyl 4'-((N-(3-(3-methoxy-3-oxoprop-1-en-1-yl)phenyl)cyclohexanecarboxamido)methyl)-[1,1'-biphenyl]-3-carboxylate;
(E)-Methyl 4'-((N-(3-(3-methoxy-3-oxoprop-1-en-1-yl)phenyl)cyclohexanecarboxamido)methyl)-[1,1'-biphenyl]-4-carboxylate;
(E)-Methyl 3-(3-(N-((4'-(methylsulfonyl)-[1,1'-biphenyl]-4-yl)methyl)cyclohexanecarboxamido)phenyl)acrylate;
(E)-tert-Butyl 4-(((4'-methoxy-3'-methyl-[1,1'-biphenyl]-4-yl)methyl)(3-(3-methoxy-3-oxoprop-1-en-1-yl)phenyl)carbamoyl)piperidine-1-carboxylate;
(E)-Methyl 3-(3-(N-((3'-(hydroxymethyl)-[1,1'-biphenyl]-4-yl)methyl)cyclohexanecarboxamido)phenyl)acrylate;
(E)-Methyl 3-(3-(N-((4'-(hydroxymethyl)-[1,1'-biphenyl]-4-yl)methyl)cyclohexanecarboxamido)phenyl)acrylate;
(E)-Methyl 3-(3-(N-((3'-(methylsulfonyl)-[1,1'-biphenyl]-4-yl)methyl)cyclohexanecarboxamido)phenyl)acrylate;
(E)-Methyl 3-(3-(N-(4-(benzo[d][1,3]dioxol-5-yl)benzyl)cyclohexanecarboxamido)phenyl)acrylate;
(E)-Methyl 3-(3-(N-((3'-chloro-4'-methoxy-[1,1'-biphenyl]-4-yl)methyl)cyclohexanecarboxamido)phenyl)acrylate;
(E)-Methyl 3-(3-(N-((2-cyano-4'-(dimethylamino)-[1,1'-biphenyl]-4-yl)methyl)cyclohexanecarboxamido)phenyl)acrylate;

(E)-Methyl 3-(3-(N-((3-cyano-4'-(dimethylamino)-[1,1'-biphenyl]-4-yl)methyl)cyclohexanecarboxamido)phenyl)acrylate;
(E)-Methyl 3-(3-(N-((4'-(dimethylamino)-2-ethyl-[1,1'-biphenyl]-4-yl)methyl)cyclohexanecarboxamido)phenyl)acrylate;
(E)-Methyl 3-(3-(N-((4'-(dimethylamino)-3-ethyl-[1,1'-biphenyl]-4-yl)methyl)cyclohexanecarboxamido)phenyl)acrylate;
(E)-Methyl 3-(3-(N-((4'-methoxy-3'-methyl-[1,1'-biphenyl]-4-yl)methyl)piperidine-4-carboxamido)phenyl)acrylate;
(E)-Methyl 3-(3-(1-acetyl-N-((4'-methoxy-3'-methyl-[1,1'-biphenyl]-4-yl)methyl)piperidine-4-carboxamido)phenyl)acrylate;
(E)-Methyl 3-(3-(N-((4'-methoxy-3'-methyl-[1,1'-biphenyl]-4-yl)methyl)-1-(methylsulfonyl)piperidine-4-carboxamido)phenyl)acrylate;
(E)-Methyl 3-(3-(N-((4'-(dimethylamino)-[1,1'-biphenyl]-4-yl)methyl)cyclohexanecarboxamido)phenyl)-2-methylacrylate;
(E)-Methyl 3-(3-(N-((3'-cyano-4'-methoxy-[1,1'-biphenyl]-4-yl)methyl)cyclohexanecarboxamido)phenyl)acrylate;
(E)-Methyl 3-(3-(N-(4-(pyridin-2-yl)benzyl)cyclohexanecarboxamido)phenyl)acrylate;
(E)-Methyl 3-(3-(N-((2'-cyano-[1,1'-biphenyl]-4-yl)methyl)cyclohexanecarboxamido)phenyl)acrylate;
(E)-Methyl 3-(3-(N-(4-(thiazol-2-yl)benzyl)cyclohexanecarboxamido)phenyl)acrylate;
(E)-Methyl 3-(3-(N-(4-(thiazol-4-yl)benzyl)cyclohexanecarboxamido)phenyl)acrylate;
(E)-Methyl 3-(3-(N-(4-(thiazol-5-yl)benzyl)cyclohexanecarboxamido)phenyl)acrylate;
(E)-Methyl 3-(3-(N-((4'-isopropyl-[1,1'-biphenyl]-4-yl)methyl)cyclohexanecarboxamido)phenyl)acrylate;
(E)-Methyl 3-(3-(N-((4'-(prop-1-en-2-yl)-[1,1'-biphenyl]-4-yl)methyl)cyclohexanecarboxamido)phenyl)acrylate;
(E)-Methyl 3-(3-(N-((3'-cyano-4'-(dimethylamino)-[1,1'-biphenyl]-4-yl)methyl)cyclohexanecarboxamido)phenyl)acrylate;
(E)-Methyl 3-(3-(N-((4'-(dimethylamino)-3'-fluoro-[1,1'-biphenyl]-4-yl)methyl)cyclohexanecarboxamido)phenyl)acrylate;
(E)-Methyl 3-(3-(N-(4-(1-methyl-1H-benzo[d]imidazol-5-yl)benzyl)cyclohexanecarboxamido)phenyl)acrylate;
(E)-methyl 3-(3-(N-((4'-(dimethylamino)-3'-methoxy-[1,1'-biphenyl]-4-yl)methyl)cyclohexanecarboxamido)phenyl)acrylate;
(E)-Methyl 3-(3-(N-(4-(1-methyl-1H-benzo[d][1,2,3]triazol-5-yl)benzyl)cyclohexanecarboxamido)phenyl)acrylate;
(E)-Methyl 3-(3-(N-((4'-(azetidin-1-yl)-[1,1'-biphenyl]-4-yl)methyl)cyclohexanecarboxamido)phenyl)acrylate;
(E)-Methyl 3-(3-(N-(4-(2-(dimethylamino)pyrimidin-5-yl)benzyl)cyclohexanecarboxamido)phenyl)acrylate;
(E)-Methyl 3-(3-(N-(4-(5-(dimethylamino)pyrazin-2-yl)benzyl)cyclohexanecarboxamido)phenyl)acrylate;
(E)-Methyl 3-(3-(N-(4-(6-(dimethylamino)pyridazin-3-yl)benzyl)cyclohexanecarboxamido)phenyl)acrylate;
(E)-Methyl 3-(3-(N-((4'-(N-methylmethylsulfonamido)-[1,1'-biphenyl]-4-yl)methyl)cyclohexanecarboxamido)phenyl)acrylate;
(E)-Methyl 3-(3-(N-((3'-fluoro-4'-(methylsulfonyl)-[1,1'-biphenyl]-4-yl)methyl)cyclohexanecarboxamido)phenyl)acrylate;
(E)-Methyl 3-(3-(N-((2'-fluoro-4'-(methylsulfonyl)-[1,1'-biphenyl]-4-yl)methyl)cyclohexanecarboxamido)phenyl)acrylate;
(E)-Methyl 3-(3-(N-(4-(benzo[d]thiazol-6-yl)benzyl)cyclohexanecarboxamido)phenyl)acrylate;
(E)-Methyl 3-(3-(N-((3'-chloro-4'-(methylsulfonyl)-[1,1'-biphenyl]-4-yl)methyl)cyclohexanecarboxamido)phenyl)acrylate;
(E)-Methyl 3-(3-(N-(4-(benzo[d]oxazol-5-yl)benzyl)cyclohexanecarboxamido)phenyl)acrylate;
(E)-Methyl 3-(3-(N-(4-(benzo[d]oxazol-6-yl)benzyl)cyclohexanecarboxamido)phenyl)acrylate;
(E)-Methyl 3-(3-(N-(4-(benzo[d]isoxazol-6-yl)benzyl)cyclohexanecarboxamido)phenyl)acrylate;
(E)-Methyl 3-(3-(N-(4-(benzo[d]thiazol-5-yl)benzyl)cyclohexanecarboxamido)phenyl)acrylate;
(E)-Methyl 3-(3-(N-(4-(benzo[d]isoxazol-5-yl)benzyl)cyclohexanecarboxamido)phenyl)acrylate;
(E)-Methyl 3-(3-(N-(4-(benzo[d]isothiazol-6-yl)benzyl)cyclohexanecarboxamido)phenyl)acrylate;
(E)-Methyl 3-(3-(N-(4-(benzo[d]isothiazol-5-yl)benzyl)cyclohexanecarboxamido)phenyl)acrylate;
(E)-Methyl 3-(3-(N-(4-(3-fluoro-1-methyl-1H-indazol-5-yl)benzyl)cyclohexanecarboxamido)phenyl)acrylate;
(E)-Methyl 3-(3-(N-(4-(3-methylbenzo[d]isothiazol-6-yl)benzyl)cyclohexanecarboxamido)phenyl)acrylate;
(E)-Methyl 3-(3-(N-(4-(4-methylpiperazin-1-yl)benzyl)cyclohexanecarboxamido)phenyl)acrylate;
(E)-Methyl 3-(3-(N-(4-morpholinobenzyl)cyclohexanecarboxamido)phenyl)acrylate;
(E)-Methyl 3-(3-(N-(4-(piperidin-1-yl)benzyl)cyclohexanecarboxamido)phenyl)acrylate;
(E)-Methyl 3-(3-(N-(4-(piperazin-1-yl)benzyl)cyclohexanecarboxamido)phenyl) acrylate;
(E)-Methyl 3-(3-(N-(naphthalen-1-ylmethyl)cyclohexanecarboxamido)phenyl)acrylate;
(E)-Methyl 3-(3-(N-([1,1'-biphenyl]-2-ylmethyl)cyclohexanecarboxamido)phenyl)acrylate;
(E)-Methyl 3-(3-(N-([1,1'-biphenyl]-3-ylmethyl)cyclohexanecarboxamido)phenyl)acrylate;
(E)-iso-Propyl 3-(3-(N-((4'-(dimethylamino)-[1,1'-biphenyl]-4-yl)methyl)cyclohexanecarboxamido)phenyl)acrylate;
(E)-Ethyl 3-(3-(N-((4'-(dimethylamino)-[1,1'-biphenyl]-4-yl)methyl)cyclohexanecarboxamido)phenyl)acrylate;
(E)-Methyl 3-(3-(N-((4'-(dimethylamino)-[1,1'-biphenyl]-4-yl)methyl)cyclohexanecarboxamido)-5-ethylphenyl)acrylate;
(E)-2-Hydroxyethyl 3-(3-(N-((4'-(dimethylamino)-[1,1'-biphenyl]-4-yl)methyl)cyclohexanecarboxamido)phenyl)acrylate;
(E)-Cyclohexyl 3-(3-(N-((4'-(dimethylamino)-[1,1'-biphenyl]-4-yl)methyl)cyclohexanecarboxamido)phenyl)acrylate;
(E)-Isobutyl 3-(3-(N-((4'-(dimethylamino)-[1,1'-biphenyl]-4-yl)methyl)cyclohexanecarboxamido)phenyl)acrylate;
(E)-2-Methoxyethyl 3-(3-(N-((4'-(dimethylamino)-[1,1'-biphenyl]-4-yl)methyl)cyclohexanecarboxamido)phenyl)acrylate;
(E)-2-(Dimethylamino)ethyl 3-(3-(N-((4'-(dimethylamino)-[1,1'-biphenyl]-4-yl)methyl)cyclohexanecarboxamido)phenyl)acrylate;
(E)-(Tetrahydrofuran-2-yl)methyl 3-(3-(N-((4'-(dimethylamino)-[1,1'-biphenyl]-4-yl)methyl)cyclohexanecarboxamido)phenyl)acrylate;

(E)-2,2,2-Trifluoroethyl 3-(3-(N-((4'-(dimethylamino)-[1,1'-biphenyl]-4-yl)methyl)cyclohexanecarboxamido)phenyl)acrylate;
(E)-Benzyl 3-(3-(N-((4'-(dimethylamino)-[1,1'-biphenyl]-4-yl)methyl)cyclohexanecarboxamido)phenyl)acrylate;
(E)-Methyl 3-(3-(N-((4'-(dimethylamino)-[1,1'-biphenyl]-4-yl)methyl)cyclohexanecarboxamido)-5-methoxyphenyl)acrylate;
(E)-Methyl 3-(3-cyano-5-(N-((4'-(dimethylamino)-[1,1'-biphenyl]-4-yl)methyl)cyclohexanecarboxamido)phenyl)acrylate;
(E)-Methyl 3-(3-chloro-5-(N-((4'-(dimethylamino)-[1,1'-biphenyl]-4-yl)methyl)cyclohexanecarboxamido)phenyl)acrylate;
(E)-Methyl 3-(3-(N-((4'-(dimethylamino)-[1,1'-biphenyl]-4-yl)methyl)cyclohexanecarboxamido)-5-(trifluoromethyl)phenyl)acrylate;
Methyl 3-(3-(N-((4'-(Dimethylamino)-[1,1'-biphenyl]-4-yl)methyl)cyclohexanecarboxamido)phenyl)propiolate;
(E)-3-(3-(N-((4'-(dimethylamino)-[1,1'-biphenyl]-4-yl)methyl)cyclohexane carboxamido)phenyl)acrylic acid;
(E)-3-(3-((1s,4s)-N-((4'-(Dimethylamino)-[1,1'-biphenyl]-4-yl)methyl)-4-hydroxycyclohexanecarboxamido)phenyl)acrylic acid;
Methyl 3-(3-(N-((4'-(dimethylamino)-[1,1'-biphenyl]-4-yl)methyl)cyclohexanecarboxamido)-5-methylphenyl)propanoate;
Methyl 3-(5-(N-((4'-(dimethylamino)-[1,1'-biphenyl]-4-yl)methyl)cyclohexanecarboxamido)-2-methylphenyl)propanoate;
Methyl 3-(3-(N-((4'-(dimethylamino)-[1,1'-biphenyl]-4-yl)methyl)cyclohexanecarboxamido)-2-methylphenyl)propanoate;
Methyl 3-(3-(N-((4'-(dimethylamino)-[1,1'-biphenyl]-4-yl)methyl)cyclohexanecarboxamido)-4-methylphenyl)propanoate;
Methyl 3-(3-(N-((4'-(dimethylamino)-[1,1'-biphenyl]-4-yl)methyl)cyclohexanecarboxamido)phenyl)butanoate;
Methyl 3-(3-(N-((4'-(dimethylamino)-[1,1'-biphenyl]-4-yl)methyl)cyclohexanecarboxamido)phenyl)-2-methylpropanoate;
(E)-Methyl 3-(3-(trans-4-((tert-butoxycarbonyl)amino)-N-((4'-(dimethylamino)-[1,1'-biphenyl]-4-yl)methyl)cyclohexanecarboxamido)phenyl)acrylate;
(E)-Methyl 3-(3-(trans-4-amino-N-((4'-(dimethylamino)-[1,1'-biphenyl]-4-yl)methyl)cyclohexanecarboxamido)phenyl)acrylate;
(E)-Methyl 3-(3-(trans-4(4'-(dimethylamino)-[1,1'-biphenyl]-4-yl)methyl)-4-((methoxycarbonyl)amino)cyclohexanecarboxamido)phenyl)acrylate;
trans-(E)-Methyl 3-(3-(4-acetamido-N-((4'-(dimethylamino)-[1,1'-biphenyl]-4-yl)methyl)cyclohexanecarboxamido)phenyl)acrylate;
trans-(E)-Methyl 3-(3-(N-((4'-(dimethylamino)-[1,1'-biphenyl]-4-yl)methyl)-4-(methylsulfonamido)cyclohexanecarboxamido)phenyl)acrylate;
N-((4'-(Dimethylamino)-[1,1'-biphenyl]-4-yl)methyl)-N-(3-(3-methylbut-2-en-1-yl)phenyl)cyclohexanecarboxamide;
(E)-Methyl 3-(3-(N-(4-benzamidobenzyl)cyclohexanecarboxamido)phenyl)acrylate;
(E)-Methyl 3-(3-(N-(4-(N-methylbenzamido)benzyl)cyclohexanecarboxamido)phenyl)acrylate;
(E)-Methyl 3-(3-(N-(4-(benzylamino)benzyl)cyclohexanecarboxamido)phenyl)acrylate; and
(E)-Methyl 3-(3-(N-(4-(benzyl(methyl)amino)benzyl)cyclohexanecarboxamido)phenyl)acrylate;
or a pharmaceutically acceptable salt, or solvate thereof.

16. A pharmaceutical composition comprising a compound of claim 1, or a pharmaceutically acceptable salt, or solvate thereof, and at least one pharmaceutically acceptable excipient.

17. A method of treating or preventing a liver disease or condition in a subject, comprising administering to the subject a therapeutically effective amount of one or more of the compounds of claim 1, or a pharmaceutically acceptable salt or solvate thereof.

18. The method of claim 17, wherein the liver disease or condition is primary biliary cirrhosis, primary sclerosing cholangitis, cholestasis, nonalcoholic steatohepatitis (NASH), or nonalcoholic fatty liver disease (NAFLD).

* * * * *